(12) United States Patent
    Delgado et al.

(10) Patent No.: US 12,588,997 B2
(45) Date of Patent: Mar. 31, 2026

(54) HEART VALVE SEALING DEVICES AND DELIVERY DEVICES THEREFOR

(71) Applicant: Edwards Lifesciences Corporation, Irvine, CA (US)

(72) Inventors: Sergio Delgado, Irvine, CA (US); Eric Michael Oberwise, Newport Beach, CA (US); Michael J. Popp, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 842 days.

(21) Appl. No.: 17/721,068

(22) Filed: Apr. 14, 2022

(65) Prior Publication Data

US 2022/0233312 A1     Jul. 28, 2022

Related U.S. Application Data

(63) Continuation of application No. PCT/US2020/055482, filed on Oct. 14, 2020.

(60) Provisional application No. 62/915,589, filed on Oct. 15, 2019.

(51) Int. Cl.
    *A61F 2/24*          (2006.01)

(52) U.S. Cl.
    CPC ............ *A61F 2/2454* (2013.01); *A61F 2/246* (2013.01); *A61F 2/2466* (2013.01); *A61F 2220/0016* (2013.01); *A61F 2230/0093* (2013.01)

(58) Field of Classification Search
    CPC ....... A61F 2/246; A61F 2/2466; A61F 2/2454
    See application file for complete search history.

(56) References Cited

U.S. PATENT DOCUMENTS

| | | | |
|---|---|---|---|
| 3,874,388 | A | 4/1975 | King et al. |
| 4,011,947 | A | 3/1977 | Sawyer |
| 4,340,091 | A | 7/1982 | Skelton et al. |
| 4,506,669 | A | 3/1985 | Blake, III |
| 4,590,937 | A | 5/1986 | Deniega |
| 4,693,248 | A | 9/1987 | Failla |
| 4,803,983 | A | 2/1989 | Siegel |
| 5,125,895 | A | 6/1992 | Buchbinder et al. |
| 5,171,252 | A | 12/1992 | Friedland |
| 5,195,962 | A | 3/1993 | Martin et al. |
| 5,292,326 | A | 3/1994 | Green et al. |
| 5,327,905 | A | 7/1994 | Avitall |
| 5,363,861 | A | 11/1994 | Edwards et al. |

(Continued)

FOREIGN PATENT DOCUMENTS

| | | |
|---|---|---|
| CN | 1142351 A | 2/1997 |
| CN | 102438552 A | 5/2012 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Alvin J Stewart
(74) *Attorney, Agent, or Firm* — Anya Adams

(57)          ABSTRACT

Valve repair devices are disclosed herein. One valve repair device has a main shaft and a pair of paddles. The pair of paddles include a connection portion, an inner paddle portion, and an outer paddle portion. Each connection portion of the pair of paddles is connected to the main shaft. The pair of paddles are moveable between an open position and a closed position.

9 Claims, 133 Drawing Sheets

(56)                References Cited

U.S. PATENT DOCUMENTS

| | | | |
|---|---|---|---|
| 5,370,685 | A | 12/1994 | Stevens |
| 5,389,077 | A | 2/1995 | Melinyshyn et al. |
| 5,411,552 | A | 5/1995 | Andersen et al. |
| 5,450,860 | A | 9/1995 | O'Connor |
| 5,456,674 | A | 10/1995 | Bos et al. |
| 5,474,057 | A | 12/1995 | Makower et al. |
| 5,478,353 | A | 12/1995 | Yoon |
| 5,487,746 | A | 1/1996 | Yu et al. |
| 5,565,004 | A | 10/1996 | Christoudias |
| 5,607,462 | A | 3/1997 | Imran |
| 5,609,598 | A | 3/1997 | Laufer et al. |
| 5,611,794 | A | 3/1997 | Sauer et al. |
| 5,626,607 | A | 5/1997 | Malecki et al. |
| 5,695,504 | A | 12/1997 | Gifford, III et al. |
| 5,716,417 | A | 2/1998 | Girard et al. |
| 5,727,569 | A | 3/1998 | Benetti et al. |
| 5,741,297 | A | 4/1998 | Simon |
| 5,782,746 | A | 7/1998 | Wright |
| 5,797,960 | A | 8/1998 | Stevens et al. |
| 5,836,311 | A | 11/1998 | Borst et al. |
| 5,843,076 | A | 12/1998 | Webster, Jr. et al. |
| 5,855,590 | A | 1/1999 | Malecki et al. |
| 5,885,271 | A | 3/1999 | Hamilton et al. |
| 5,888,247 | A | 3/1999 | Benetti |
| 5,891,017 | A | 4/1999 | Swindle et al. |
| 5,891,112 | A | 4/1999 | Samson |
| 5,894,843 | A | 4/1999 | Benetti et al. |
| 5,921,979 | A | 7/1999 | Kovac et al. |
| 5,944,738 | A | 8/1999 | Amplatz et al. |
| 5,957,835 | A | 9/1999 | Anderson et al. |
| 5,972,020 | A | 10/1999 | Carpentier et al. |
| 5,980,534 | A | 11/1999 | Gimpelson |
| 6,004,329 | A | 12/1999 | Myers et al. |
| 6,010,531 | A | 1/2000 | Donlon et al. |
| 6,017,358 | A | 1/2000 | Yoon et al. |
| 6,086,600 | A | 7/2000 | Kortenbach |
| 6,120,496 | A | 9/2000 | Whayne et al. |
| 6,132,370 | A | 10/2000 | Furnish et al. |
| 6,162,239 | A | 12/2000 | Manhes |
| 6,165,183 | A | 12/2000 | Kuehn et al. |
| 6,182,664 | B1 | 2/2001 | Cosgrove |
| 6,193,732 | B1 | 2/2001 | Frantzen et al. |
| 6,193,734 | B1 | 2/2001 | Bolduc et al. |
| 6,200,315 | B1 | 3/2001 | Gaiser et al. |
| 6,228,032 | B1 | 5/2001 | Eaton et al. |
| 6,241,743 | B1 | 6/2001 | Levin et al. |
| 6,269,819 | B1 | 8/2001 | Oz et al. |
| 6,269,829 | B1 | 8/2001 | Chen et al. |
| 6,312,447 | B1 | 11/2001 | Grimes |
| 6,461,366 | B1 | 10/2002 | Seguin |
| 6,468,285 | B1 | 10/2002 | Hsu et al. |
| 6,508,806 | B1 | 1/2003 | Hoste |
| 6,508,825 | B1 | 1/2003 | Selmon et al. |
| 6,530,933 | B1 | 3/2003 | Yeung et al. |
| 6,537,290 | B2 | 3/2003 | Adams et al. |
| 6,544,215 | B1 | 4/2003 | Bencini et al. |
| 6,626,930 | B1 | 9/2003 | Allen et al. |
| 6,629,534 | B1 | 10/2003 | St. Goar et al. |
| 6,719,767 | B1 | 4/2004 | Kimblad |
| 6,764,510 | B2 | 7/2004 | Vidlund et al. |
| 6,770,083 | B2 | 8/2004 | Seguin |
| 6,837,867 | B2 | 1/2005 | Kortelling |
| 6,855,137 | B2 | 2/2005 | Bon |
| 6,913,614 | B2 | 7/2005 | Marino et al. |
| 6,939,337 | B2 | 9/2005 | Parker et al. |
| 6,945,956 | B2 | 9/2005 | Waldhauser et al. |
| 7,048,754 | B2 | 5/2006 | Martin et al. |
| 7,101,395 | B2 | 9/2006 | Tremulis et al. |
| 7,125,421 | B2 | 10/2006 | Tremulis et al. |
| 7,288,097 | B2 | 10/2007 | Seguin |
| 7,371,210 | B2 | 5/2008 | Brock et al. |
| 7,464,712 | B2 | 12/2008 | Oz et al. |
| 7,509,959 | B2 | 3/2009 | Oz et al. |
| 7,569,062 | B1 | 8/2009 | Kuehn et al. |
| 7,618,449 | B2 | 11/2009 | Tremulis et al. |
| 7,682,369 | B2 | 3/2010 | Seguin |
| 7,731,706 | B2 | 6/2010 | Potter |
| 7,744,609 | B2 | 6/2010 | Allen et al. |
| 7,748,389 | B2 | 7/2010 | Salahieh et al. |
| 7,753,932 | B2 | 7/2010 | Gingrich et al. |
| 7,758,596 | B2 | 7/2010 | Oz et al. |
| 7,780,723 | B2 | 8/2010 | Taylor |
| 7,803,185 | B2 | 9/2010 | Gabbay |
| 7,824,443 | B2 | 11/2010 | Salahieh et al. |
| 7,981,123 | B2 | 7/2011 | Seguin |
| 7,988,724 | B2 | 8/2011 | Salahieh et al. |
| 8,052,750 | B2 | 11/2011 | Tuval et al. |
| 8,070,805 | B2 | 12/2011 | Vidlund et al. |
| 8,096,985 | B2 | 1/2012 | Legaspi et al. |
| 8,104,149 | B1 | 1/2012 | McGarity |
| 8,133,239 | B2 | 3/2012 | Oz et al. |
| 8,147,542 | B2 | 4/2012 | Maisano et al. |
| 8,172,856 | B2 | 5/2012 | Eigler et al. |
| 8,206,437 | B2 | 6/2012 | Bonhoeffer et al. |
| 8,216,301 | B2 | 7/2012 | Bonhoeffer et al. |
| 8,303,653 | B2 | 11/2012 | Bonhoeffer et al. |
| 8,313,525 | B2 | 11/2012 | Tuval et al. |
| 8,348,995 | B2 | 1/2013 | Tuval et al. |
| 8,348,996 | B2 | 1/2013 | Tuval et al. |
| 8,414,643 | B2 | 4/2013 | Tuval et al. |
| 8,425,404 | B2 | 4/2013 | Wilson et al. |
| 8,449,599 | B2 | 5/2013 | Chau et al. |
| 8,449,606 | B2 | 5/2013 | Eliasen et al. |
| 8,460,368 | B2 | 6/2013 | Taylor et al. |
| 8,470,028 | B2 | 6/2013 | Thornton et al. |
| 8,480,730 | B2 | 7/2013 | Maurer et al. |
| 8,540,767 | B2 | 9/2013 | Zhang |
| 8,579,965 | B2 | 11/2013 | Bonhoeffer et al. |
| 8,585,756 | B2 | 11/2013 | Bonhoeffer et al. |
| 8,652,202 | B2 | 2/2014 | Alon et al. |
| 8,668,733 | B2 | 3/2014 | Haug et al. |
| 8,721,665 | B2 | 5/2014 | Oz et al. |
| 8,740,918 | B2 | 6/2014 | Seguin |
| 8,771,347 | B2 | 7/2014 | DeBoer et al. |
| 8,778,017 | B2 | 7/2014 | Eliasen et al. |
| 8,834,564 | B2 | 9/2014 | Tuval et al. |
| 8,840,663 | B2 | 9/2014 | Salahieh et al. |
| 8,876,894 | B2 | 11/2014 | Tuval et al. |
| 8,876,895 | B2 | 11/2014 | Tuval et al. |
| 8,945,177 | B2 | 2/2015 | Dell et al. |
| 9,034,032 | B2 | 5/2015 | McLean et al. |
| 9,198,757 | B2 | 12/2015 | Schroeder et al. |
| 9,220,507 | B1 | 12/2015 | Patel et al. |
| 9,259,317 | B2 | 2/2016 | Wilson et al. |
| 9,282,972 | B1 | 3/2016 | Patel et al. |
| 9,301,834 | B2 | 4/2016 | Tuval et al. |
| 9,308,360 | B2 | 4/2016 | Bishop et al. |
| 9,387,071 | B2 | 7/2016 | Tuval et al. |
| 9,427,327 | B2 | 8/2016 | Parrish |
| 9,439,763 | B2 | 9/2016 | Geist et al. |
| 9,510,837 | B2 | 12/2016 | Seguin |
| 9,510,946 | B2 | 12/2016 | Chau et al. |
| 9,572,660 | B2 | 2/2017 | Braido et al. |
| 9,642,704 | B2 | 5/2017 | Tuval et al. |
| 9,700,445 | B2 | 7/2017 | Martin et al. |
| 9,775,963 | B2 | 10/2017 | Miller |
| D809,139 | S | 1/2018 | Marsot et al. |
| 9,889,002 | B2 | 2/2018 | Bonhoeffer et al. |
| 9,949,824 | B2 | 4/2018 | Bonhoeffer et al. |
| 10,076,327 | B2 | 9/2018 | Ellis et al. |
| 10,076,415 | B1 | 9/2018 | Metchik et al. |
| 10,099,050 | B2 | 10/2018 | Chen et al. |
| 10,105,221 | B2 | 10/2018 | Siegel |
| 10,105,222 | B1 | 10/2018 | Metchik et al. |
| 10,111,751 | B1 | 10/2018 | Metchik et al. |
| 10,123,873 | B1 | 11/2018 | Metchik et al. |
| 10,130,475 | B1 | 11/2018 | Metchik et al. |
| 10,136,993 | B1 | 11/2018 | Metchik et al. |
| 10,159,570 | B1 | 12/2018 | Metchik et al. |
| 10,226,309 | B2 | 3/2019 | Ho et al. |
| 10,231,837 | B1 | 3/2019 | Metchik et al. |
| 10,238,493 | B1 | 3/2019 | Metchik et al. |
| 10,238,494 | B2 | 3/2019 | McNiven et al. |
| 10,238,495 | B2 | 3/2019 | Marsot et al. |

(56)　　　　　References Cited

U.S. PATENT DOCUMENTS

| | | |
|---|---|---|
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251177 A1 | 11/2005 | Saadat et al. |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0024818 A1 | 2/2010 | Stenzler et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0222136 A1 | 8/2014 | Geist et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277403 A1 | 9/2014 | Peter |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |

(56) References Cited

U.S. PATENT DOCUMENTS

| | | |
|---|---|---|
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0071487 A1 | 3/2018 | Khuu et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126119 A1 | 5/2018 | McNiven et al. |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0344490 A1 | 12/2018 | Fox et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142579 A1 | 5/2019 | Delgado et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0323668 A1 | 10/2020 | Diedering et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0257196 A1 | 8/2022 | Massmann |
| 2022/0287841 A1 | 9/2022 | Freschauf et al. |

(56) References Cited

U.S. PATENT DOCUMENTS

| | | | |
|---|---|---|---|
| 2022/0296248 A1 | 9/2022 | Abunassar et al. | |
| 2022/0313433 A1 | 10/2022 | Ma et al. | |
| 2023/0014540 A1 | 1/2023 | Metchik et al. | |
| 2023/0149170 A1 | 5/2023 | Giese et al. | |
| 2023/0218291 A1 | 7/2023 | Zarbatany et al. | |
| 2023/0270549 A1 | 8/2023 | Guidotti et al. | |
| 2024/0148505 A1 | 5/2024 | Datta et al. | |

FOREIGN PATENT DOCUMENTS

| | | | |
|---|---|---|---|
| CN | 106175845 A | 12/2016 | |
| CN | 106491245 A | 3/2017 | |
| CN | 107789017 A | 3/2018 | |
| CN | 109953779 A | 7/2019 | |
| CN | 110338857 A | 10/2019 | |
| CN | 110495972 A | 11/2019 | |
| CN | 110537946 A | 12/2019 | |
| CN | 110664515 A | 1/2020 | |
| CN | 209996540 U | 1/2020 | |
| CN | 211243911 U | 8/2020 | |
| CN | 211723546 U | 10/2020 | |
| CN | 111870398 A | 11/2020 | |
| CN | 111904660 A | 11/2020 | |
| CN | 112120831 A | 12/2020 | |
| CN | 112168427 A | 1/2021 | |
| CN | 112190367 A | 1/2021 | |
| CN | 212346813 U | 1/2021 | |
| CN | 212415988 U | 1/2021 | |
| CN | 212490263 U | 2/2021 | |
| CN | 213489553 U | 6/2021 | |
| CN | 113476182 A | 10/2021 | |
| CN | 113855328 A | 12/2021 | |
| CN | 215019733 U | 12/2021 | |
| EP | 0098100 A2 | 1/1984 | |
| FR | 2146050 A5 | 2/1973 | |
| FR | 9711600 | 3/1997 | |
| JP | 2018518245 A | 7/2018 | |
| WO | WO-2005112827 A2 | 12/2005 | |
| WO | WO-2010108079 A1 | 9/2010 | |
| WO | WO-2014064694 A2 | 5/2014 | |
| WO | 2017015632 A1 | 1/2017 | |
| WO | 2018013856 A1 | 1/2018 | |
| WO | 2018050200 A1 | 3/2018 | |
| WO | 2018050203 A1 | 3/2018 | |
| WO | WO-2018081461 A1 | 5/2018 | |
| WO | 2018195015 A1 | 10/2018 | |
| WO | 2018195201 A1 | 10/2018 | |
| WO | 2018195215 A2 | 10/2018 | |
| WO | WO-2018209021 A1 | 11/2018 | |
| WO | WO-2019051180 A2 | 3/2019 | |
| WO | 2019139904 A1 | 7/2019 | |
| WO | 2020106705 A1 | 5/2020 | |
| WO | 2020106827 A1 | 5/2020 | |
| WO | 2020112622 A1 | 6/2020 | |
| WO | 2020167677 A1 | 8/2020 | |
| WO | 2020168081 A1 | 8/2020 | |
| WO | 2020172224 A1 | 8/2020 | |
| WO | 2020176410 A1 | 9/2020 | |
| WO | WO-2021196580 A1 | 10/2021 | |
| WO | WO-2021227412 A1 | 11/2021 | |
| WO | WO-2022006087 A2 | 1/2022 | |
| WO | WO-2022036209 A1 | 2/2022 | |
| WO | WO-2022051241 A1 | 3/2022 | |
| WO | WO-2022052506 A1 | 3/2022 | |
| WO | WO-2022068188 A1 | 4/2022 | |
| WO | WO-2022101817 A2 | 5/2022 | |
| WO | WO-2022140175 A1 | 6/2022 | |
| WO | WO-2022153131 A1 | 7/2022 | |
| WO | WO-2022155298 A2 | 7/2022 | |
| WO | WO-2022157592 A1 | 7/2022 | |
| WO | WO-2022212172 A1 | 10/2022 | |
| WO | WO-2023003755 A1 | 1/2023 | |
| WO | WO-2023004098 A1 | 1/2023 | |
| WO | WO-2023278663 A2 | 1/2023 | |
| WO | WO-2023288003 A1 | 1/2023 | |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer- Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.

Reul RM et al., "Mitral valve reconstruction for mitral insufficiency", Prog Cardiovasc Dis., vol. 39, Issue—6, May-Jun. 1997.

Rösch et al., "The Birth, Early Years and Future of Interventional Radiology," Journal of Vascular and Interventional Radiology, vol. 14, No. 7, pp. 841-853, Jul. 1, 2003, Elsevier, United States.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

(56)             References Cited

OTHER PUBLICATIONS

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, @ 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Umaña JP et al., Bow-tie 'mitral valve repair: an adjuvant technique for ischemic mitral regurgitation', Ann Thorac Surg., vol. 66, Issue-6, pp. 1640-1646, Nov. 1998.

Urban, Philip MD, "Coronary Artery Stenting", pp. 5-47, @ 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

Grasso C., et al., "The Pascal Transcatheter Mitral Valve Repair System for the Treatment of Mitral Regurgitation: Another Piece to the Puzzle of Edge-to-edge Technique," Journal of Thoracic Disease, AME Publishing Company, Hong Kong, China, Dec. 2017, vol. 9, No. 12, pp. 4856-4859, DOI: 10.21037/jtd.2017.10.156.

Pavcnik D., et al., "Development and Initial Experimental Evaluation of a Prosthetic Aortic Valve for Transcatheter Placement," Cardiovascular Radiology, Apr. 1, 1992, vol. 183, No. 1, pp. 151-154.

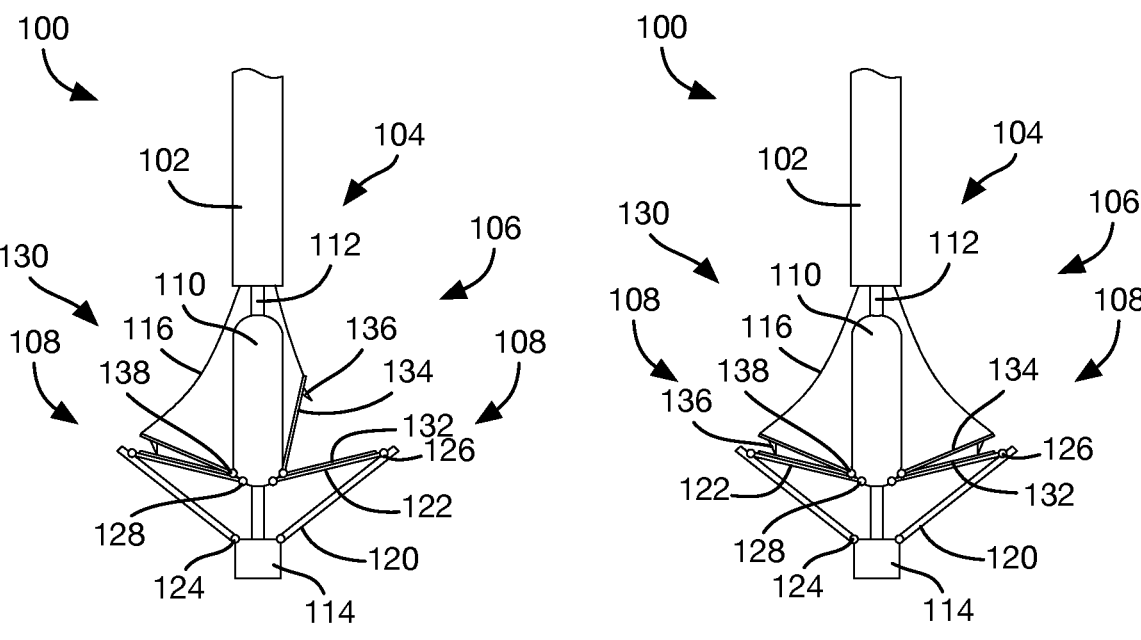
FIG. 12                  FIG. 13
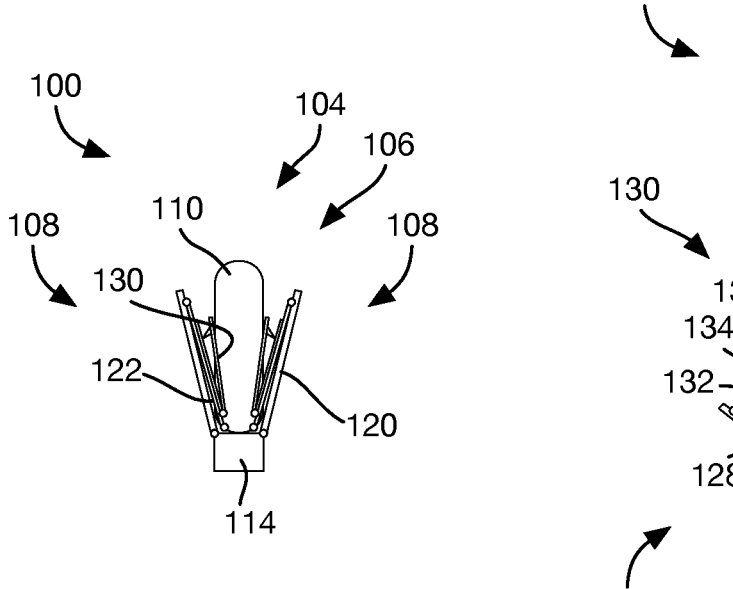
FIG. 14
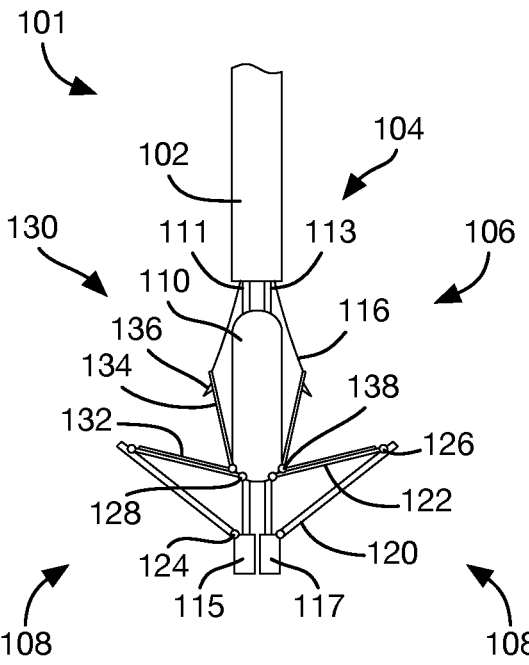
FIG. 15

H

100

106

104        LA        108

108        22

20

MV        LV

106

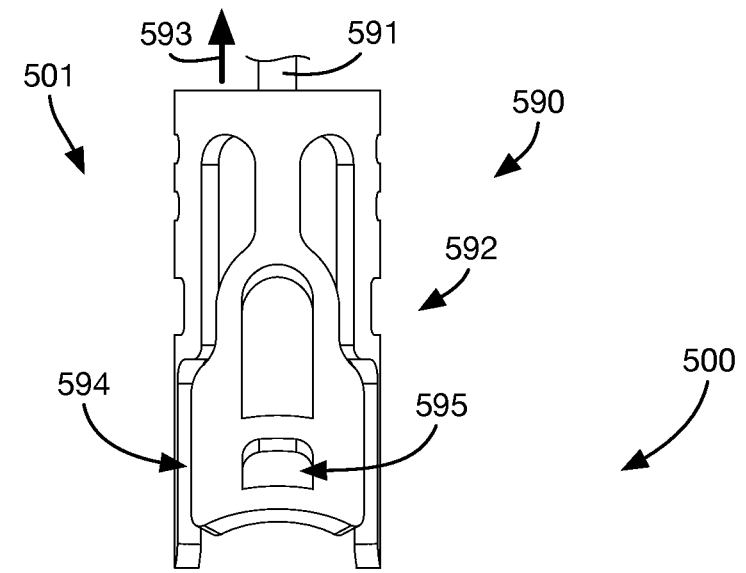
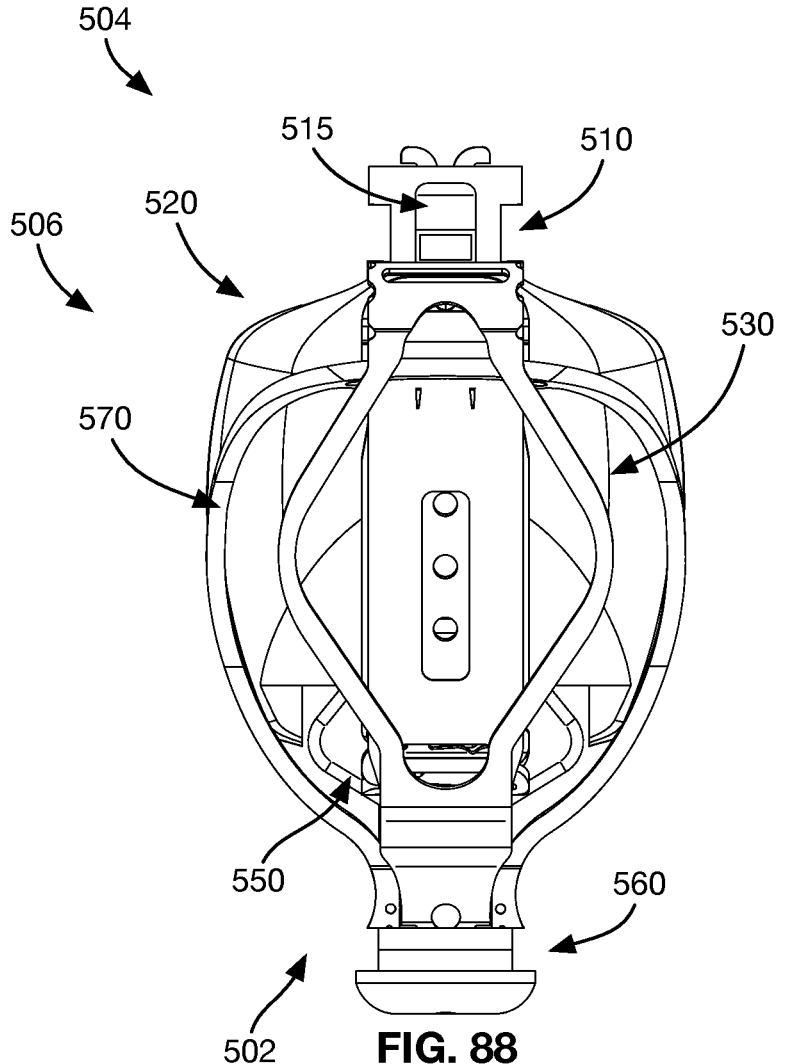
FIG. 88

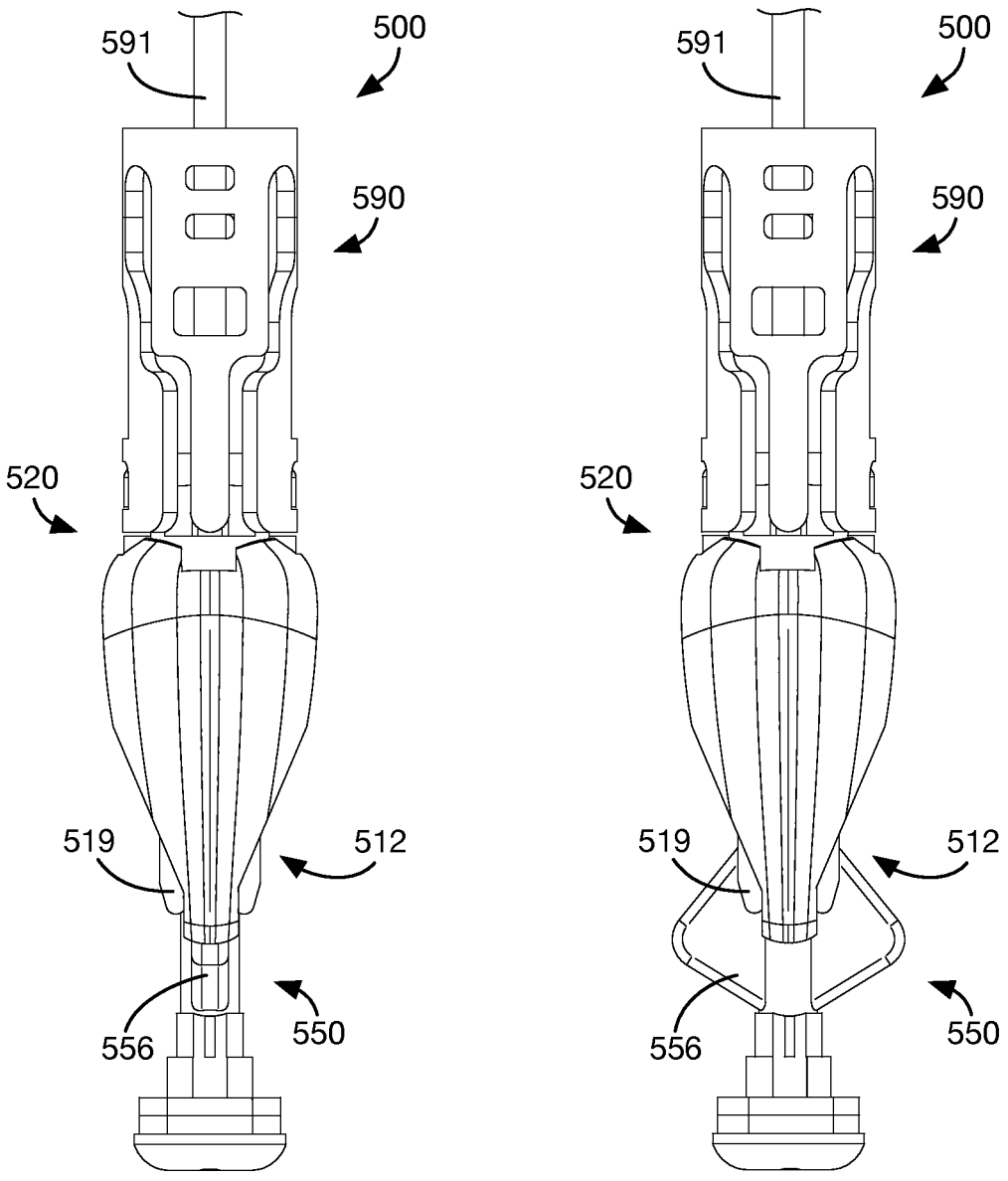
FIG. 176              FIG. 177

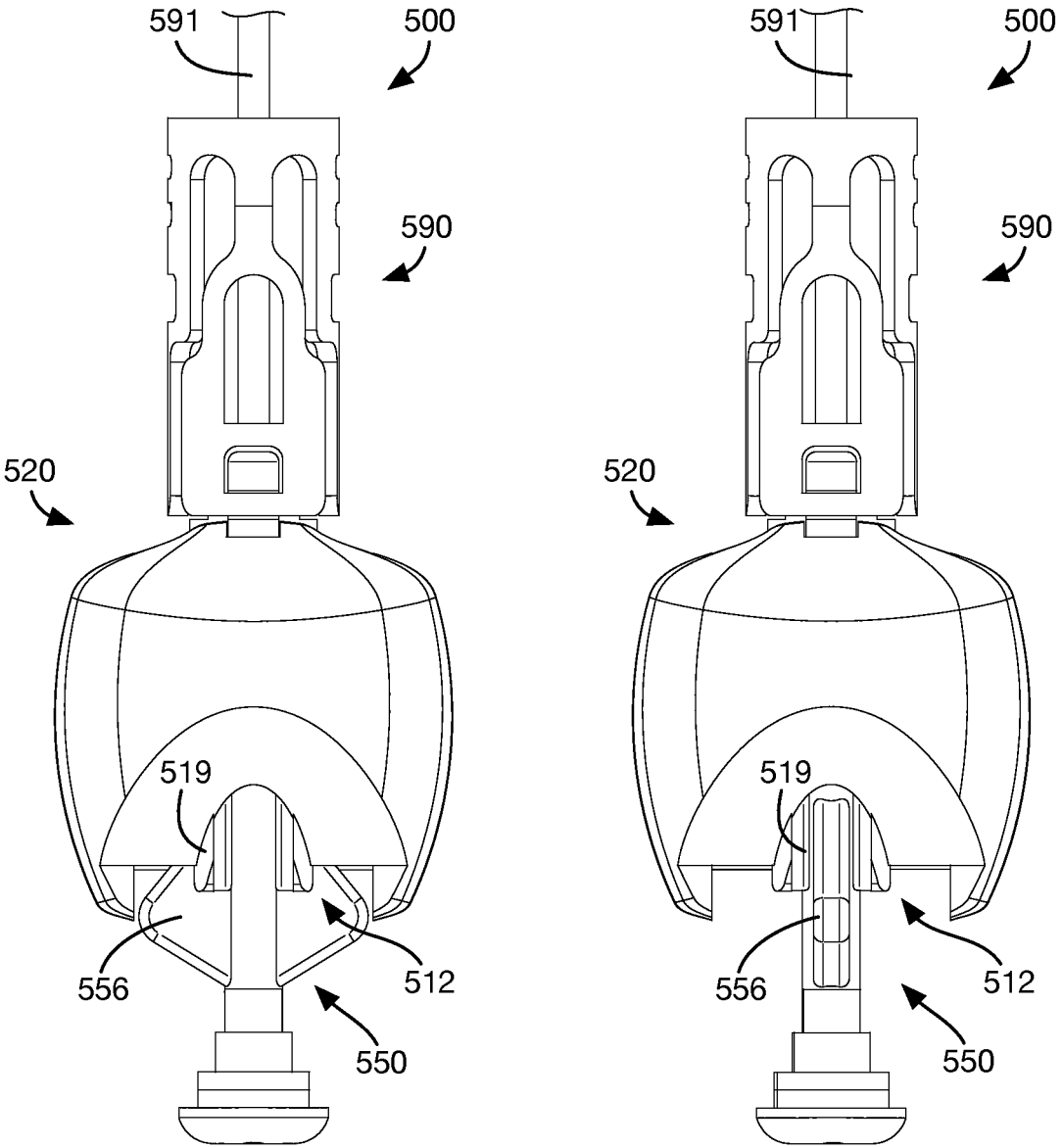
FIG. 178                    FIG. 179

HEART VALVE SEALING DEVICES AND DELIVERY DEVICES THEREFOR

RELATED APPLICATIONS

The present application is a continuation of PCT/US2020/055482, filed on Oct. 14, 2020, which claims the benefit of U.S. Provisional Patent Application No. 62/915,589, filed on Oct. 15, 2019, titled "Heart Valve Sealing Devices and Delivery Devices Therefor," which are incorporated herein by reference in their entireties for all purposes.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive and complications may occur. Transvascular techniques can be used to introduce and implant prosthetic devices in a manner that is much less invasive than open heart surgery. As one example, a transseptal technique could be used, e.g., comprising inserting a catheter into the right femoral vein, up the inferior vena cava and into the right atrium, puncturing the septum, and passing the catheter into the left atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present.

A technique for treating mitral and other valvular regurgitation in patients may include securing edges of the native valve leaflets directly to one another. For example, a catheter delivered clip may be used to attempt to clip the sides of the leaflets together at the end portions of the leaflets. But significant challenges exist. For example, multiple clips may be required to eliminate or reduce regurgitation to an acceptable level, but in some circumstances, this can result in longer operation times and may result in over-restricted flow or undesirable stresses on the native anatomy.

Despite these prior techniques, there is a continuing need for improved devices and methods for treating valvular regurgitation.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

An example implantable prosthetic device has a coaption element and at least one anchor. The coaption element is configured to be positioned within the native heart valve orifice to help fill a space where the native valve is regurgitant and form a more effective seal. The coaption element can have a structure that is impervious to blood (or otherwise inhibits blood) and that allows the native leaflets to close around the coaption element during ventricular systole to block blood from flowing from the left or right ventricle back into the left or right atrium, respectively. The coaption element can be connected to leaflets of the native valve by the anchor.

In one example embodiment, a valve repair device for repairing a native valve of a patient includes a coaption element, and one or more anchor portions. The coaption element can be formed from a solid or hollow piece of material by a variety of different processes, such as molding, three-dimensional printing, casting, etc. The one or more anchor portions are moveable between an open position and a closed position.

In one example embodiment, a valve repair device for repairing a native valve of a patient includes a main shaft, a coaption member, at least one paddle, at least one clasp, an actuation shaft, and a cap. An attachment projection extends outward from the main shaft.

In some embodiments, the coaption member includes a central opening, a groove along the central opening, and at least one engagement recess. The central opening can be configured to receive the main shaft. The groove along the central opening can be configured to allow the attachment projection of the main shaft to pass through the coaption portion.

In some embodiments, the at least one engagement recess receives the attachment projection of the main shaft.

In some embodiments, the actuation shaft extends through the main shaft.

In some embodiments, the cap is attached to the actuation shaft such that the cap can be moved by the actuation shaft away from the main shaft.

The paddle portions are moveable between an open position and a closed position.

In some embodiments, the least one clasp is attached to each of the paddle portions.

In some embodiments, movement of the cap toward the main shaft causes the paddle portions to move to the closed position, and movement of the cap away from the main shaft causes the paddle portions to move to the open position.

In one example embodiment, a valve repair device for repairing a native valve of a patient includes a main shaft, a coaption member, an actuation shaft, a cap, and one or more paddles. In some embodiments, the main shaft has at least one paddle opening.

In some embodiments, an attachment projection extends outward from the main shaft.

In some embodiments, the actuation shaft extends through the main shaft.

In some embodiments, the cap is attached to the actuation shaft such that the cap can be moved by the actuation shaft away from the main shaft.

In some embodiments, the cap includes one or more paddle openings.

In some embodiments, the plurality of paddle portions are moveable between an open position and a closed position.

In some embodiments, a proximal end of each paddle is inserted into one of the plurality of paddle openings in the main shaft.

In some embodiments, a distal end of each paddle is inserted into a paddle opening in the cap.

In some embodiments, movement of the cap toward the main shaft causes the paddle portions to move to the closed position, and movement of the cap away from the main shaft causes the paddle portions to move to the open position.

In one example embodiment, a valve repair device for repairing a native valve of a patient includes a main shaft, a coaption member, one or more paddles, an actuation shaft, and a spreading member. The actuation shaft extends through the main shaft. The spreading member is moveable between an engaged position and a disengaged position. The one or more paddles are moveable between an open position and a closed position. The cam portion is moveable to causes the cam portion to engage the paddles to spread the paddles apart.

In one example embodiment, a valve repair device includes a coaption element and an anchor portion. The coaption element including a plurality of cutouts or openings that allow the coaption element to be compressed to fit within a delivery catheter.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which:

FIGS. 8-14 show an example embodiment of an implantable prosthetic device, in various stages of deployment;

FIG. 15 shows an example embodiment of an implantable prosthetic device that is similar to the device illustrated by FIGS. 8-14, but where the paddles are independently controllable;

FIG. 88 shows a front view of the implantable prosthetic device of FIG. 82;

FIG. 152 shows a top perspective view of the components of FIG. 149 with the paddle frames in a shape setting position;

FIG. 153 shows a top perspective view of paddles, paddle frames, and a distal nut assembly in an assembled condition;

FIG. 154 shows a bottom perspective view of the components of FIG. 153;

FIG. 155 shows a side view of the components of FIG. 153;

FIG. 156 shows a top perspective, partially cutaway, view of components of an example implantable device;

FIG. 157 shows a bottom perspective, partially cutaway, view of the components of an implantable device of FIG. 156;

FIG. 158 shows a side, partially sectioned, view of the components of an implantable device of FIG. 156;

FIG. 159 shows an enlarged detail view of the area 159 of FIG. 156;

FIG. 160 shows an enlarged detail view of the area 160 of FIG. 157;

FIG. 161 shows a top perspective view of paddles of an example implantable device;

FIG. 162 shows a bottom perspective view of the paddles of FIG. 161;

FIG. 163 shows a top perspective view of a bottom portion of paddles, paddle frames, and a distal nut assembly of an example implantable device in a disassembled condition;

Figure 164:
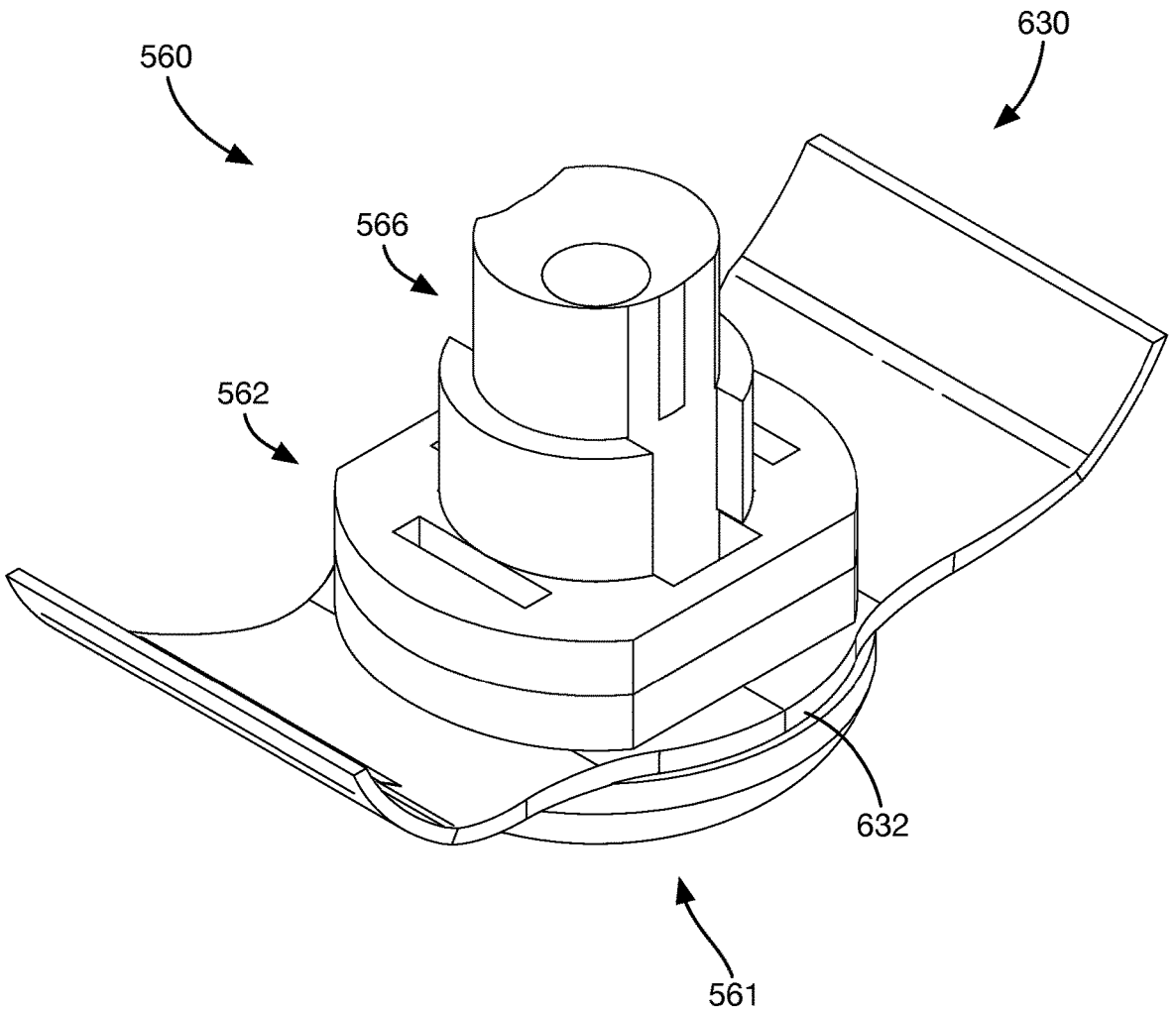
Figure 165:
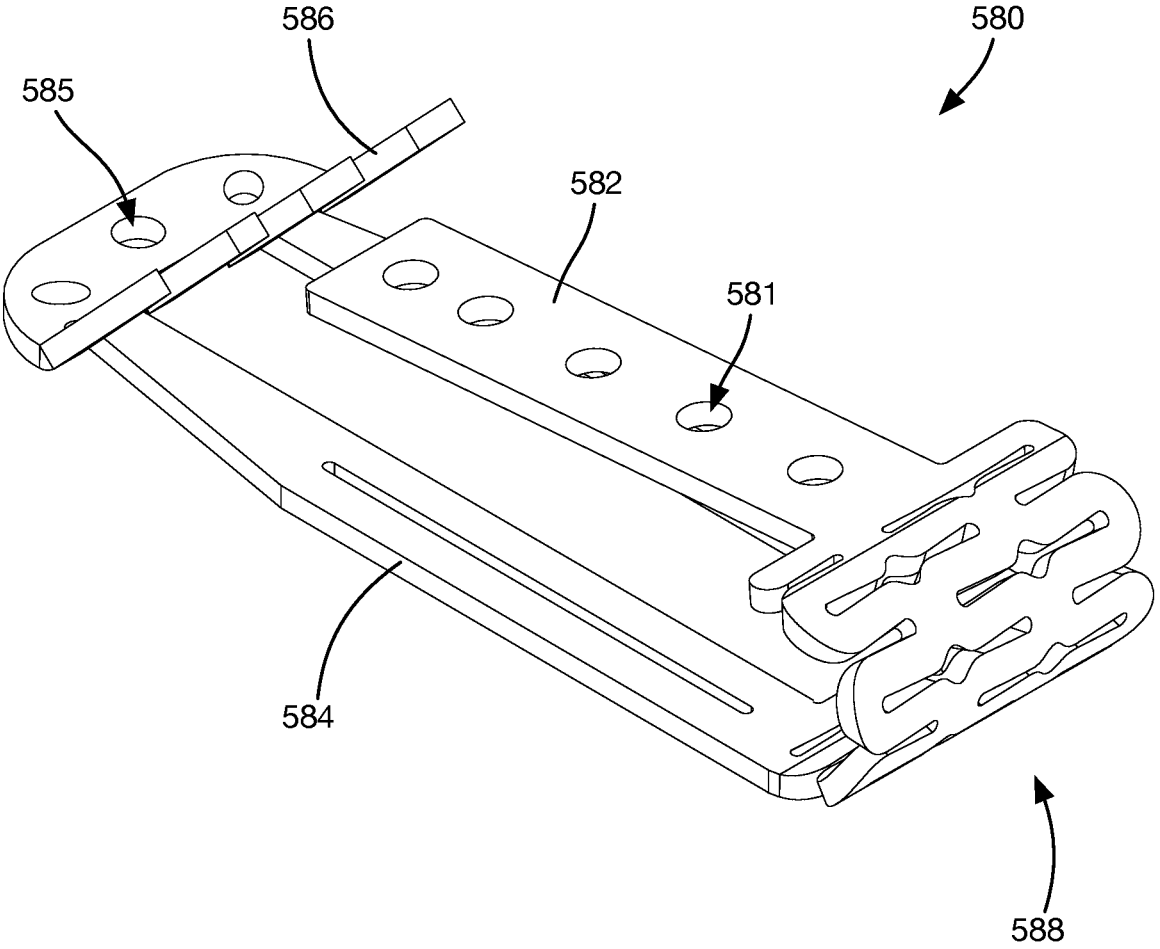
Figure 166:
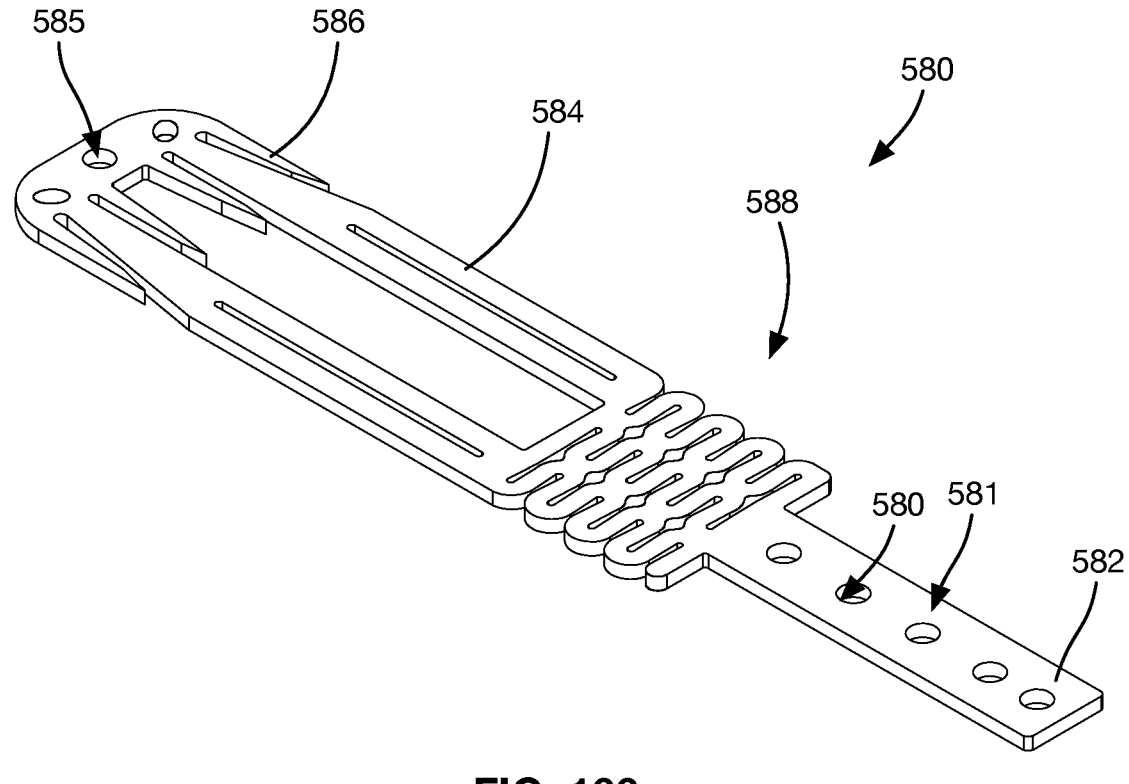
Figure 167:
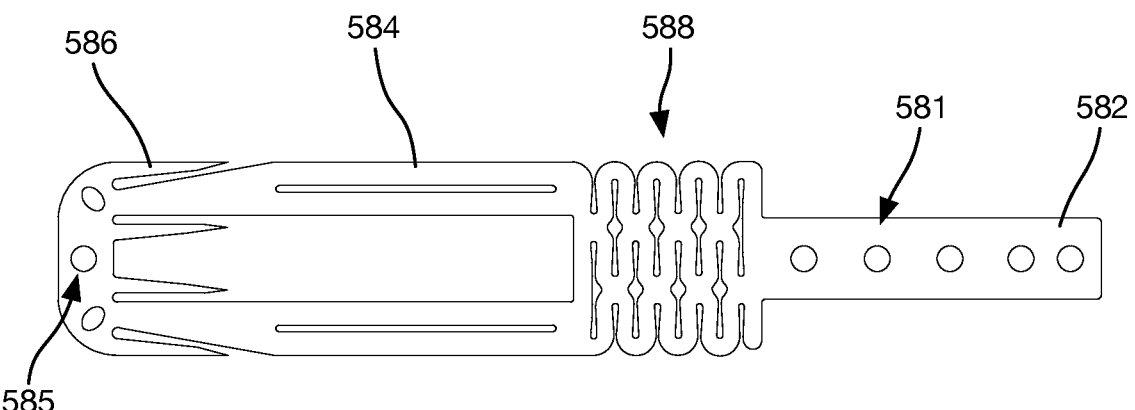
Figure 180:
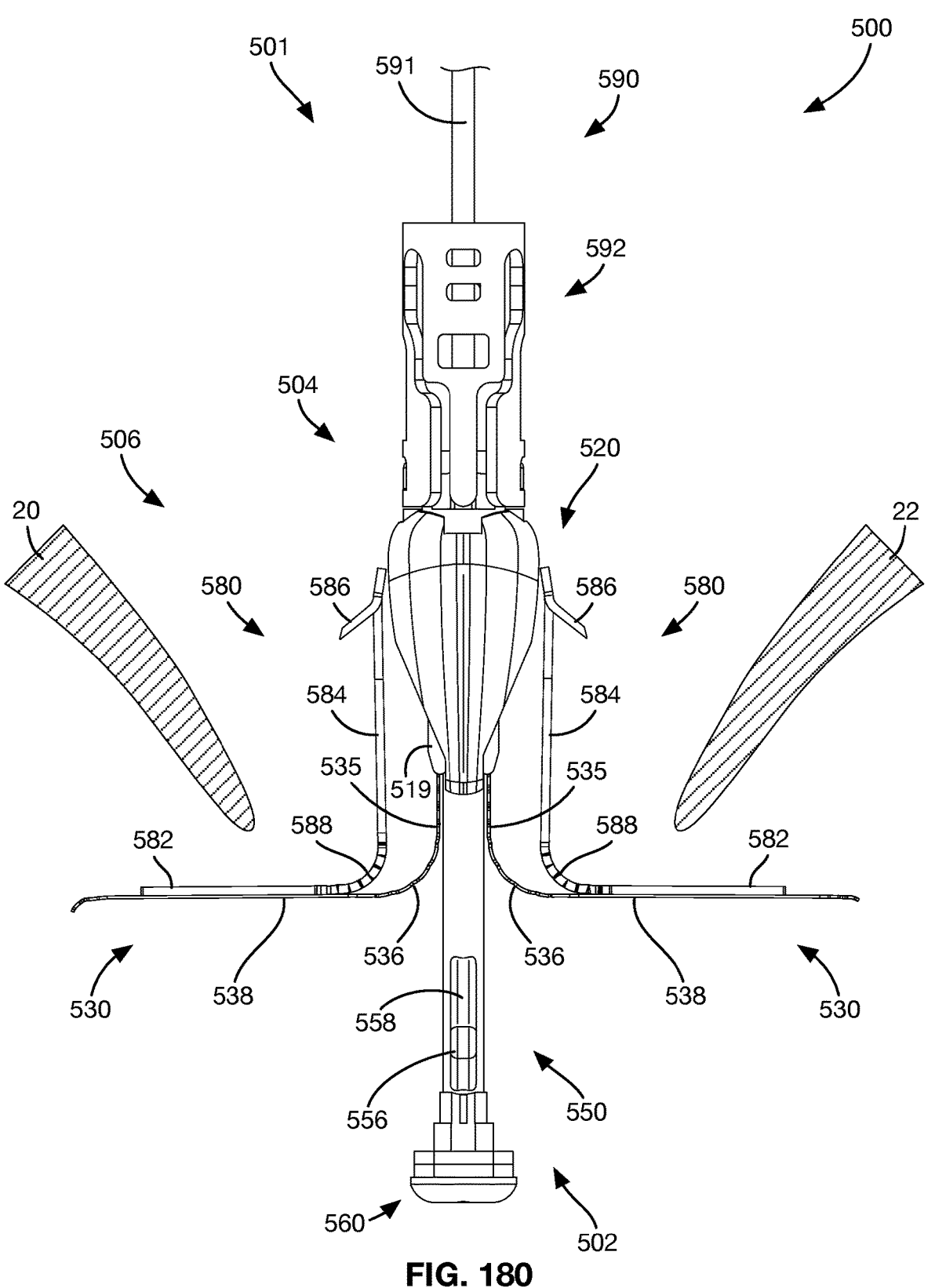
Figure 181:
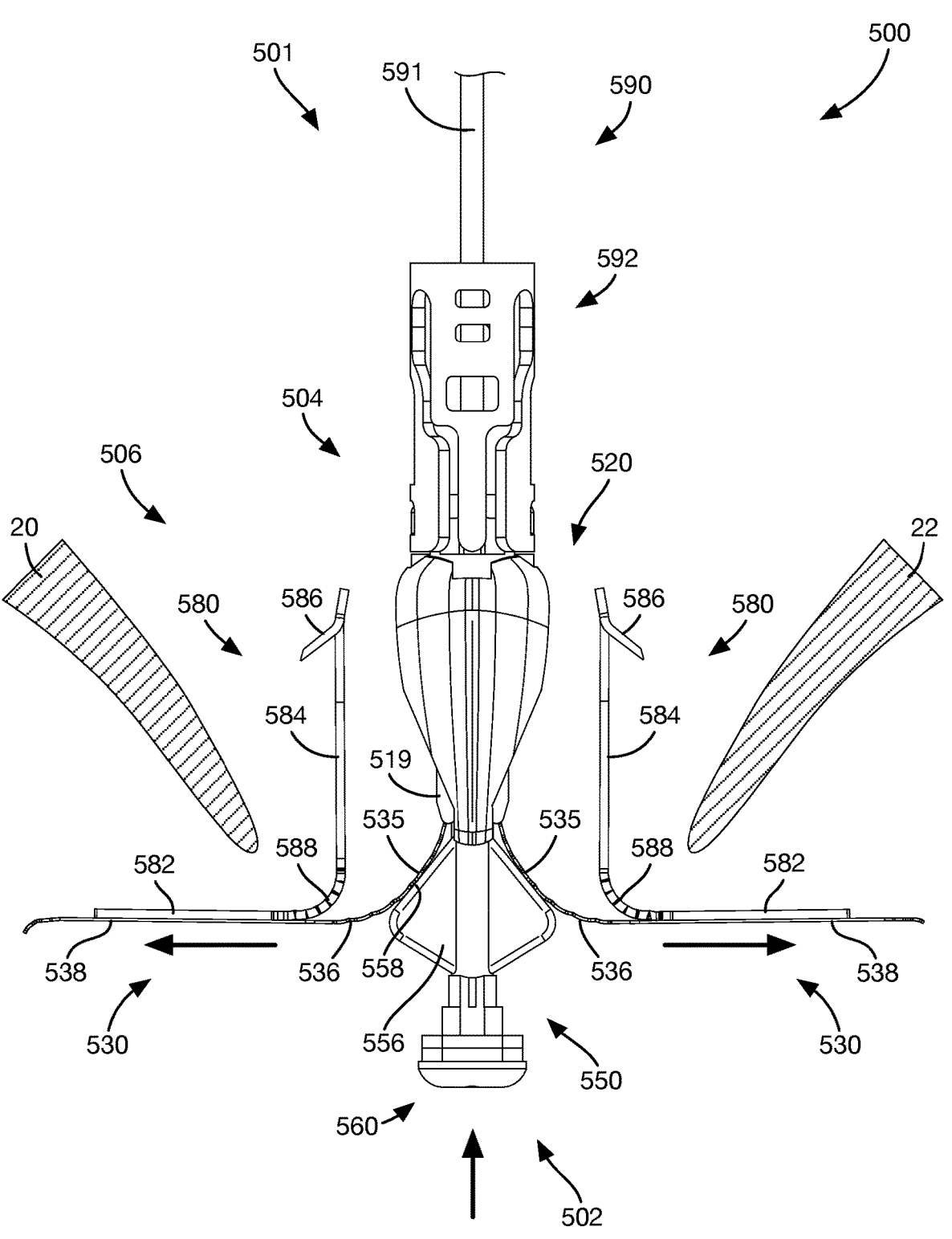
Figure 182:
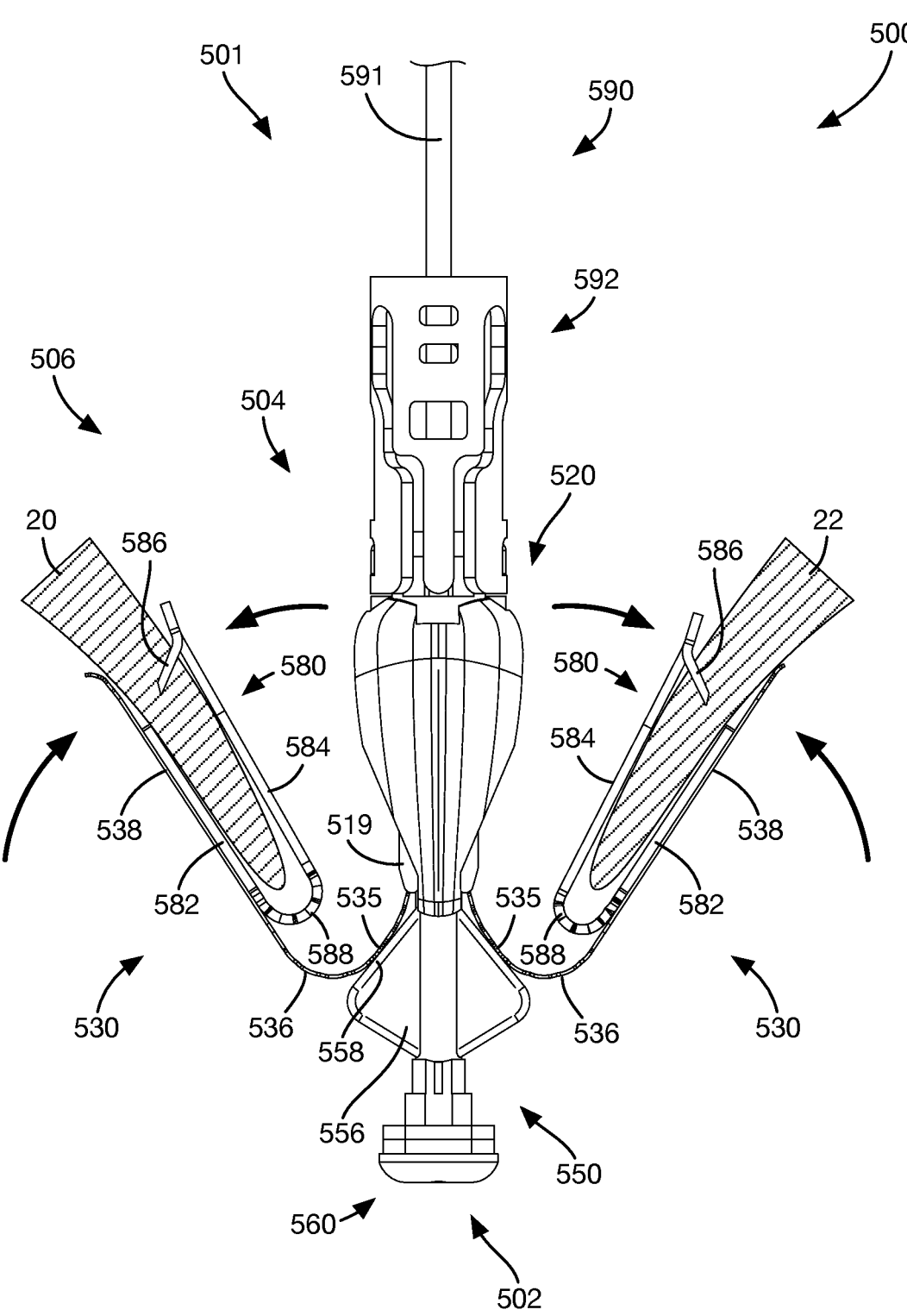
Figure 183:
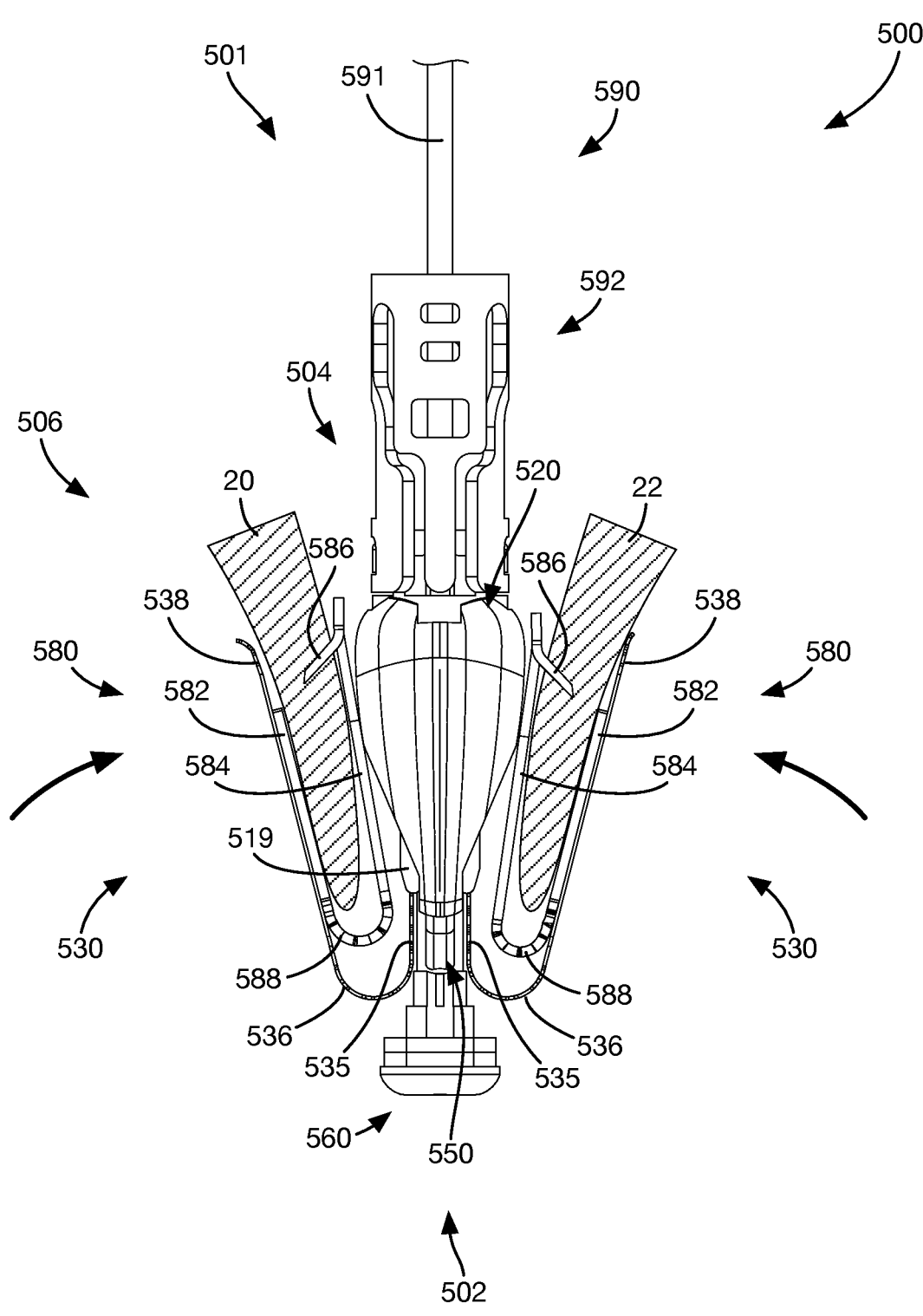
Figure 184:
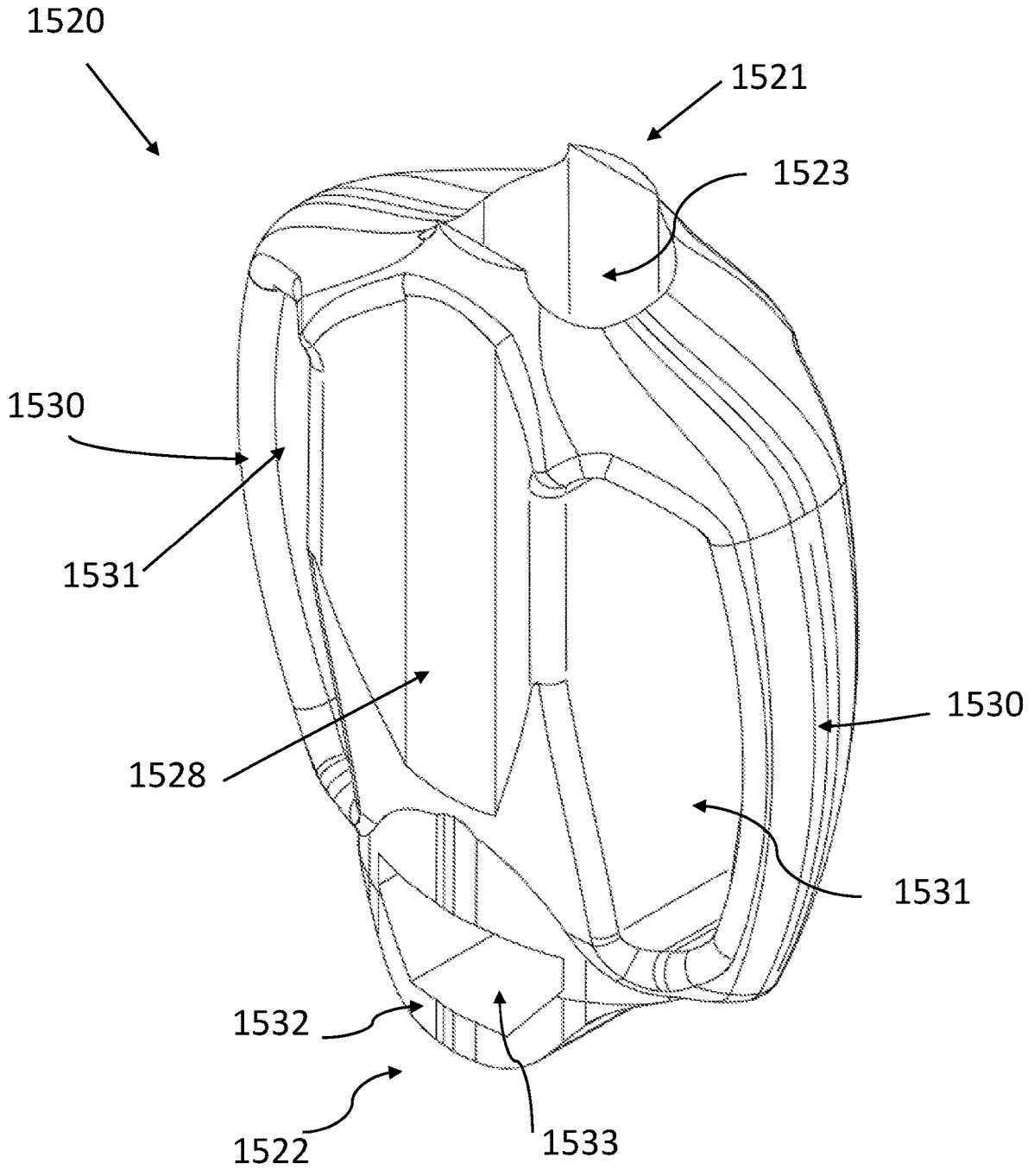
Figure 186:
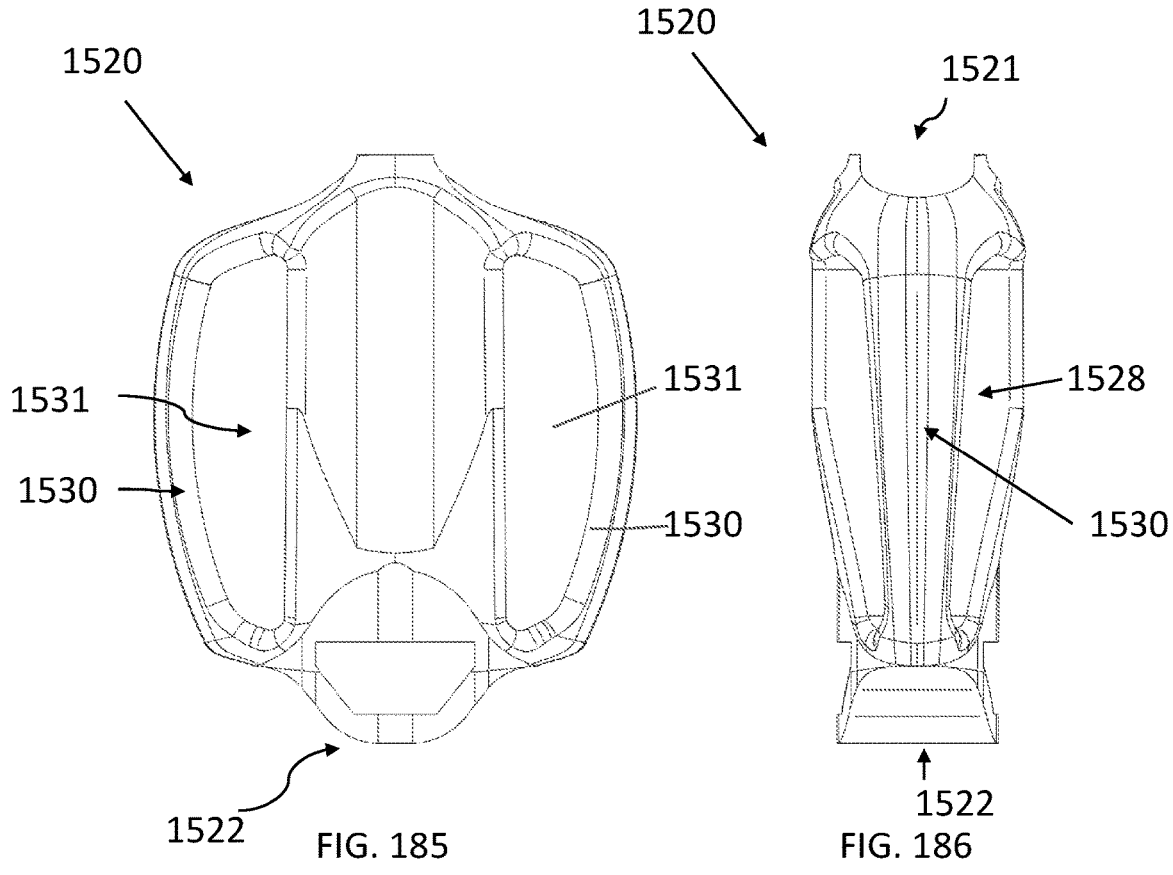
Figure 187:
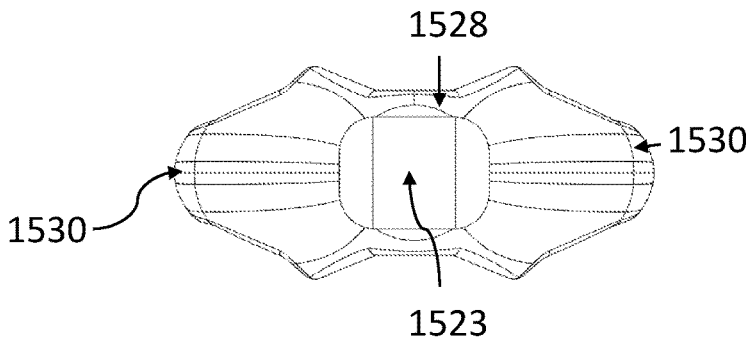
Figure 188:
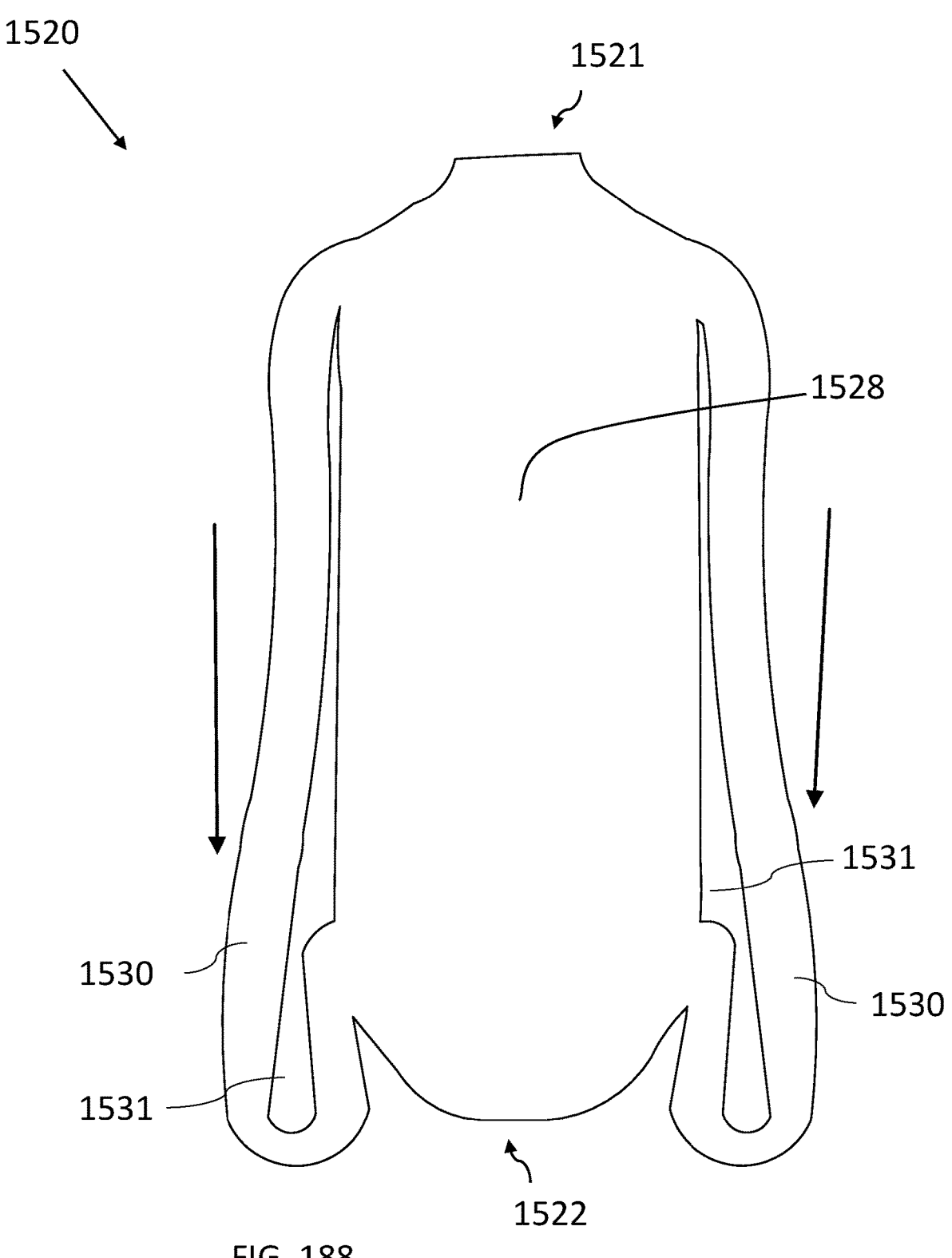
Figure 189:
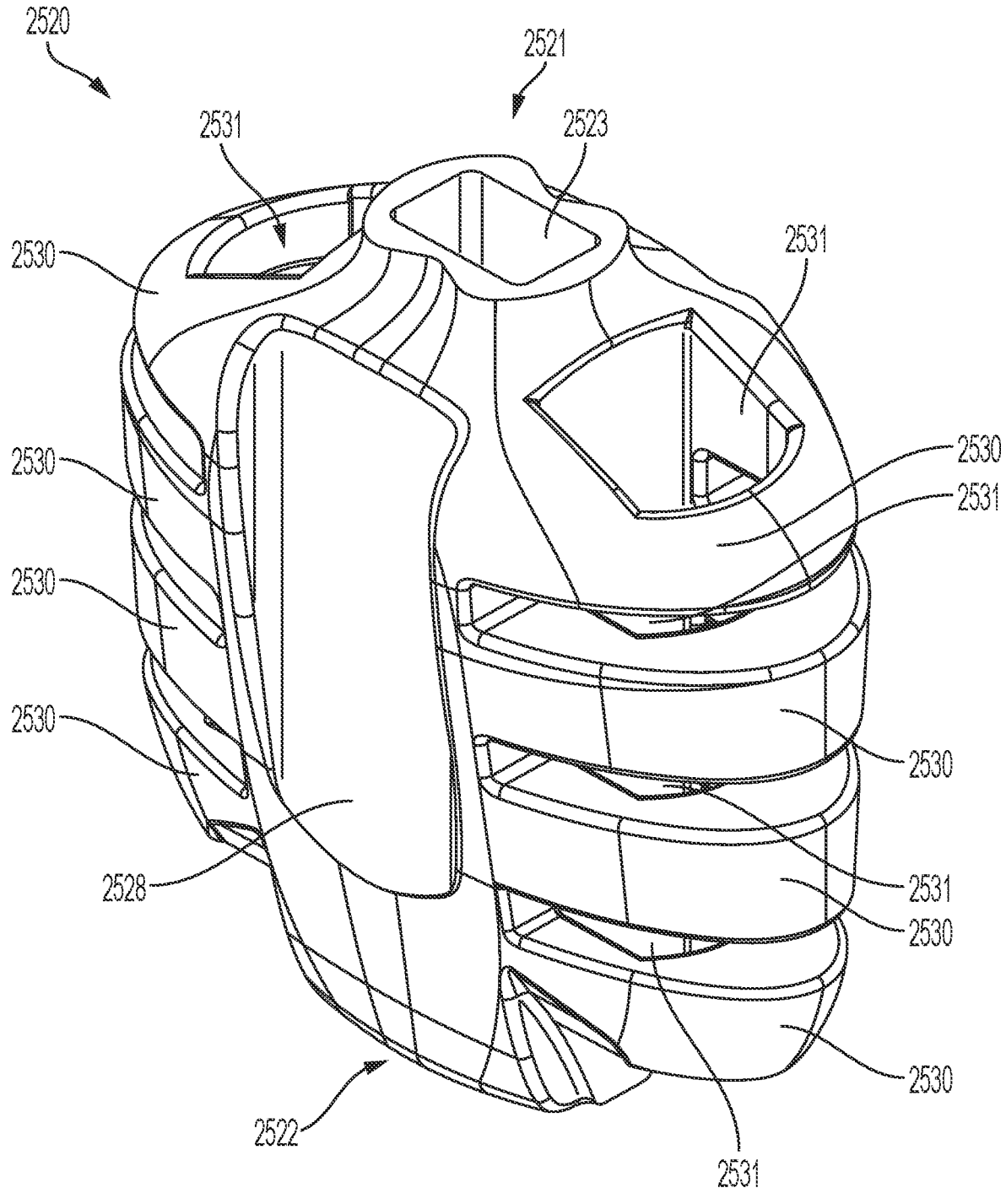
Figures 190, 191:
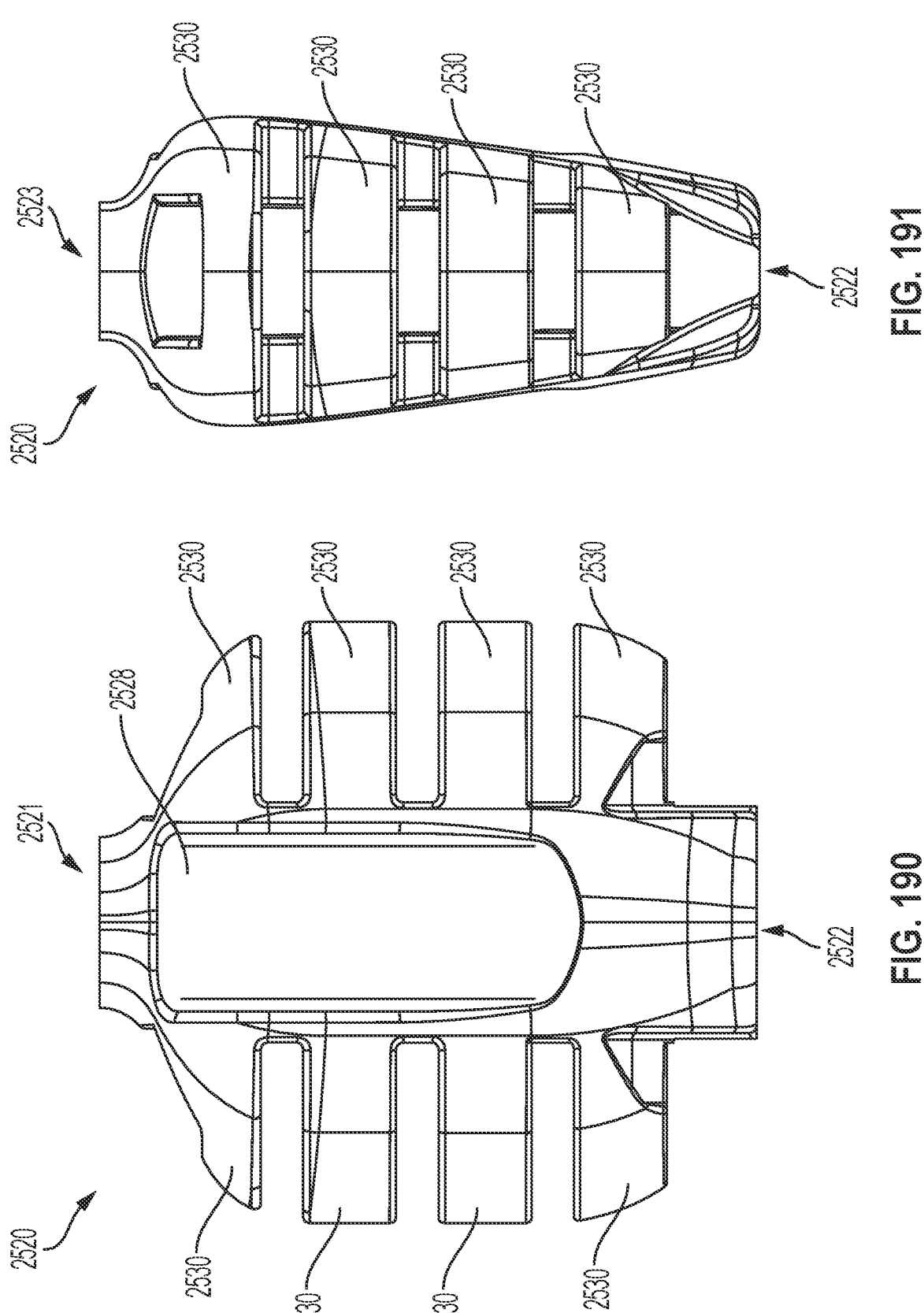
Figures 192, 193:
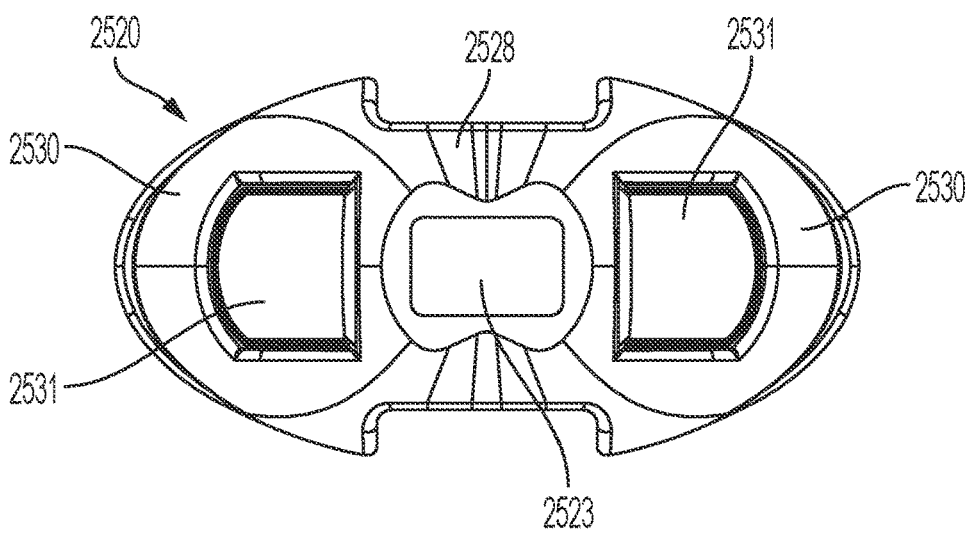
Figure 194:
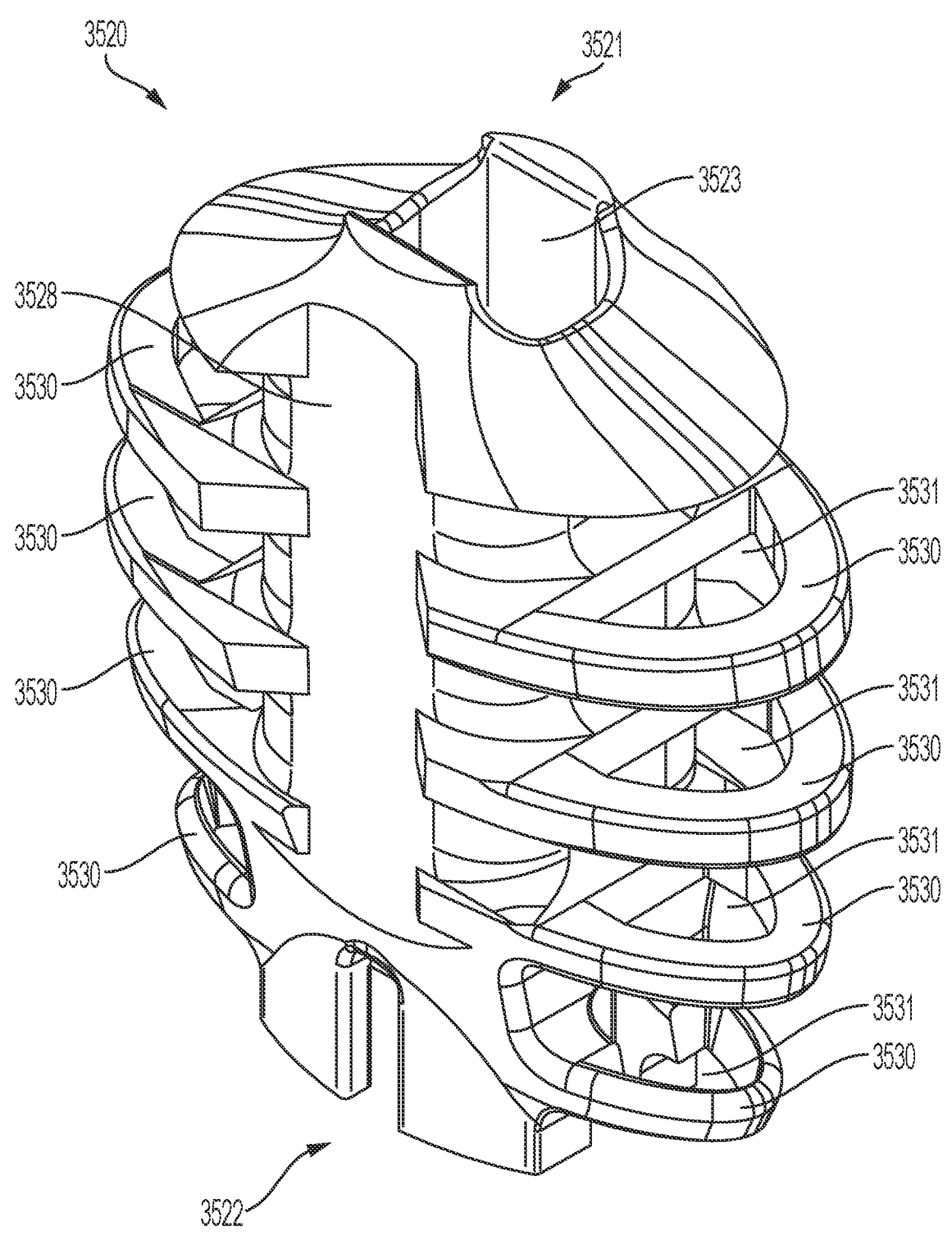
Figures 195, 196:
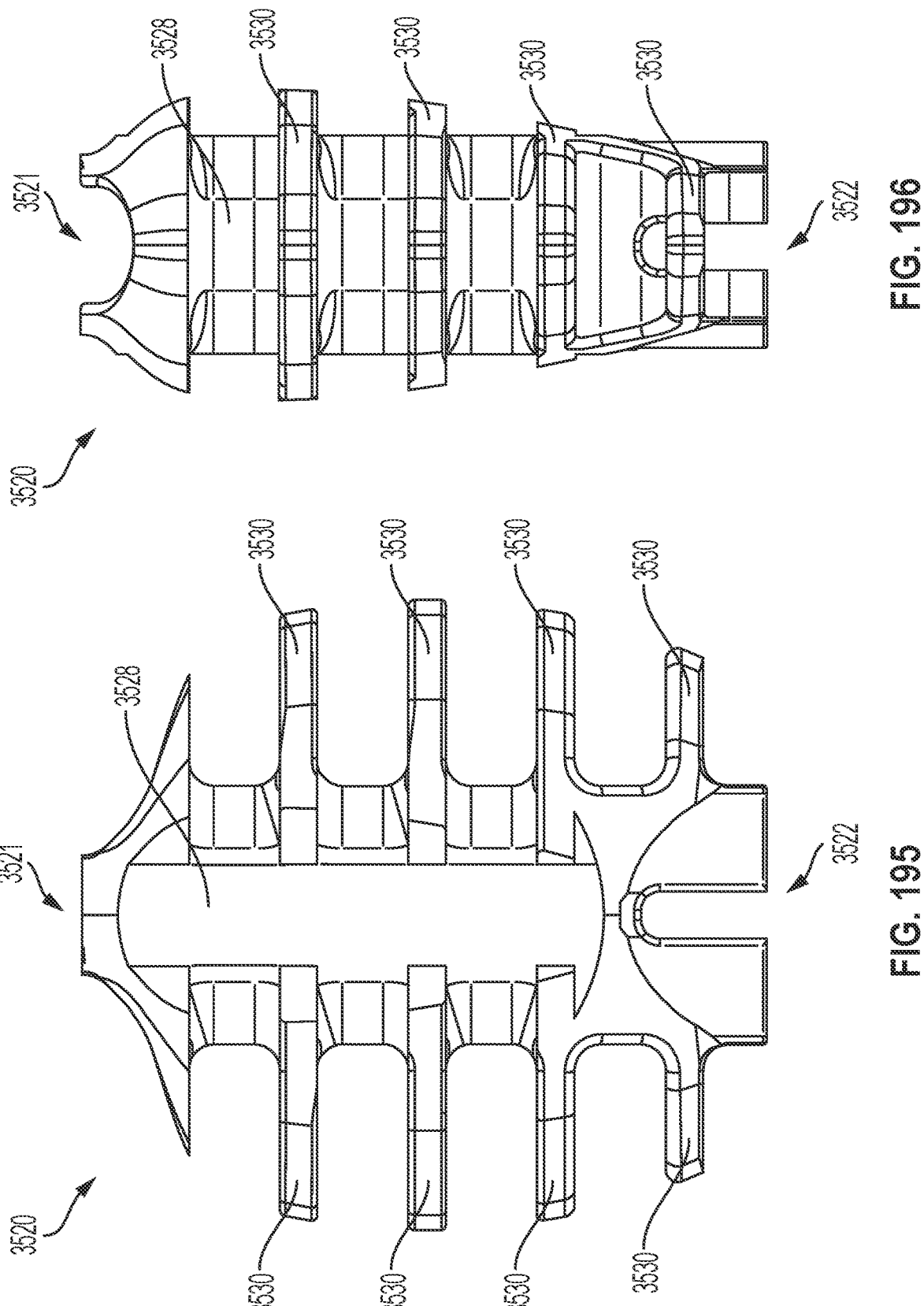
Figure 197:
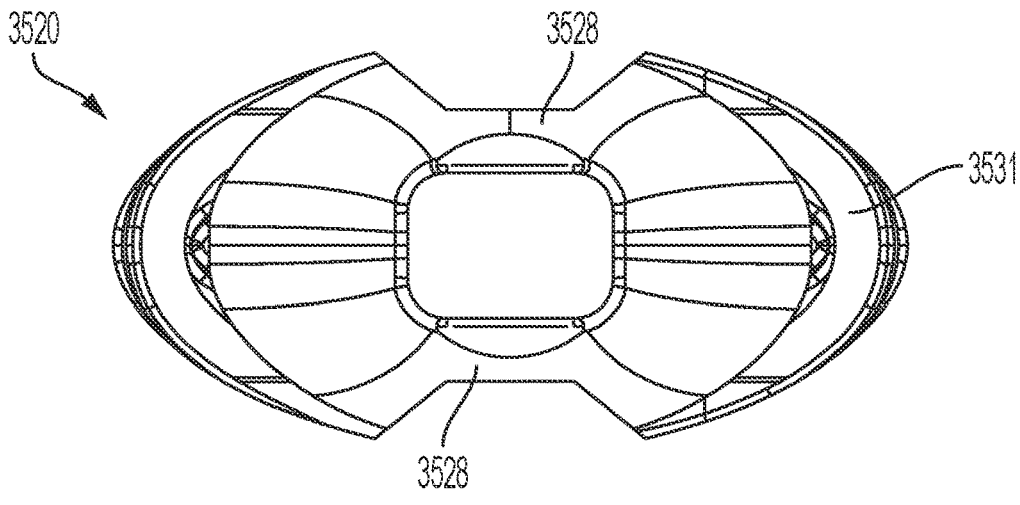
Figure 198:
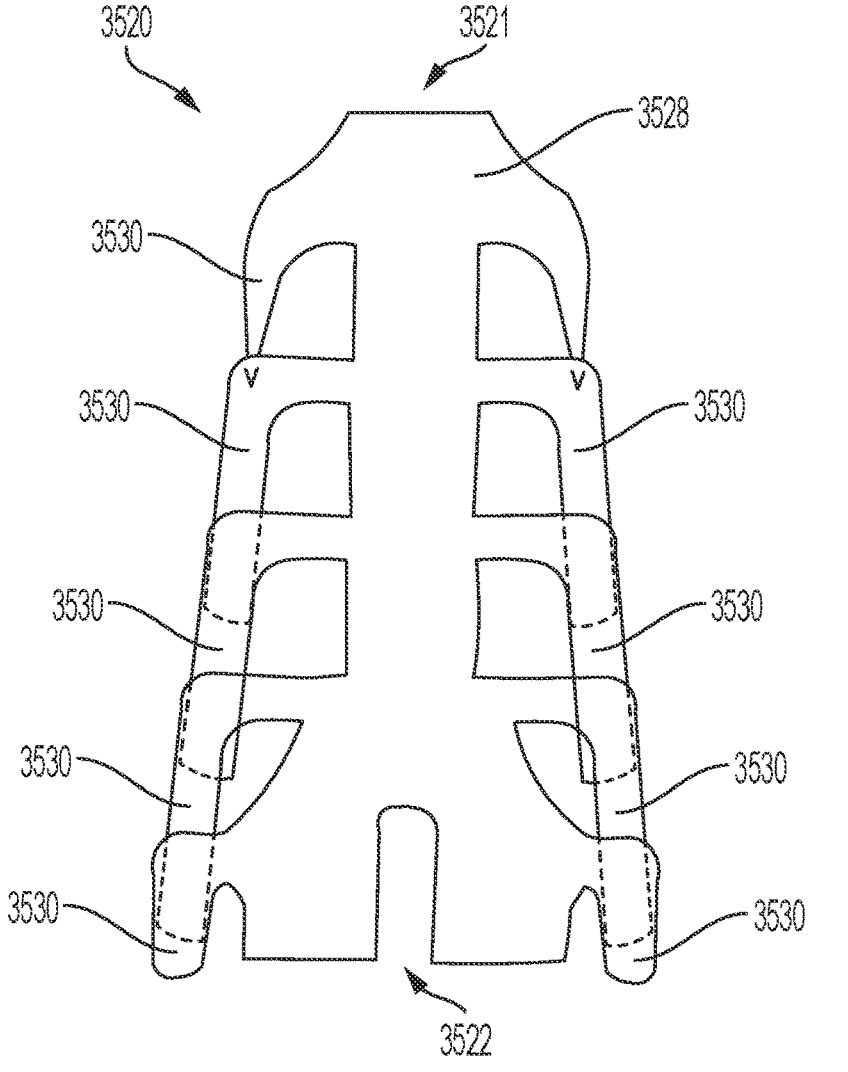
Figure 199:
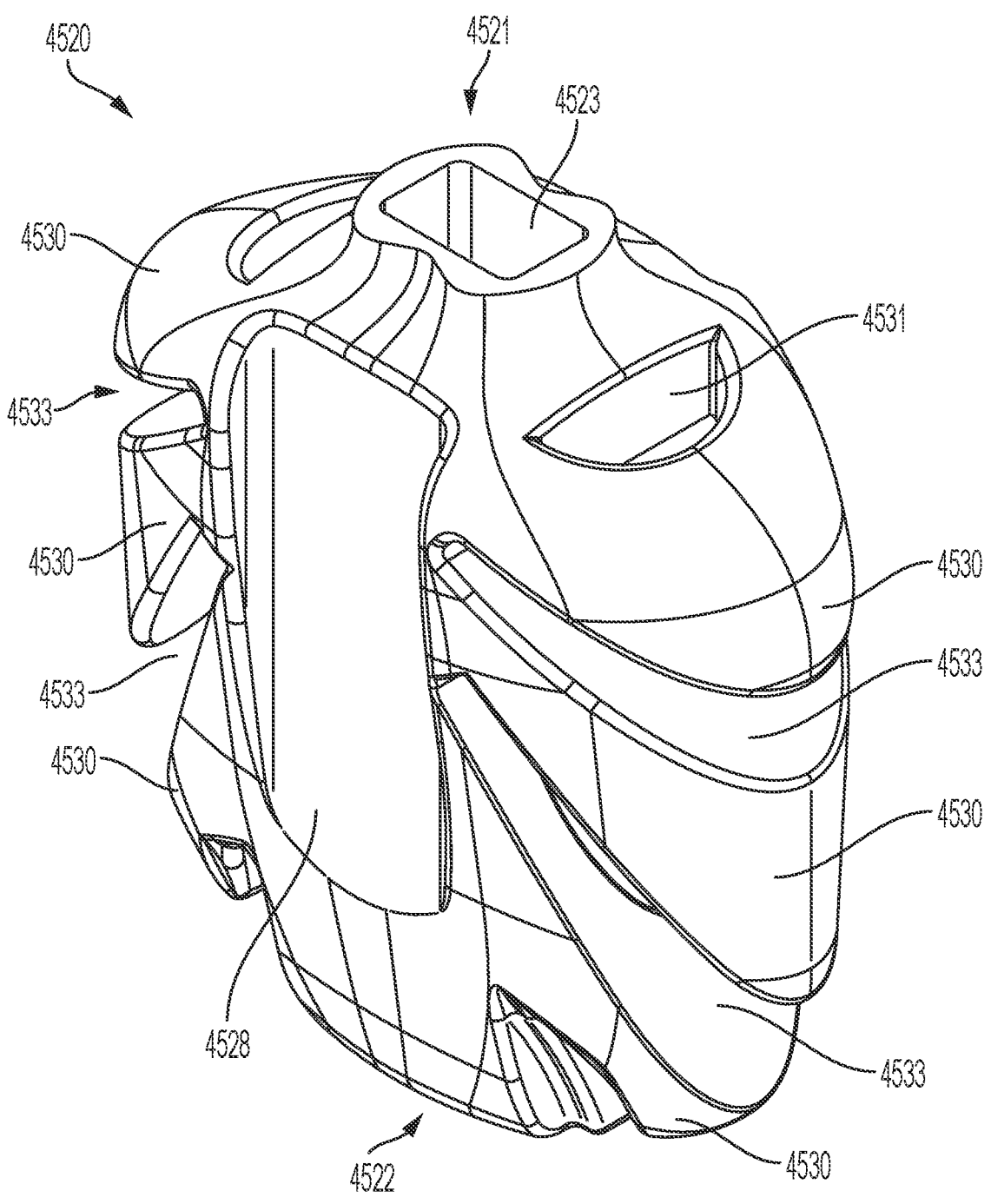
Figures 200, 201:
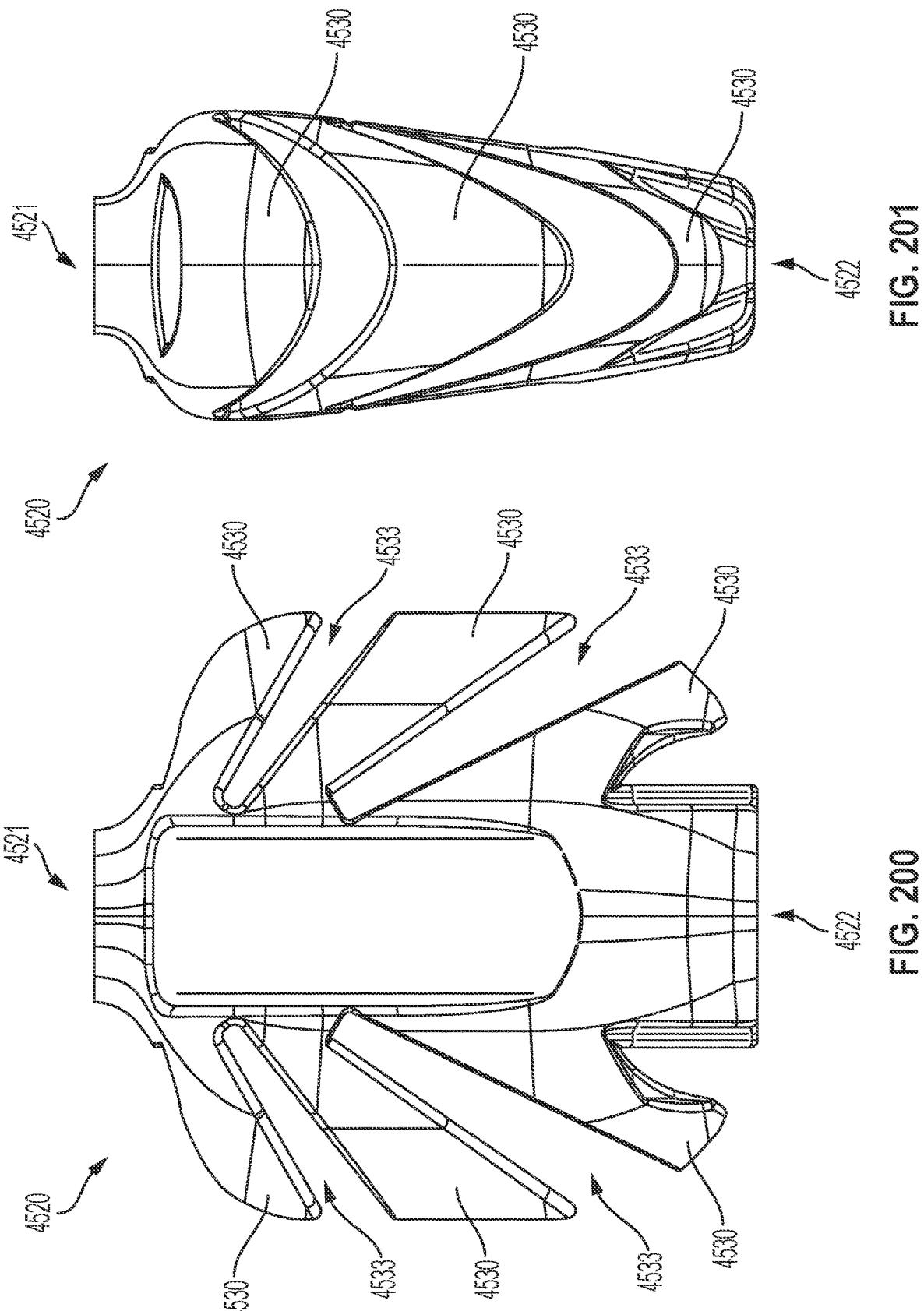
Figure 202:
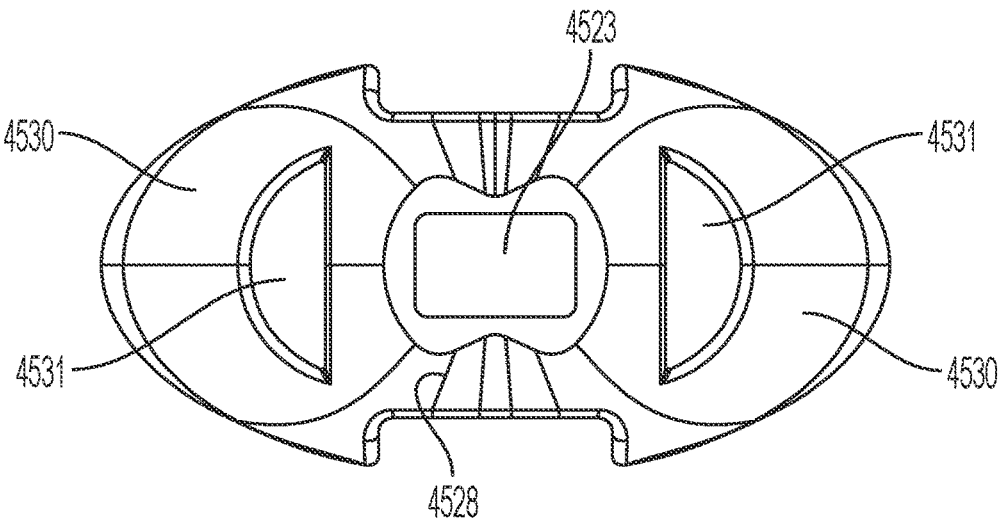
Figure 203:
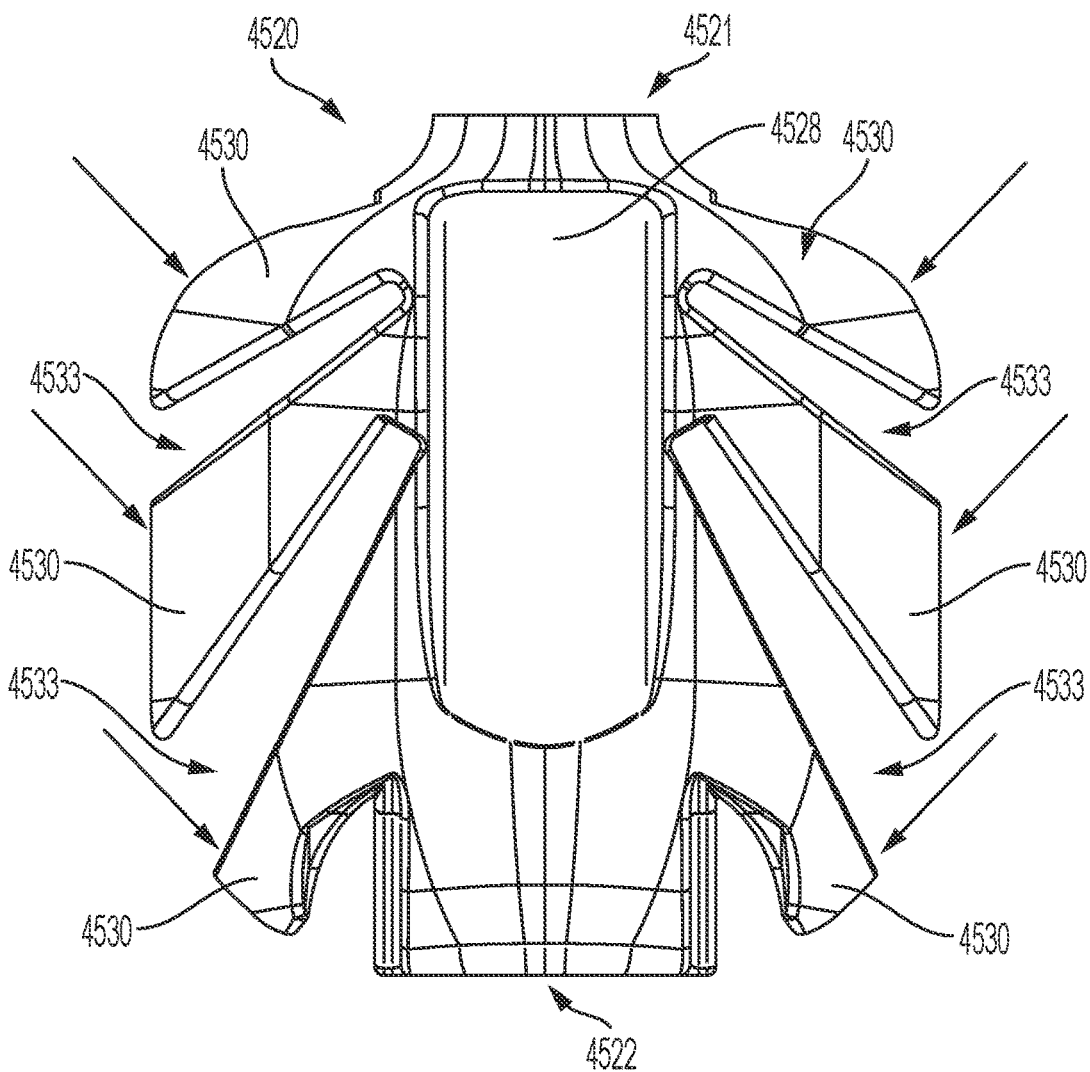
Figure 204:
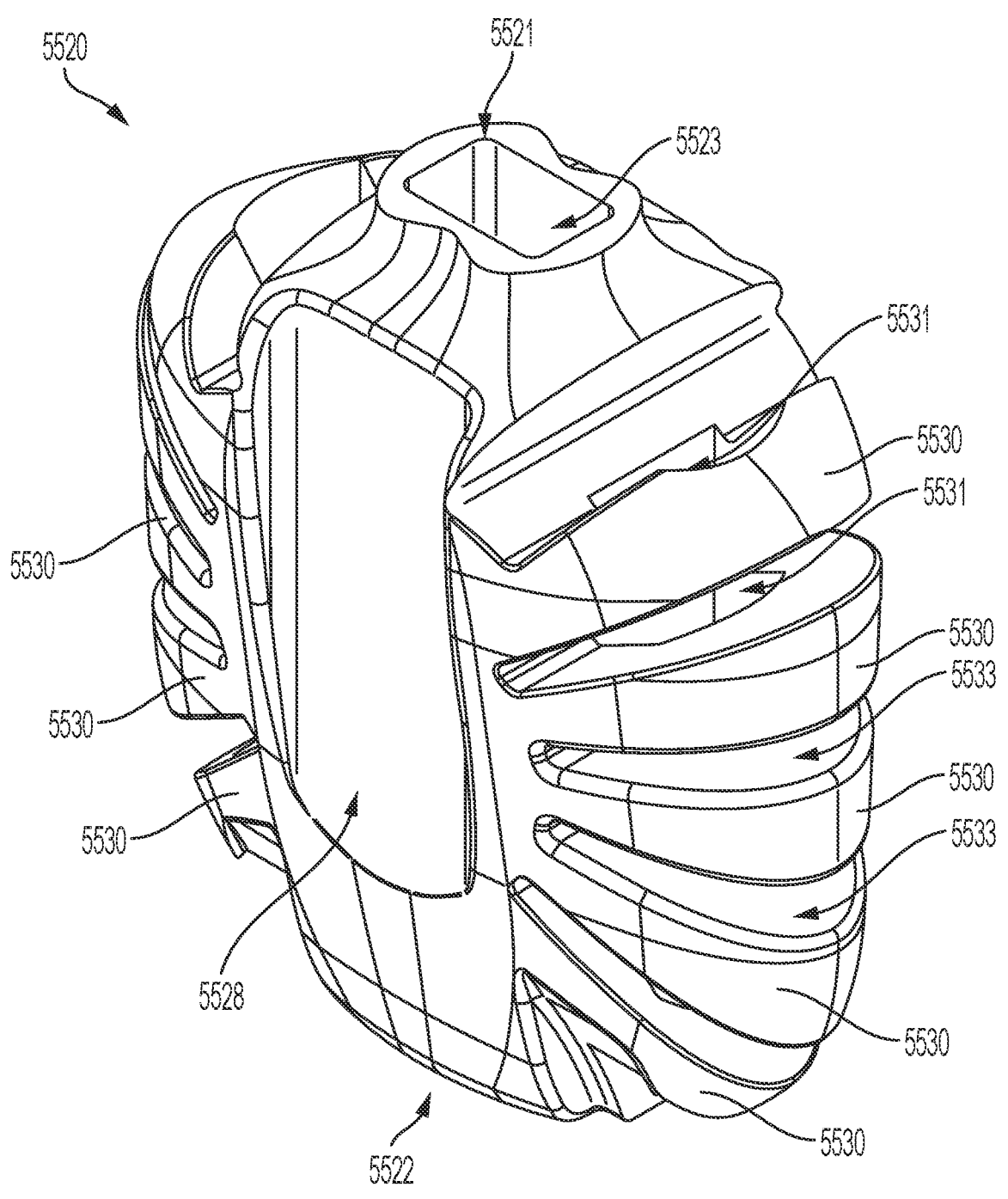
Figures 205, 206:
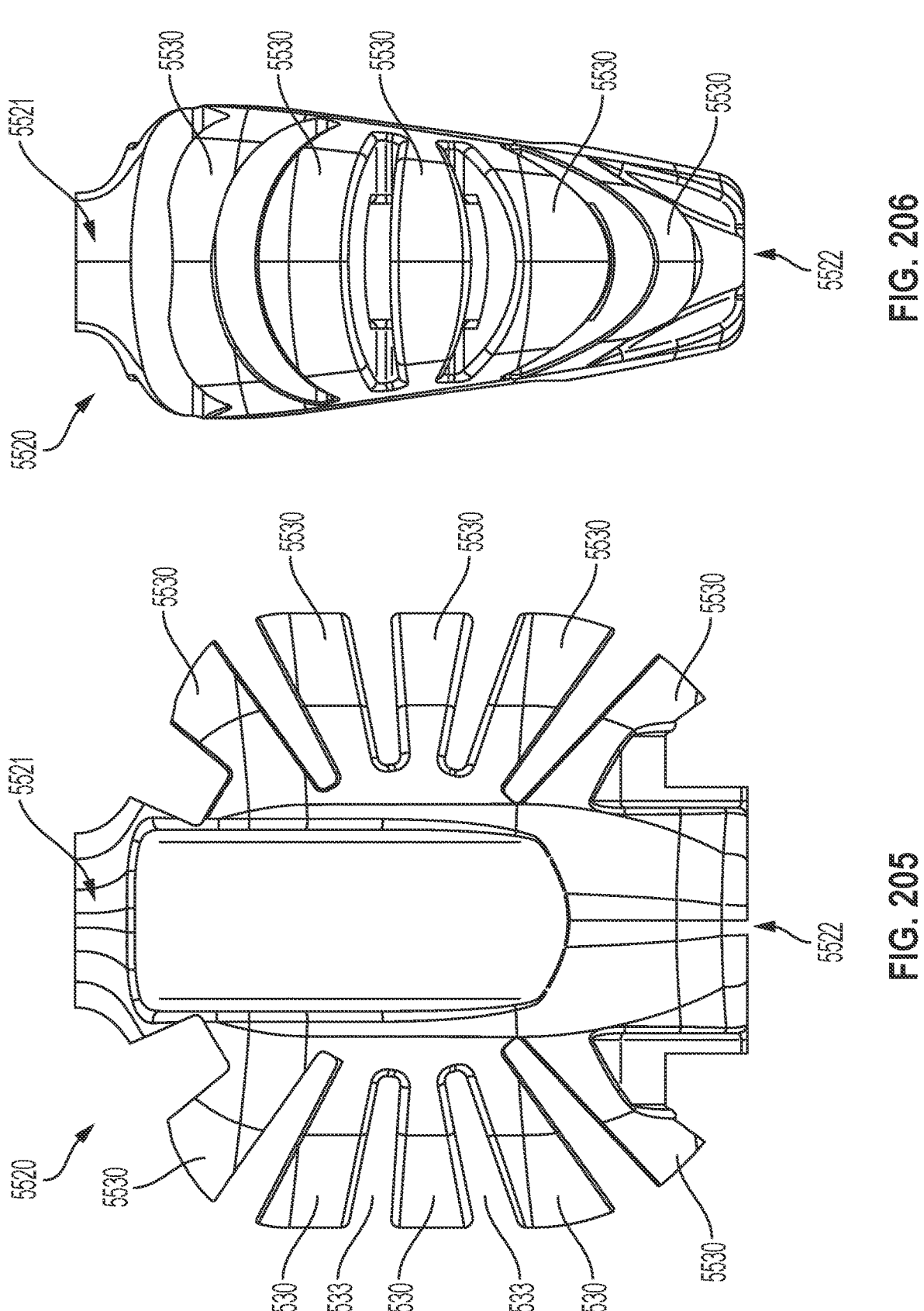
Figure 207:
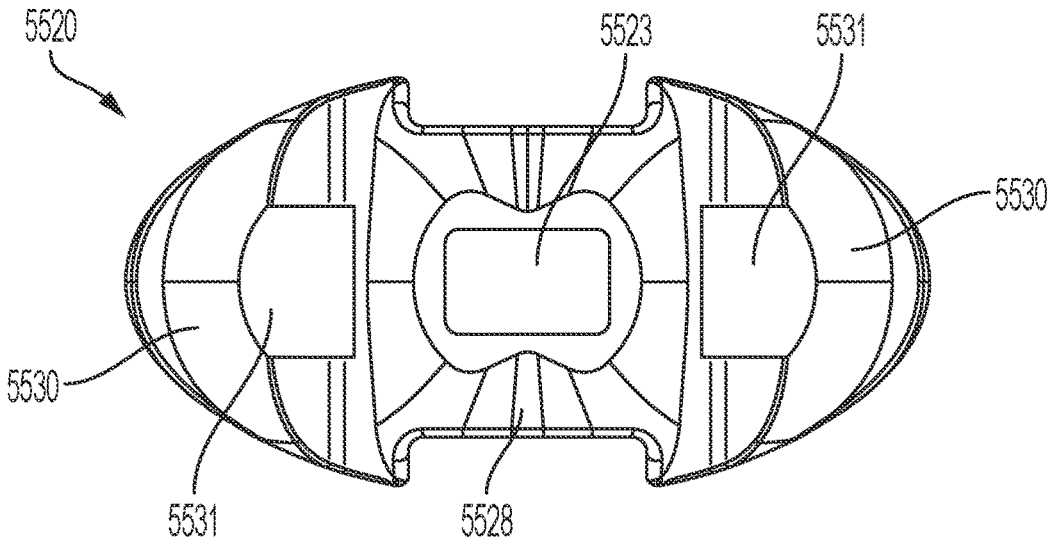
Figure 208:
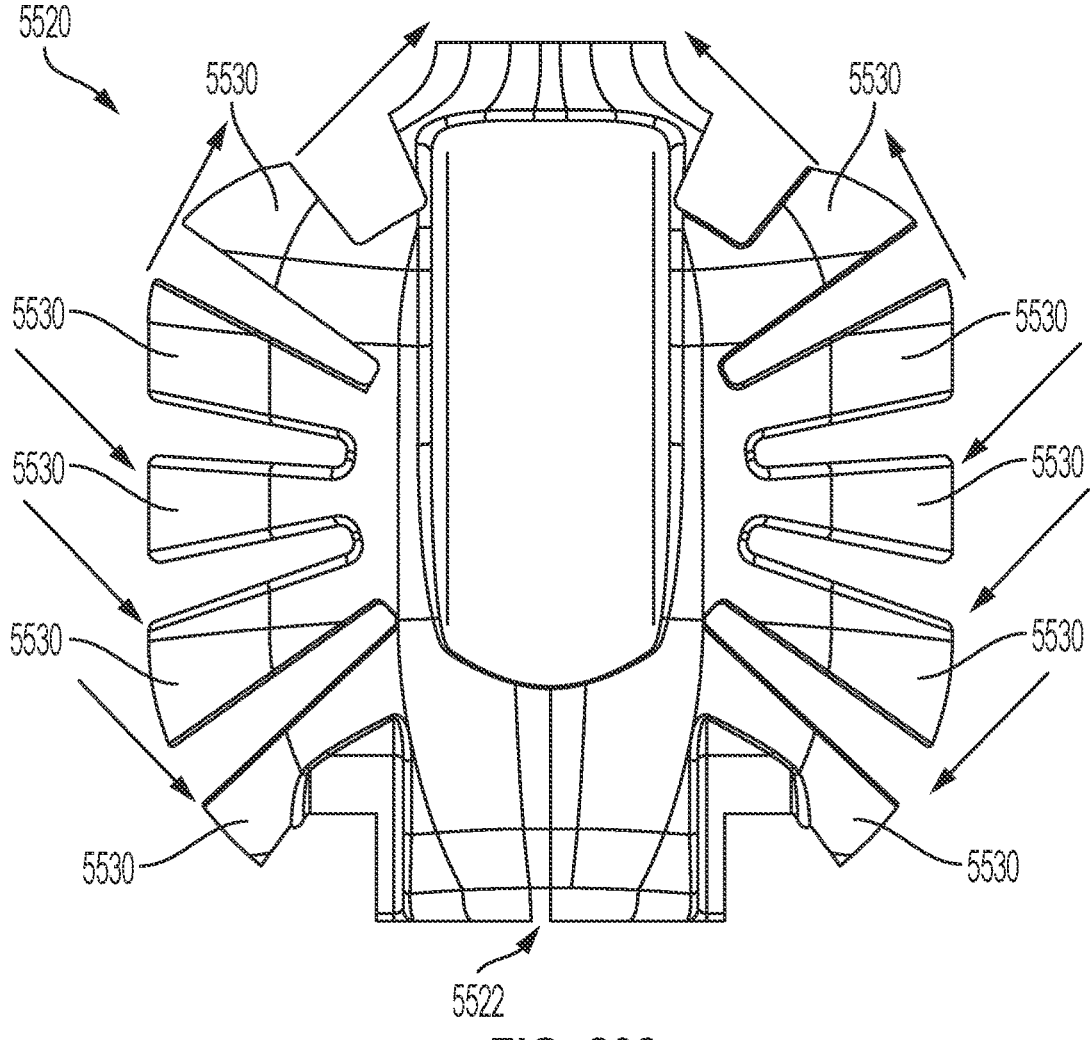
Figure 209:
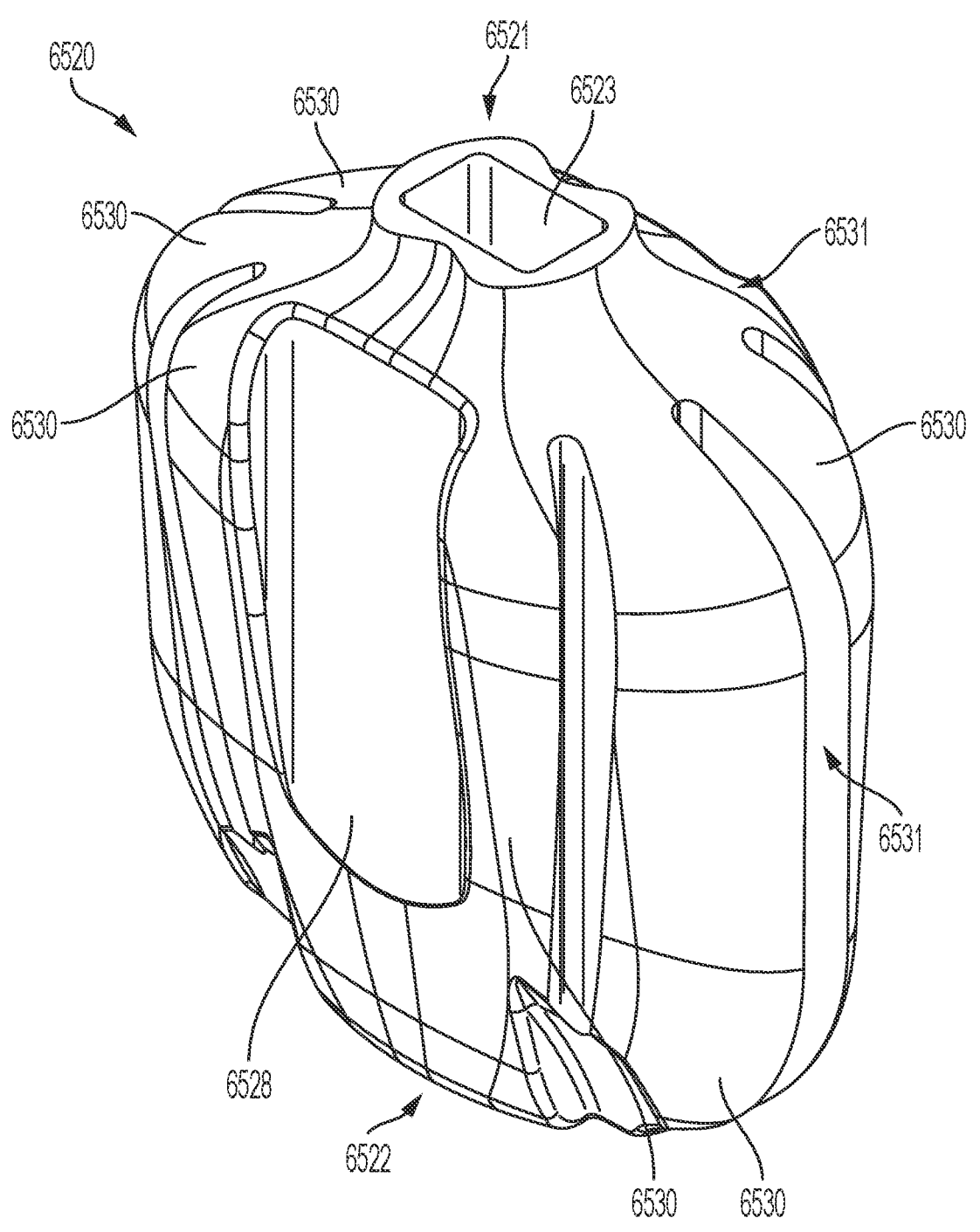
Figures 210, 211:
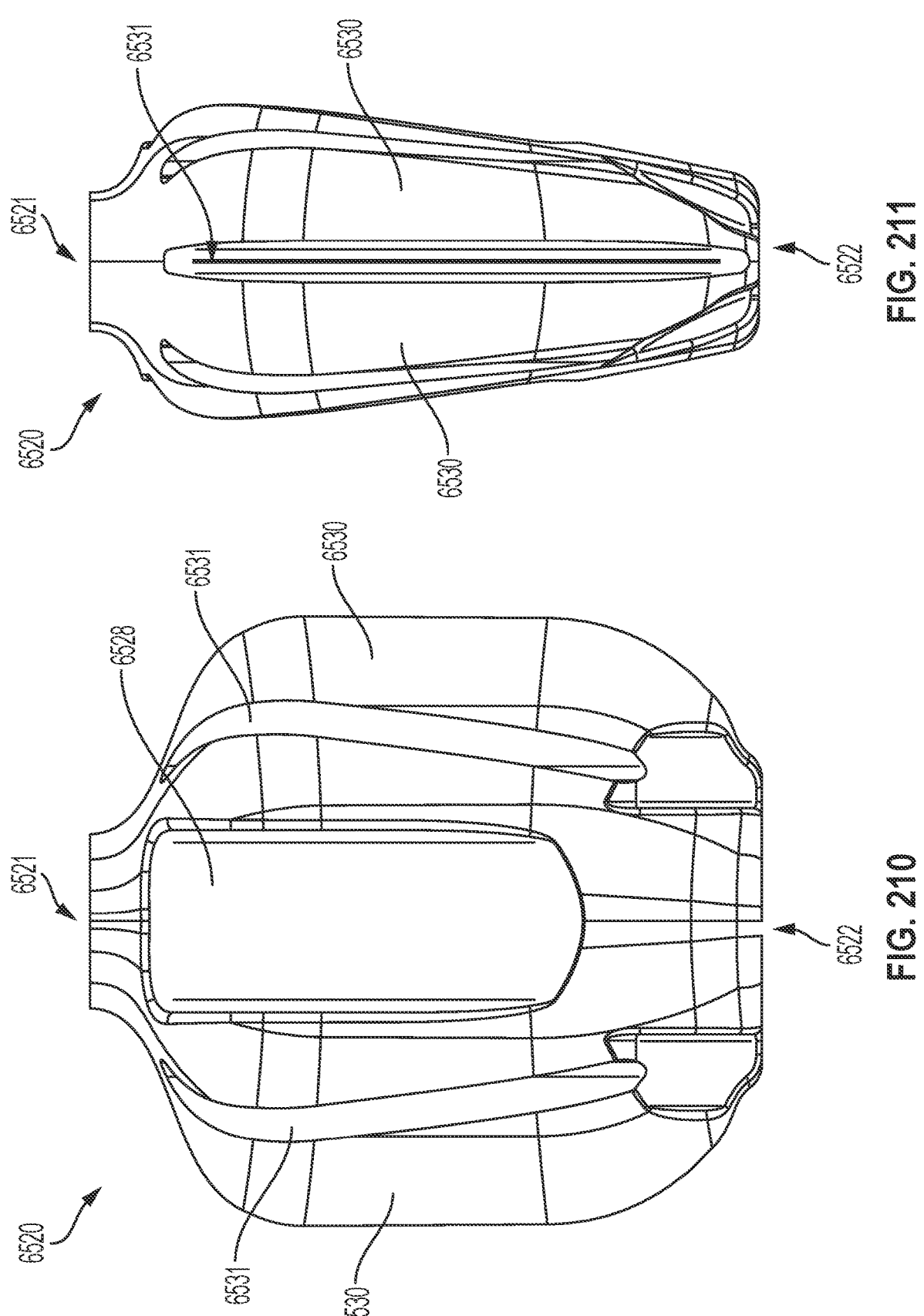
Figure 212:
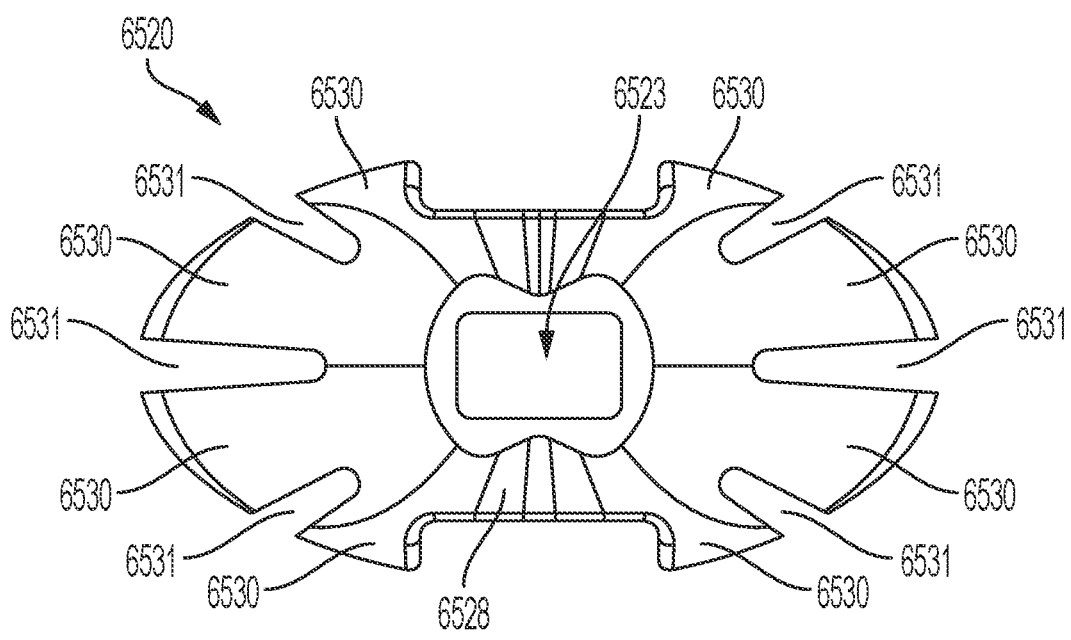
Figure 213:
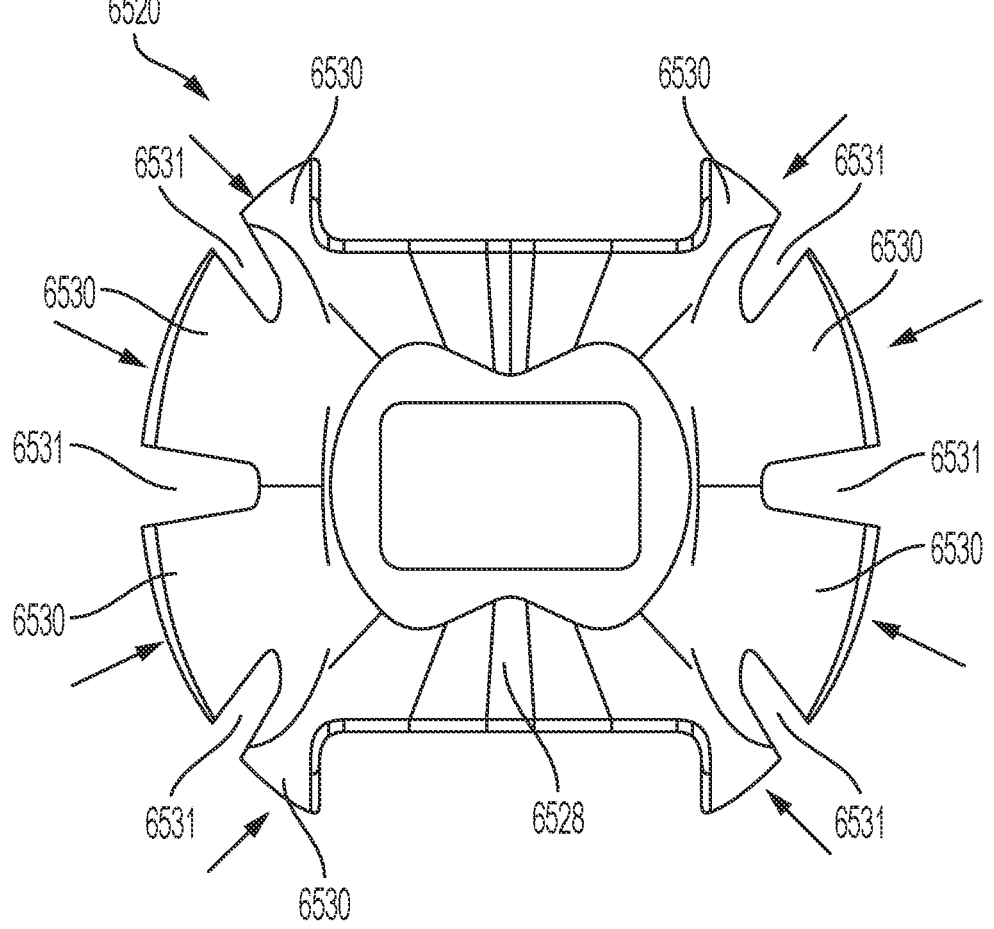

FIG. 164 shows a top perspective view of a portion of paddles, paddle frames, and a distal nut assembly of an example implantable device in an assembled condition;

FIG. 165 shows a top perspective view of a barbed clasp of an example implantable device;

FIG. 166 shows a top perspective view of a laser cut blank for the barbed clasp of FIG. 165;

FIG. 167 shows a top view of the barbed clasp blank of FIG. 166;

FIGS. 168-171 show a top perspective view of the deployment of a spreading member of an example implantable device;

FIGS. 172-175 show a bottom perspective view of the deployment of a spreading member of an example implantable device;

FIG. 176 shows a front view of an example implantable device with a spreading member in a stowed condition;

FIG. 177 shows a front view of an example implantable device with a spreading member in a deployed condition;

FIG. 178 shows a side view of the example implantable device of FIG. 176;

FIG. 179 shows a side view of the example implantable device of FIG. 177;

FIG. 180 shows a front view of an example implantable device with some of the components removed and with the paddles and barbed claps in a capture-ready condition;

FIG. 181 shows a front view of the example implantable device of FIG. 180 with paddles engaged by a deployed spreading member;

FIG. 182 shows a front view of the example implantable device of FIG. 180 with barbed clasps closed and paddles partially closed to capture the native leaflets; and FIG. 183 shows a front view of the example implantable device of FIG. 180 in a fully closed condition and with the spreading member in a stowed condition;

FIG. 184 shows a top perspective view of an example compressible coaption element;

FIG. 185 shows a side view of the compressible coaption element of FIG. 184;

FIG. 186 shows a front view of the compressible coaption element of FIG. 184;

FIG. 187 shows a top view of the compressible coaption element of FIG. 184;

FIG. 188 shows a front schematic view of the compressible coaption element of FIG. 185 in a compressed state;

FIG. 189 shows a top perspective view of an example compressible coaption element;

FIG. 190 shows a side view of the compressible coaption element of FIG. 189;

FIG. 191 shows a front view of the compressible coaption element of FIG. 189;

FIG. 192 shows a top view of the compressible coaption element of FIG. 189;

FIG. 193 shows a front schematic view of the compressible coaption element of FIG. 189 in a compressed state;

FIG. 194 shows a top perspective view of an example compressible coaption element;

FIG. 195 shows a side view of the compressible coaption element of FIG. 194;

FIG. 196 shows a front view of the compressible coaption element of FIG. 194;

FIG. 197 shows a top view of the compressible coaption element of FIG. 194;

FIG. 198 shows a front schematic view of the compressible coaption element of FIG. 194 in a compressed state;

FIG. 199 shows a top perspective view of an example compressible coaption element;

FIG. 200 shows a side view of the compressible coaption element of FIG. 199;

FIG. 201 shows a front view of the compressible coaption element of FIG. 199;

FIG. 202 shows a top view of the compressible coaption element of FIG. 199;

FIG. 203 shows a front schematic view of the compressible coaption element of FIG. 199 being moved to a compressed state;

FIG. 204 shows a top perspective view of an example compressible coaption element;

FIG. 205 shows a side view of the compressible coaption element of FIG. 204;

FIG. 206 shows a front view of the compressible coaption element of FIG. 204;

FIG. 207 shows a top view of the compressible coaption element of FIG. 204;

FIG. 208 shows a front schematic view of the compressible coaption element of FIG. 204 being moved to a compressed state;

FIG. 209 shows a top perspective view of an example compressible coaption element;

FIG. 210 shows a side view of the compressible coaption element of FIG. 209;

FIG. 211 shows a front view of the compressible coaption element of FIG. 209;

FIG. 212 shows a top view of the compressible coaption element of FIG. 209; and FIG. 213 shows a top schematic view of the compressible coaption element of FIG. 209 being moved to a compressed state.

DETAILED DESCRIPTION

The following description refers to the accompanying drawings, which illustrate specific embodiments of the present disclosure. Other embodiments having different structures and operation do not depart from the scope of the present disclosure.

Example embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

The implantable prosthetic devices disclosed herein can take on a wide variety of forms and can incorporate a wide variety of features and methods of operation of implantable prosthetic devices as shown and described in International Application No. PCT/US2018/028171, filed on Apr. 18, 2018, International Application No. PCT/US2019/028041, filed on Apr. 18, 2019, U.S. patent application Ser. No. 16/123,105, filed on Sep. 6, 2018, International Application No. PCT/US2018/031959, filed on May 10, 2018, International Application No. PCT/US2018/028189, Filed on Apr. 18, 2018, International Application No. PCT/US2018/045985, filed on Aug. 9, 2018, U.S. Provisional Patent Application Ser. No. 62/744,031, filed on Oct. 10, 2018, U.S. Provisional Patent Application Ser. No. 62/803,854, filed on Feb. 11, 2019, U.S. Provisional Patent Application Ser. No. 62/809,856, flied on Feb. 25, 2019, U.S. Provisional Patent Application Ser. No. 62/808,377, Filed on Feb. 21, 2019, U.S. Provisional Patent Application Ser. No. 62/805, 847, filed on 14 Feb. 2019, and International Application No. PCT/US16/32462, Filed on May 13, 2016, each of which are incorporated herein by reference in its entirety, which are incorporated herein by reference in their entirety.

Figure 1:
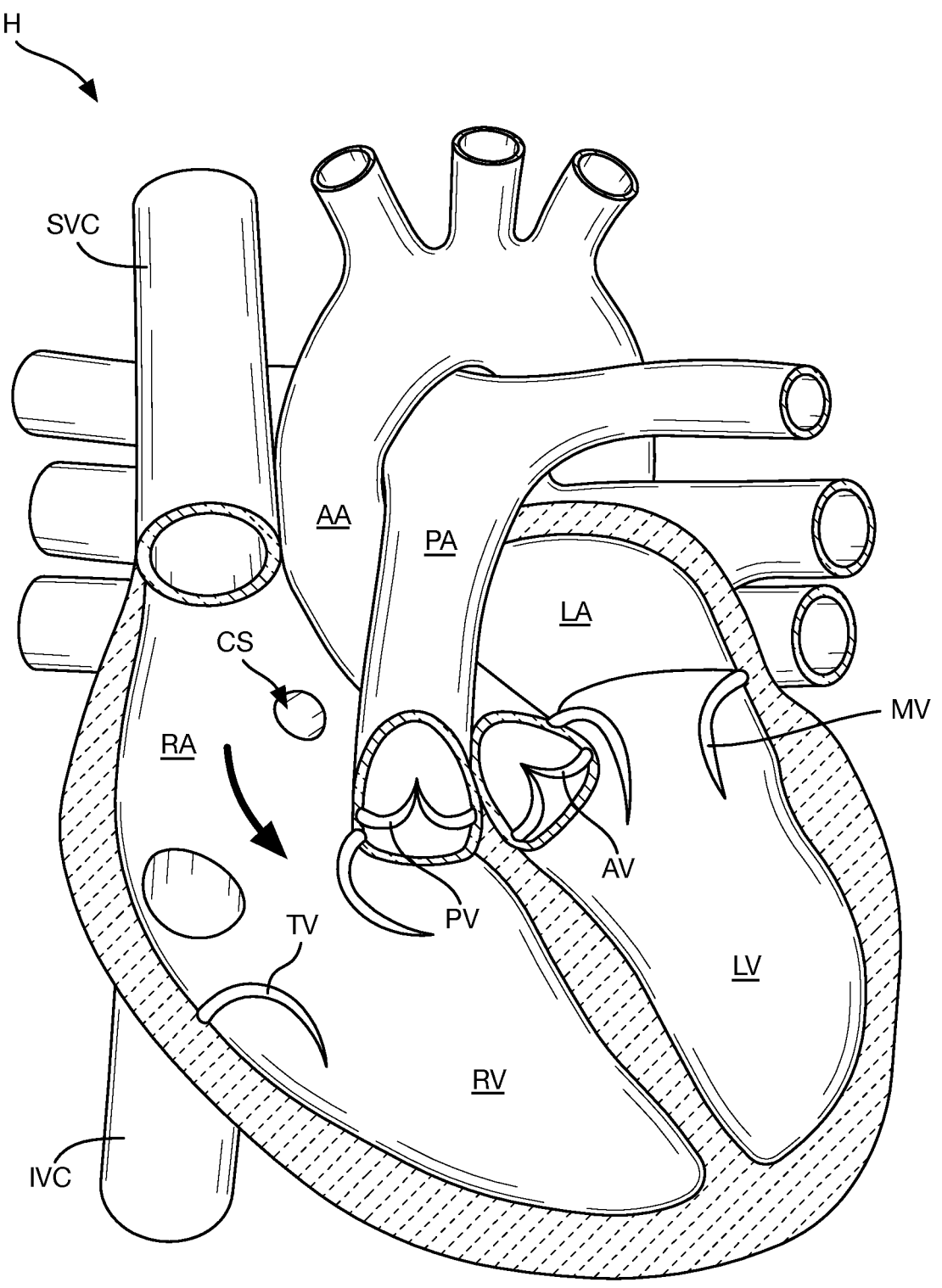
FIG. 1 illustrates a cutaway view of the human heart in a diastolic phase.
Figure 2:
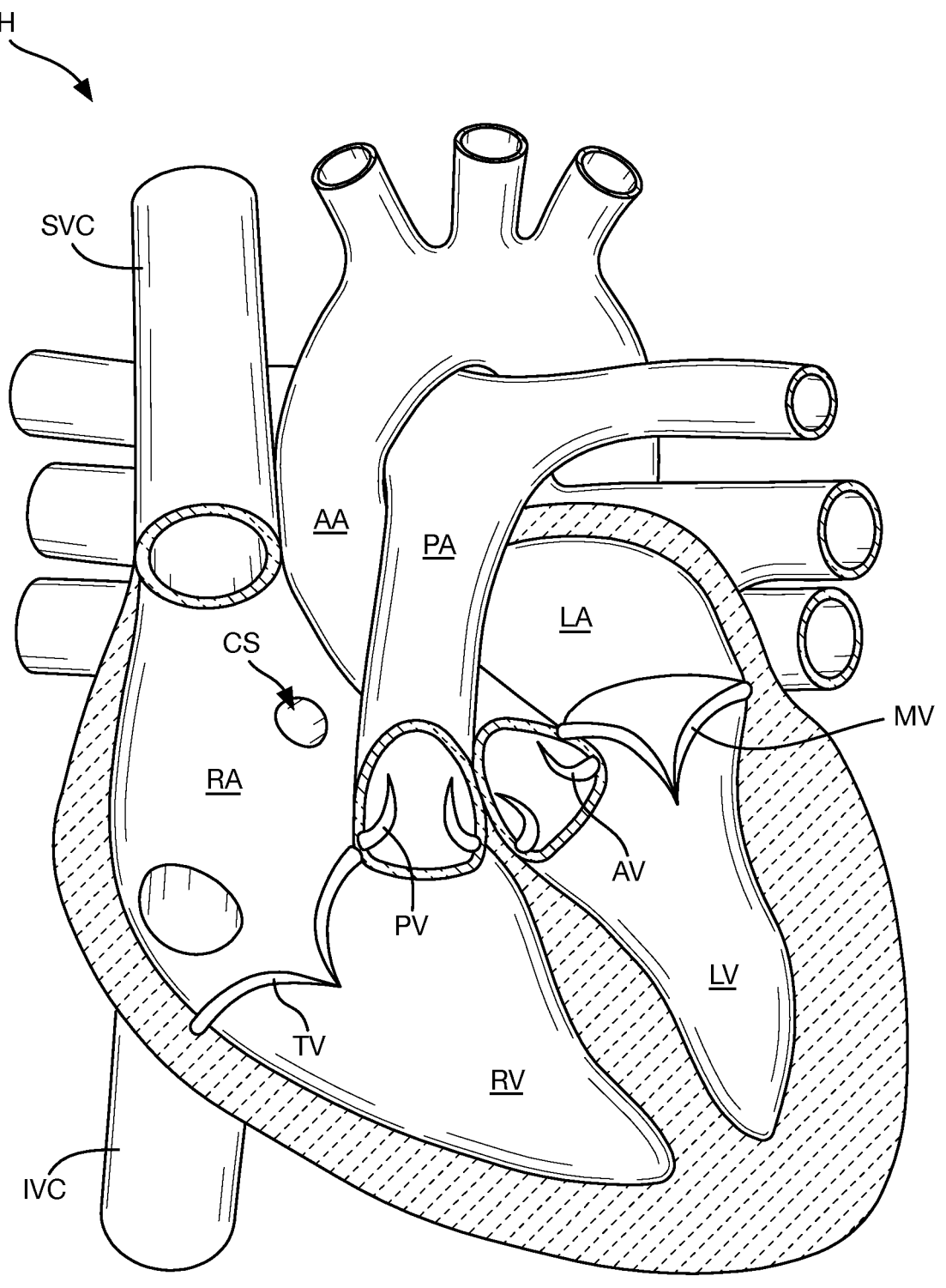
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 3-7) extending inward across the respective orifices that come together or "coapt" in the flow stream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV back into the left atrium LA and blood is collected in the left atrium from the pulmonary vein. In one example embodiment, the devices described by the present application are used to repair the function of a defective mitral valve MV. That is, the devices are configured to help close the leaflets of the mitral valve to prevent blood from regurgitating from the left ventricle LV and back into the left atrium LA. The devices described in the present application are designed to easily grasp and secure the native leaflets around an optional coaption element or spacer that acts as a filler in the regurgitant orifice to prevent or inhibit back flow or regurgitation during systole. In this application, the terms coaption element, spacer, spacer element, and coaptation element and refers to a component that fills a portion of a space between a native heart valve, such as a mitral valve or a tricuspid valve.

Figure 3:
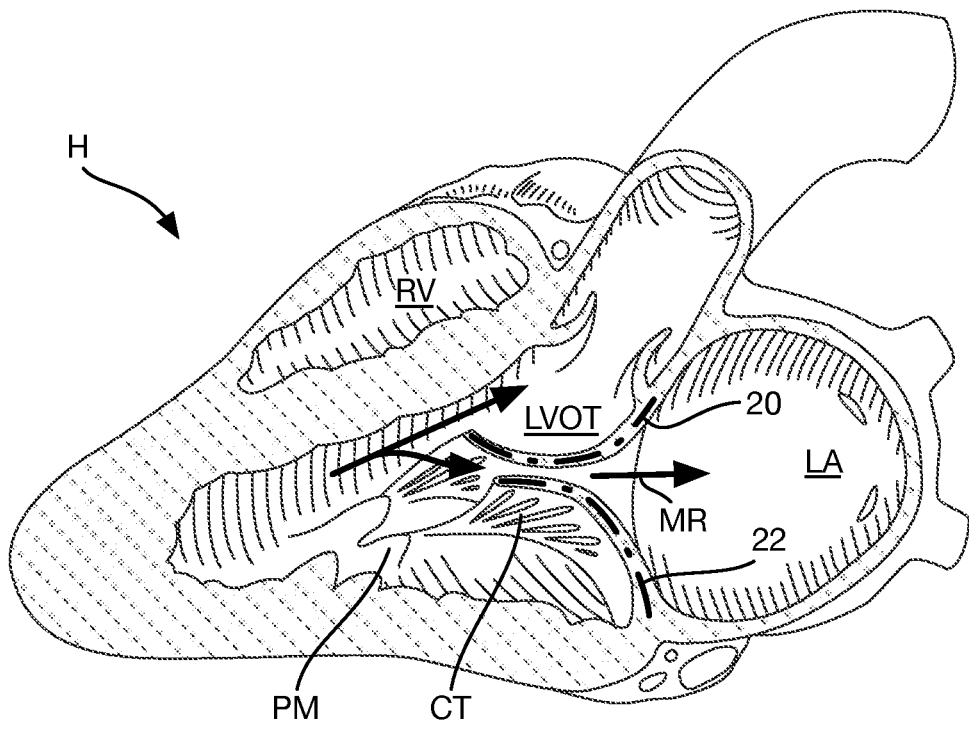
FIG. 3 is another cutaway view of the human heart in a systolic phase showing mitral regurgitation.
Figure 4:
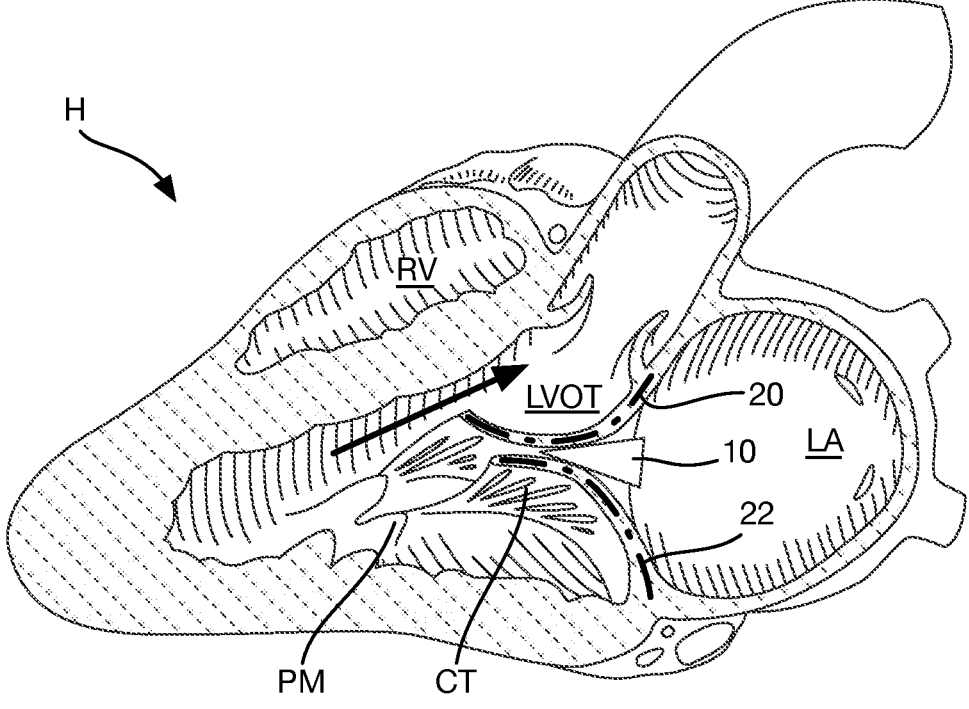
FIG. 4 is the cutaway view of FIG. 3 annotated to illustrate a natural shape of mitral valve leaflets in the systolic phase.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIGS. 3 and 4, the mitral valve MV is anchored to the wall of the left ventricle LV by chordae tendineae CT. The chordae tendineae CT are cord-like tendons that connect the papillary muscles PM (i.e., the muscles located at the base of the chordae tendineae CT and within the walls of the left ventricle LV) to the leaflets 20, 22 of the mitral valve MV. The papillary muscles PM serve to limit the movements of leaflets 20, 22 of the mitral valve MV to prevent the mitral valve MV from being reverted. The mitral valve MV opens and closes in response to relative pressure changes in the left atrium LA and the left ventricle LV. The papillary muscles PM do not open or close the mitral valve MV. Rather, the papillary muscles PM support or brace the leaflets 20, 22 against the high pressure necessary to circulate blood throughout the body. Together the papillary muscles PM and the chordae tendineae CT are known as the subvalvular apparatus, which functions to keep the mitral valve MV from prolapsing into the left atrium LA when the mitral valve closes. As seen from a Left Ventricular Outflow Tract (LVOT) view shown in FIG. 3, the anatomy of the leaflets 20, 22 is such that the inner sides of the leaflets coapt at the free end portions and the leaflets 20, 22 start receding or spreading apart from each other. The leaflets 20, 22 spread apart in the atrial direction, until each leaflet meets with the mitral annulus.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow. The second type of valve malfunction, valve regurgitation, occurs when the leaflets of the valve do not close completely thereby causing blood to leak back into the prior chamber (e.g., causing blood to leak from the left ventricle to the left atrium).

There are three main mechanisms by which a native valve becomes regurgitant—or incompetent—which include Carpentier's type I, type II, and type III malfunctions. A Carpentier's type I malfunction involves the dilation of the annulus such that normally functioning leaflets are distracted from each other and fail to form a tight seal—i.e., the leaflets do not coapt properly. Included in a type I mechanism malfunction are perforations of the leaflets, as are present in endocarditis. A Carpentier's type II malfunction involves prolapse of one or more leaflets of a native valve above a plane of coaption. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (Mb).

Figure 5:
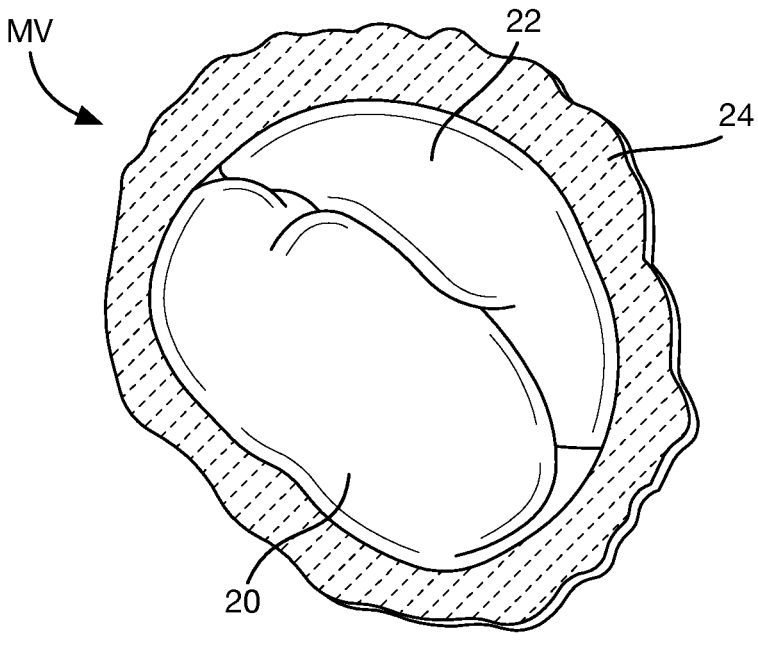
FIG. 5 illustrates a healthy mitral valve with the leaflets closed as viewed from an atrial side of the mitral valve.
Figure 6:
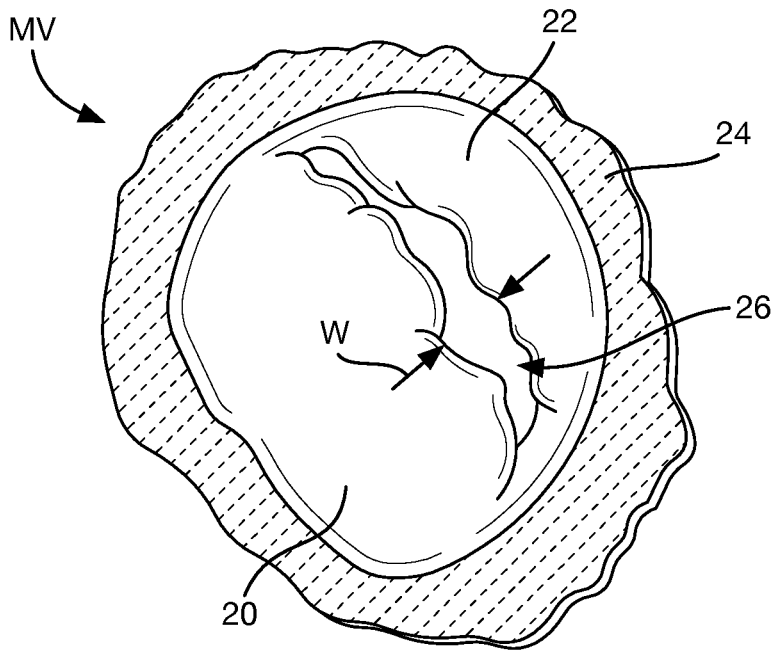
FIG. 6 illustrates a dysfunctional mitral valve with a visible gap between the leaflets as viewed from an atrial side of the mitral valve.
Figure 7:
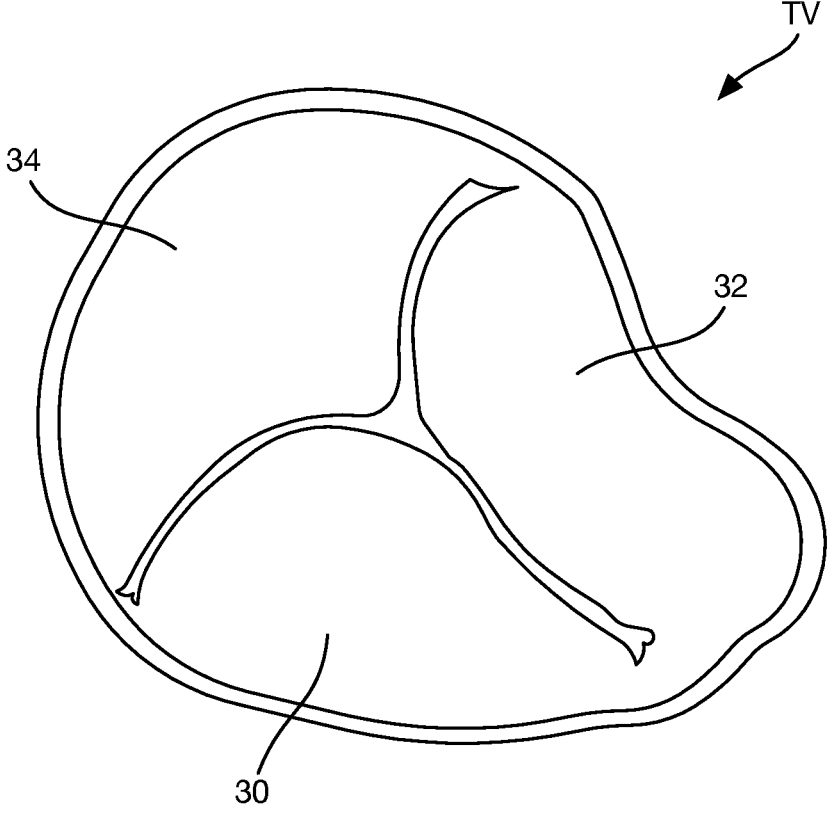
FIG. 7 illustrates a tricuspid valve viewed from an atrial side of the tricuspid valve.

Referring to FIG. 5, when a healthy mitral valve MV is in a closed position, the anterior leaflet 20 and the posterior leaflet 22 coapt, which prevents blood from leaking from the left ventricle LV to the left atrium LA. Referring to FIGS. 3 and 6, mitral regurgitation MR when the edges of the leaflets 20, 22 are not in contact with each other. This failure to coapt causes a gap 26 between the anterior leaflet 20 and the posterior leaflet 22, which allows blood to flow back into the left atrium LA from the left ventricle LV during systole, as illustrated by the mitral regurgitation MR flow path shown in FIG. 3. The gap 26 can have a width W between about 2.5 mm and about 17.5 mm, between about 5 mm and about 15 mm, between about 7.5 mm and about 12.5 mm, or about 10 mm. In some situations, the gap 26 can have a width W greater than 15 mm. As set forth above, there are several different ways that a leaflet (e.g. leaflets 20, 22 of mitral valve MV) may malfunction, which can thereby lead to regurgitation.

In any of the above-mentioned situations, a valve repair device is desired that is capable of engaging the anterior leaflet 20 and the posterior leaflet 22 to close the gap 26 and prevent regurgitation of blood through the mitral valve MV. As can be seen in FIG. 4, an abstract representation of a valve repair device 10 is shown implanted between the leaflets 20, 22 such that regurgitation does not occur during systole (compare FIG. 4 with FIG. 3). In particular, the coaption element of the device 10 has a generally tapered or triangular shape that naturally adapts to the native valve geometry and to its expanding leaflet nature (toward the annulus).

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart is primarily responsible for circulating the flow of blood throughout the body, substantially higher pressures are experienced by the left side heart structures (i.e., the left atrium LA, the left ventricle LV, the mitral valve MV, and the aortic valve AV). Accordingly, malfunction of the mitral valve MV or the aortic valve AV can be particularly problematic and often life threatening.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV (FIG. 7) are more prone to deformation of leaflets, which, as described above, prevents the mitral valve MV or tricuspid valve TV from closing properly and allows for regurgitation or back flow of blood from the ventricle into the atrium (e.g., a deformed mitral valve MV may allow for mitral regurgitation MR or back flow from the left ventricle LV to the left atrium LA as shown in FIG. 3). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae CT becoming dysfunctional (e.g., the chordae tendineae CT may stretch or rupture), which allows the anterior leaflet 20 and the posterior leaflet 22 to be reverted such that blood is regurgitated into the left atrium LA. The problems occurring due to dysfunctional chordae tendineae CT can be repaired by repairing the chordae tendineae CT or the structure of the mitral valve MV (e.g., by securing the leaflets 20, 22 at the affected portion of the mitral valve).

The devices and procedures disclosed herein often make reference to repairing a mitral valve for illustration. However, it should be understood that the devices and concepts provided herein can be used to repair any native valve, as well as any component of a native valve. For example, such devices can be used between the leaflets 20, 22 of the mitral valve MV to prevent or inhibit regurgitation of blood from the left ventricle into the left atrium. With respect to the tricuspid valve TV (FIG. 5), such devices can be used between any two of the anterior leaflet 30, septal leaflet 32, and posterior leaflet 34 to prevent or inhibit regurgitation of blood from the right ventricle into the right atrium. In addition, any of the devices and concepts provided herein can be used on all three of the leaflets 30, 32, 34 together to prevent or inhibit regurgitation of blood from the right ventricle to the right atrium. That is, the valve repair devices provided herein can be centrally located between the three leaflets 30, 32, 34.

An example implantable prosthetic device has a coaption element and at least one anchor. The coaption element is configured to be positioned within the native heart valve orifice to help fill the space between the leaflets and form a more effective seal, thereby reducing or preventing regurgitation described above. The coaption element can have a structure that is impervious or resistant to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device can be used in the native mitral (bicuspid) and tricuspid valves. The coaption element is sometimes referred to herein as a spacer because the coaption element can fill a space between improperly functioning native mitral leaflets 20, 22 or tricuspid leaflets 30, 32, 34 that do not close completely.

The coaption element (e.g., spacer, coaptation element, etc.) can have various shapes. In some embodiments, the coaption element can have an elongated cylindrical shape having a round cross-sectional shape. In some embodiments, the coaption element can have an oval cross-sectional shape, a crescent cross-sectional shape, a rectangular cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular portion of the coaption element. In some embodiments, the anchor can attach to an actuation element, such as a shaft or actuation wire, to which the coaption element is also attached. In some embodiments, the anchor and the coaption element can be positioned independently with respect to each other by separately moving each of the anchor and the coaption element along the longitudinal axis of the actuation element (e.g., actuation shaft, actuation wire, etc.). In some embodiments, the anchor and the coaption element can be positioned simultaneously by moving the anchor and the coaption element together along the longitudinal axis of the actuation element, e.g., shaft or actuation wire. The anchor can be configured to be positioned behind a native leaflet when implanted such that the leaflet is grasped by the anchor.

The prosthetic device can be configured to be implanted via a delivery sheath. The coaption element and the anchor can be compressible to a radially compressed state and can be self-expandable to a radially expanded state when compressive pressure is released. The device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are optionally configured to self-expand. The implantation methods for various embodiments can be different and are more fully discussed below with respect to each embodiment. Additional information regarding these and other delivery methods can be found in U.S. Pat. No. 8,449,599 and U.S. Patent Application Publication Nos. 2014/0222136, and 2014/0067052, 2016/0331523 each of which is incorporated herein by reference in its entirety. These methods can be performed on a living animal or on a simulation, such as on a cadaver, cadaver heart, simulator (e.g. with the body parts, tissue, etc. being simulated), etc.

The disclosed prosthetic devices can be configured such that the anchor is connected to a leaflet, taking advantage of the tension from native chordae tendineae to resist high systolic pressure urging the device toward the left atrium. During diastole, the devices can rely on the compressive and retention forces exerted on the leaflet that is grasped by the anchor.

Referring now to FIGS. 8-15, a schematically illustrated implantable prosthetic device 100 (e.g., a prosthetic spacer device, etc.) is shown in various stages of deployment. The device 100 can include any other features for an implantable prosthetic device discussed in the present application, and the device 100 can be positioned to engage valve tissue 20, 22 as part of any suitable valve repair system (e.g., any valve repair system disclosed in the present application).

The device 100 is deployed from a delivery sheath or means for delivery 102 and includes a coapting portion or coaptation portion 104 and an anchor portion 106. The coaptation portion 104 of the device 100 includes a coaption element or means for coapting 110 that is adapted to be implanted between the leaflets of a native valve (e.g., a native mitral valve, tricuspid valve, etc.) and is slidably attached to an actuation element 112 (e.g., actuation wire, actuation shaft, actuation tube, etc.). The anchor portion 106 is actuatable between open and closed conditions and can take a wide variety of forms, such as, for example, paddles, gripping elements, or the like. Actuation of the actuation element or means for actuating 112 opens and closes the anchor portion 106 of the device 100 to grasp the native valve leaflets during implantation. The actuation element 112 (e.g., wire, shaft, tube, screw, line, etc.) can take a wide variety of different forms. For example, the actuation element can be threaded such that rotation of the actuation element (e.g., wire, shaft, tube, screw, etc.) moves the anchor portion 106 relative to the coaption portion 104. Or, the actuation element can be unthreaded, such that pushing or pulling the actuation element 112 moves the anchor portion 106 relative to the coaption portion 104.

The anchor portion 106 and/or anchors 108 of the device 100 include outer paddles 120 and inner paddles 122 that are connected between a cap 114 and the coaption element or means for coapting 110 by portions 124, 126, 128. The connection portions 124, 126, 128 can be jointed and/or flexible to move between all of the positions described below. The interconnection of the outer paddles 120, the inner paddles 122, the coaption element or means for coapting 110, and the cap 114 by the portions 124, 126, and 128 can constrain the device to the positions and movements illustrated herein.

In some implementations, the actuation element or means for actuating 112 (e.g., actuation wire, actuation shaft, etc.) extends through the delivery sheath and the coaption element or means for coapting 110 to the cap 114 at the distal connection of the anchor portion 106. Extending and retracting the actuation element or means for actuating 112 increases and decreases the spacing between the coaption element or means for coapting 110 and the cap 114, respectively. A collar or other attachment element removably attaches the coaption element or means for coapting 110 to the delivery sheath or means for delivery 102 so that the actuation element or means for actuating 112 slides through the collar or other attachment element and through the coaption element or means for coapting 110 during actuation to open and close the paddles 120, 122.

The anchor portion 106 and/or anchors 108 include attachment portions or gripping members. The illustrated gripping members comprise barbed clasps 130 that include a base or fixed arm 132, a moveable arm 134, optional barbs or means for securing 136, and a joint portion 138. The fixed arms 132 are attached to the inner paddles 122, with the joint portion 138 disposed proximate the coaption element or means for coapting 110. The barbed clasps 130 have flat surfaces and do not fit in a recess of the inner paddle 122. Rather, the flat portions of the barbed clasps 130 are disposed against the surface of the inner paddle 122. The joint portion 138 provides a spring force between the fixed and moveable arms 132, 134 of the barbed clasp 130. The joint portion 138 can be any suitable joint, such as a flexible joint, a spring joint, a pivot joint, or the like. In some embodiments, the joint portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the barbed clasps 130 and expose the barbs or means for securing 136.

The barbed clasps 130 can be opened by applying tension to actuation lines 116 attached to the moveable arms 134, thereby causing the moveable arms 134 to rotate, flex, or pivot on the joint portions 138. The actuation lines 116 extend through the delivery sheath or means for delivery 102. The actuation line 116 can take a wide variety of forms, such as, for example, a line, a suture, a wire, a rod, a catheter, or the like. The barbed clasps 130 can be spring loaded so that in the closed position the barbed clasps 130 continue to provide a pinching force on the grasped native leaflet. This pinching force remains constant regardless of the position of the inner paddles 122. Barbs or means for securing 136 of the barbed clasps 130 can pierce the native leaflets to further secure the native leaflets.

During implantation, the paddles 120, 122 can be opened and closed, for example, to grasp the native leaflets or native mitral valve leaflets between the paddles 120, 122 and the coaption element or means for coapting 110. The barbed clasps 130 can be used to grasp and/or further secure the native leaflets by engaging the leaflets with barbs or means for securing 136 and pinching the leaflets between the moveable and fixed arms 134, 132. The barbs or means for securing 136 of the barbed clasps 130 increase friction with the leaflets or may partially or completely puncture the leaflets. The actuation lines 116 can be actuated separately so that each barbed clasp 130 can be opened and closed separately. Separate operation allows one leaflet to be grasped at a time, or for the repositioning of a clasp 130 on a leaflet that was insufficiently grasped, without altering a successful grasp on the other leaflet. The barbed clasps 130 can be opened and closed relative to the position of the inner paddle 122 (as long as the inner paddle is in an open position), thereby allowing leaflets to be grasped in a variety of positions as the particular situation requires.

Figure 8:
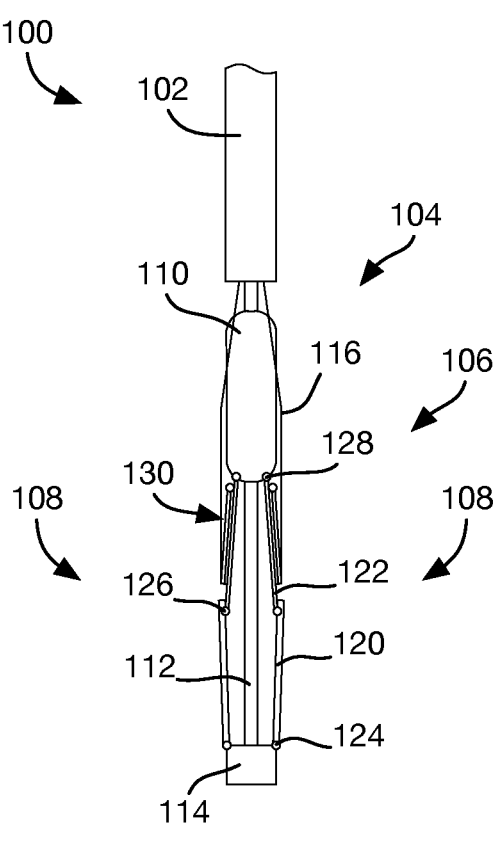

Referring now to FIG. 8, the device 100 is shown in an elongated or fully open condition for deployment from the delivery sheath. The device 100 is loaded in the delivery sheath in the fully open position, because the fully open position takes up the least space and allows the smallest catheter to be used (or the largest device 100 to be used for a given catheter size). In the elongated condition the cap 114 is spaced apart from the coaption element or means for
coapting 110 such that the paddles 120, 122 are fully
extended. In some embodiments, an angle formed between
the interior of the outer and inner paddles 120, 122 is
approximately 180 degrees. The barbed clasps 130 are kept
in a closed condition during deployment through the deliv-
ery sheath or means for delivery 102 so that the barbs or
means for securing 136 (FIG. 9) do not catch or damage the
sheath or tissue in the patient's heart.

Figure 9:
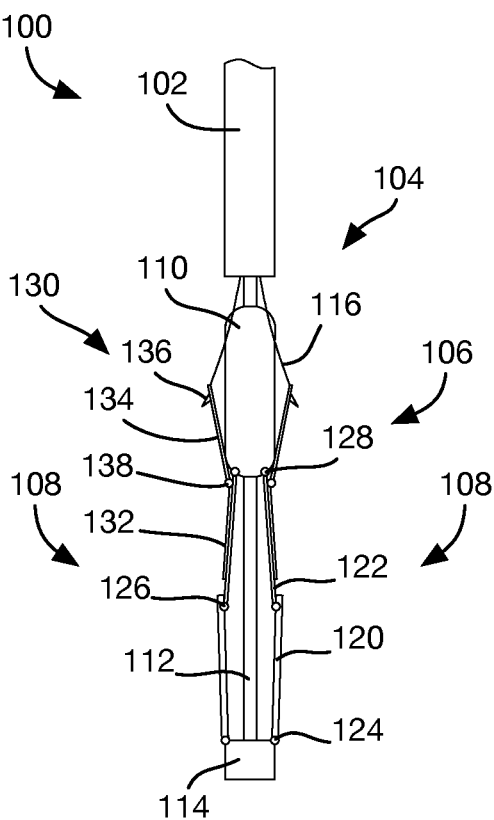

Referring now to FIG. 9, the device 100 is shown in an
elongated detangling condition, similar to FIG. 8, but with
the barbed clasps 130 in a fully open position, ranging from
about 140 degrees to about 200 degrees, to about 170
degrees to about 190 degrees, or about 180 degrees between
fixed and moveable portions 132, 134 of the barbed clasps
130. Fully opening the paddles 120, 122 and the clasps 130
has been found to improve ease of detanglement or detach-
ment from anatomy of the patient, such as the chordae
tendineae CT, during implantation of the device 100.

Figure 10:
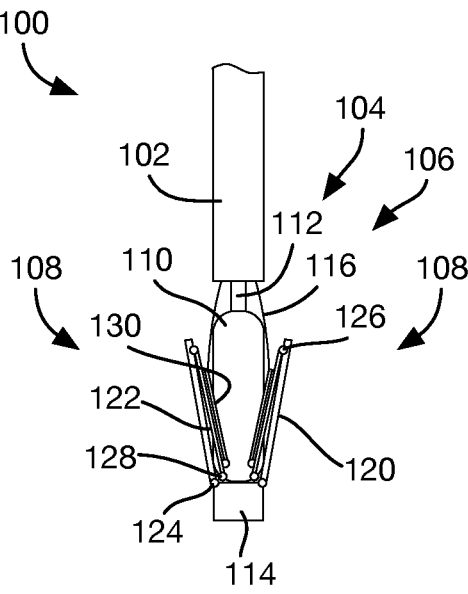

Referring now to FIG. 10, the device 100 is shown in a
shortened or fully closed condition. The compact size of the
device 100 in the shortened condition allows for easier
maneuvering and placement within the heart H. To move the
device 100 from the elongated condition to the shortened
condition, the actuation element or means for actuating 112
is retracted to pull the cap 114 towards the coaption element
or means for coapting 110. The connection portion 126 (e.g.,
joint, flexible connection, etc.) between the outer paddle 120
and inner paddle 122 is constrained in movement such that
compression forces acting on the outer paddle 120 from the
cap 114 being retracted towards the coaption element or
means for coapting 110 causes the paddles 120, 122 to move
radially outward. During movement from the open to closed
position, the outer paddles 120 maintain an acute angle with
the actuation element or means for actuating 112. The outer
paddles 120 can optionally be biased toward a closed
position. The inner paddles 122 during the same motion
move through a considerably larger angle as they are ori-
ented away from the coaption element or means for coapting
110 in the open condition and collapse along the sides of the
coaption element or means for coapting 110 in the closed
condition. In some embodiments, the inner paddles 122 are
thinner and/or narrower than the outer paddles 120, and the
connection portions 126, 128 (e.g., joints, flexible connec-
tions, etc.) connected to the inner paddles 122 can be thinner
and/or more flexible. For example, this increased flexibility
can allow more movement than the connection portion 124
connecting the outer paddle 120 to the cap 114. In some
embodiments, the outer paddles 120 are narrower than the
inner paddles 122. The connection portions 126, 128 con-
nected to the inner paddles 122 can be more flexible, for
example, to allow more movement than the connection
portion 124 connecting the outer paddle 120 to the cap 114.
In some embodiments, the inner paddles 122 can be the
same or substantially the same width as the outer paddles
120.

Figure 11:
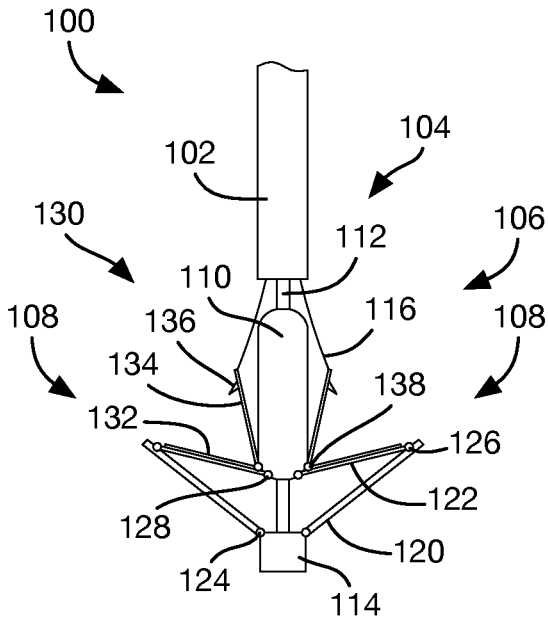

Referring now to FIGS. 11-13, the device 100 is shown in
a partially open, grasp-ready condition. To transition from
the fully closed to the partially open condition, the actuation
element or means for actuating 112 is extended to push the
cap 114 away from the coaption element or means for
coapting 110, thereby pulling on the outer paddles 120,
which in turn pull on the inner paddles 122, causing the
anchors 108 of the anchor portion 106 to partially unfold.
The actuation lines 116 are also retracted to open the clasps
130 so that the leaflets can be grasped. Also, the positions of
the clasps 130 are dependent on the positions of the paddles

122, 120. For example, referring to FIG. 10, closing the
paddles 122, 120 also closes the clasps 130.

Referring now to FIG. 12, one of the actuation lines 116
is extended to allow one of the clasps 130 to close. Referring
now to FIG. 13, the other actuation line 116 is extended to
allow the other clasp 130 to close. Either or both of the
actuation lines 116 can be repeatedly actuated to repeatedly
open and close the barbed clasps 130.

Referring now to FIG. 14, the device 100 is shown in a
fully closed and deployed condition. The delivery sheath or
means for delivery 102 and actuation element or means for
actuating 112 are retracted and the paddles 120, 122 and
clasps 130 remain in a fully closed position. Once deployed,
the device 100 can be maintained in the fully closed position
with a mechanical latch or may be biased to remain closed
through the use of spring materials, such as steel, other
metals, plastics, composites, etc. or shape-memory alloys
such as Nitinol. For example, the connection portions 124,
126, 128, the joint portions 138, and/or the inner and outer
paddles 122, and/or an additional biasing component (not
shown) can be formed of metals such as steel or shape-
memory alloy, such as Nitinol—produced in a wire, sheet,
tubing, or laser sintered powder—and are biased to hold the
outer paddles 120 closed around the coaption element or
means for coapting 110 and the barbed clasps 130 pinched
around native leaflets. Similarly, the fixed and moveable
arms 132, 134 of the barbed clasps 130 are biased to pinch
the leaflets. In certain embodiments, the connection portions
124, 126, 128, joint portions 138, and/or the inner and outer
paddles 122, and/or an additional biasing component (not
shown) can be formed of any other suitably elastic material,
such as a metal or polymer material, to maintain the device
in the closed condition after implantation.

FIG. 15 illustrates an example embodiment where the
paddles 120, 122 are independently controllable. The device
101 illustrated by FIG. 15 is similar to the device illustrated
by FIG. 11, except the device 101 of FIG. 15 includes two
independent actuation elements or actuation wires 111, 113
that are coupled to two independent caps 115, 117. To
transition a first inner paddle 122 and a first outer paddle 120
from the fully closed to the partially open condition, the
actuation element or means for actuating 111 is extended to
push the cap 115 away from the coaption element or means
for coapting 110, thereby pulling on the outer paddle 120,
which in turn pulls on the inner paddle 122, causing the first
anchor 108 to partially unfold. To transition a second inner
paddle 122 and a second outer paddle 120 from the fully
closed to the partially open condition, the actuation element
or means for actuating 113 is extended to push the cap 115
away from the coaption element or means for coapting 110,
thereby pulling on the outer paddle 120, which in turn pulls
on the inner paddle 122, causing the second anchor 108 to
partially unfold. The independent paddle control illustrated
by FIG. 15 can be implemented on any of the devices
disclosed by the present application. For comparison, in the
example illustrated by FIG. 11, the pair of inner and outer
paddles 122, 120 are moved in unison, rather than indepen-
dently, by a single actuation element or means for actuating
112.

Referring now to FIGS. 16-21, the implantable device 100
of FIGS. 8-14 is shown being delivered and implanted
within the native mitral valve MV of the heart H, though
similar steps can be used on other valves. The methods and
steps shown and/or discussed can be performed on a living
animal or on a simulation, such as on a cadaver, cadaver
heart, simulator (e.g. with the body parts, heart, tissue, etc.
being simulated), etc.

Figure 16:
FIGS. 16-21 show the implantable prosthetic device of FIGS. 8-14 being delivered and implanted within the native mitral valve.
Figure 17:
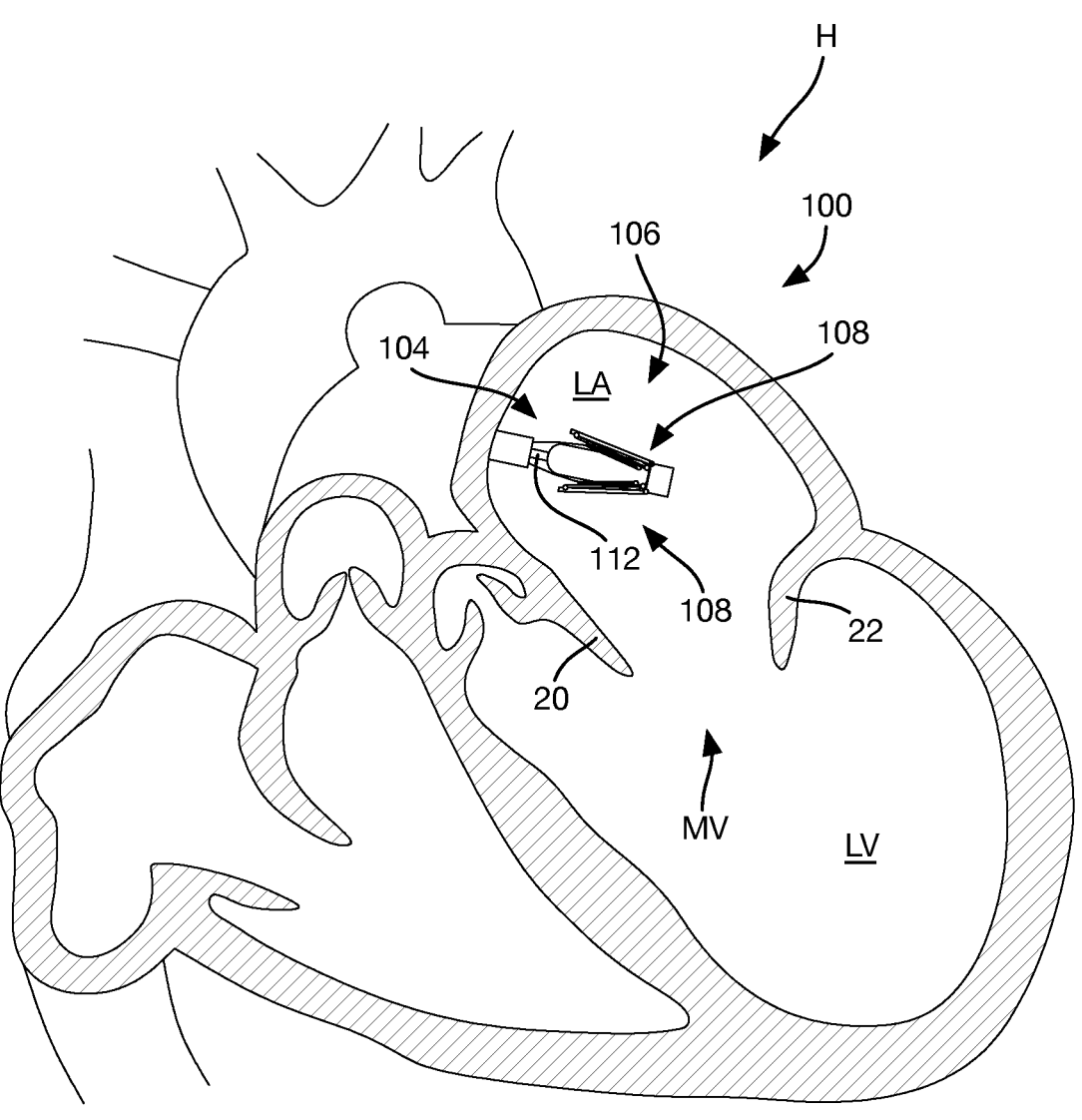
Figure 18:
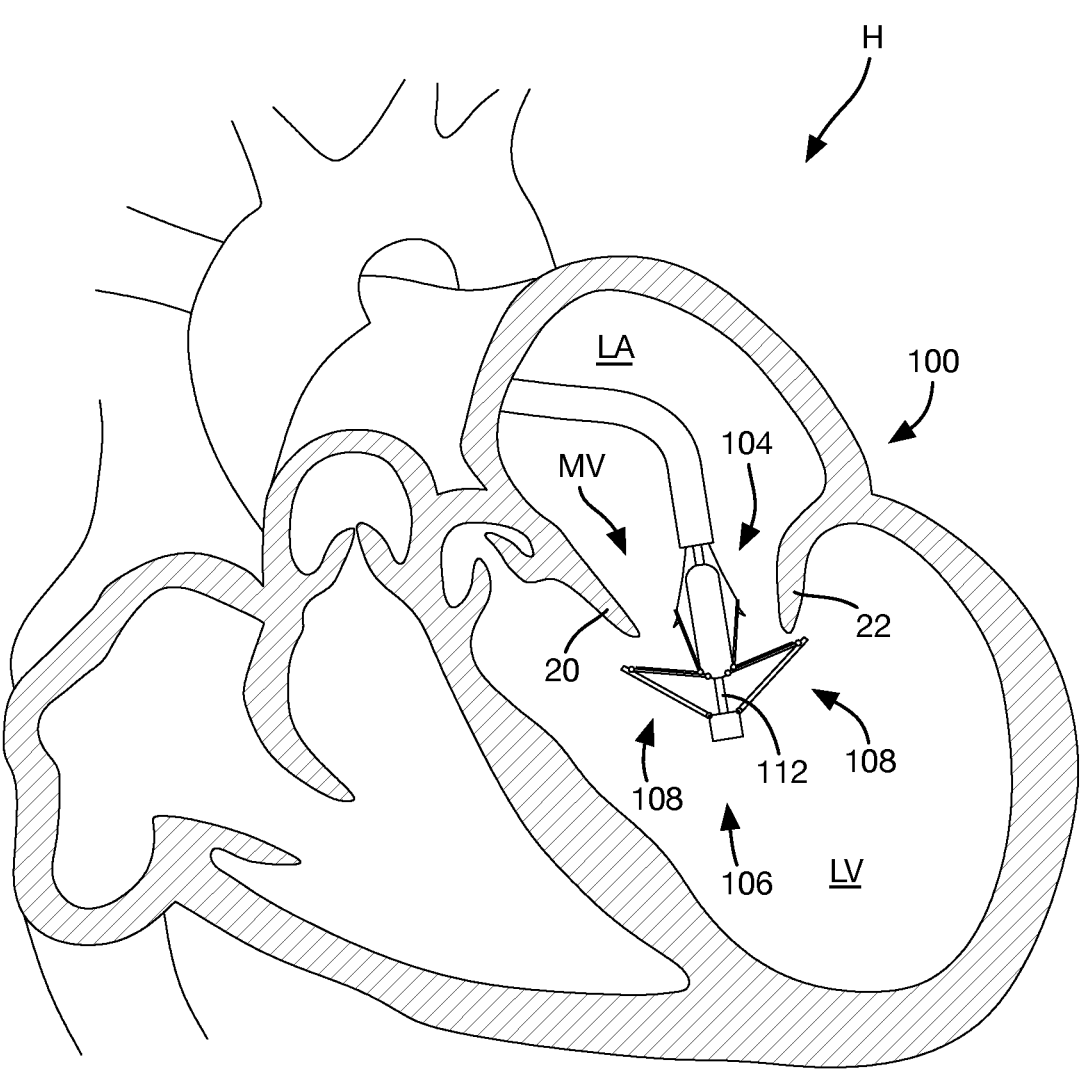
Figure 19:
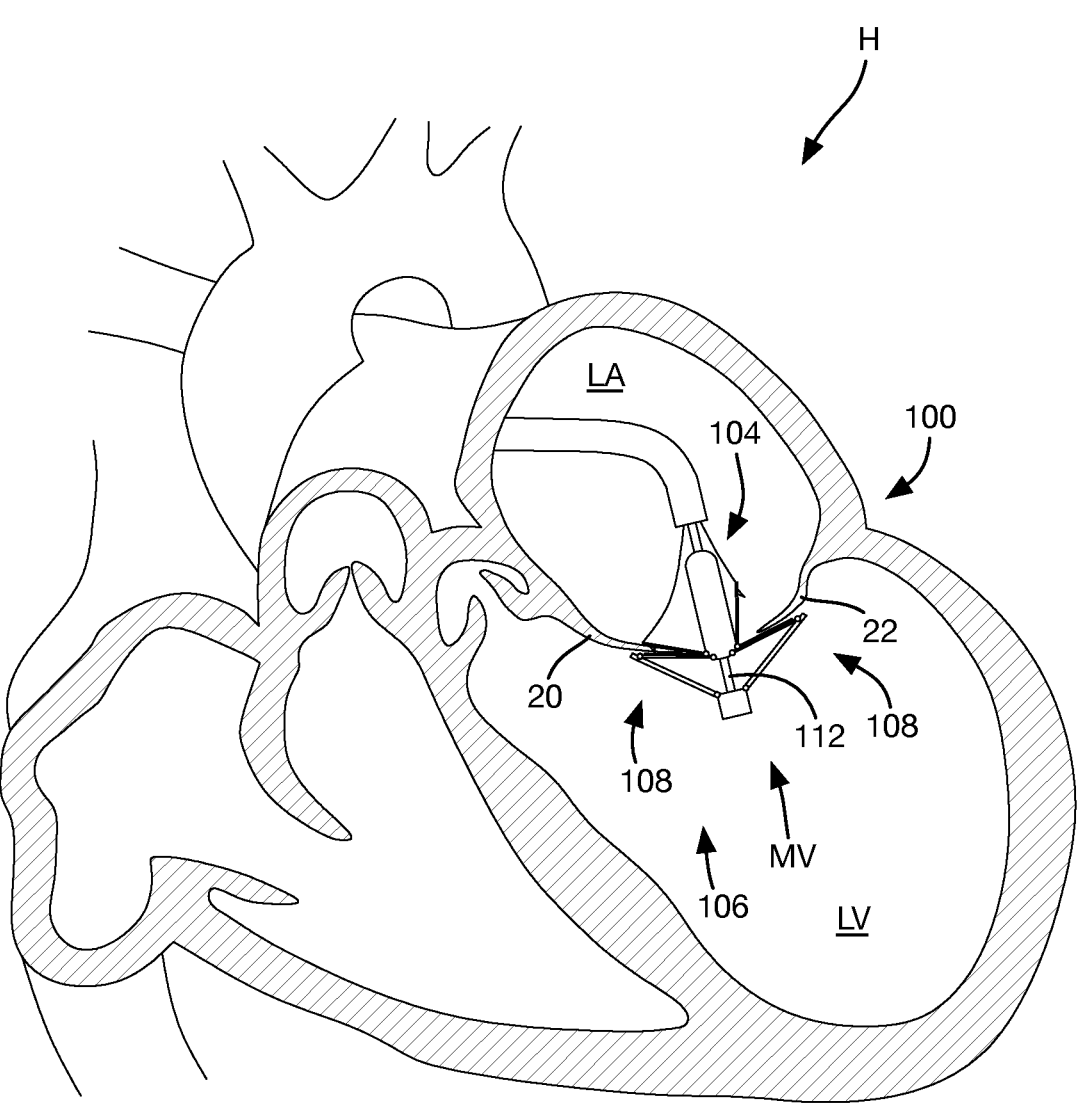
Figure 20:
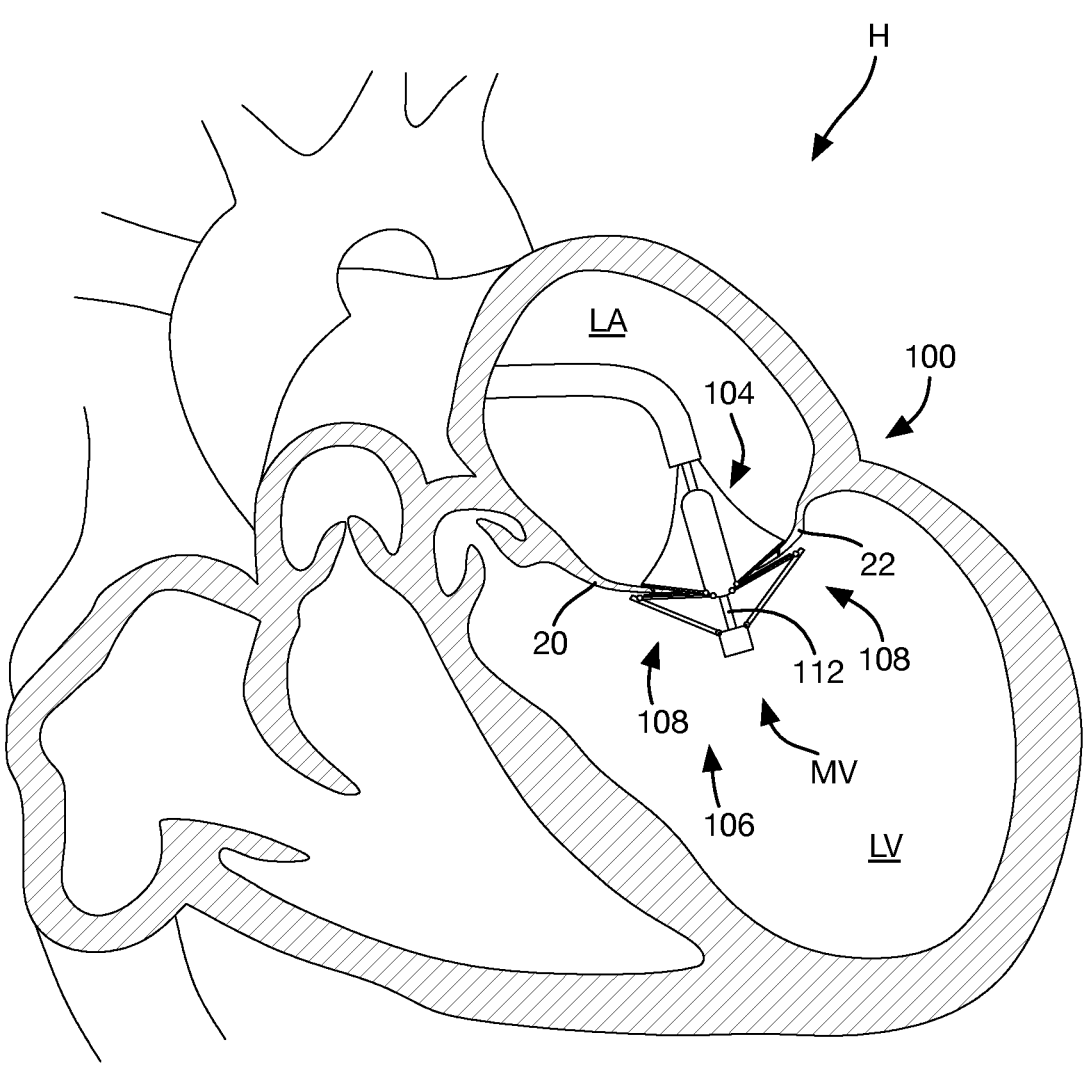
Figure 21:
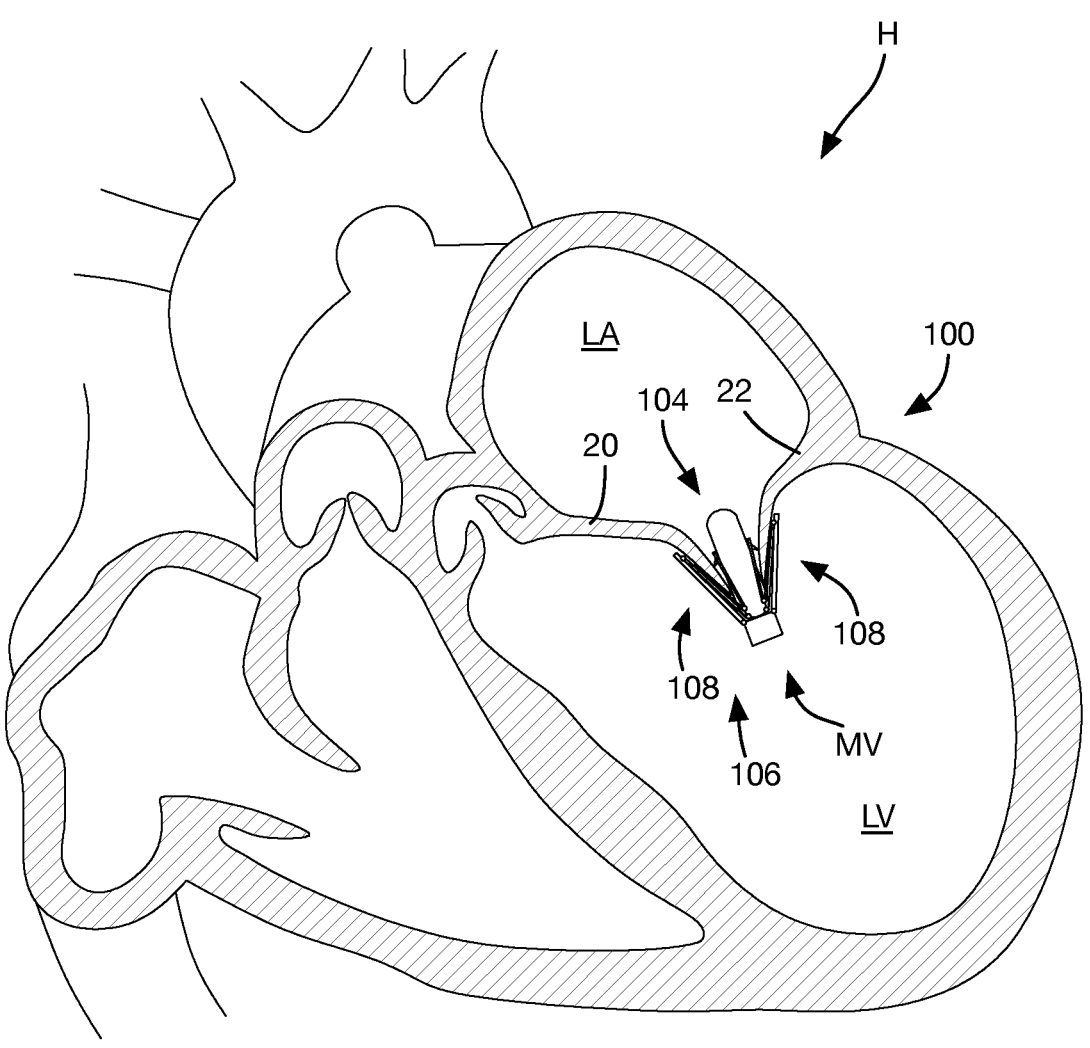
Figure 22:
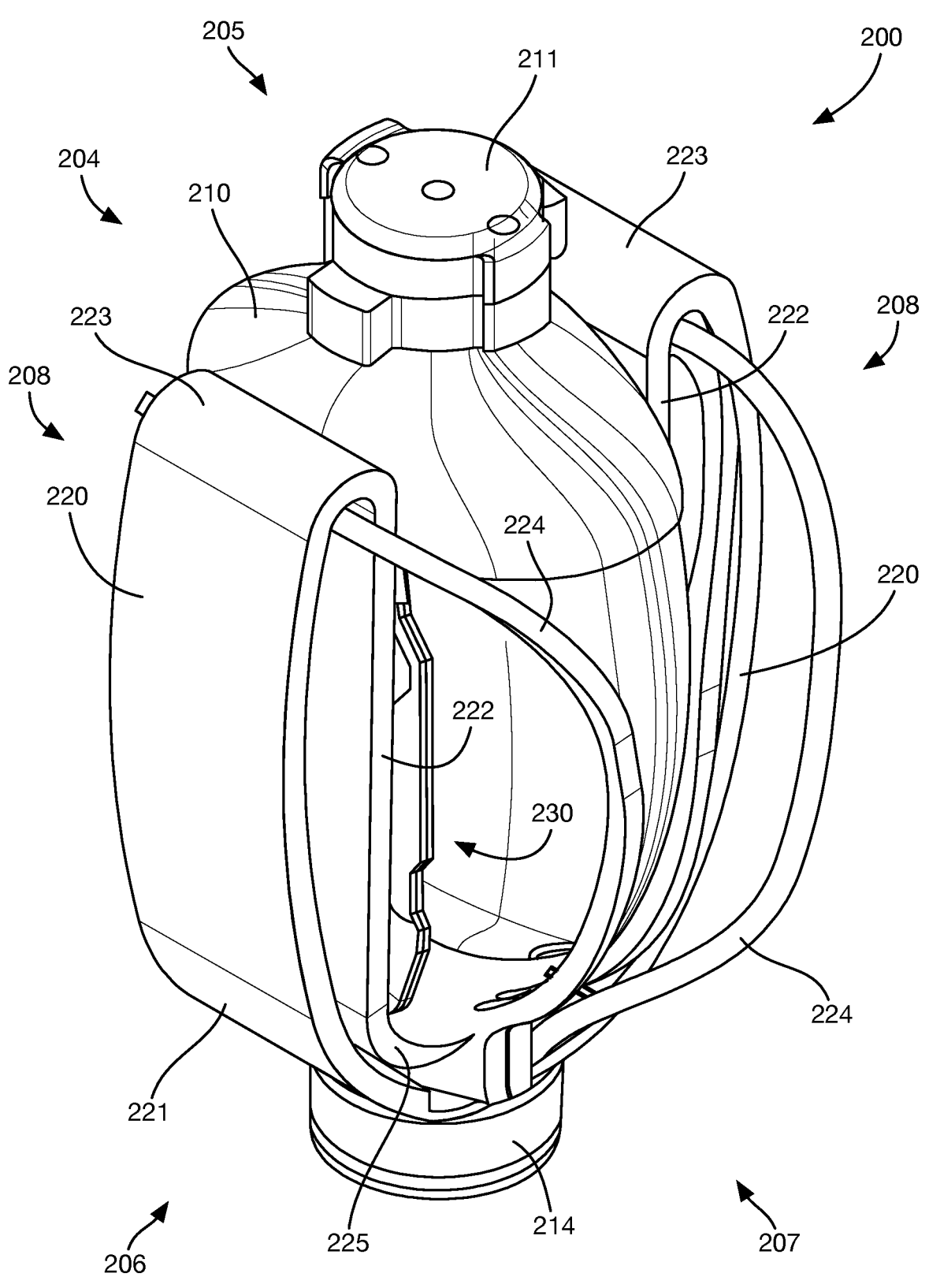
FIG. 22 shows a perspective view of an example implantable prosthetic device in a closed position.
Figure 23:
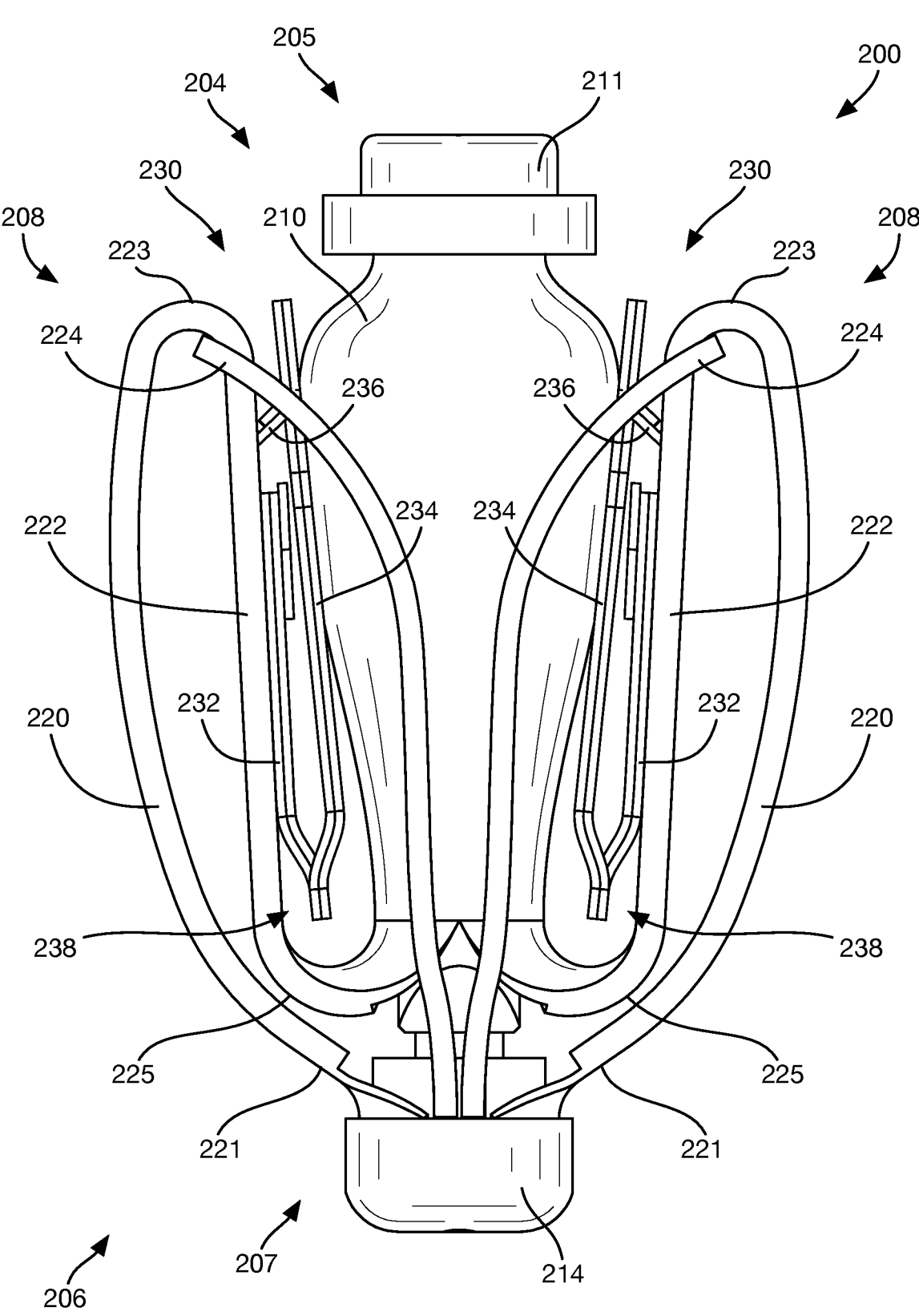
FIG. 23 shows a front view of the implantable prosthetic device of FIG. 22.

Referring now to FIG. 16, the delivery sheath is inserted into the left atrium LA through the septum and the device 100 is deployed from the delivery sheath in the fully open condition. The actuation element or means for actuating 112 is then retracted to move the device 100 into the fully closed condition shown in FIG. 17. As can be seen in FIG. 18, the device 100 is moved into position within the mitral valve MV into the ventricle LV and partially opened so that the leaflets 20, 22 can be grasped. Referring now to FIG. 19, an actuation line 116 is extended to close one of the clasps 130, capturing a leaflet 20. FIG. 20 shows the other actuation line 116 being then extended to close the other clasp 130, capturing the remaining leaflet 22. As can be seen in FIG. 21, the delivery sheath or means for delivery 102 and actuation element or means for actuating 112 and actuation lines 116 are then retracted and the device 100 is fully closed and deployed in the native mitral valve MV.

Referring now to FIGS. 22-27, an example embodiment of an implantable prosthetic spacer device 200 is shown. The implantable device 200 is one of the many different configurations that the device 100 that is schematically illustrated in FIGS. 8-14 can take. The device 200 can include any other features for an implantable prosthetic device discussed in the present application, and the device 200 can be positioned to engage valve tissue 20, 22 as part of any suitable valve repair system (e.g., any valve repair system disclosed in the present application).

The implantable prosthetic spacer device 200 includes a coaption portion 204, a proximal or attachment portion 205, an anchor portion 206, and a distal portion 207. The coaption portion 204 of the device includes a coaption element 210 for implantation between the leaflets 20, 22 of the native mitral valve MV. The anchor portion 206 includes a plurality of anchors 208, each anchor 208 including outer paddles 220, inner paddles 222, paddle extension members or paddle frames 224, and clasps 230. The attachment portion 205 includes a first or proximal collar 211 for engaging with a capture mechanism 213 (FIGS. 43-49) of a delivery sheath or system 202 (FIGS. 38-42 and 49).

The coaption element 210 and paddles 220, 222 are formed from a flexible material that can be a metal fabric, such as a mesh, woven, braided, or formed in any other suitable way or a laser cut or otherwise cut flexible material. The material can be cloth, shape-memory alloy wire—such as Nitinol—to provide shape-setting capability, or any other flexible material suitable for implantation in the human body.

An element 212 (e.g., actuation wire, shaft, etc.) extends from the delivery sheath or system 202 to engage and enable actuation of the implantable prosthetic device 200. The actuation element 212 extends through the capture mechanism 213, proximal collar 211, and coaption element 210 to engage a cap 214 of the distal portion 207. The actuation element 212 can be configured to removably engage the cap 214 with a threaded connection, or the like, so that the actuation element 212 can be disengaged and removed from the device 200 after implantation.

The coaption element 210 extends from the proximal collar 211 to the inner paddles 222. The coaption element 210 has a generally elongated and round shape. In particular, the coaption element 210 has an elliptical shape or cross-section when viewed from above (FIG. 51) and has a tapered shape or cross-section when seen from a front view (e.g., FIG. 23) and a round shape or cross-section when seen from a side view (e.g., FIG. 24). A blend of these three geometries can result in the three-dimensional shape of the illustrated coaption element 210 that achieves the benefits described herein. The round shape of the coaption element 210 can also be seen, when viewed from above, to substantially follow or be close to the shape of the paddle frames 570.

The size of the coaption element 210 can be selected to minimize the number of implants that a single patient will require (preferably one), while at the same time maintaining low transvalvular gradients. In one example embodiment, the anterior-posterior distance at the top of the spacer is about 5 mm, and the medial-lateral distance of the spacer at its widest is about 10 mm. In one example embodiment, the overall geometry of the device 200 can be based on these two dimensions and the overall shape strategy described above. It should be readily apparent that the use of other anterior-posterior distance anterior-posterior distance and medial-lateral distance as starting points for the device will result in a device having different dimensions. Further, using other dimensions and the shape strategy described above will also result in a device having different dimensions.

The outer paddles 220 are jointably attached to the cap 214 of the distal portion 207 by connection portions 221 and to the inner paddles 222 by connection portions 223. The inner paddles 222 are jointably attached to the coaption element by connection portions 225. In this manner, the anchors 208 are configured similar to legs in that the inner paddles 222 are like upper portions of the legs, the outer paddles 220 are like lower portions of the legs, and the connection portions 223 are like knee portions of the legs.

The inner paddles 222 are stiff, relatively stiff, rigid, have rigid portions and/or are stiffened by a stiffening member or a fixed portion 232 of the clasps 230. The stiffening of the inner paddle allows the device to move to the various different positions shown and described herein. The inner paddle 222, the outer paddle 220, and the coaption element can all be interconnected as described herein, such that the device 200 is constrained to the movements and positions shown and described herein.

The paddle frames 224 are attached to the cap 214 at the distal portion 207 and extend to the connection portions 223 between the inner and outer paddles 222, 220. In some embodiments, the paddle frames 224 are formed of a material that is more rigid and stiff than the material forming the paddles 222, 220 so that the paddle frames 224 provide support for the paddles 222, 220.

Figure 51:
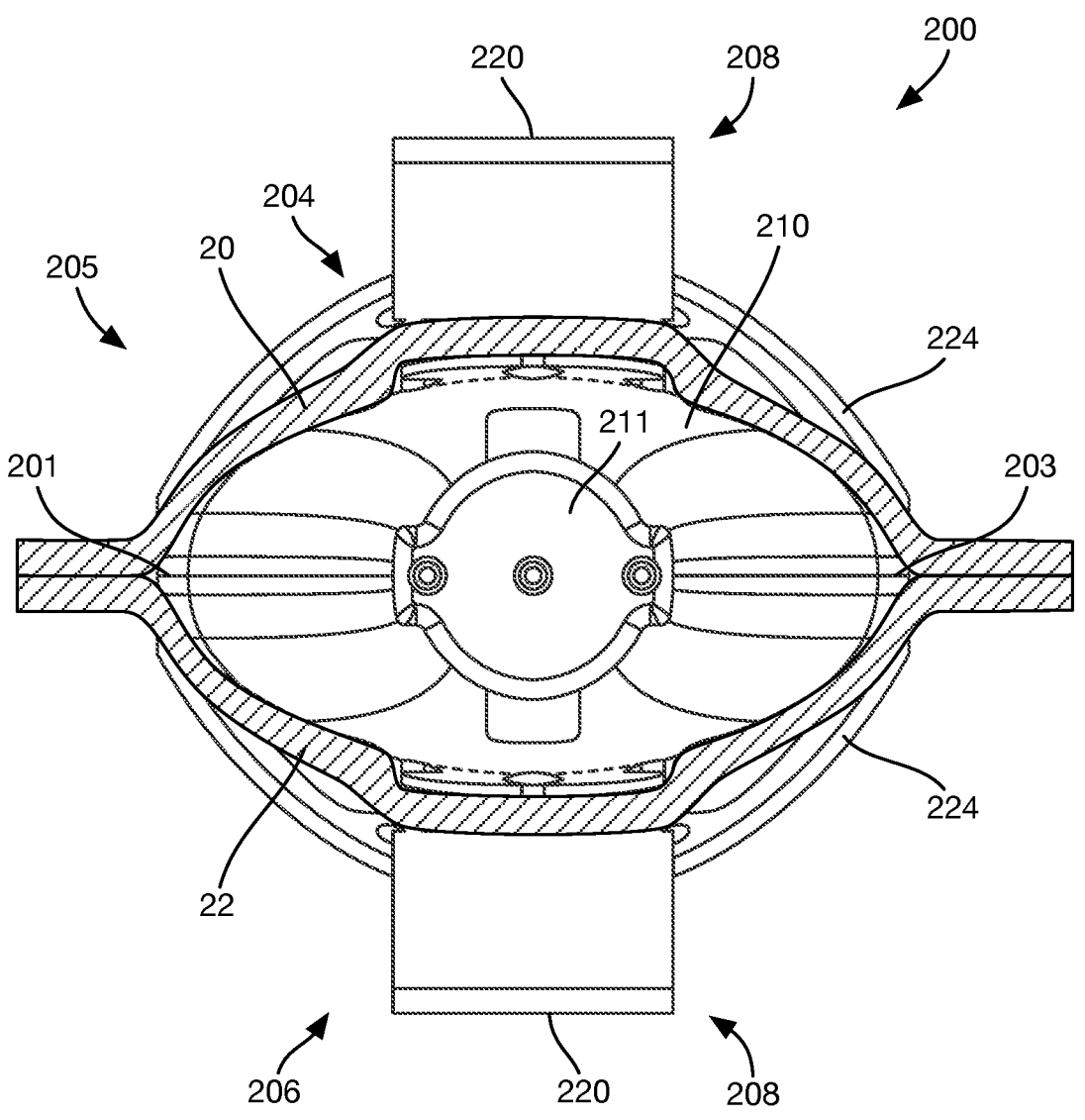
FIG. 51 is a top schematic view illustrating a path of native valve leaflets around a coaption element of a valve repair device.
Figure 52:
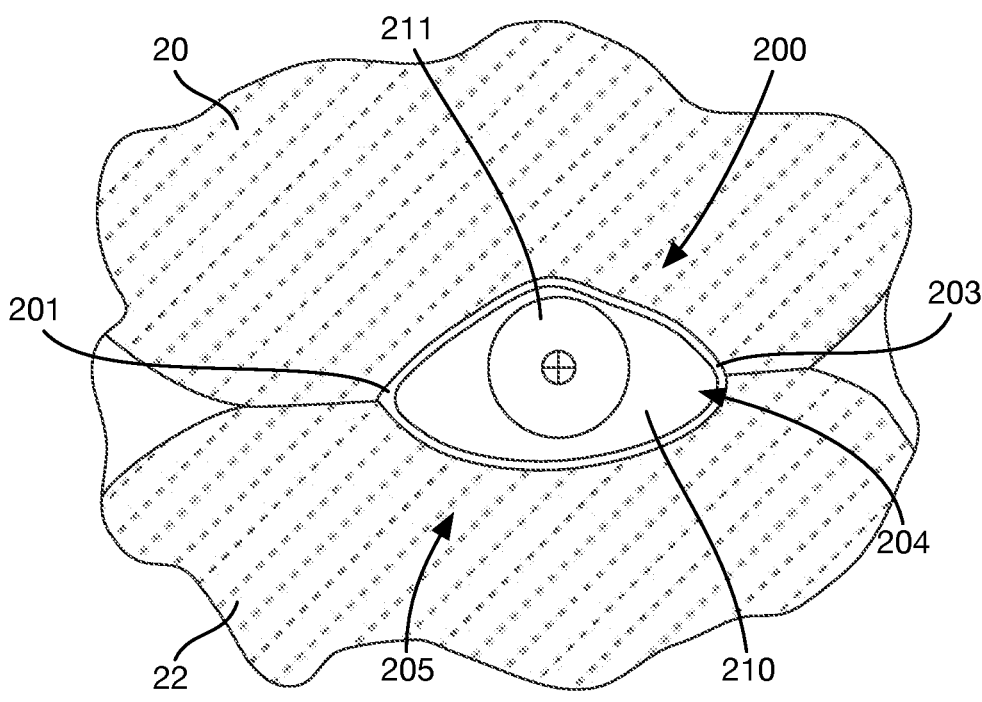
FIG. 52 illustrates a coaption element in the gap of the mitral valve as viewed from an atrial side of the mitral valve.
Figure 53:
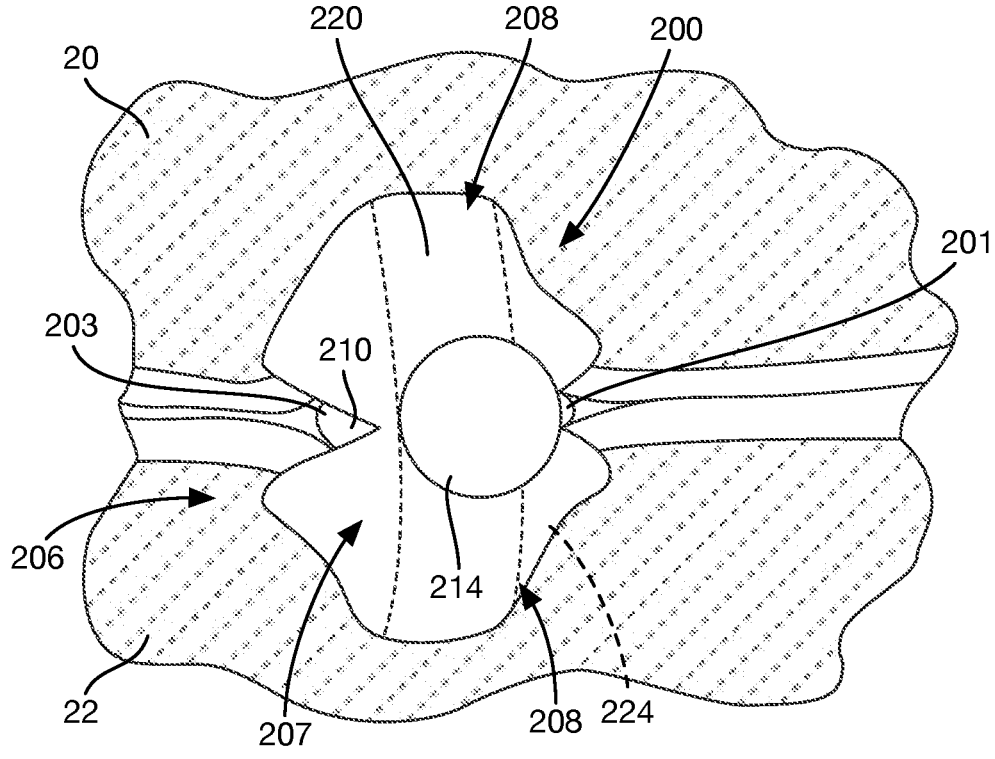
FIG. 53 illustrates a valve repair device attached to mitral valve leaflets with the coaption element in the gap of the mitral valve as viewed from a ventricular side of the mitral valve.

The paddle frames 224 provide additional pinching force between the inner paddles 222 and the coaption element 210 and assist in wrapping the leaflets around the sides of the coaption element 210 for a better seal between the coaption element 210 and the leaflets, as can be seen in FIG. 51. That is, the paddle frames 224 can be configured with a round three-dimensional shape extending from the cap 214 to the connection portions 223 of the anchors 208. The connections between the paddle frames 224, the outer and inner paddles 220, 222, the cap 214, and the coaption element 210 can constrain each of these parts to the movements and positions described herein. In particular the connection portion 223 is constrained by its connection between the outer and inner paddles 220, 222 and by its connection to the paddle frame 224. Similarly, the paddle frame 224 is constrained by its attachment to the connection portion 223 (and thus the inner and outer paddles 222, 220) and to the cap 214.

Configuring the paddle frames 224 in this manner provides increased surface area compared to the outer paddles 220 alone. This can, for example, make it easier to grasp and secure the native leaflets. The increased surface area can also distribute the clamping force of the paddles 220 and paddle frames 224 against the native leaflets over a relatively larger surface of the native leaflets in order to further protect the native leaflet tissue. Referring again to FIG. 51, the increased surface area of the paddle frames 224 can also allow the native leaflets 20, 22 to be clamped to the implantable prosthetic spacer device 200, such that the native leaflets 20, 22 coapt entirely around the coaption member 210. This can, for example, improve sealing of the native leaflets 20, 22 and thus prevent or further reduce valvular regurgitation.

The barbed clasps 230 include a base or fixed arm 232, a moveable arm 234, barbs 236, and a joint portion 238. The fixed arms 232 are attached to the inner paddles 222, with the joint portion 238 disposed proximate the coaption element 210. The joint portion 238 is spring-loaded so that the fixed and moveable arms 232, 234 are biased toward each other when the barbed clasp 230 is in a closed condition.

The fixed arms 232 are attached to the inner paddles 222 through holes or slots 231 with sutures (not shown). The fixed arms 232 can be attached to the inner paddles 222 with any suitable means, such as screws or other fasteners, crimped sleeves, mechanical latches or snaps, welding, adhesive, or the like. The fixed arms 232 remain substantially stationary relative to the inner paddles 222 when the moveable arms 234 are opened to open the barbed clasps 230 and expose the barbs 236. The barbed clasps 230 are opened by applying tension to actuation lines 216 (FIGS. 43-48) attached to holes 235 in the moveable arms 234, thereby causing the moveable arms 234 to move, pivot, flex, etc. on the joint portions 238.

Figure 29:
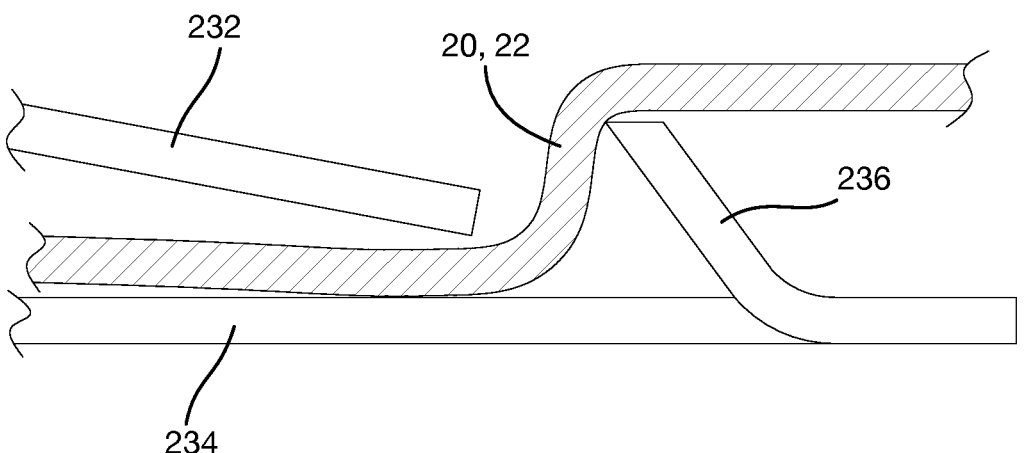
FIG. 29 shows a portion of native valve tissue grasped by a barbed clasp.

Referring now to FIG. 29, a close-up view of one of the leaflets 20, 22 grasped by a barbed clasp such as clasp 230 is shown. The leaflet 20, 22 is grasped between the moveable and fixed arms 234, 232 of the clasp 230. The tissue of the leaflet 20, 22 is not pierced by the barbs 236, though in some embodiments the barbs 236 may partially or fully pierce through the leaflet 20, 22. The angle and height of the barbs 236 relative to the moveable arm 234 helps to secure the leaflet 20, 22 within the clasp 230. In particular, a force pulling the implant off of the native leaflet 20, 22 will encourage the barbs 236 to further engage the tissue, thereby ensuring better retention. Retention of the leaflet 20, 22 in the clasp 230 is further improved by the position of fixed arm 232 near the barbs 236 when the clasp 230 is closed. In this arrangement, the tissue is formed by the fixed arms 232 and the moveable arms 234 and the barbs 236 into an S-shaped torturous path. Thus, forces pulling the leaflet 20, 22 away from the clasp 230 will encourage the tissue to further engage the barbs 236 before the leaflets 20, 22 can escape. For example, leaflet tension during diastole can encourage the barbs 236 to pull toward the end portion of the leaflet 20, 22. Thus, the S-shaped path can utilize the leaflet tension during diastole to more tightly engage the leaflets 20, 22 with the barbs 236.

Figure 25:
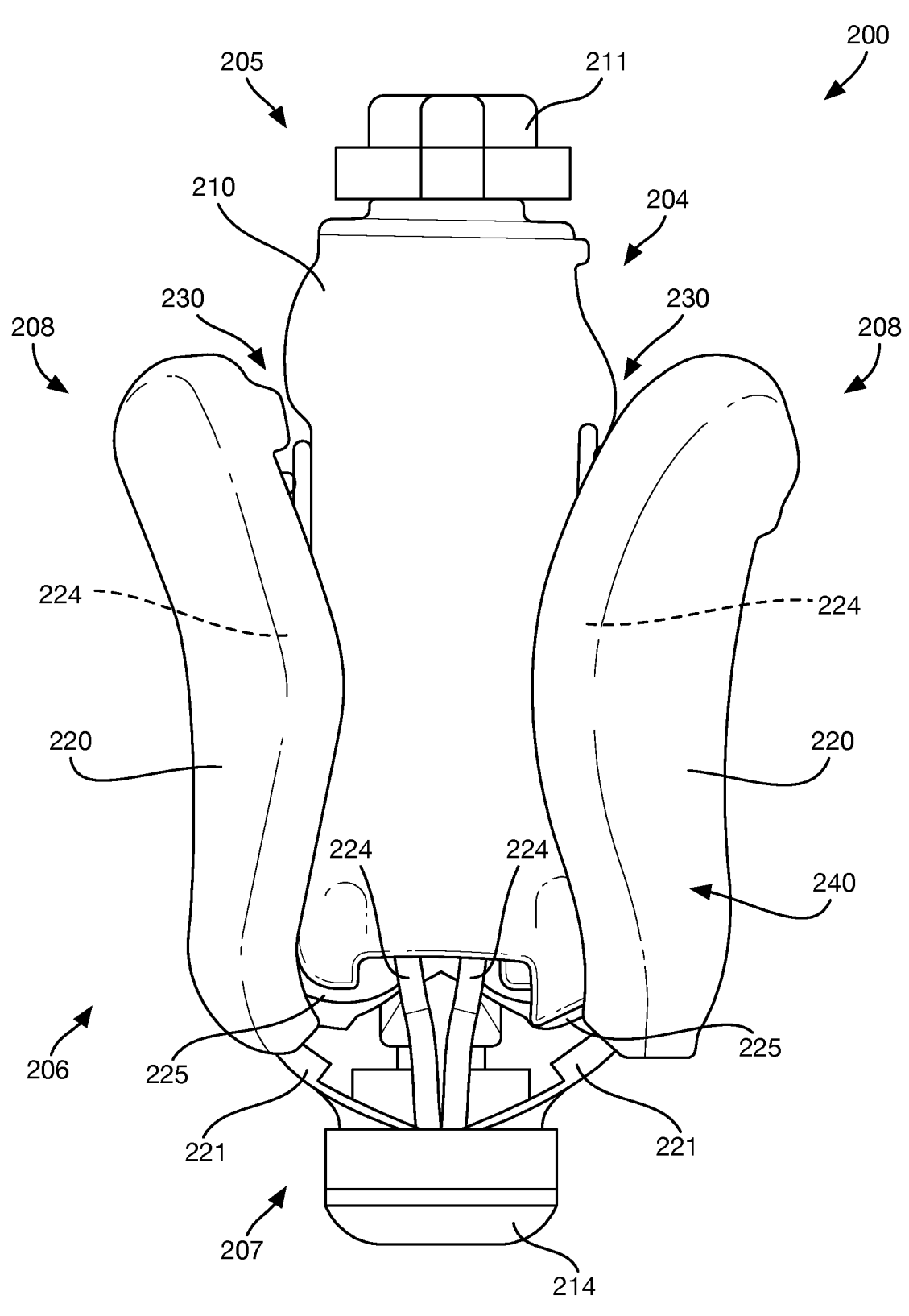
FIG. 25 shows a front view of the implantable prosthetic device of FIG. 22 with a cover covering the paddles and coaption element.
Figure 26:
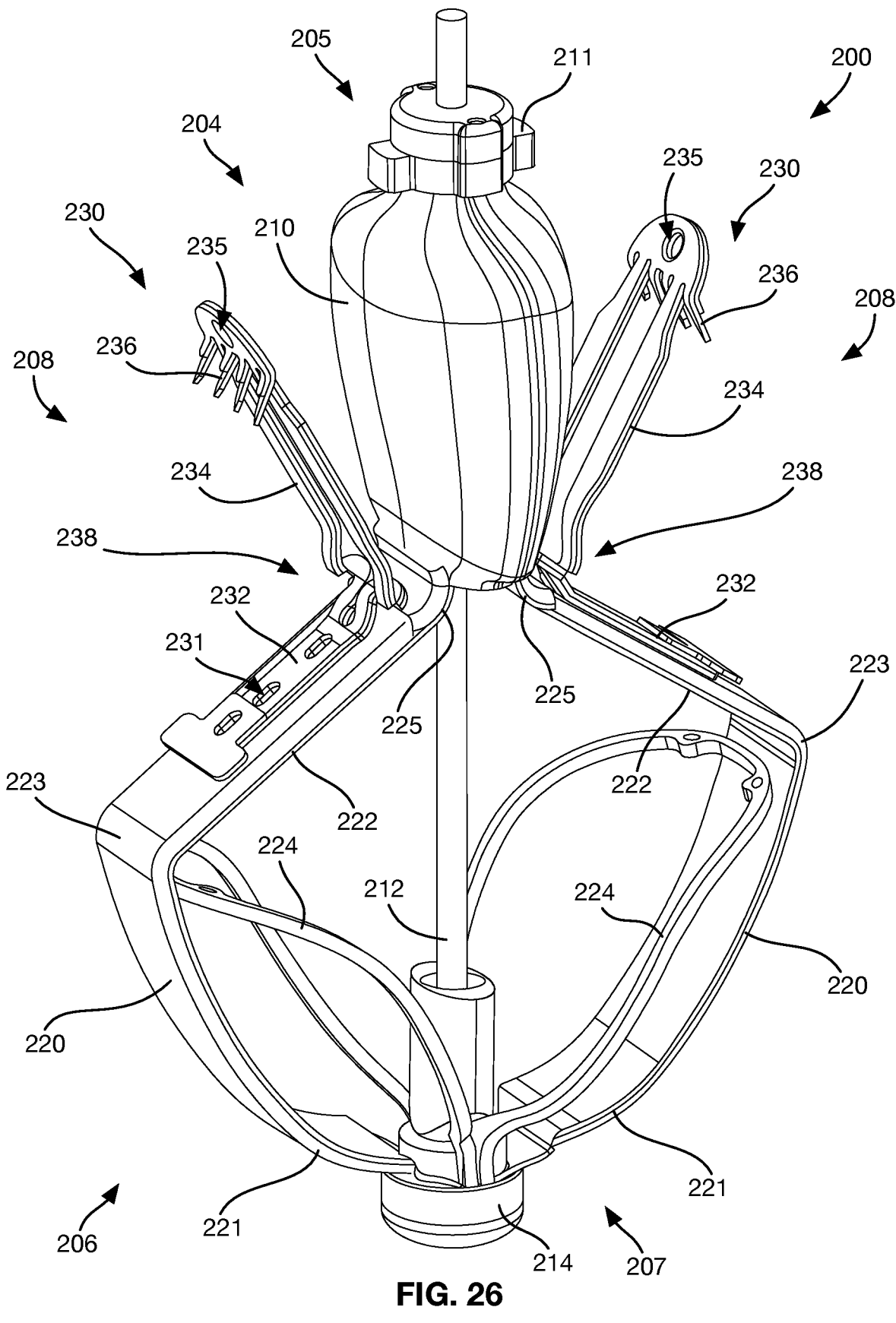
FIG. 26 shows a top perspective view of the implantable prosthetic device of FIG. 22 in an open position.
Figure 27:
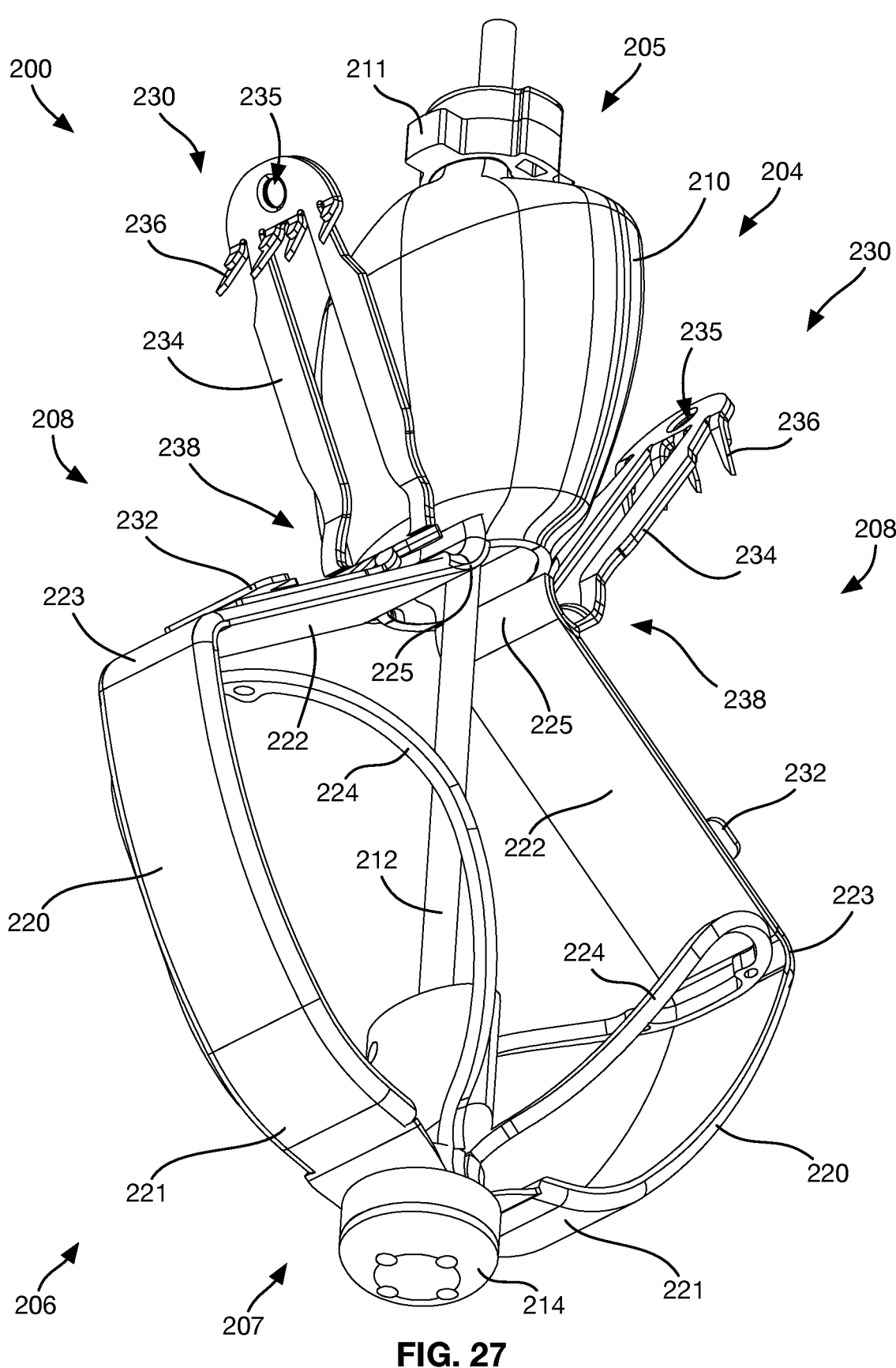
FIG. 27 shows a bottom perspective view of the implantable prosthetic device of FIG. 22 in an open position.
Figure 28:
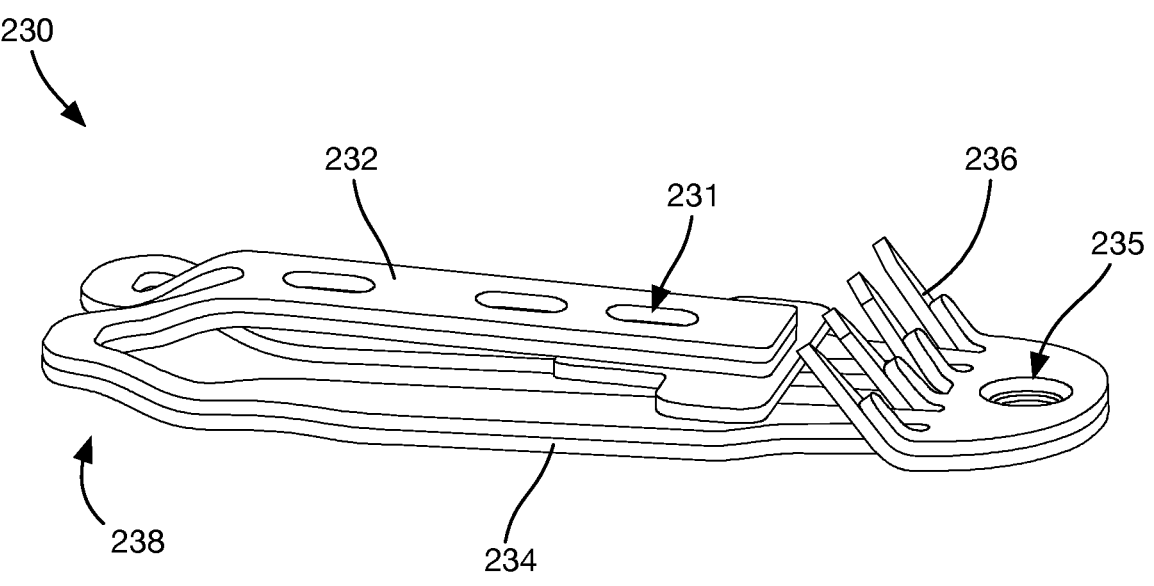
FIG. 28 shows a barbed clasp for use in an implantable prosthetic device.

Referring to FIG. 25, the prosthetic spacer device 200 can also include a cover 240. In some embodiments, the cover 240 can be disposed on the coaption member 210, the outer and inner paddles 220, 222, and/or the paddle frames 224. The cover 240 can be configured to prevent or reduce blood-flow through the prosthetic spacer device 200 and/or to promote native tissue ingrowth. In some embodiments, the cover 240 can be a cloth or fabric such as PET, velour, or other suitable fabric. In some embodiments, in lieu of or in addition to a fabric, the cover 240 can include a coating (e.g., polymeric, silicone, etc.) that is applied to the implantable prosthetic spacer device 200.

During implantation, the paddles 220, 222 of the anchors 208 are opened and closed to grasp the native valve leaflets 20, 22 between the paddles 220, 222 and the coaption element 210. The anchors 208 are moved between a closed position (FIGS. 22-25) to various open positions (FIGS. 26-37) by extending and retracting the actuation element, wire, or shaft 212. Extending and retracting the actuation element 212 increases and decreases the spacing between the coaption element 210 and the cap 214, respectively. The proximal collar 211 and the coaption element 210 slide along the actuation element 212 during actuation so that changing of the spacing between the coaption element 210 and the cap 214 causes the paddles 220, 220 to move between different positions to grasp the native valve leaflets 20, 22 during implantation.

As the device 200 is opened and closed, the pair of inner and outer paddles 222, 220 are moved in unison, rather than independently, by a single actuation element 212. Also, the positions of the clasps 230 are dependent on the positions of the paddles 222, 220. For example, the clasps 230 are arranged such that closure of the anchors 208 simultaneously closes the clasps 230. In one example embodiment, the device 200 can be made to have the paddles 220, 222 be independently controllable in the same manner as the device 100 illustrated in FIG. 15.

The barbed clasps 230 further secure the native leaflets 20, 22 by engaging the leaflets 20, 22 with barbs 236 and pinching the leaflets 20, 22 between the moveable and fixed arms 234, 232. The barbs 236 of the barbed clasps 230 increase friction with or may partially or completely puncture the leaflets 20, 22. The actuation lines 216 (FIGS. 43-48) can be actuated separately so that each barbed clasp 230 can be opened and closed separately. Separate operation allows one leaflet 20, 22 to be grasped at a time, or for the repositioning of a clasp 230 on a leaflet 20, 22 that was insufficiently grasped, without altering a successful grasp on the other leaflet 20, 22. The barbed clasps 230 can be fully opened and closed when the inner paddle 222 is not closed, thereby allowing leaflets 20, 22 to be grasped in a variety of positions as the particular situation requires.

Referring now to FIGS. 22-25, the device 200 is shown in a closed position. When closed, the inner paddles 222 are disposed between the outer paddles 220 and the coaption element 210. The clasps 230 are disposed between the inner paddles 222 and the coaption element 210. Upon successful capture of native leaflets 20, 22 the device 200 is moved to and retained in the closed position so that the leaflets 20, 22 are secured within the device 200 by the clasps 230 and are pressed against the coaption element 210 by the paddles 220, 222. The outer paddles 220 have a wide curved shape that fits around the curved shape of the coaption element 210 to more securely grip the leaflets 20, 22 when the device 200 is closed, as can be seen in FIG. 51. The curved shape and rounded edges of the outer paddle 220 also prohibits tearing of the leaflet tissue.

Referring now to FIGS. 30-37, the implantable prosthetic device 200 described above is shown in various positions and configurations ranging from partially open to fully open. The paddles 220, 222 of the device 200 transition between each of the positions shown in FIGS. 30-37 from the closed position shown in FIGS. 22-25 through to the fully open position upon extension of the actuation element 212 (e.g., wire, shaft, etc.) from a fully retracted position to a fully extended position of the actuation element.

Figures 30, 31:
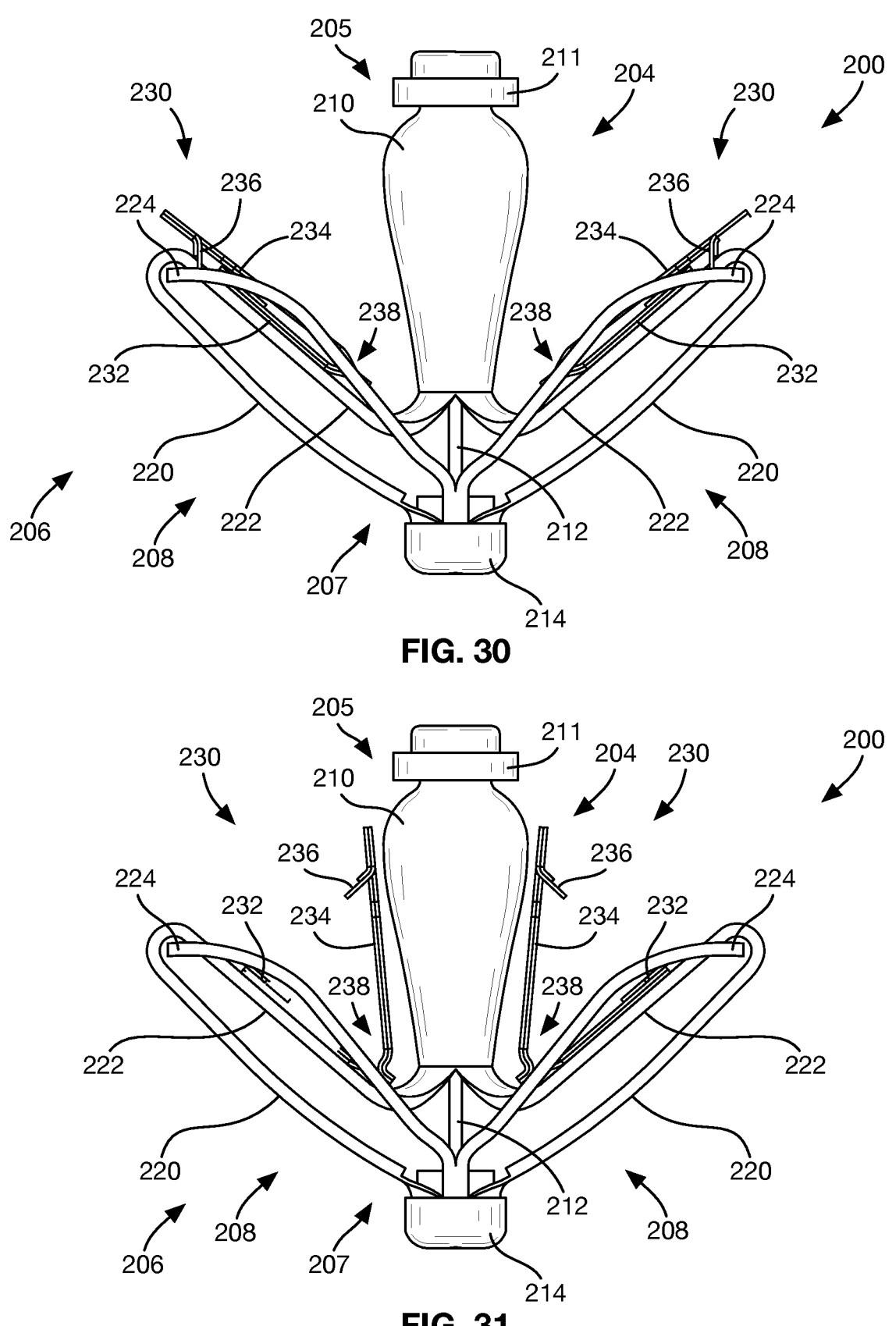
FIG. 30 shows a side view of an example implantable prosthetic device in a partially-open position with barbed clasps in a closed position.
FIG. 31 shows a side view of an example implantable prosthetic device in a partially-open position with barbed clasps in an open position.

Referring now to FIGS. 30-31, the device 200 is shown in a partially open position. The device 200 is moved into the partially open position by extending the actuation element 212. Extending the actuation element 212 pulls down on the bottom portions of the outer paddles 220 and paddle frames 224. The outer paddles 220 and paddle frames 224 pull down on the inner paddles 222, where the inner paddles 222 are connected to the outer paddles 220 and the paddle frames 224. Because the proximal collar 212 and coaption element 210 are held in place by the capture mechanism 213, the inner paddles 222 are caused to move, pivot, flex, etc. in an opening direction. The inner paddles 222, the outer paddles 220, and the paddle frames all flex to the position shown in FIGS. 30-31. Opening the paddles 222, 220 and frames 224 forms a gap between the coaption element 210 and the inner paddle 222 that can receive and grasp the native leaflets 20, 22. This movement also exposes the barbed clasps 230 that can be moved between closed (FIG. 30) and open (FIG. 31) positions to form a second gap for grasping the native leaflets 20, 22. The extent of the gap between the fixed and moveable arms 232, 234 of the clasp 230 is limited to the extent that the inner paddle 222 has spread away from the coaption element 210.

Figures 32, 33:
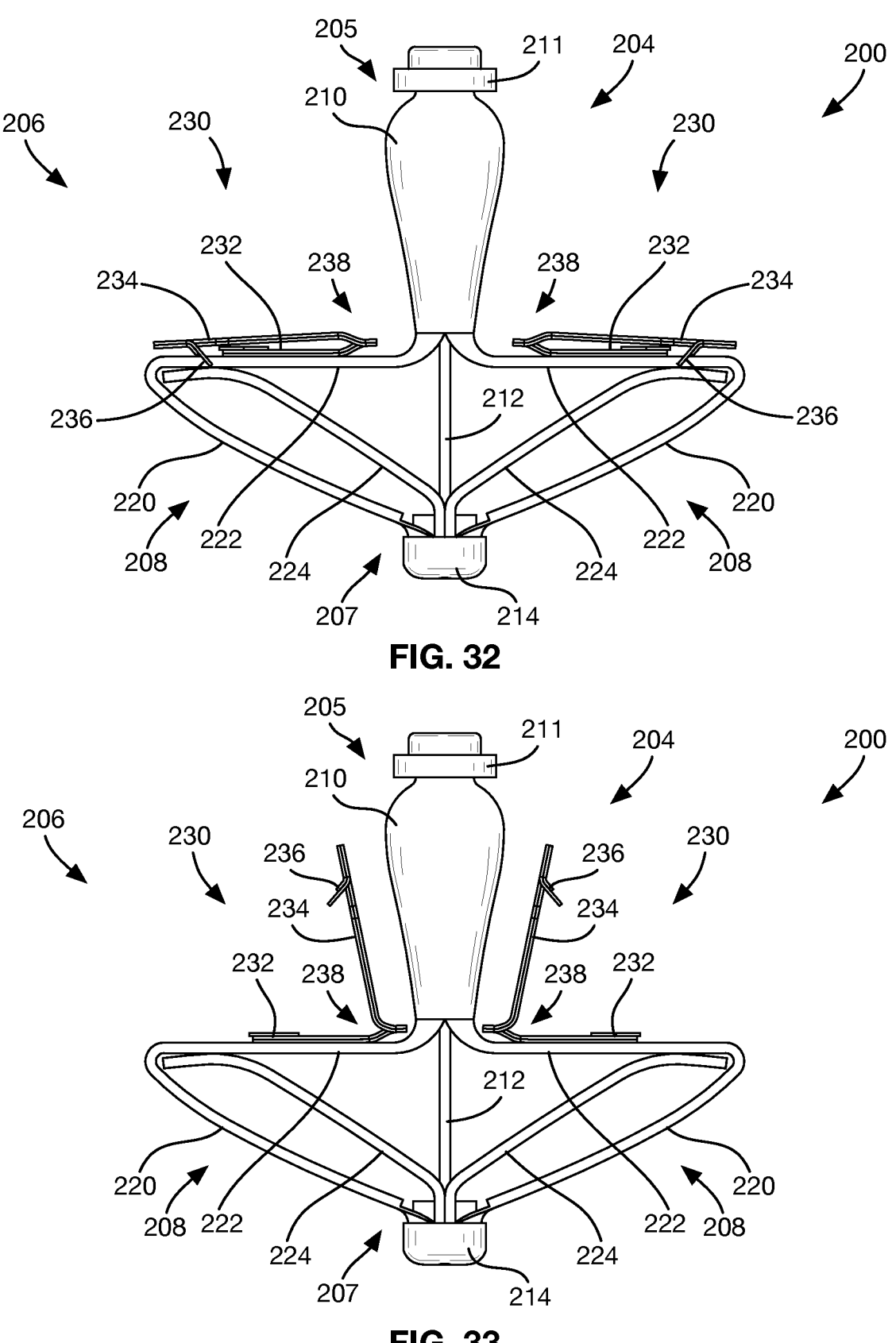
FIG. 32 shows a side view of an example implantable prosthetic device in a half-open position with barbed clasps in a closed position.
FIG. 33 shows a side view of an example implantable prosthetic device in a half-open position with barbed clasps in an open position.

Referring now to FIGS. 32-33, the device 200 is shown in a laterally extended or open position. The device 200 is moved into the laterally extended or open position by continuing to extend the actuation element 212 described above, thereby increasing the distance between the coaption element 210 and the cap 214 of the distal portion 207. Continuing to extend the actuation element 212 pulls down on the outer paddles 220 and paddle frames 224, thereby causing the inner paddles 222 to spread apart further from the coaption element 210. In the laterally extended or open position, the inner paddles 222 extend horizontally more than in other positions of the device 200 and form an approximately 90-degree angle with the coaption element 210. Similarly, the paddle frames 224 are at their maximum spread position when the device 200 is in the laterally extended or open position. The increased gap between the coaption element 210 and inner paddle 222 formed in the laterally extended or open position allows clasps 230 to open further (FIG. 33) before engaging the coaption element 210, thereby increasing the size of the gap between the fixed and moveable arms 232, 234.

Figure 34:
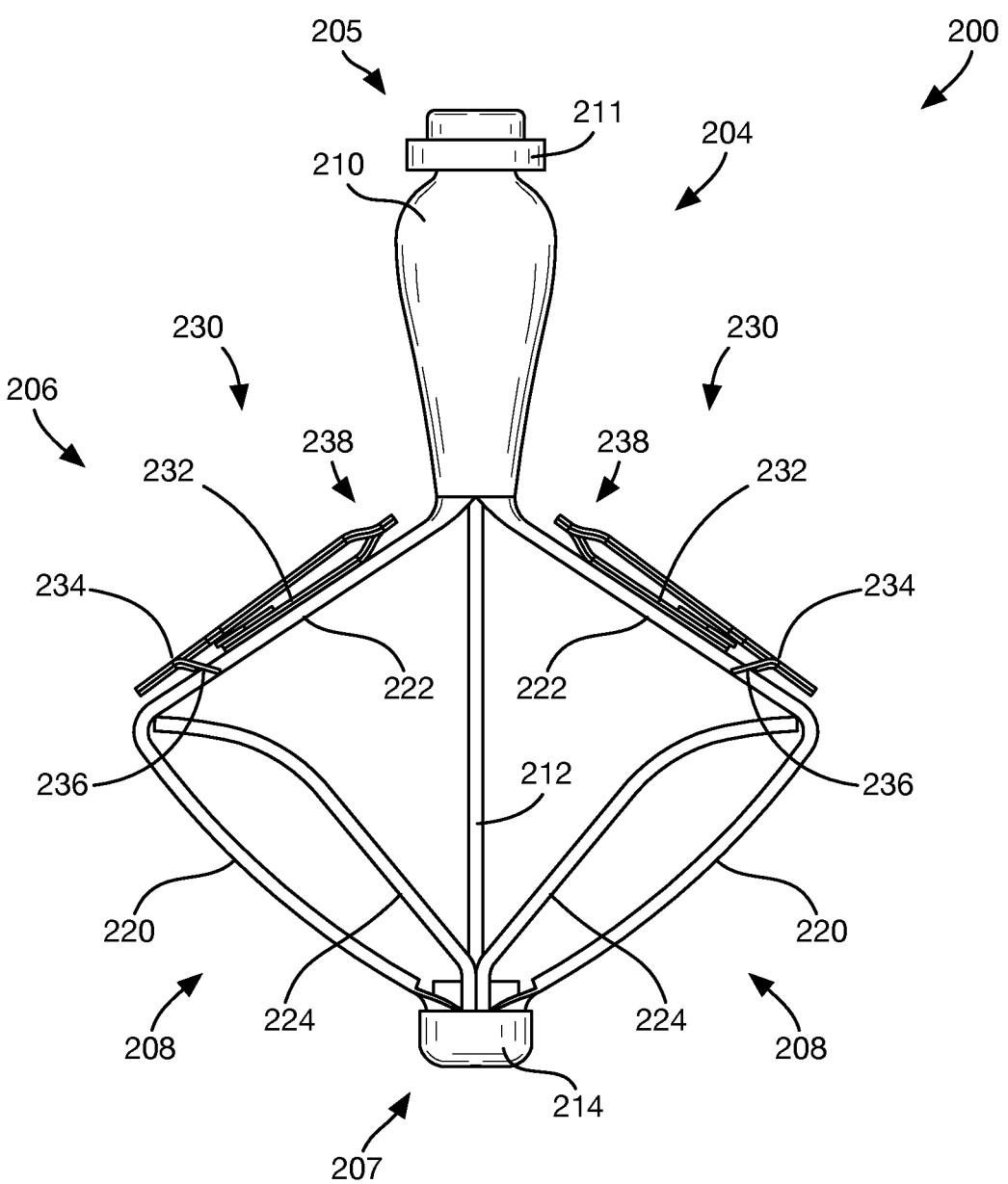
FIG. 34 shows a side view of an example implantable prosthetic device in a three-quarters-open position with barbed clasps in a closed position.
Figure 35:
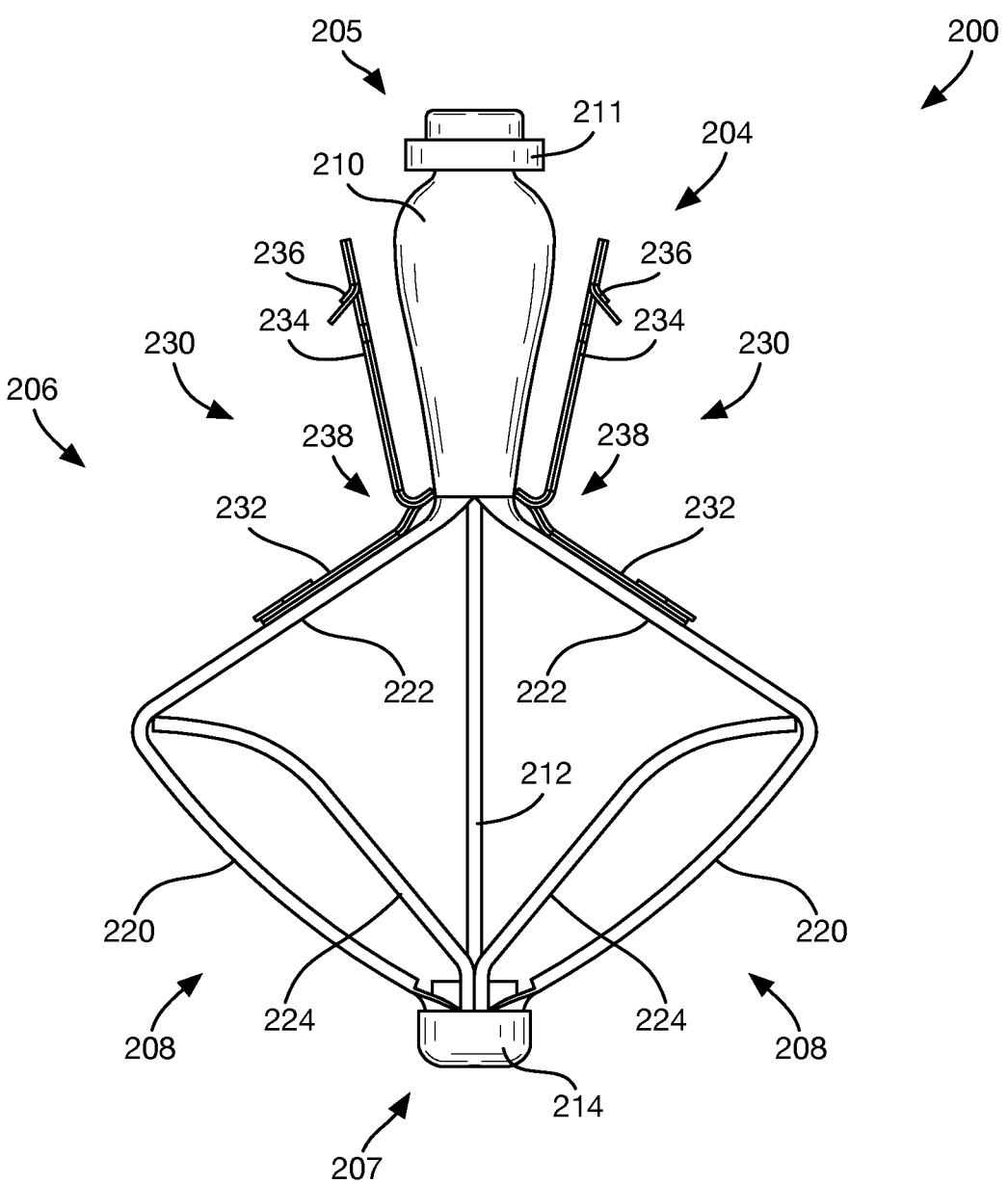
FIG. 35 shows a side view of an example implantable prosthetic device in a three-quarters-open position with barbed clasps in an open position.

Referring now to FIGS. 34-35, the device 200 is shown in a three-quarters extended position. The device 200 is moved into the three-quarters extended position by continuing to extend the actuation element 212 described above, thereby increasing the distance between the coaption element 210 and the cap 214 of the distal portion 207. Continuing to extend the actuation element 212 pulls down on the outer paddles 220 and paddle frames 224, thereby causing the inner paddles 222 to spread apart further from the coaption element 210. In the three-quarters extended position, the inner paddles 222 are open beyond 90 degrees to an approximately 135-degree angle with the coaption element 210. The paddle frames 224 are less spread than in the laterally extended or open position and begin to move inward toward the actuation element 212 as the actuation element 212 extends further. The outer paddles 220 also flex back toward the actuation element 212. As with the laterally extended or open position, the increased gap between the coaption element 210 and inner paddle 222 formed in the laterally extended or open position allows clasps 230 to open even further (FIG. 35), thereby increasing the size of the gap between the fixed and moveable arms 232, 234.

Figure 36:
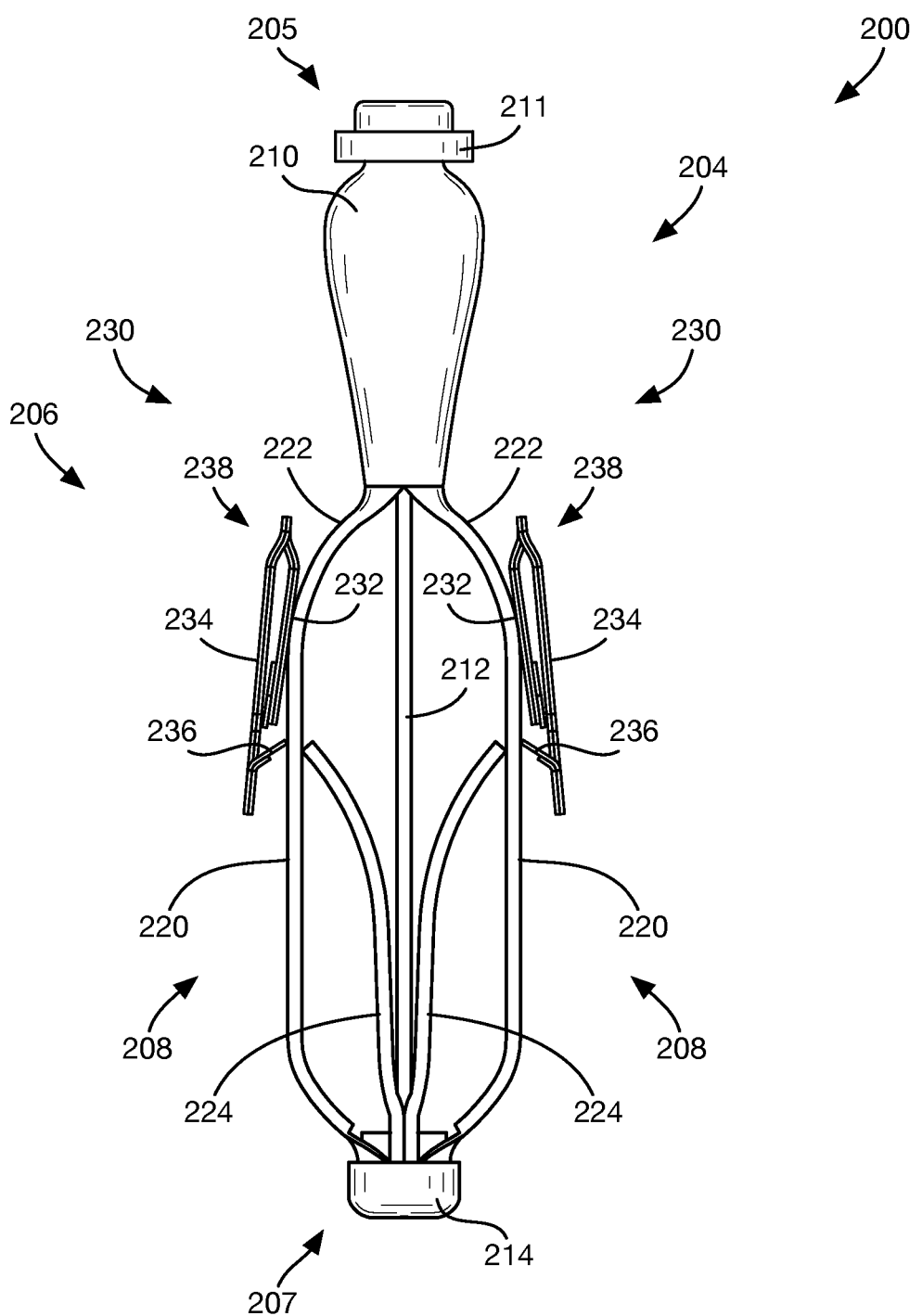
FIG. 36 shows a side view of an example implantable prosthetic device in a full bailout position with barbed clasps in a closed position.
Figure 37:
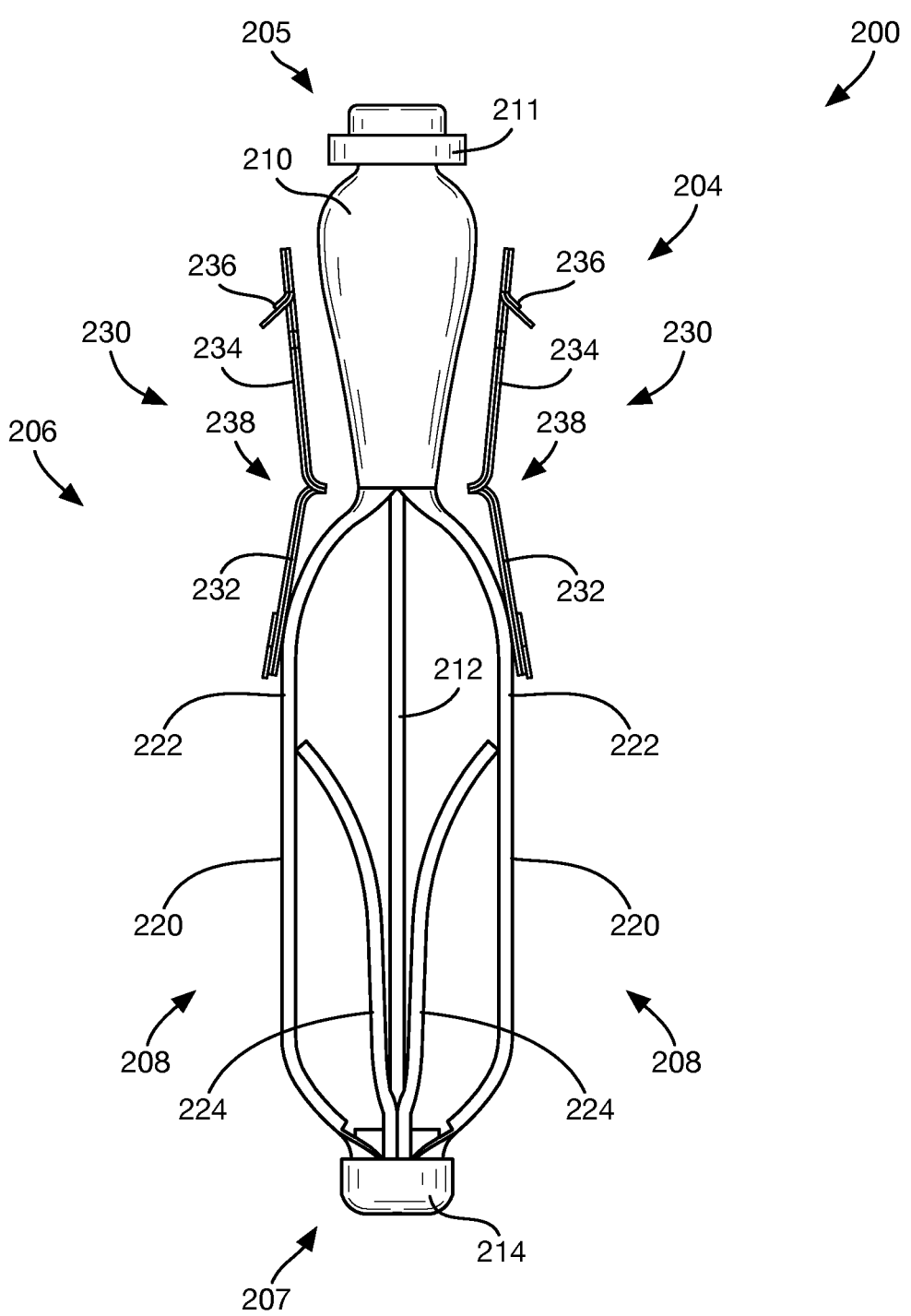
FIG. 37 shows a side view of an example implantable prosthetic device in a full bailout position with barbed clasps in an open position.

Referring now to FIGS. 36-37, the device 200 is shown in a fully extended position. The device 200 is moved into the fully extended position by continuing to extend the actuation element 212 described above, thereby increasing the distance between the coaption element 210 and the cap 214 of the distal portion 207 to a maximum distance allowable by the device 200. Continuing to extend the actuation element 212 pulls down on the outer paddles 220 and paddle frames 224, thereby causing the inner paddles 222 to spread apart further from the coaption element 210. The outer paddles 220 and paddle frames 224 move to a position where they are close to the actuation element. In the fully extended position, the inner paddles 222 are open to an approximately 180-degree angle with the coaption element 210. The inner and outer paddles 222, 220 are stretched straight in the fully extended position to form an approximately 180-degree angle between the paddles 222, 220. The fully extended position of the device 200 provides the maximum size of the gap between the coaption element 210 and inner paddle 222, and, in some embodiments, allows clasps 230 to also open fully to approximately 180 degrees (FIG. 37) between the fixed and moveable arms 232, 234 of the clasp 230. The position of the device 200 is the longest and the narrowest configuration. Thus, the fully extended position of the device 200 may be a desirable position for bailout of the device 200 from an attempted implantation or may be a desired position for placement of the device in a delivery catheter, or the like.

Configuring the prosthetic spacer device 200 such that the anchors 208 can extend to a straight or approximately straight configuration (e.g. approximately 120-180 degrees relative to the coaption element 210) can provide several advantages. For example, this configuration can reduce the radial crimp profile of the prosthetic spacer device 200. It can also make it easier to grasp the native leaflets 20, 22 by providing a larger opening between the coaption element 210 and the inner paddles 222 in which to grasp the native leaflets 20, 22. Additionally, the relatively narrow, straight configuration can prevent or reduce the likelihood that the prosthetic spacer device 200 will become entangled in native anatomy (e.g., chordae tendineae CT shown in FIGS. 3 and 4) when positioning and/or retrieving the prosthetic spacer device 200 into the delivery apparatus 202.

Referring now to FIGS. 38-49, the implantable device 200 is shown being delivered and implanted within the native mitral valve MV of the heart H, though similar steps can be used on other valves. The methods and steps shown and/or discussed can be performed on a living animal or on a simulation, such as on a cadaver, cadaver heart, simulator (e.g. with the body parts, heart, tissue, etc. being simulated), etc.

As described above, the device 200 shown in FIGS. 38-49 includes the optional covering 240 (e.g., FIG. 25) over the coaption element 210, clasps 230, inner paddles 222 and/or the outer paddles 220. The device 200 is deployed from a delivery sheath 202, is retained by a capture mechanism 213 (See FIGS. 43-49) and is actuated by extending or retracting the actuation element, wire, or shaft 212. Fingers of the capture mechanism 213 removably attach the collar 211 to the delivery sheath 202. In some embodiments, the capture mechanism 213 is held closed around the collar 211 by the actuation element 212, such that removal of the actuation element 212 allows the fingers of the capture mechanism 213 to open and release the collar 211 to decouple the capture mechanism 213 from the device 200 after the device 200 has been successfully implanted.

Figure 38:
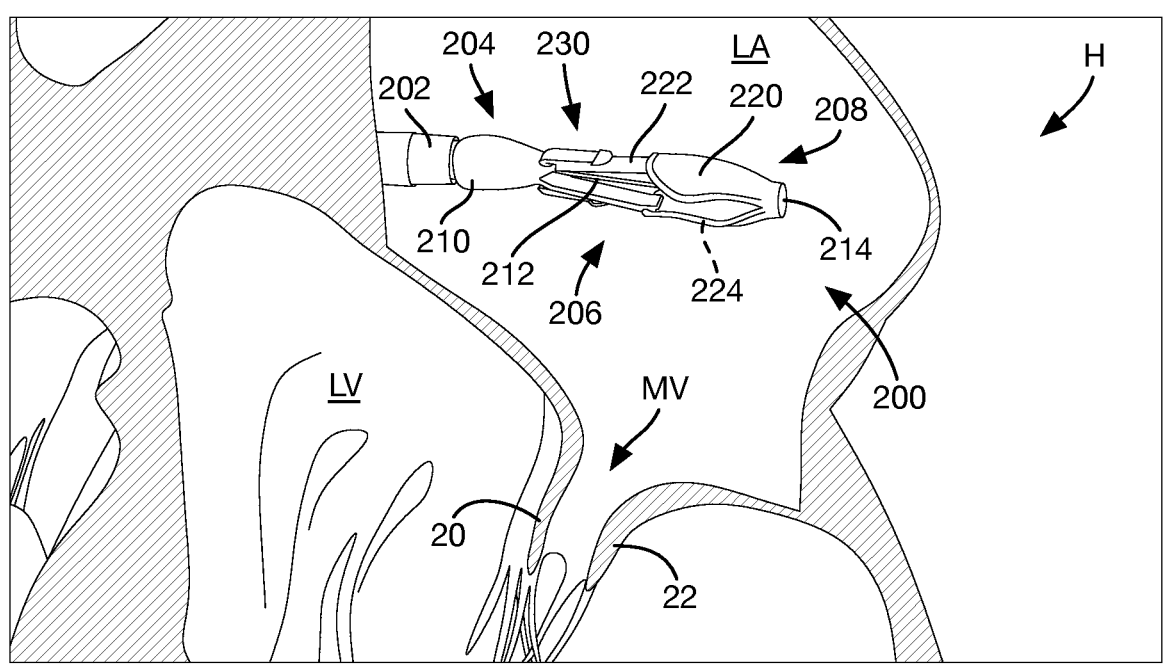
FIGS. 38-49 show the implantable prosthetic device of FIGS. 30-38, including a cover, being delivered and implanted within the native mitral valve.
Figure 39:
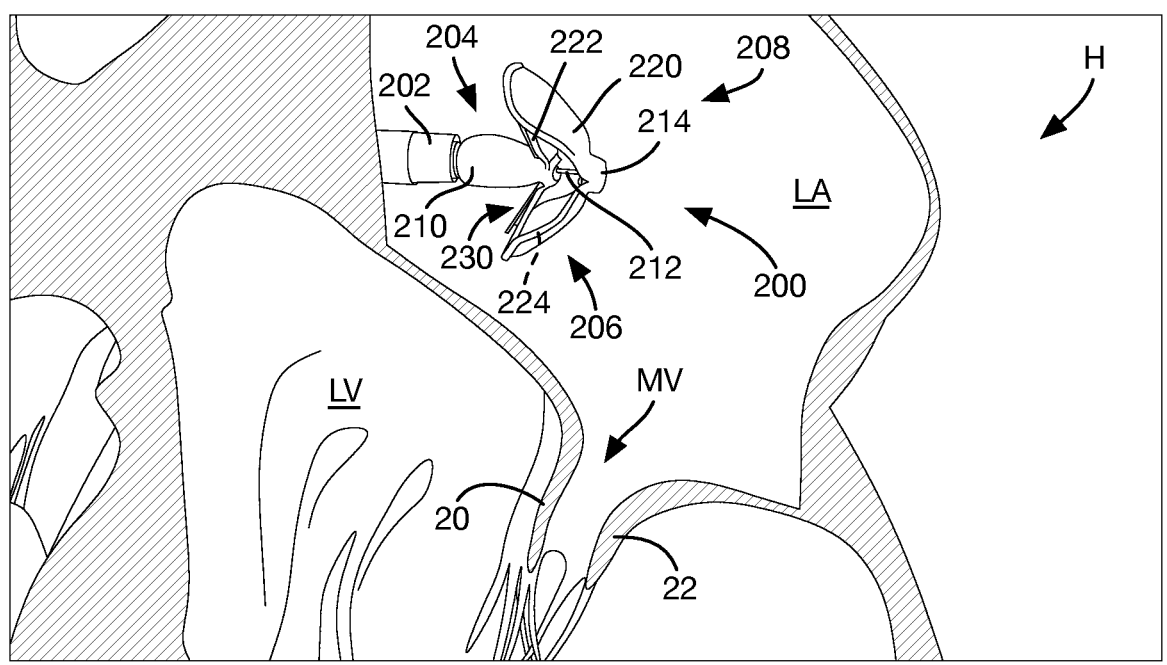
Figure 40:
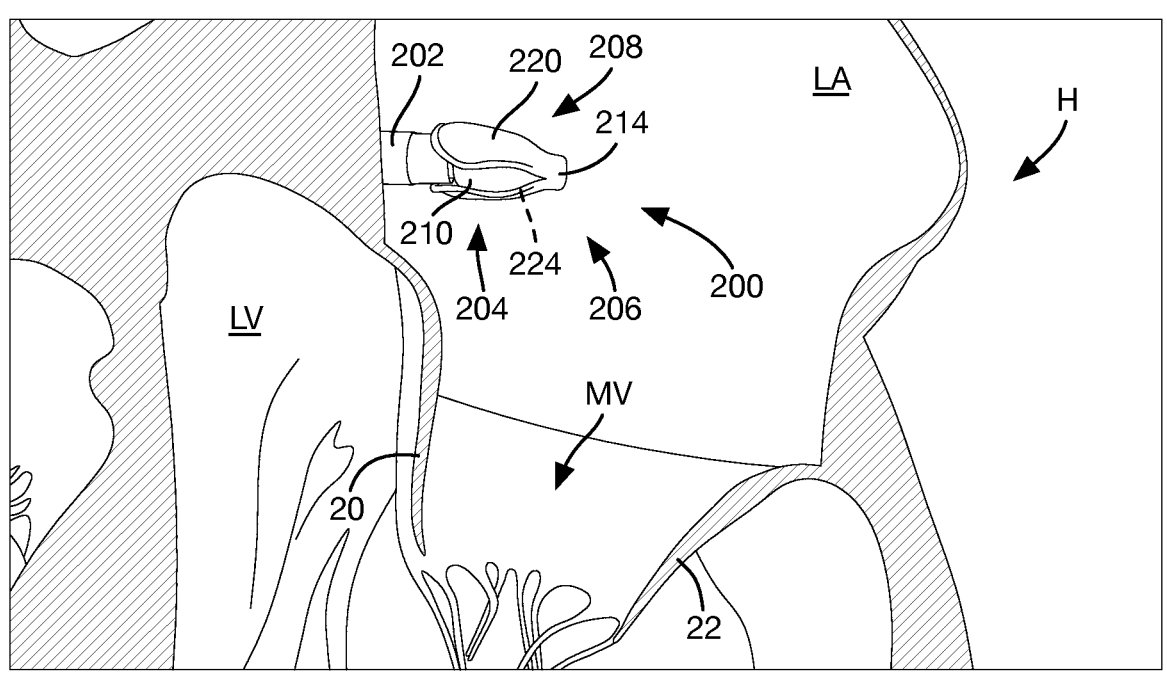
Figure 41:
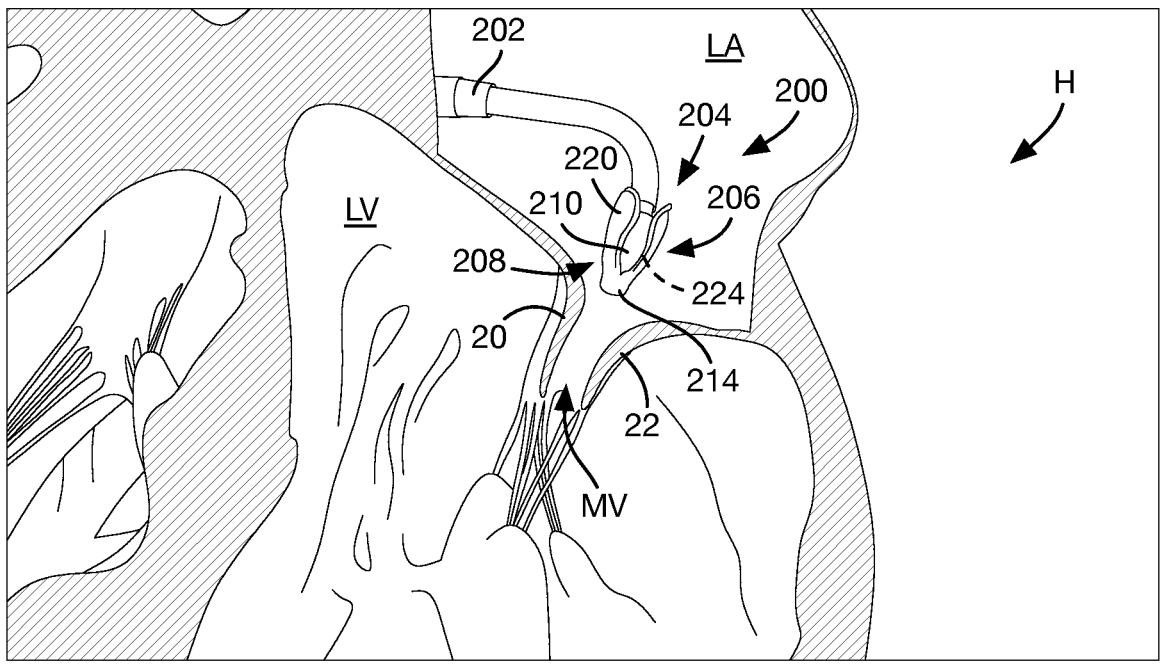
Figure 42:
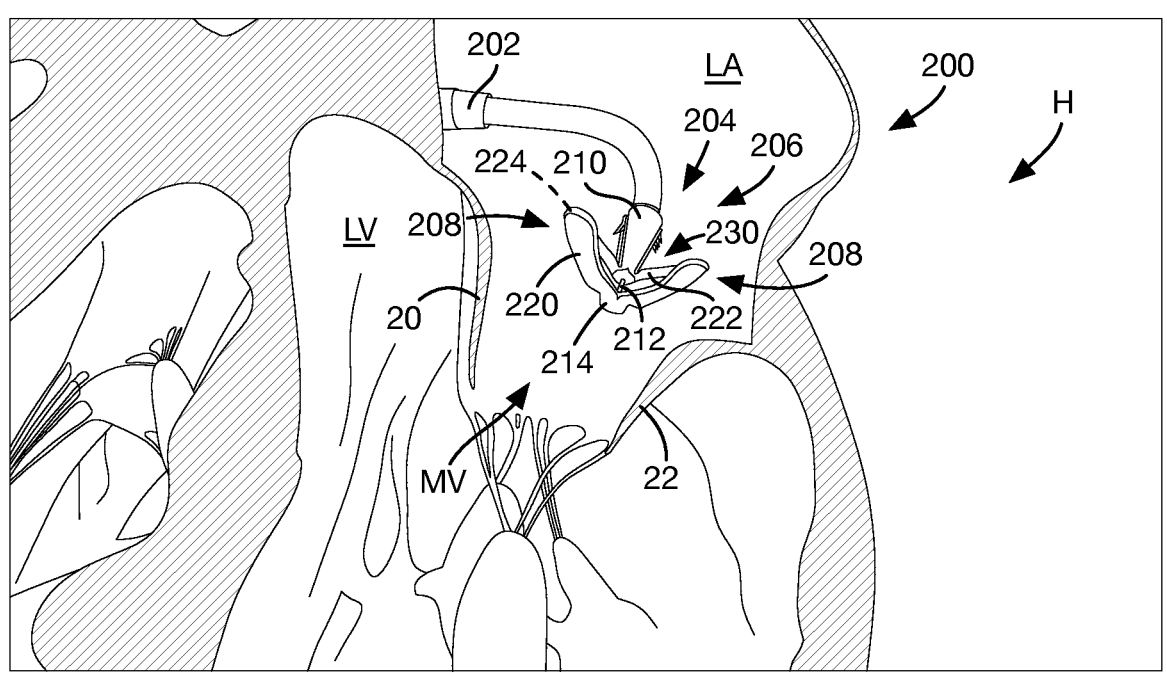
Figure 43:
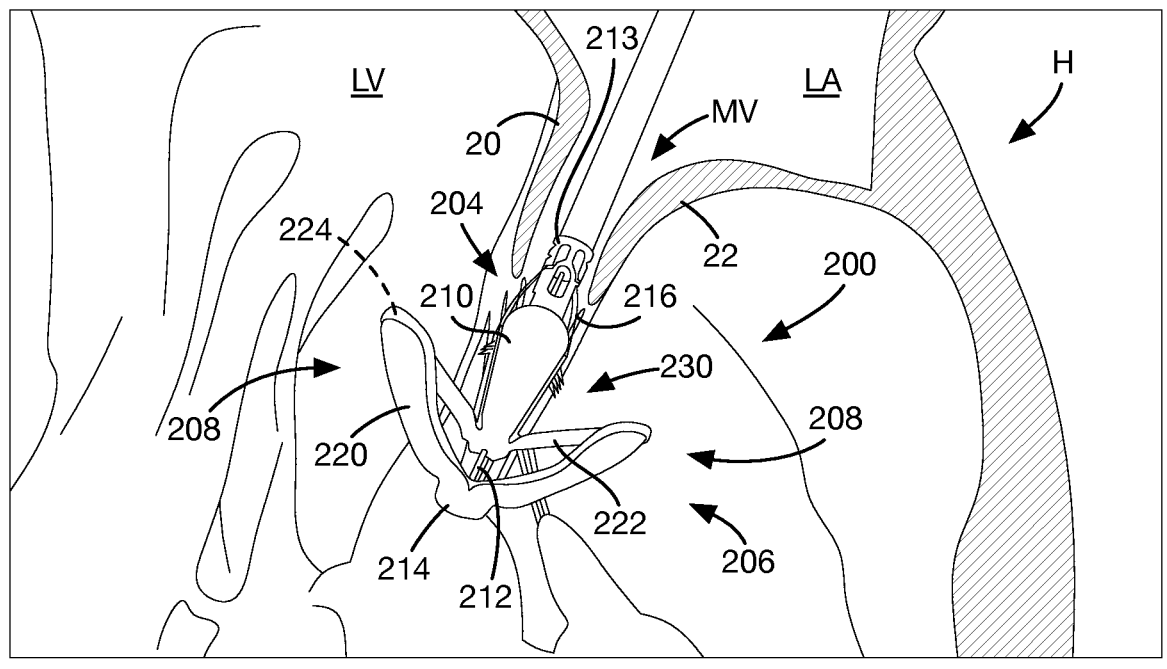
Figure 44:
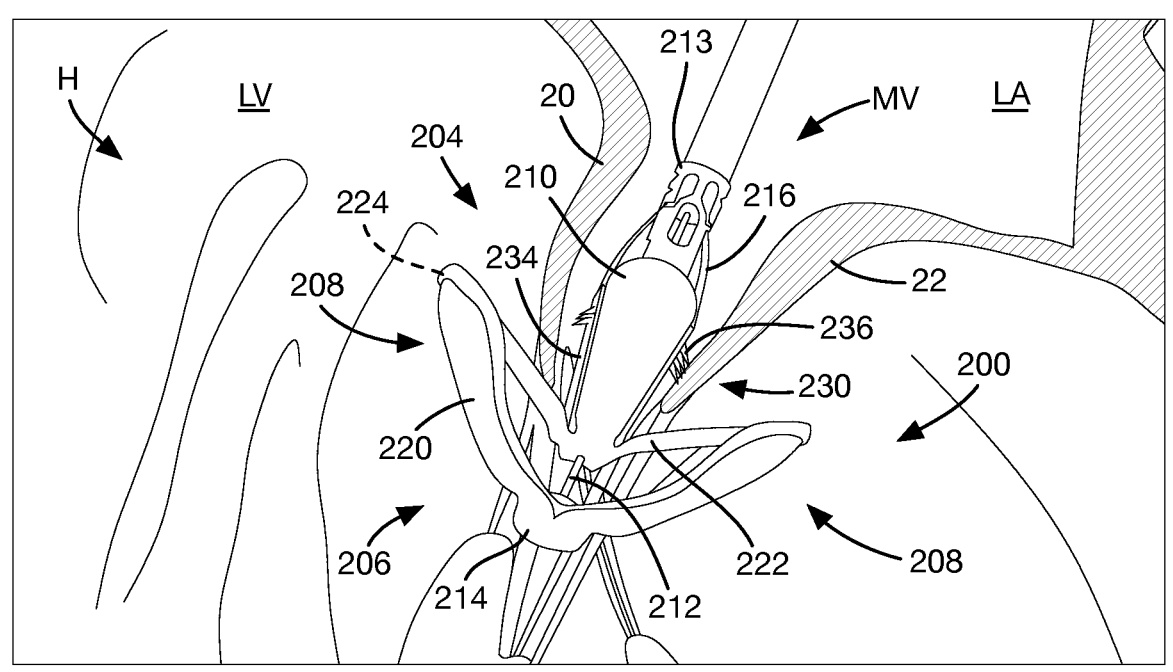
Figure 45:
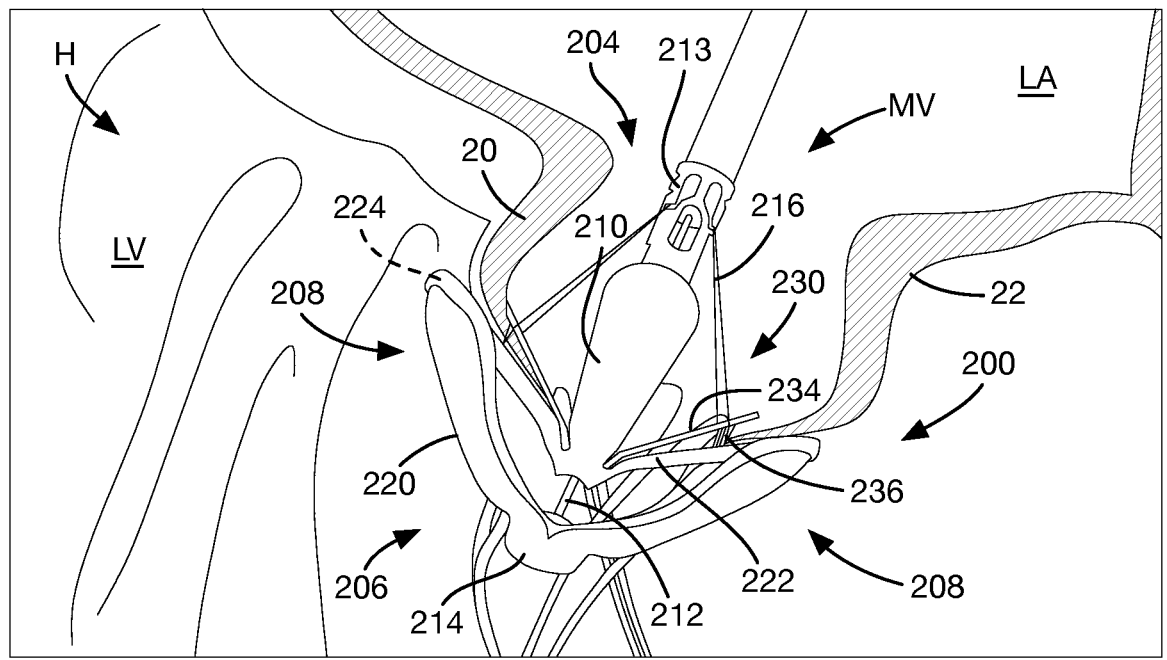
Figure 46:
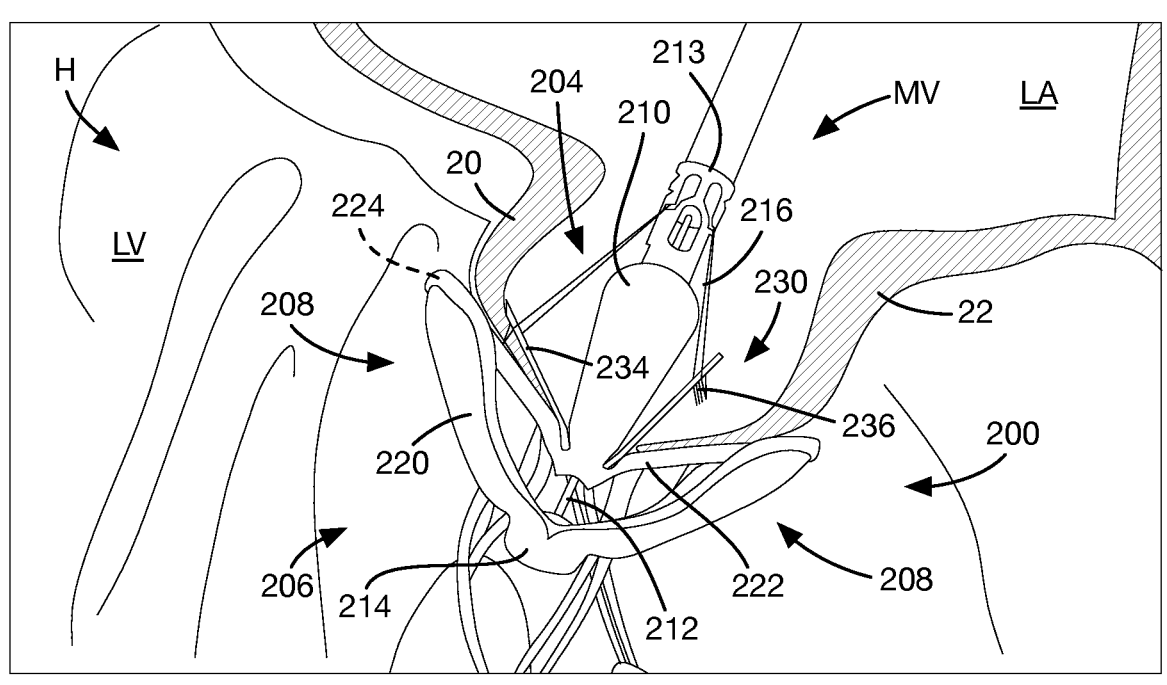
Figure 47:
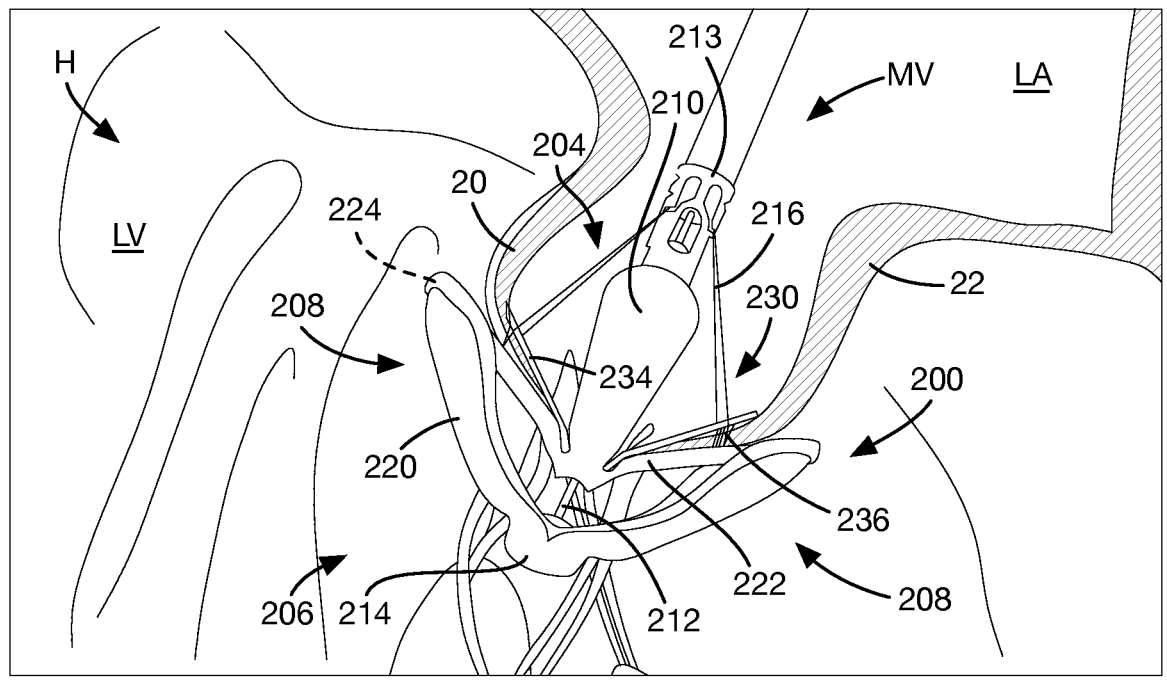
Figure 48:
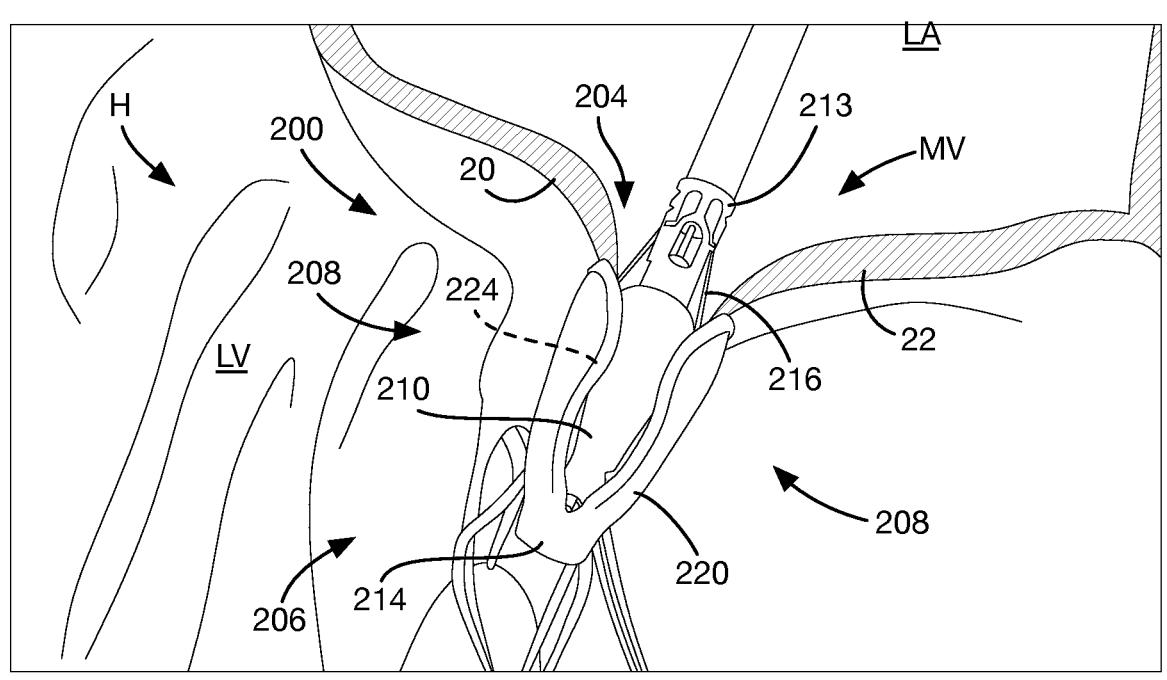
Figure 49:
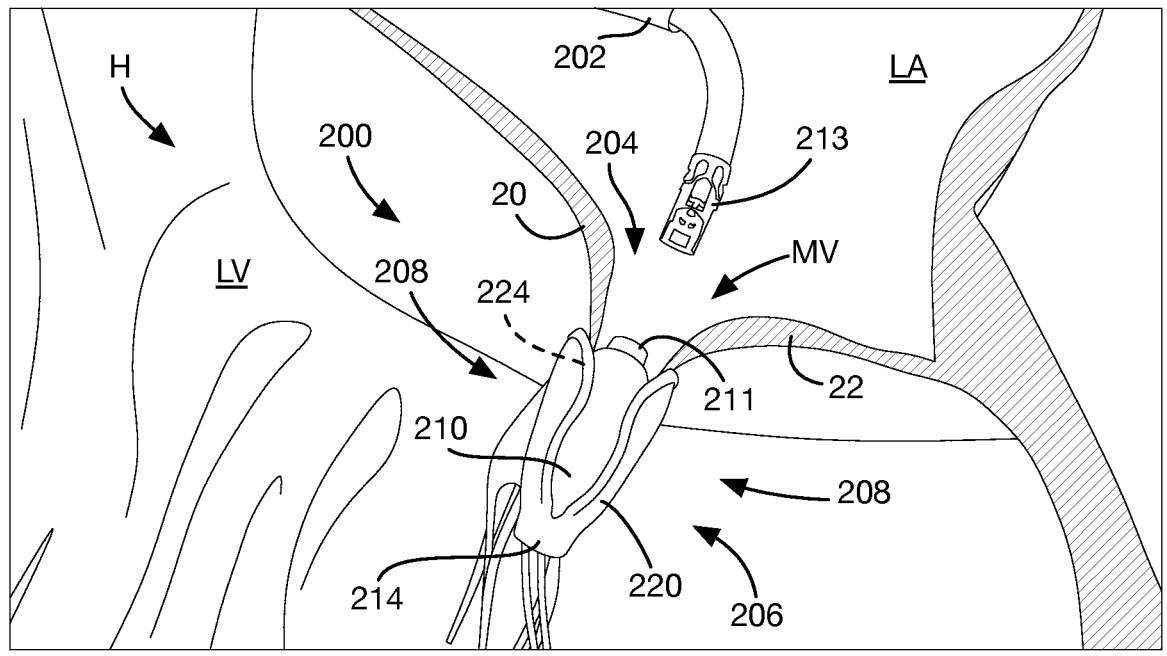

Referring now to FIG. 38, the delivery sheath 202 is inserted into the left atrium LA through the septum and the device 200 is deployed from the delivery sheath 202 in the fully open condition for the reasons discussed above with respect to the device 100. The actuation element 212 is then retracted to move the device 200 through the partially closed condition (FIG. 39) and to the fully closed condition shown in FIGS. 40-41 and then maneuvered towards the mitral valve MV as shown in FIG. 41. Referring now to FIG. 42, when the device 200 is aligned with the mitral valve MV, the actuation element 212 is extended to open the paddles 220, 222 into the partially opened position and the actuation lines 216 (FIGS. 43-48) are retracted to open the barbed clasps 230 to prepare for leaflet grasp. Next, as shown in FIGS. 43-44, the partially open device 200 is inserted through the mitral valve MV until leaflets 20, 22 are properly positioned in between the inner paddles 222 and the coaption element 210 and inside the open barbed clasps 230. FIG. 45 shows the device 200 with both clasps 230 closed, though the barbs 236 of one clasp 230 missed one leaflet 22. As can be seen in FIGS. 45-47, the out of position clasp 230 is opened and closed again to properly grasp the missed leaflet 22. When both leaflets 20, 22 are grasped properly, the actuation element 212 is retracted to move the device 200 into the fully closed position shown in FIG. 48. With the device 200 fully closed and implanted in the native mitral valve MV, the actuation element 212 is disengaged from the cap 214 and is withdrawn to release the capture mechanism 213 from the proximal collar 211 so that the capture mechanism 213 can be withdrawn into the delivery sheath 202, as shown in FIG. 49. Once deployed, the device 200 can be maintained in the fully closed position with a mechanical means such as a latch or can be biased to remain closed through the use of spring material, such as steel, and/or shape-memory alloys such as Nitinol. For example, the paddles 220, 222 can be formed of steel or Nitinol shape-memory alloy—produced in a wire, sheet, tubing, or laser sintered powder—and are biased to hold the outer paddles 220 closed around the inner paddles 222, coaption element 210, and the barbed clasps 230 pinched around native leaflets 20, 22.

Referring to FIGS. 50-54, once the device 200 is implanted in the native mitral valve MV, the coaption element 210 functions as a gap filler in the valve regurgitant orifice, such as the gap 26 in the mitral valve MV illustrated by FIG. 6. When the device 200 has been deployed between the two opposing valve leaflets 20, 22, the leaflets 20, 22 no longer coapt against each other in the area of the coaption element 210, but instead coapt against the coaption element 210. This reduces the distance the leaflets 20, 22 need to be approximated to close the mitral valve MV during systole, thereby facilitating repair of functional valve disease that may be causing mitral regurgitation. A reduction in leaflet approximation distance can result in several other advantages as well. For example, the reduced approximation distance required of the leaflets 20, 22 reduces or minimizes the stress experienced by the native valve. Shorter approximation distance of the valve leaflets 20, 22 can also require less approximation forces which can result in less tension experienced by the leaflets 20, 22 and less diameter reduction of the valve annulus. The smaller reduction of the valve annulus—or none at all—can result in less reduction in valve orifice area as compared to a device without a spacer. In this way, the coaption element 210 can reduce the transvalvular gradients.

To adequately fill the gap 26 between the leaflets 20, 22, the device 200 and the components thereof can have a wide variety of different shapes and sizes. For example, the outer paddles 220 and paddle frames 224 can be configured to conform to the shape or geometry of the coaption element 210 as is shown in FIGS. 50-54. As a result, the outer paddles 220 and paddle frames 224 can mate with both the coaption element 210 and the native valve leaflets 20, 22. That is, when the leaflets 20, 22 are coapted against the coaption element 210, the leaflets 20, 22 fully surround or "hug" the coaption element 210 in its entirety, thus small leaks at lateral and medial aspects 201, 203 of the coaption element 210 can be prevented or inhibited. The interaction of the leaflets 20, 22 and the device 200 is made clear in FIG. 51, which shows a schematic atrial or surgeon's view that shows the paddle frame 224 (which would not actually be visible from a true atrial view, e.g., FIG. 52), conforming to the coaption element 210 geometry. The opposing leaflets 20, 22 (the ends of which would also not be visible in the true atrial view, e.g., FIG. 52) being approximated by the paddle frames 224, to fully surround or "hug" the coaption element 210.

This coaption of the leaflets 20, 22 against the lateral and medial aspects 201, 203 of the coaption element 210 (shown from the atrial side in FIG. 52, and the ventricular side in FIG. 53) would seem to contradict the statement above that the presence of a coaption element 210 minimizes the distance the leaflets need to be approximated. However, the distance the leaflets 20, 22 need to be approximated is still minimized if the coaption element 210 is placed precisely at a regurgitant gap 26 and the regurgitant gap 26 is less than the width (medial-lateral) of the coaption element 210.

Figure 50:
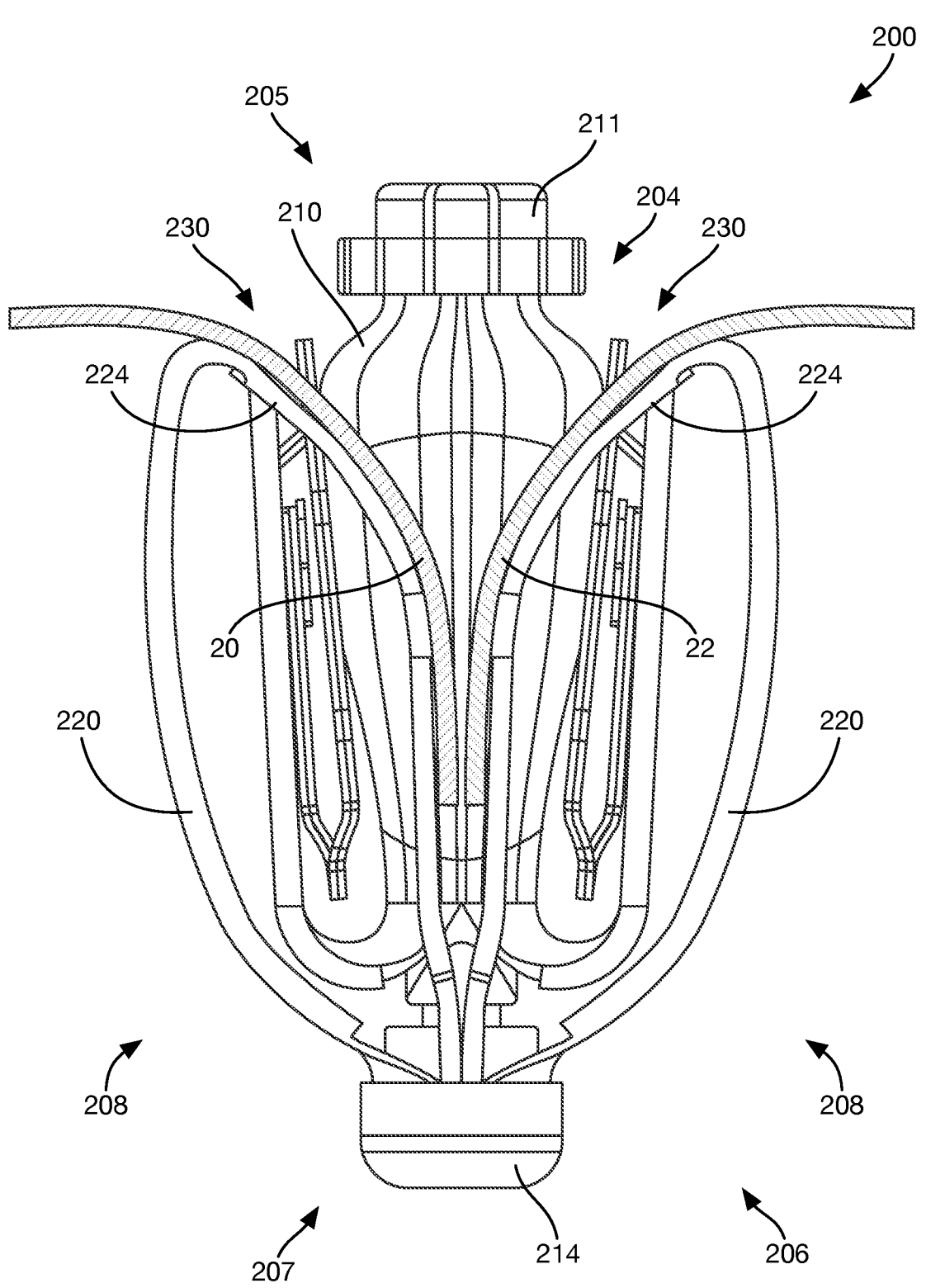
FIG. 50 is a schematic view illustrating a path of native valve leaflets along each side of a coaption element of valve repair device.

FIG. 50 illustrates the geometry of the coaption element 210 and the paddle frame 224 from an LVOT perspective. As can be seen in this view, the coaption element 210 has a tapered shape being smaller in dimension in the area closer to where the inside surfaces of the leaflets 20, 22 are required to coapt and increase in dimension as the coaption element 210 extends toward the atrium. Thus, the depicted native valve geometry is accommodated by a tapered coaption element geometry. Still referring to FIG. 50, the tapered coaption element geometry, in conjunction with the illustrated expanding paddle frame 224 shape (toward the valve annulus) can help to achieve coaption on the lower end of the leaflets, reduce stress, and minimize transvalvular gradients.

Figure 24:
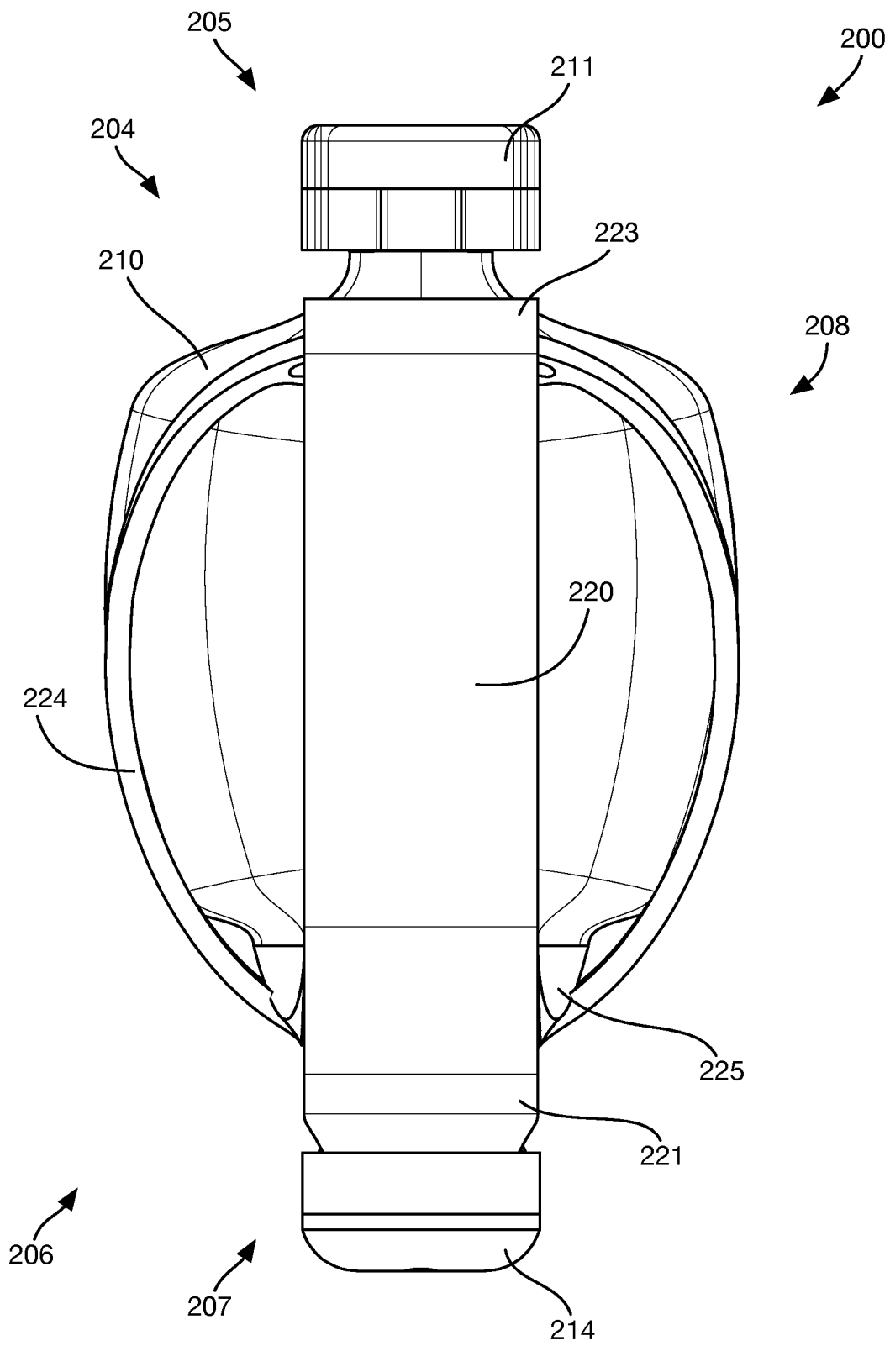
FIG. 24 shows a side view of the implantable prosthetic device of FIG. 22.
Figure 54:
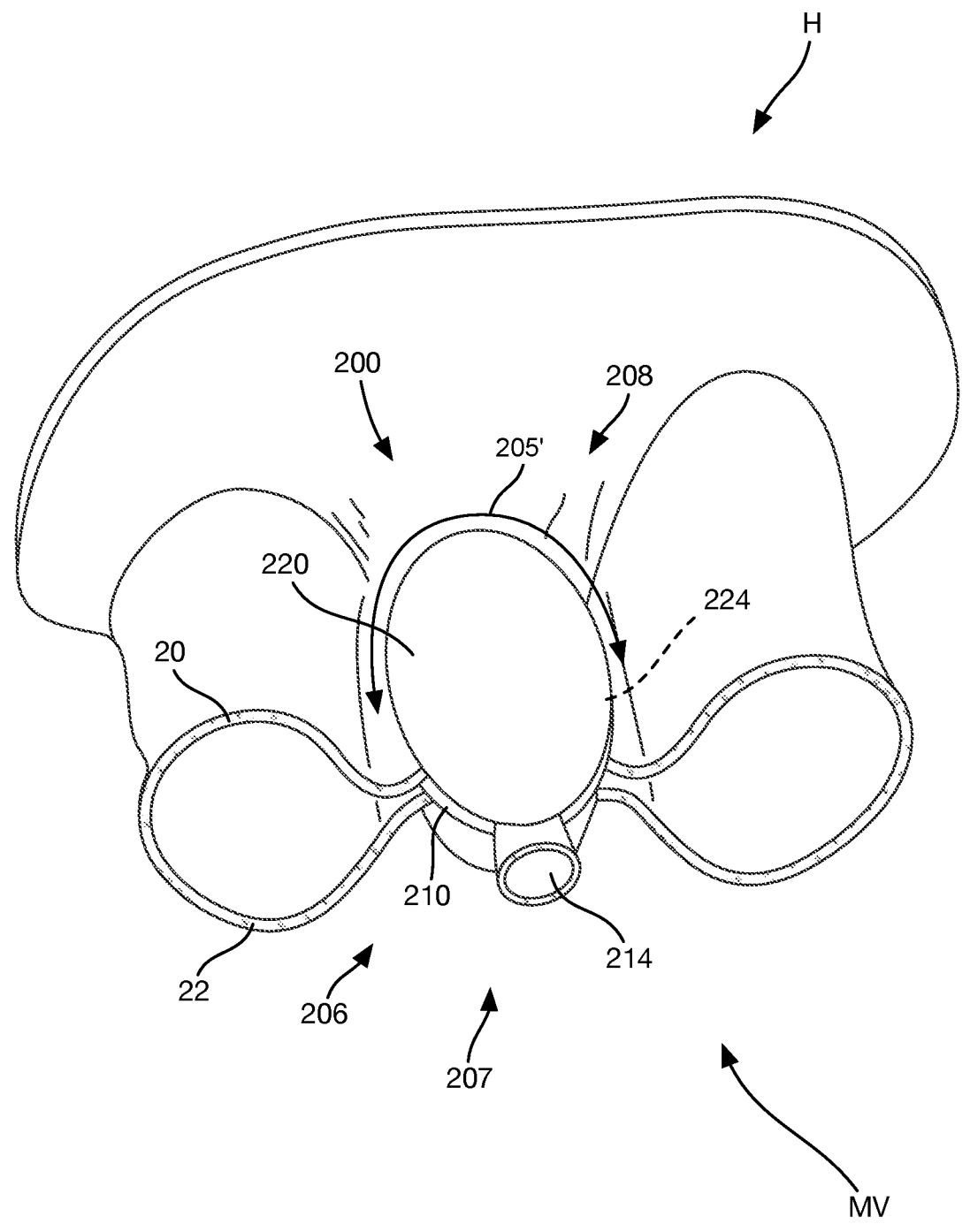
FIG. 54 is a perspective view of a valve repair device attached to mitral valve leaflets with the coaption element in the gap of the mitral valve shown from a ventricular side of the mitral valve.

Referring to FIG. 54, the shape of the coaption element 210 and the paddle frames 224 can be defined based on an Intra-Commissural view of the native valve and the device 200. Two factors of these shapes are leaflet coaption against the coaption element 210 and reduction of stress on the leaflets due to the coaption. Referring to FIGS. 54 and 24, to both coapt the valve leaflets 20, 22 against the coaption element 210 and reduce the stress applied to the valve leaflets 20, 22 by the coaption element 210 and/or the paddle frames 224, the coaption element 210 can have a round or rounded shape and the paddle frames 224 can have a full radius that spans nearly the entirety of the paddle frame 224. The round shape of the coaption element 210 and/or the illustrated fully rounded shape of the paddle frames 224 distributes the stresses on the leaflets 20, 22 across a large, curved engagement area 205'. For example, in FIG. 54, the force on the leaflets 20, 22 by the paddle frames is spread along the entire rounded length of the paddle frame 224, as the leaflets 20 try to open during the diastole cycle.

Figure 55:
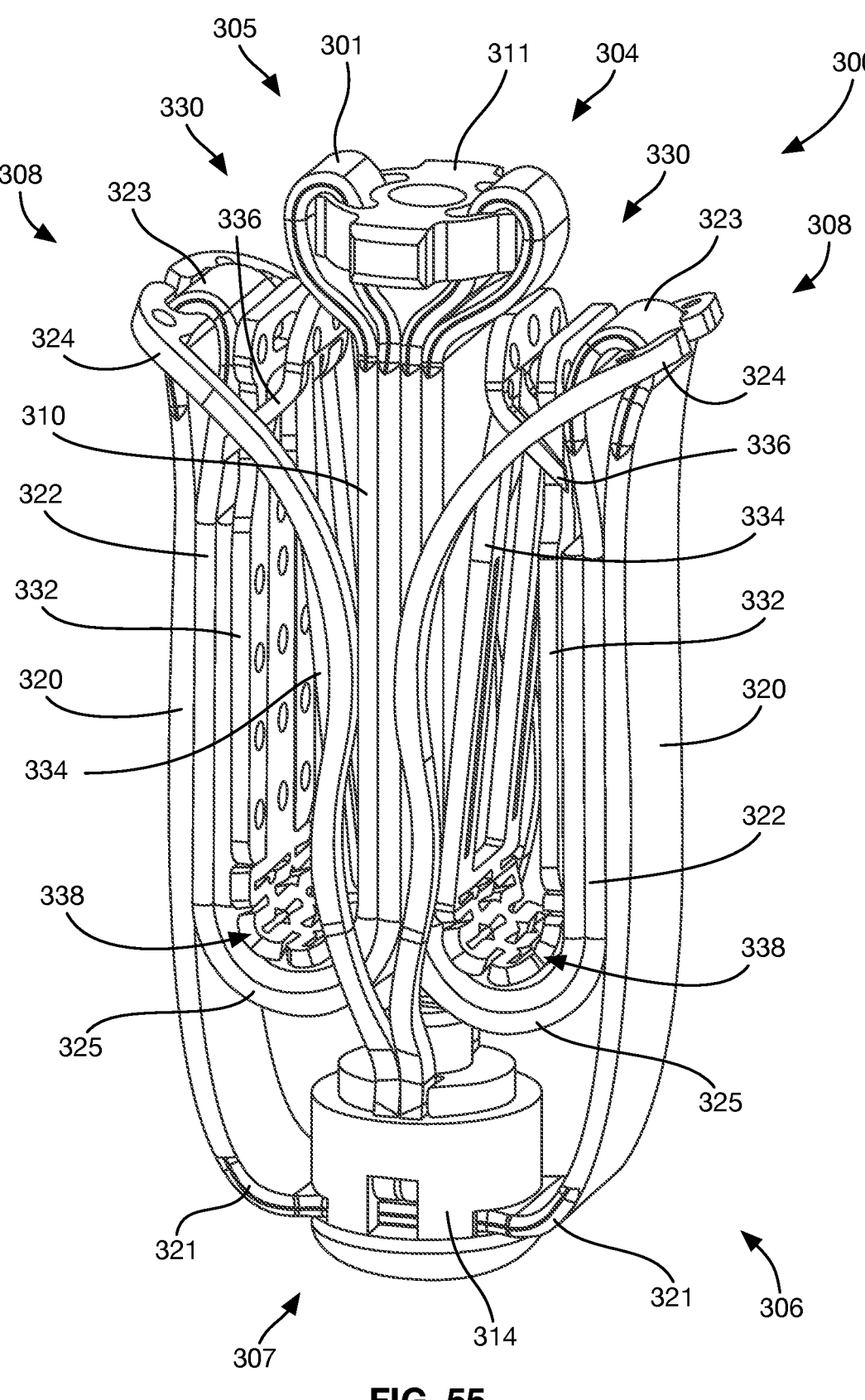
FIG. 55 shows a perspective view of an example implantable prosthetic device in a closed position.

Referring now to FIG. 55, an example embodiment of an implantable prosthetic spacer device 300 is shown. The implantable device 300 is one of the many different configurations that the device 100 that is schematically illustrated in FIGS. 8-14 can take. The device 300 can include any other features for an implantable prosthetic device discussed in the present application, and the device 300 can be positioned to engage valve tissue 20, 22 as part of any suitable valve repair system (e.g., any valve repair system disclosed in the present application).

The implantable prosthetic spacer device 300 includes a coaption portion 304, a proximal or attachment portion 305, an anchor portion 306, and a distal portion 307. The coaption portion 304 of the device includes a coaption element 310 for implantation between the leaflets 20, 22 of the native valve. The anchor portion 306 includes a plurality of anchors 308, each anchor 308 including outer paddles 320, inner paddles 322, paddle extension members or paddle frames 324, and clasps 330. The attachment portion 305 includes a first or proximal collar 311 for engaging with a capture mechanism (e.g., a capture mechanism such as the capture mechanism 213 shown in FIGS. 43-49) of a delivery sheath or system (e.g., a delivery sheath or system such as the delivery sheath or system 202 shown in FIGS. 38-42 and 49).

The anchors 308 are attached to the coaption member 310 by connection portions 325 and to the cap 314 by connection portions 321. The anchors 308 can comprise first portions or outer paddles 320 and second portions or inner paddles 322 separated by connection portions 323. The connection portions 323 can be attached to paddle frames 324 that are hingeably attached to the cap 314. In this manner, the anchors 308 are configured similar to legs in that the inner paddles 322 are like upper portions of the legs, the outer paddles 320 are like lower portions of the legs, and the connection portions 323 are like knee portions of the legs.

The coaption member 310 and the anchors 308 can be coupled together in various ways. For example, as shown in the illustrated embodiment, the coaption member 310 and the anchors 308 can be coupled together by integrally forming the coaption member 310 and the anchors 308 as a single, unitary component. This can be accomplished, for example, by forming the coaption member 310 and the anchors 308 from a continuous strip 301 of a braided or woven material, such as braided or woven nitinol wire. In some embodiments, such as in the illustrated example, the coaption member 310, the outer paddle portions 320, the inner paddle portions 322, and the connection portions 321, 323, 325 are formed from the continuous strip of material 301.

Like the anchors 208 of the implantable prosthetic device 200 described above, the anchors 308 can be configured to move between various configurations by axially moving the cap 314 relative to the proximal collar 311 and thus the anchors 308 relative to the coaption member 310 along a longitudinal axis extending between the cap 314 and the proximal collar 311. For example, the anchors 308 can be positioned in a fully extended or straight configuration (e.g., similar to the configuration of device 200 shown in FIG. 36) by moving the cap 314 away from the coaption member 310. In the straight configuration, the paddle portions 320, 322 are aligned or straight in the direction of the longitudinal axis of the device and the connection portions 323 of the anchors 308 are adjacent the longitudinal axis of the coaption member 310 (e.g., similar to the configuration of device 200 shown in FIG. 36). From the straight configuration, the anchors 308 can be moved to a fully folded configuration (e.g., FIG. 55) by moving the toward the coaption member 310. Initially, as the cap 314 moves toward the coaption member 310, the anchors 308 bend at connection portions 321, 323, 325, and the connection portions 323 move radially outwardly relative to the longitudinal axis of the device 300 and axially toward the coaption member 310 (e.g., similar to the configuration of device 200 shown in FIG. 34). As the cap 314 continues to move toward the coaption member 310, the connection portions 323 move radially inwardly relative to the longitudinal axis of the device 300 and axially toward the proximal end of the coaption member 310 (e.g., similar to the configuration of device 200 shown in FIG. 30).

Figure 56:
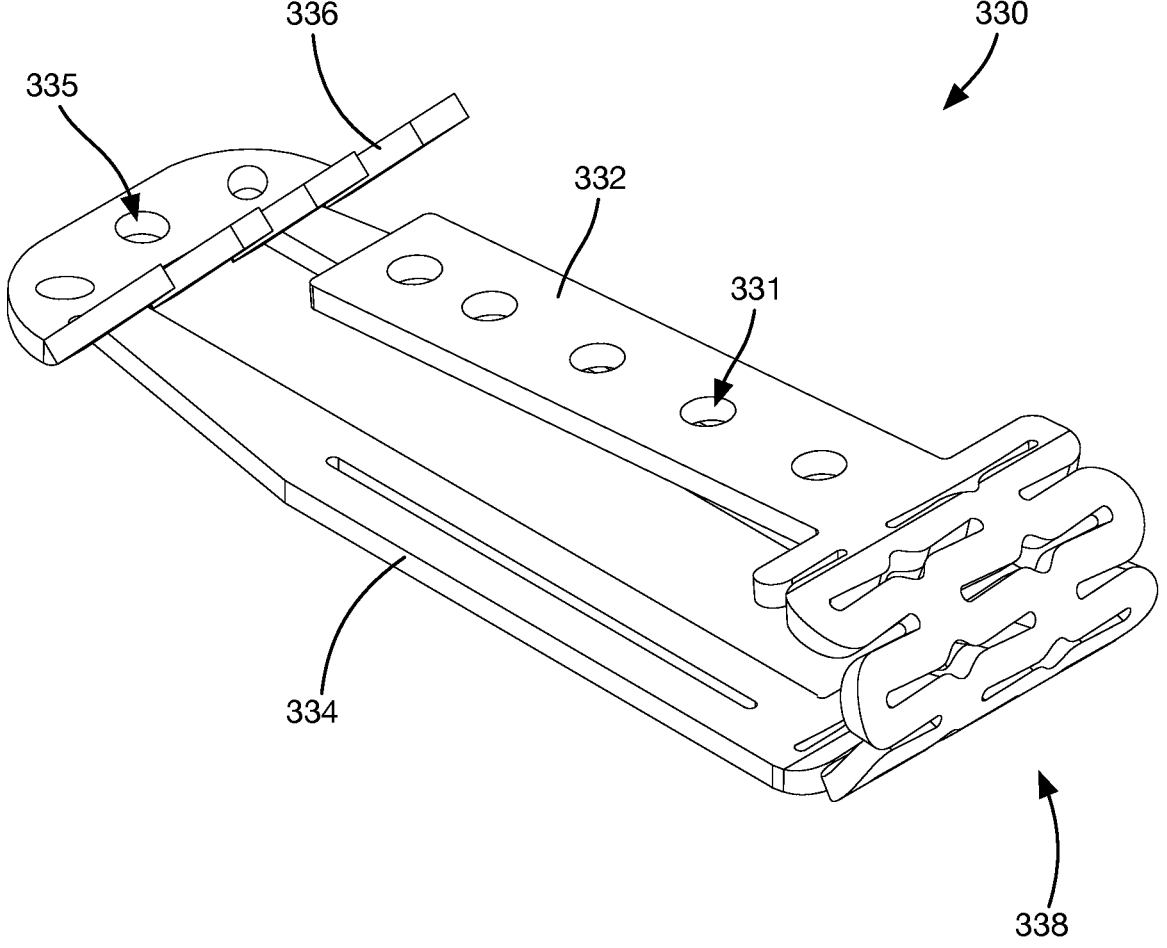
FIG. 56 shows a perspective view of an example barbed clasp of an example implantable prosthetic device in a closed position.

The barbed clasps 330 (shown in detail in FIG. 56) include a base or fixed arm 332, a moveable arm 334, barbs 336, and a joint portion 338. The fixed arms 332 are attached to the inner paddles 322, with the joint portion 338 disposed proximate the coaption element 310. The joint portion 338 is spring-loaded so that the fixed and moveable arms 332, 334 are biased toward each other when the barbed clasp 330 is in a closed condition.

The fixed arms 332 are attached to the inner paddles 322 through holes or slots 331 with sutures (not shown). The fixed arms 332 can be attached to the inner paddles 322 with any suitable means, such as screws or other fasteners, crimped sleeves, mechanical latches or snaps, welding, adhesive, or the like. The fixed arms 332 remain substantially stationary relative to the inner paddles 322 when the moveable arms 334 are opened to open the barbed clasps 330 and expose the barbs 336. The barbed clasps 330 are opened by applying tension to actuation lines (e.g., the actuation lines 216 shown in FIGS. 43-48) attached to holes 335 in the moveable arms 334, thereby causing the moveable arms 334 to move, pivot, flex, etc. on the joint portions 338.

In short, the implantable prosthetic device 300 is similar in configuration and operation to the implantable prosthetic device 200 described above, except that the coaption element 310, outer paddles 320, inner paddles 322, and connection portions 321, 323, 325 are formed from the single strip of material 301. The strip of material 301 is attached to the proximal collar 311, cap 314, and paddle frames 324 by being woven or inserted through openings in the proximal collar 311, cap 314, and paddle frames 324 that are configured to receive the continuous strip of material 301. The continuous strip 301 can be a single layer of material or can include two or more layers. In certain embodiments, portions of the device 300 have a single layer of the strip of material 301 and other portions are formed from multiple overlapping or overlying layers of the strip of material 301. For example, FIG. 55 shows the coaption member 310 and inner paddles 322 formed from multiple overlapping layers of the strip of material 301. The single continuous strip of material 301 can start and end in various locations of the device 300. The ends of the strip of material 301 can be in the same location or different locations of the device 300. For example, in the illustrated embodiment of FIG. 55, the strip of material 301 begins and ends in the location of the inner paddles 322.

As with the implantable prosthetic device 200 described above, the size of the coaption element 310 can be selected to minimize the number of implants that a single patient will require (preferably one), while at the same time maintaining low transvalvular gradients. In particular, forming many components of the device 300 from the strip of material 301 allows the device 300 to be made smaller than the device 200. For example, in one example embodiment, the anterior-posterior distance at the top of the coaption element 310 is less than 2 mm, and the medial-lateral distance of the device 300 (i.e., the width of the paddle frames 324 which are wider than the coaption element 310) at its widest is about 5 mm.

Referring now to FIGS. 57-64, an implantable device 400 is shown. The implantable device 400 has paddles 402 that open and close to grasp leaflets 20, 22 against barbed clasps or gripping devices 404. The paddles 402 move to create an opening 406 between the paddles 402 and gripping devices 404 in which the leaflets 20, 22 can be grasped. The device 400 can be configured to close a gap 26 (FIG. 6) in the native heart valve MV, TV. In addition, the implantable device 400 can include any other features for a device discussed in the present application, and the device 400 can be positioned to engage valve leaflets 20, 22 as part of any suitable valve repair system (e.g., any valve repair system disclosed in the present application). The device 400 can include any other features for an implantable prosthetic device discussed in the present application, and the device 400 can be positioned to engage valve tissue 20, 22 as part of any suitable valve repair system (e.g., any valve repair system disclosed in the present application).

Figure 57:
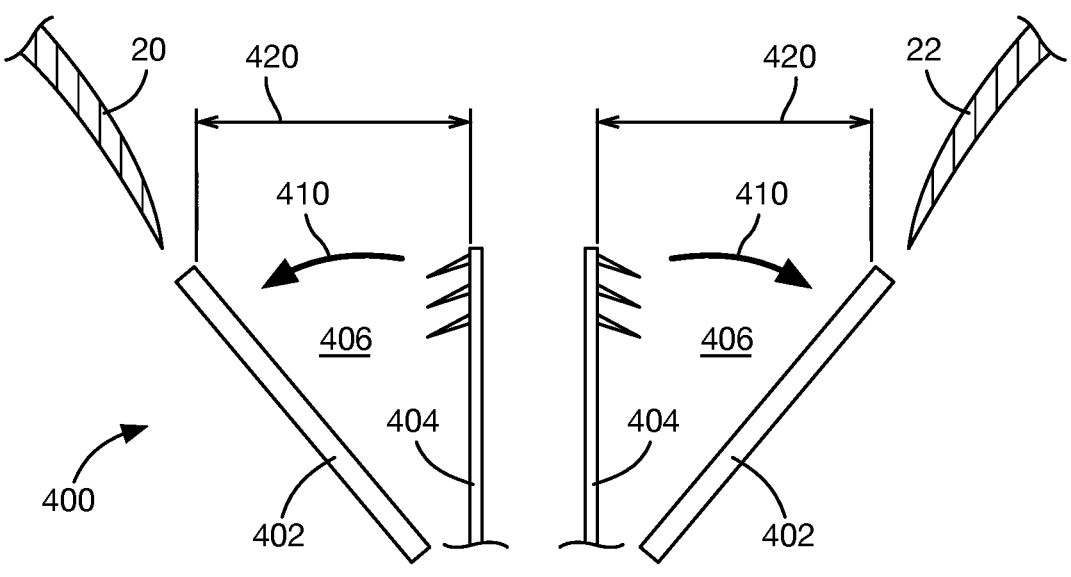
FIGS. 57-64 illustrate the movement of the paddles of an example implantable prosthetic device.

Referring to FIG. 57, the paddles 402 of the device 400 are moved, flexed, rotated, or pivoted outward in the rotational or pivot direction 410 to create the opening 406 between the paddles 402 and the gripping members 404 having a first width 420. The first width 420 can be, for example, between about 5 mm and about 15 mm, such as between 7.5 mm and about 12.5 mm, such as about 10 mm. In some embodiments, the first width 420 can be less than 5 mm or greater than 15 mm.

Figure 58:
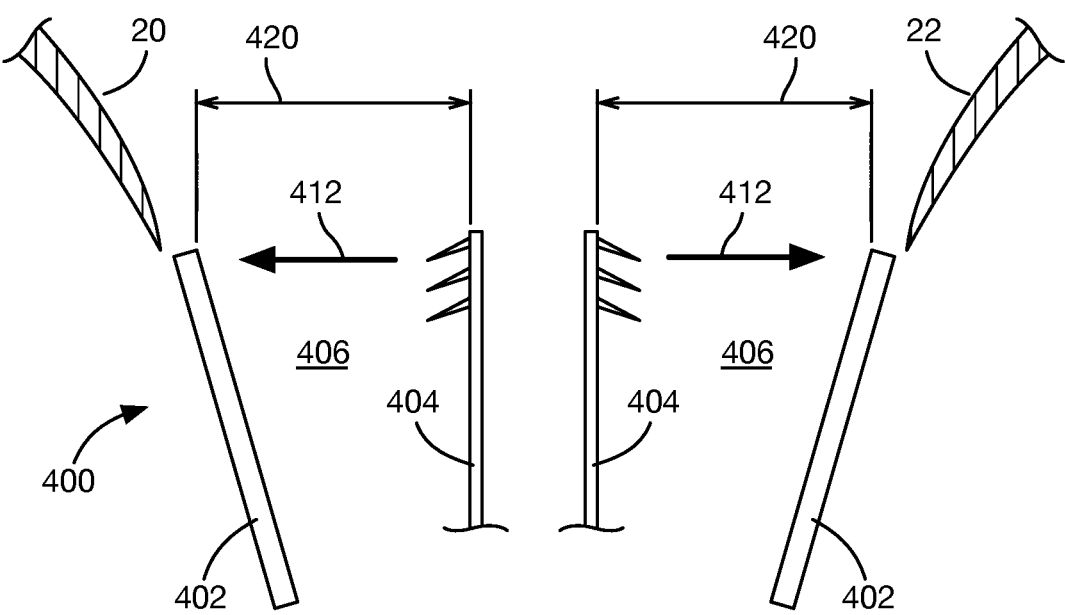

Referring to FIG. 58, the paddles 402 of the device 400 are moved outward in the translation direction 412 so that the opening 406 reaches the first width 420, instead of being rotated as shown in FIG. 57. As with the rotated paddles 402 described above, the first width 420 can be, for example, between about 5 mm and about 15 mm, such as between 7.5 mm and about 12.5 mm, such as about 10 mm. In some embodiments, the first width 420 can be less than 5 mm or greater than 15 mm. In this example, the translated paddles can then be moved, flexed, rotated, or pivoted outward to a width that is wider than the width 420.

Figure 59:
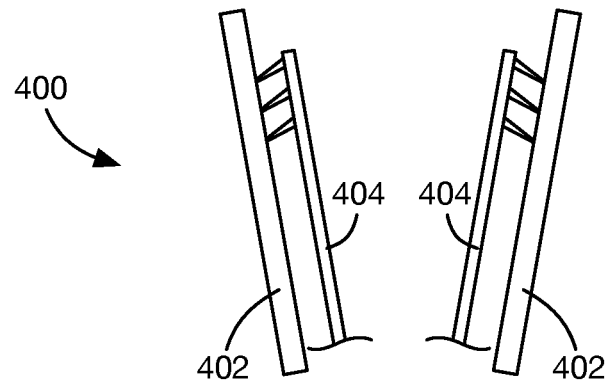
Figure 60:
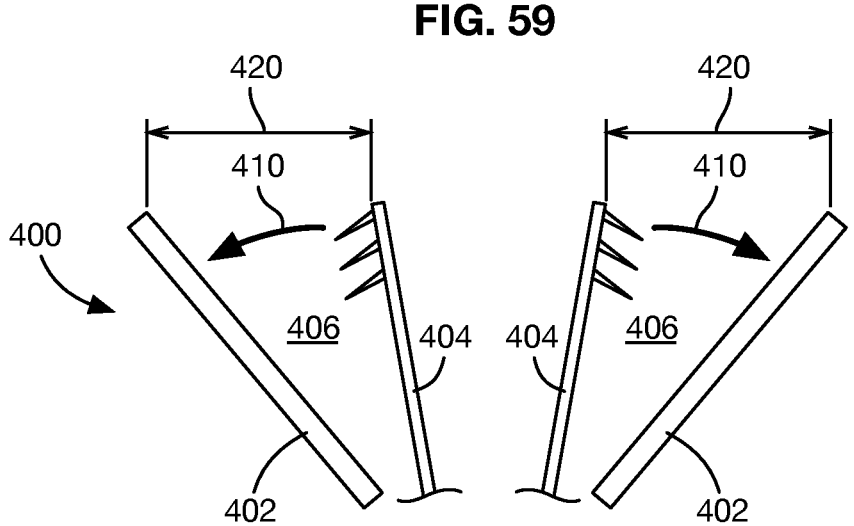
Figure 61:
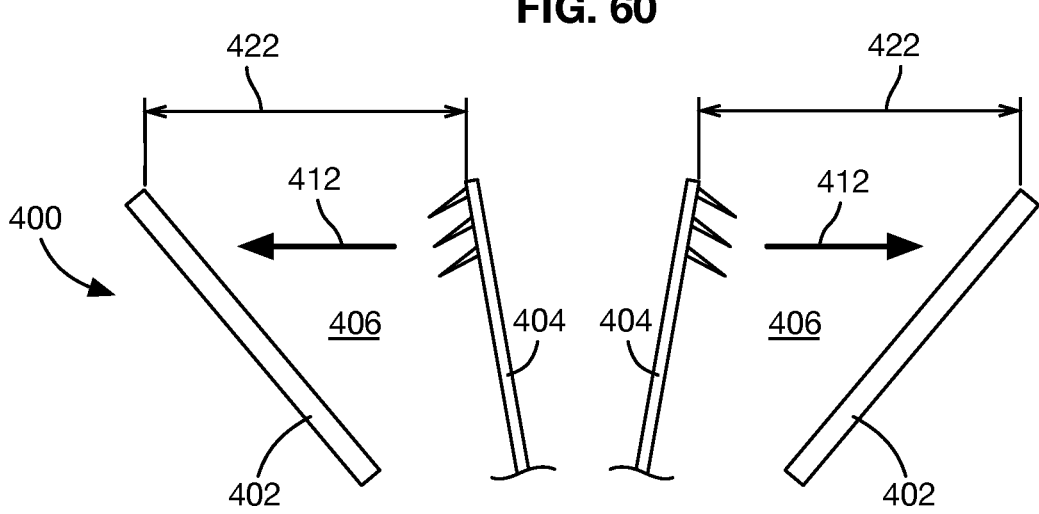

Referring to FIGS. 59-61, in one example embodiment the device 400 can be configured such that the paddles 402 are moved, flexed, rotated, or pivoted outward in the rotational or pivot direction 410 and then moved outward in the translation direction 412 to create the opening 406 having a second width 422 between the paddles 402 and the gripping members 404. The second width 422 can be, for example, between about 10 mm and about 25 mm, such as between about 10 mm and about 20 mm, such as between about 12.5 mm and about 17.5 mm, such as about 15 mm. In some embodiments, the second width 422 can be less than 10 mm or more than 25 mm. In certain embodiments, the ratio between the second width 422 and the first width 420 can be about 5 to 1 or less, such as about 4 to 1 or less such as about 3 to 1 or less, such as about 2 to 1 or less, such as about 1.5 to 1 or less, such as about 1.25 to 1 or less, such as about 1 to 1. Optionally, the device 400 can be configured such that the paddles are moved outward in the translation direction 412 and then rotated or pivoted outward in the rotational or pivot direction 410 to create the opening 406 with the second width 420 between the paddles 402 and gripping members 404. In addition, the device 400 can be configured such that the paddles 402 are moved, flexed, rotated, or pivoted outward in the rotational or pivot direction 410 and moved outward in the translation direction 412 simultaneously to create the second width 422 between the paddles 402 and the gripping members 404.

FIGS. 59-61 illustrate an implantable device 400 in which the paddles 402 are moved, flexed, rotated, or pivoted outward in the rotational or pivot direction 410, and, subsequently, moved outward in the translation direction 412 to create a wider opening 406. FIG. 59 illustrates the implantable device 400 in a closed position, such that the paddles 402 are engaging the gripping members 404. Referring to FIG. 60, the paddles 402 are moved, flexed, rotated, or pivoted outward in the rotational or pivot direction 410 to create an opening 406 having a first width 420 for receiving valve tissue. Referring to FIG. 61, after the paddles 402 are moved, flexed, rotated, or pivoted outward in the rotational or pivot direction 410, the paddles 402 are moved outward in the translation direction 412 such that the opening 406 has a second width 422. After valve tissue is received in the openings 406 between the paddles 402 and the gripping members 404, the valve repair device is moved back to the closed position (as shown in FIG. 59) to secure the valve repair device 400 to the valve tissue. The implantable device 400 can include any other features for an implantable device discussed in the present application, and the implantable device 400 can be positioned to engage valve tissue 20, 22 as part of any suitable valve repair system (e.g., any valve repair system disclosed in the present application).

Figures 62, 63, 64:
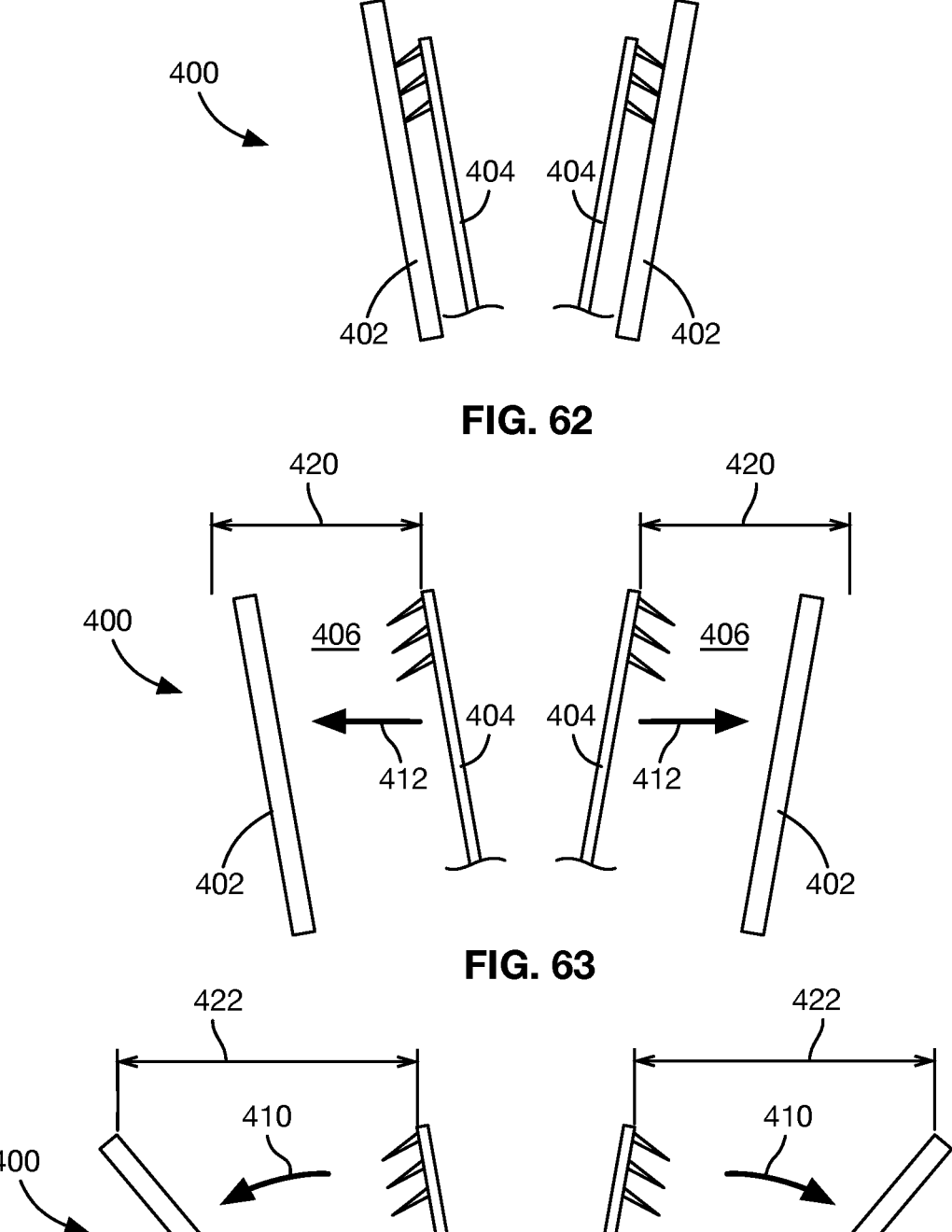

FIGS. 62-64 illustrate an implantable device 400 in which the paddles 402 are moved outward in the translation direction 412, and, subsequently, moved, flexed, rotated, or pivoted outward in the rotational or pivot direction 410 to create a wider opening 406. FIG. 62 illustrates the implantable device 400 in a closed position, such that the paddles 402 are engaging the gripping members 404. Referring to FIG. 63, the paddles 402 are moved outward in the translation direction 412 to create an opening 406 having a first width 420 for receiving valve tissue. Referring to FIG. 64, after the paddles 402 are moved outward in the translation direction 412, the paddles 402 are moved, flexed, rotated, or pivoted outward in the rotational or pivot direction 410 such that the opening 406 has a second width 422. After valve tissue is received in the openings 406 between the paddles 402 and the gripping members 404, the implantable device 400 is moved back to the closed position (as shown in FIG. 62) to secure the implantable device 400 to the valve tissue. The implantable device 400 can include any other features for an implantable device discussed in the present application, and the implantable device 400 can be positioned to engage valve tissue 20, 22 as part of any suitable valve repair system (e.g., any valve repair system disclosed in the present application).

While FIGS. 59-61 illustrate a device 400 in which the paddles 402 are rotated or pivoted and then spread apart (e.g., moved translationally away from each other), and FIGS. 62-64 illustrate a device 400 in which the paddles 402 are spread apart and then rotated or pivoted. In some embodiments, a device 400 can include paddles 402 that can be spread apart and rotated or pivoted simultaneously. In addition, in certain embodiments, the paddles 402 can be spread apart and rotated or pivoted independently of each other. That is, in the embodiments for the valve repair device 400 shown in FIGS. 59-61 and 62-64, as well as the embodiment in which the spreading apart and rotating or pivoting of each paddle 402 is completed simultaneously, the paddles 402 can be controlled independently of each other.

Figure 65:
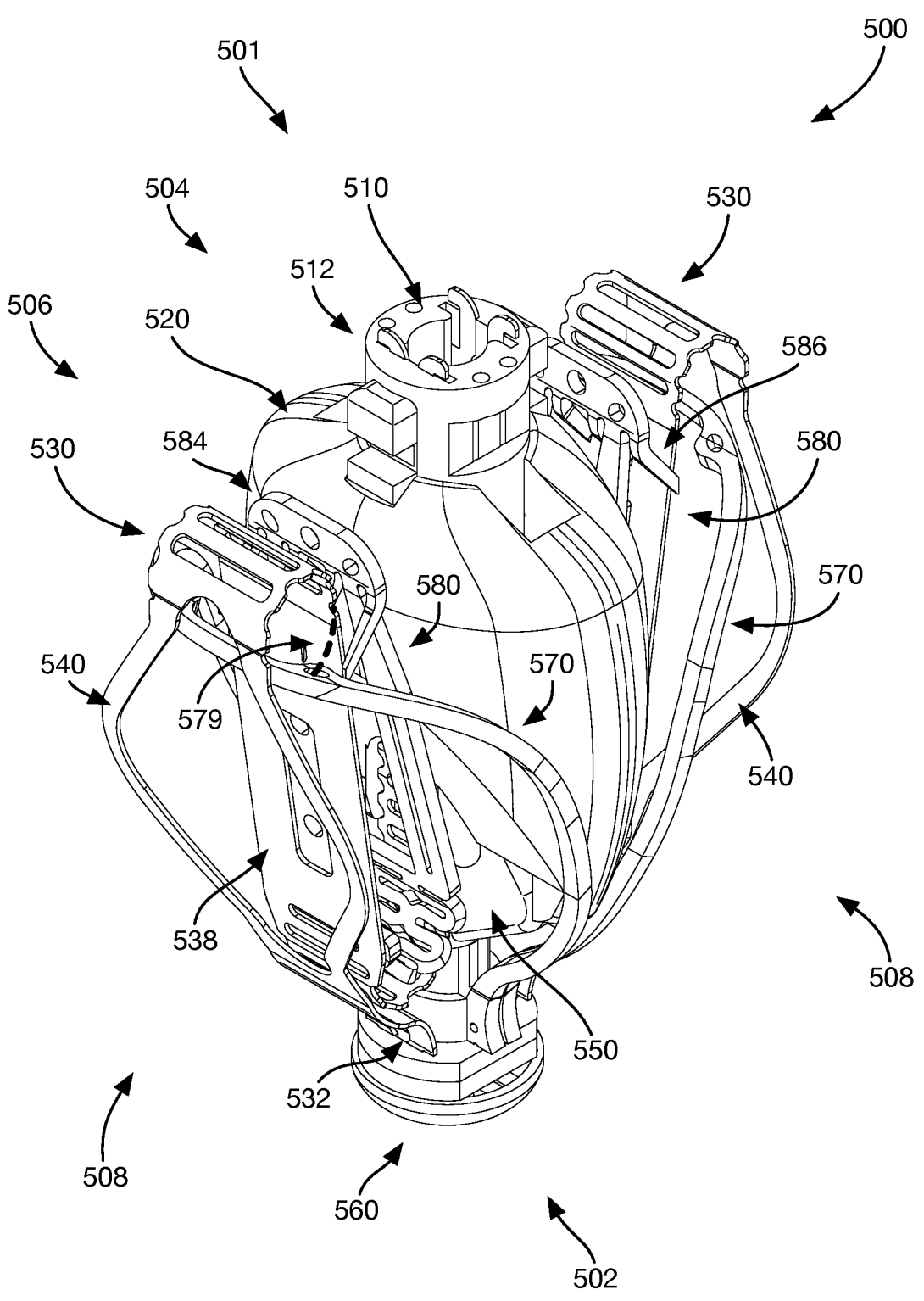
FIG. 65 shows a top perspective view of an example implantable prosthetic device in a closed position.
Figure 66:
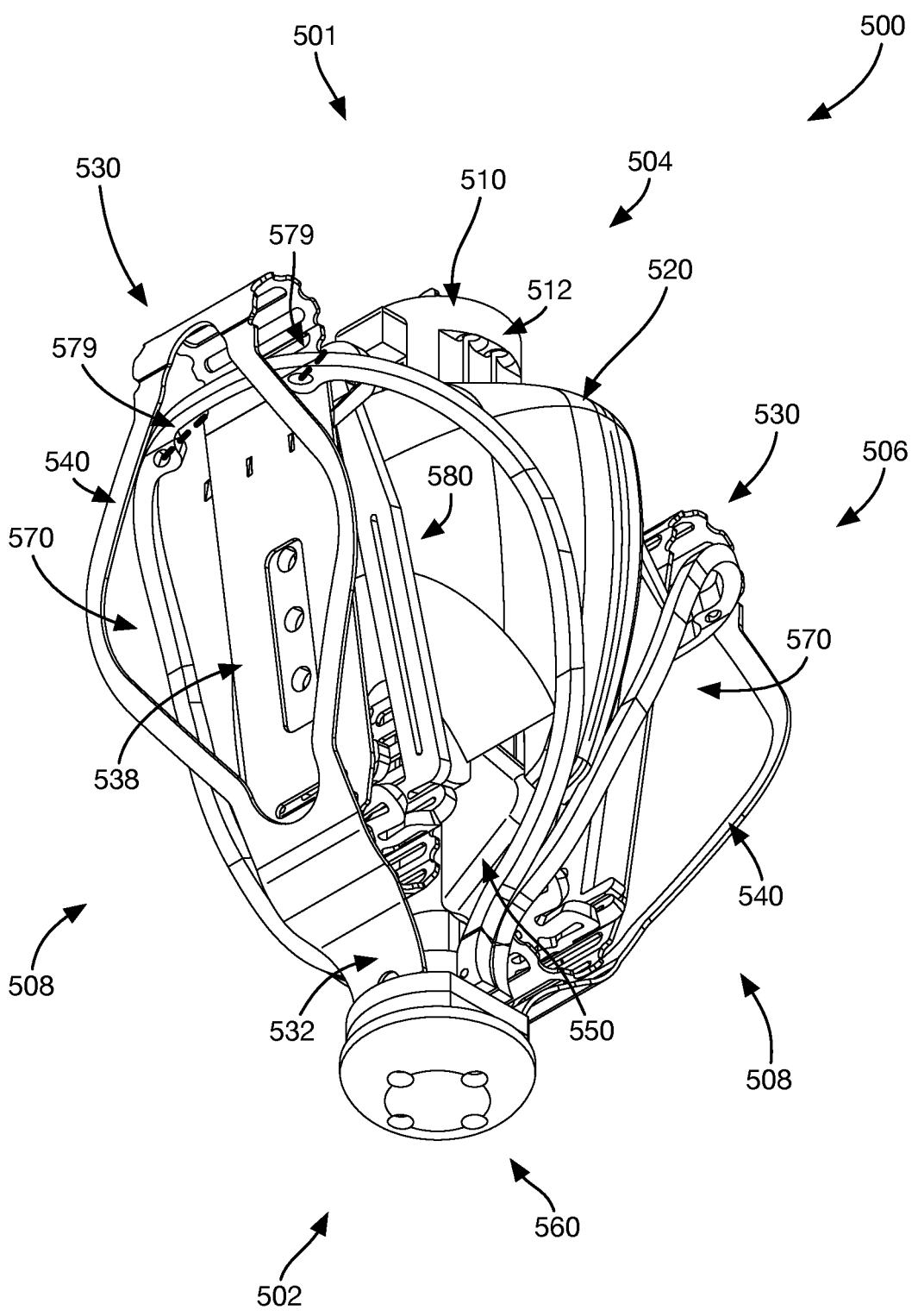
FIG. 66 shows a bottom perspective view of the implantable prosthetic device of FIG. 65.
Figure 67:
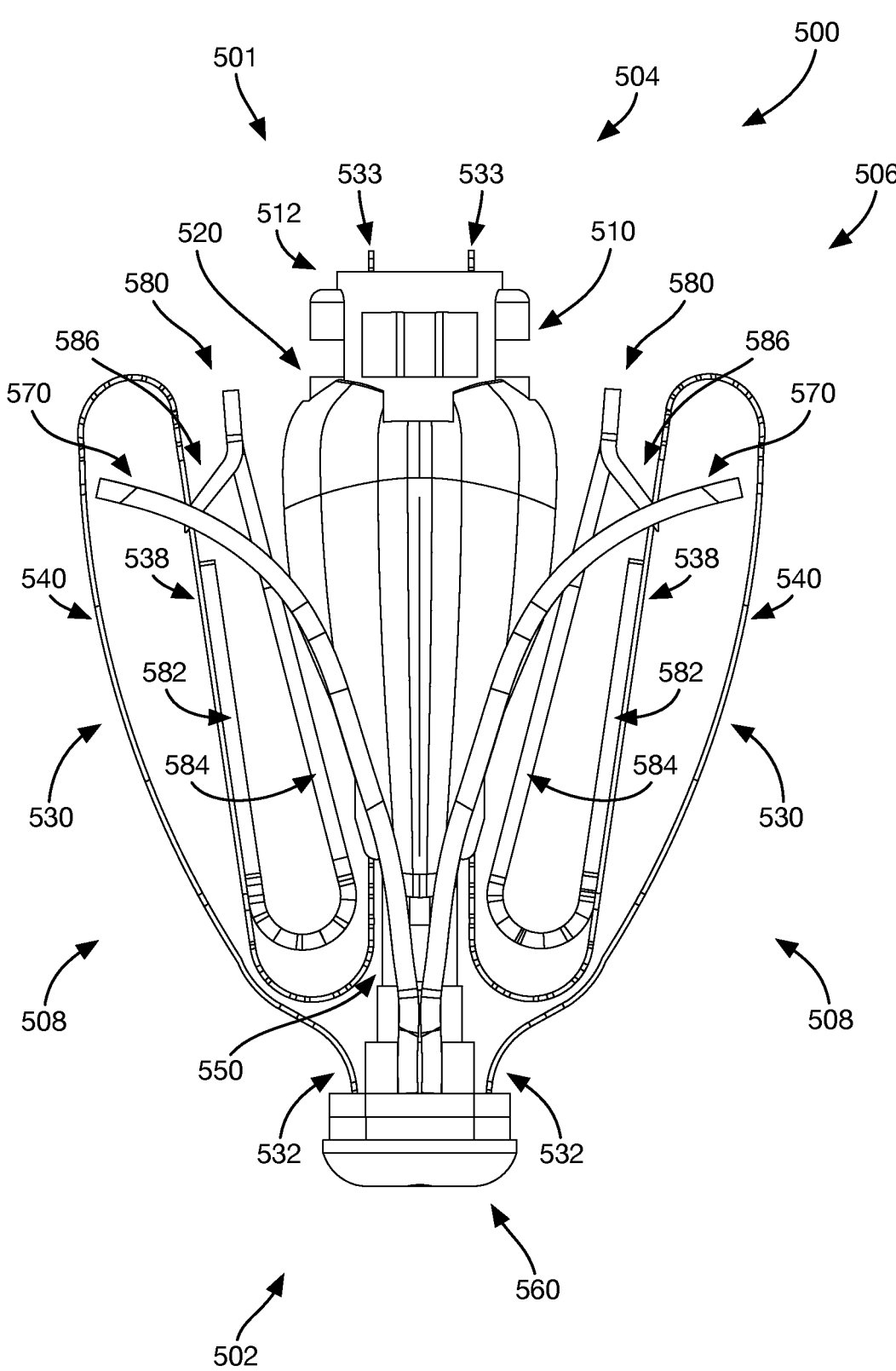
FIG. 67 shows a front view of the implantable prosthetic device of FIG. 65.
Figure 68:
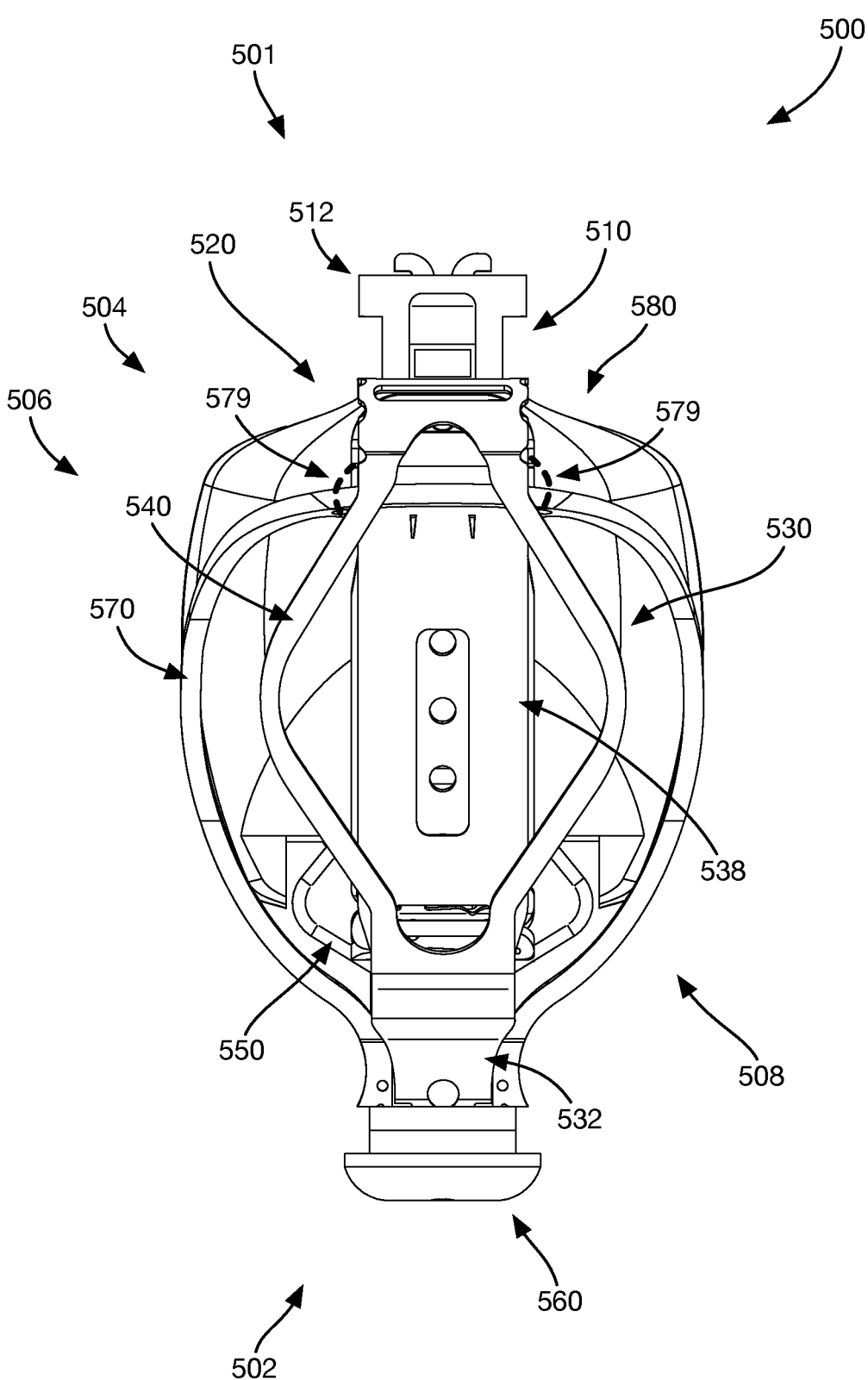
FIG. 68 shows a side view of the implantable prosthetic device of FIG. 65.
Figure 69:
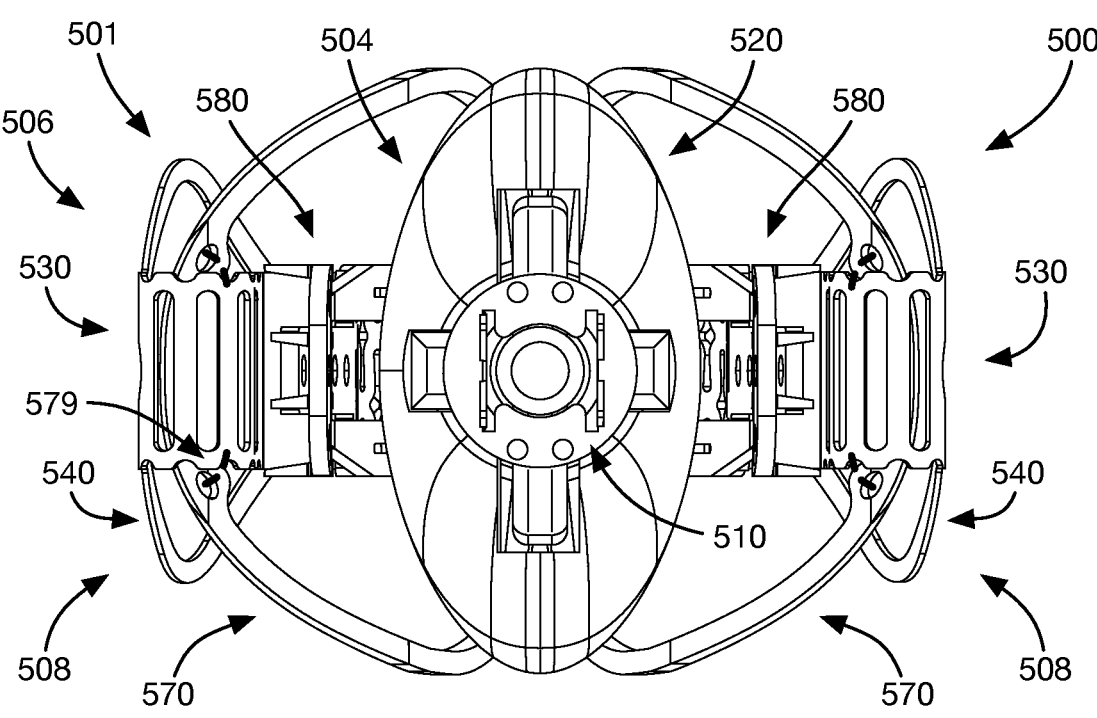
FIG. 69 shows a top view of the implantable prosthetic device of FIG. 65.
Figure 70:
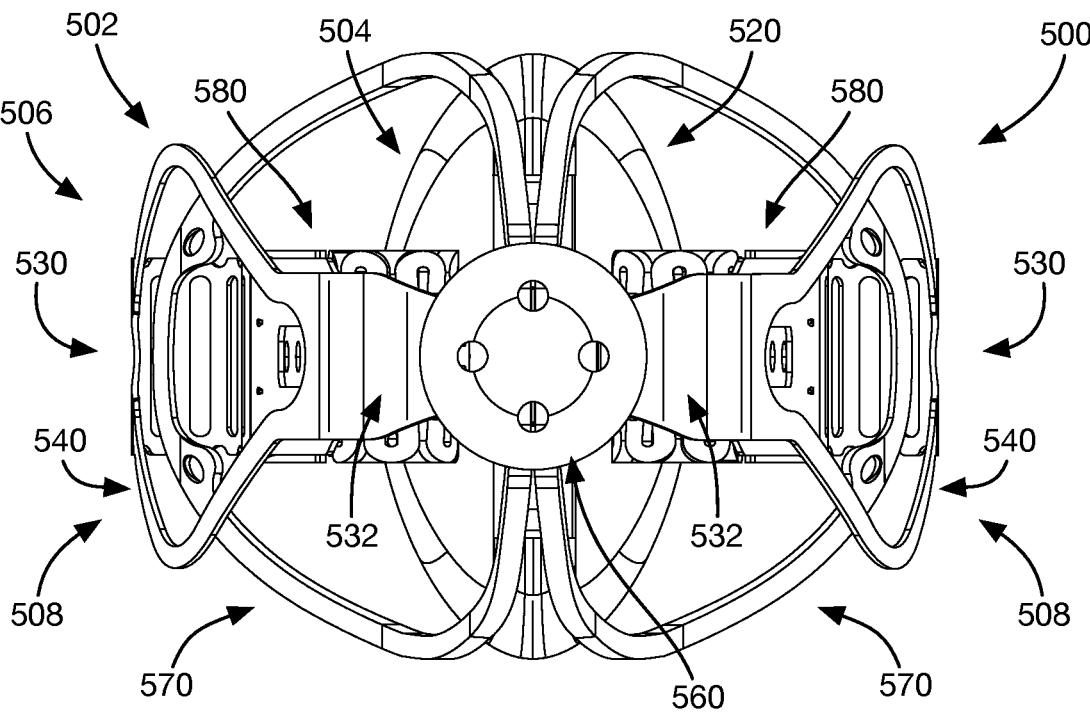
FIG. 70 shows a bottom view of the implantable prosthetic device of FIG. 65.

Referring now to FIGS. 65-183, an example embodiment of an implantable prosthetic spacer device 500 is shown. The implantable prosthetic spacer device 500 is one of the many different configurations that the device 100 that is schematically illustrated in FIGS. 8-15 can take. The device 500 can include any other features for an implantable prosthetic device discussed in the present application or any of the applications that are incorporated herein by reference, and the device 500 can be positioned to engage valve tissue 20, 22 as part of any suitable valve repair system (e.g., any valve repair system disclosed in the present application or any of the applications that are incorporated herein by reference). The various components of the implantable prosthetic spacer device 500 can be made at any suitable size to accommodate different size patient anatomy.

The implantable prosthetic spacer device 500 extends from a proximal portion 501 to a distal portion 502 and includes a coaption portion 504 and an anchor portion 506. The coaption portion 504 of the device 500 includes a central or main shaft 510 and a coaption element 520 for implantation between the leaflets 20, 22 of the native valve. The anchor portion 506 includes a plurality of anchors 508, each anchor 508 including a paddle 530, paddle extension members or paddle frames 570, and clasps 580. The anchor portion 506 can also include an optional spreading member 550 that can be actuated to adjust the position of portions of the paddles 530 and clasps 580.

Figure 72:
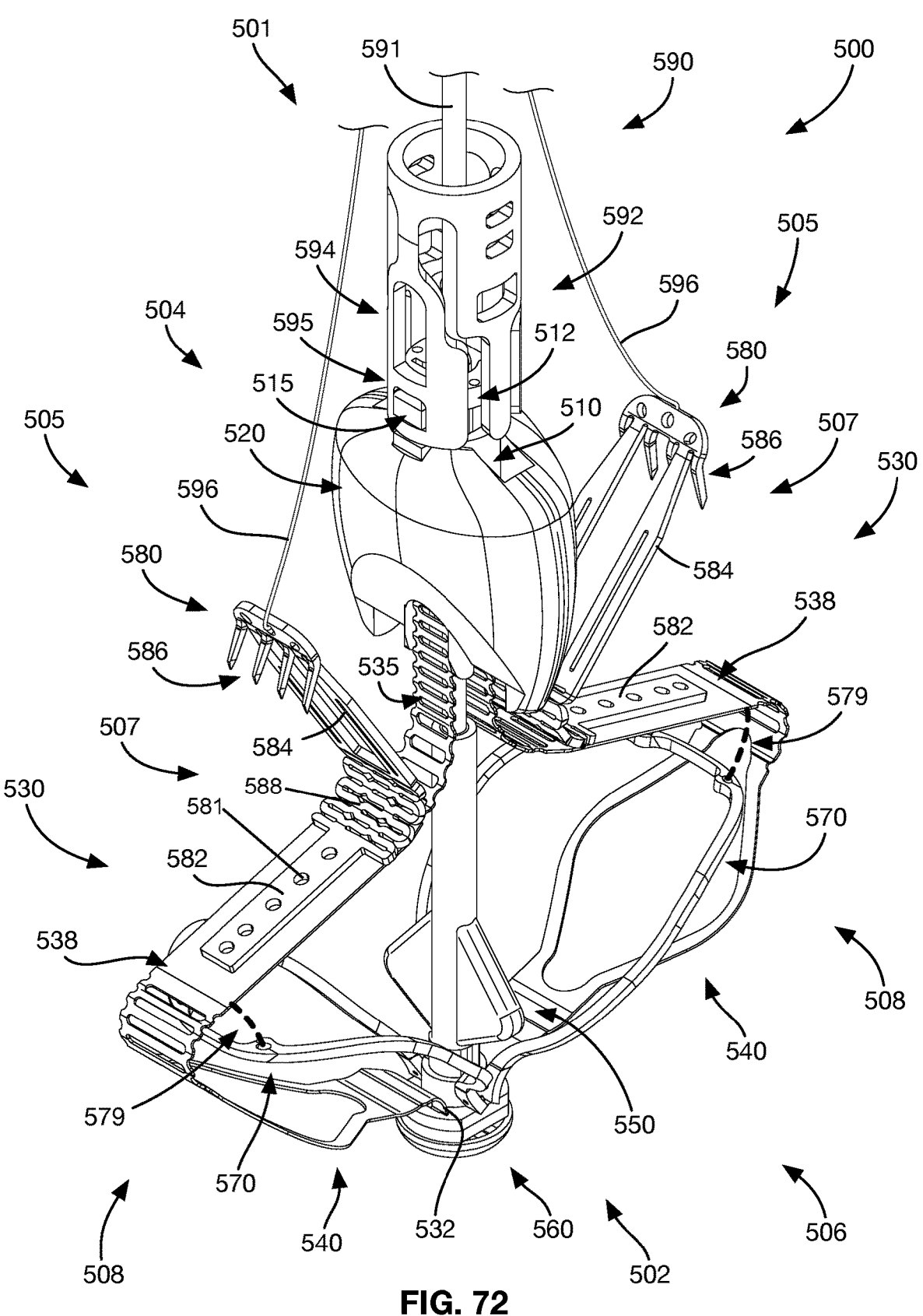
FIG. 72 shows a top perspective view of the implantable prosthetic device of FIG. 65 in an open position.
Figure 73:
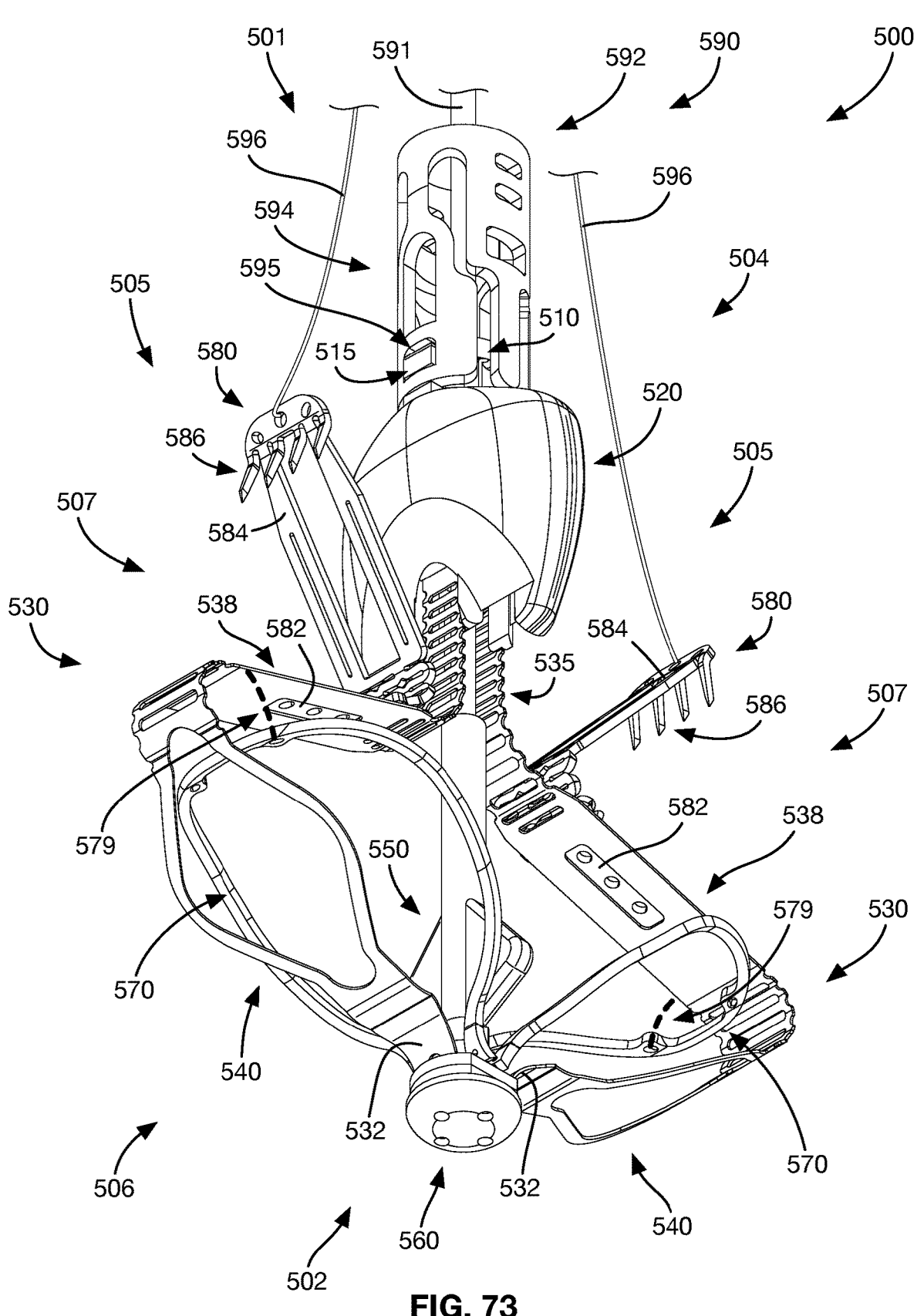
FIG. 73 shows a bottom perspective view of the implantable prosthetic device of FIG. 72.
Figure 74:
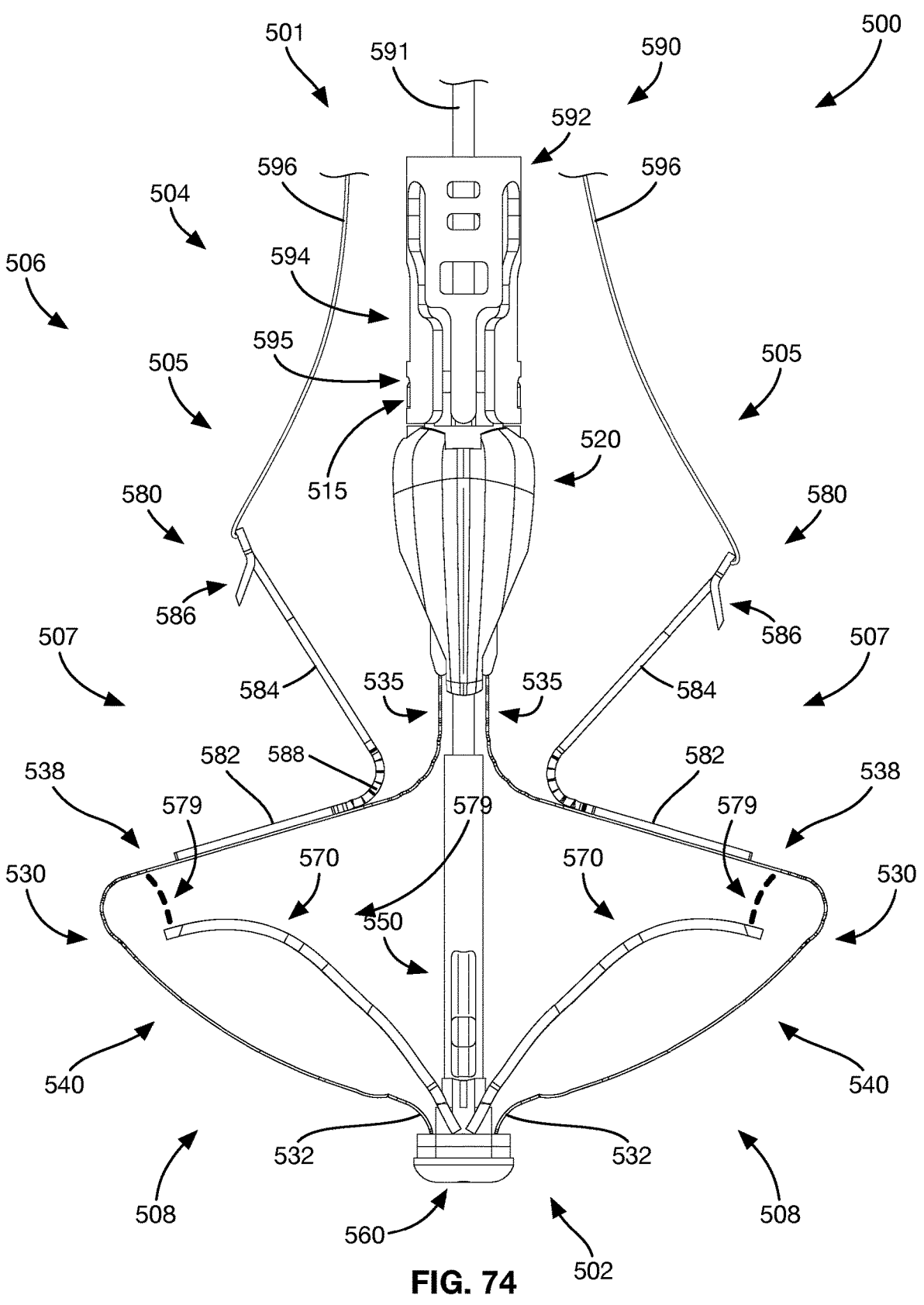
FIG. 74 shows a front view of the implantable prosthetic device of FIG. 72.
Figure 75:
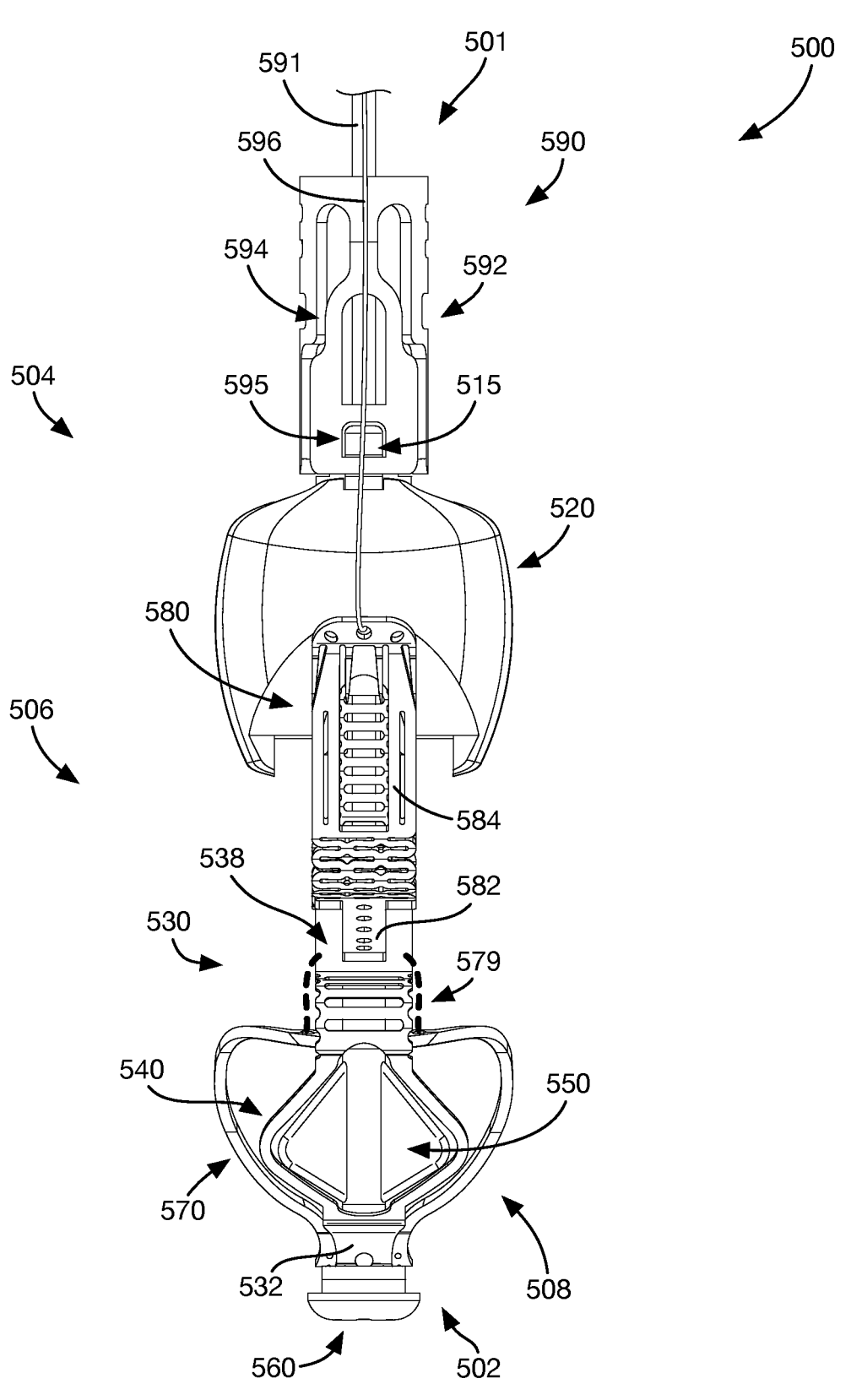
FIG. 75 shows a side view of the implantable prosthetic device of FIG. 72.
Figure 76:
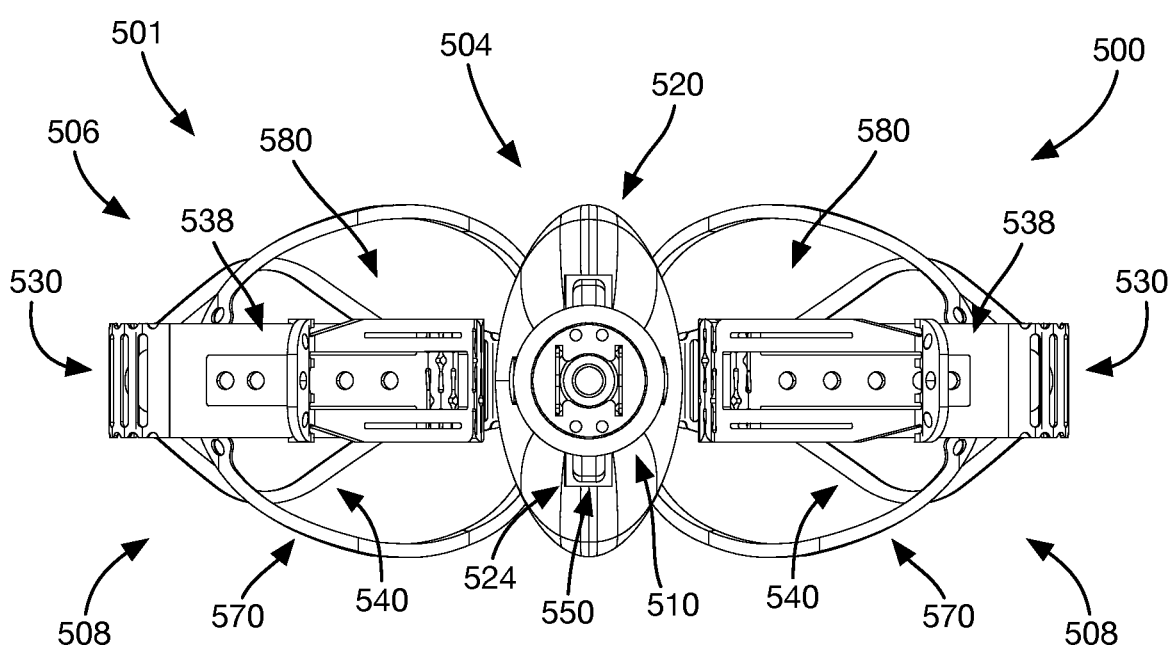
FIG. 76 shows a top view of the implantable prosthetic device of FIG. 72.
Figure 77:
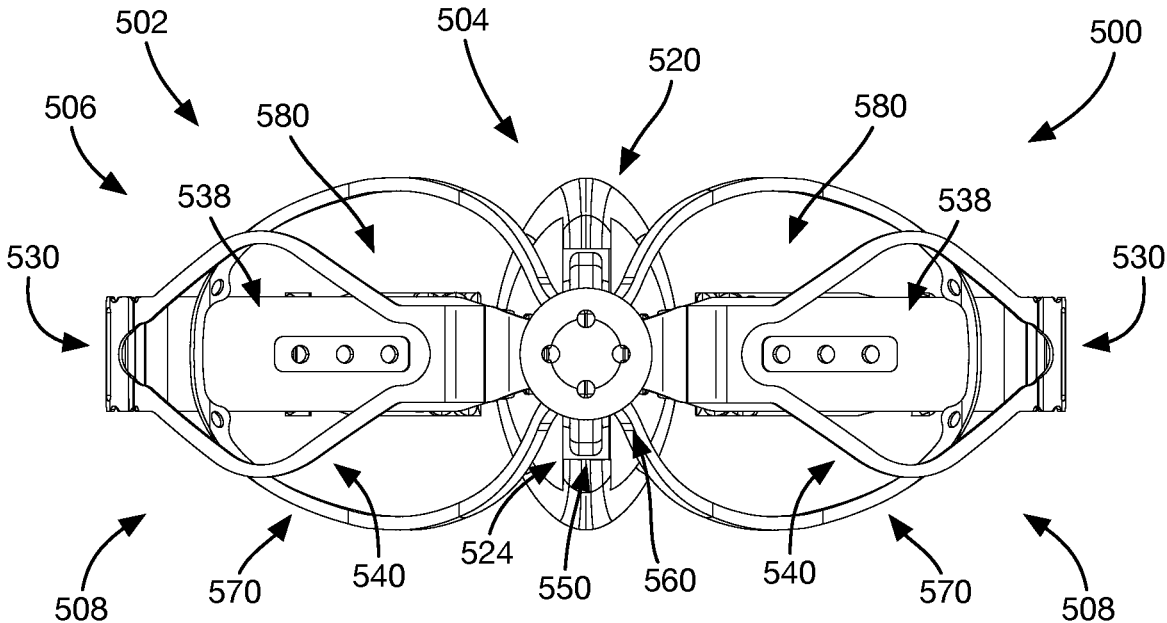
FIG. 77 shows a bottom view of the implantable prosthetic device of FIG. 72.

The implantable prosthetic spacer device 500 is implanted into the native valve in a similar fashion to the implantable prosthetic spacer device 200 described above. That is, during implantation the paddles 530 of the anchors 508 are opened and closed to grasp the native valve leaflets 20, 22 between the paddles 530 and the coaption element 520. The anchors 508 are moved between a closed position (FIGS. 65-70) to various open positions (FIGS. 72-80) by extending and retracting an actuation element 591 (e.g., wire, shaft, rod, line, etc.) extending from a delivery system 590, through the main shaft 510 and to the spreading member 550 that is connected to a distal cap assembly 560. Referring to FIG. 72, the actuation element 591 removably engages the spreading member 550 with a threaded connection, or the like, so that the actuation element 591 can be disengaged and removed from the device 500 after implantation. In embodiments without the spreading member 550, the actuation element extends to and is removably attached to the distal cap assembly 560. In these embodiments, the device illustrated by FIGS. 65-183 can be operated in substantially the same manner as any of the non-spreading devices described herein.

Extending and retracting the actuation element 591 attached to the spreading member 550 increases and decreases the spacing between the main shaft 510 and the distal cap assembly 560, respectively. The main shaft 510 slides along the spreading member 550 and actuation element 591 during actuation so that changing of the spacing between the main shaft 510 and the distal cap assembly 560 causes the paddles 530 to move between different positions to grasp the native valve leaflets 20, 22 during implantation.

In one example embodiment, as the device 500 is opened and closed, the paddles 530 are moved in unison, rather than independently, by the single actuation element or actuation wire 591. Also, the positions of the clasps 580 are dependent on the positions of the paddles 530. For example, the clasps 580 are arranged such that closure of the anchors 508 simultaneously closes the clasps 580. In any of the embodiments disclosed herein, the clasps 580 can be omitted and the native valve leaflets are captured directly between the paddles 530 and the coaption element.

In one example embodiment, the device 500 can be made to have the paddles 530 be independently controllable in the same manner as the device 100 illustrated in FIG. 15.

The barbed clasps 580 further secure the native leaflets 20, 22 by engaging the leaflets 20, 22 with barbs 586 and pinching the leaflets 20, 22 between the fixed and moveable arms 582, 584. The barbs 586 of the barbed clasps 580 increase friction with or may partially or completely puncture the leaflets 20, 22. Actuation lines 596 (FIGS. 72-75) can be actuated separately so that each barbed clasp 580 can be opened and closed separately. Separate operation of the barbed clasps 580 allows one leaflet 20, 22 to be grasped at a time, or for the repositioning of a clasp 580 on a leaflet 20, 22 that was insufficiently grasped, without altering a successful grasp on the other leaflet 20, 22. The barbed clasps 580 can be fully opened and closed when the paddle 530 is not closed, thereby allowing leaflets 20, 22 to be grasped in a variety of positions as the particular situation requires.

Referring now to FIGS. 65-70, the implantable prosthetic device 500 is shown in a closed position. When closed, inner portions 538 of the paddles 530 are disposed between the outer portions 540 of the paddles 530 and the coaption element 520. The clasps 580 are disposed between the inner portions 538 and the coaption element 520. Upon successful capture of native leaflets 20, 22 the device 500 is moved to and retained in the closed position so that the leaflets 20, 22 are secured within the device 500 by the clasps 580 and are pressed against the coaption element 520 by the paddles 530 and/or paddle frames 570. In the illustrated example, the outer portions 540 of the paddles have a wide curved shape that fits around the curved shape of the coaption element 520 to more securely grip the leaflets 20, 22 when the device 500 is closed, similar to what is shown in FIG. 51 with respect to the device 200. The curved shape and rounded edges of the outer portions 540 also inhibits tearing of the leaflet tissue. The various components of the implantable prosthetic device 500 in closed positions are shown in an exploded view in FIG. 71.

Figure 71:
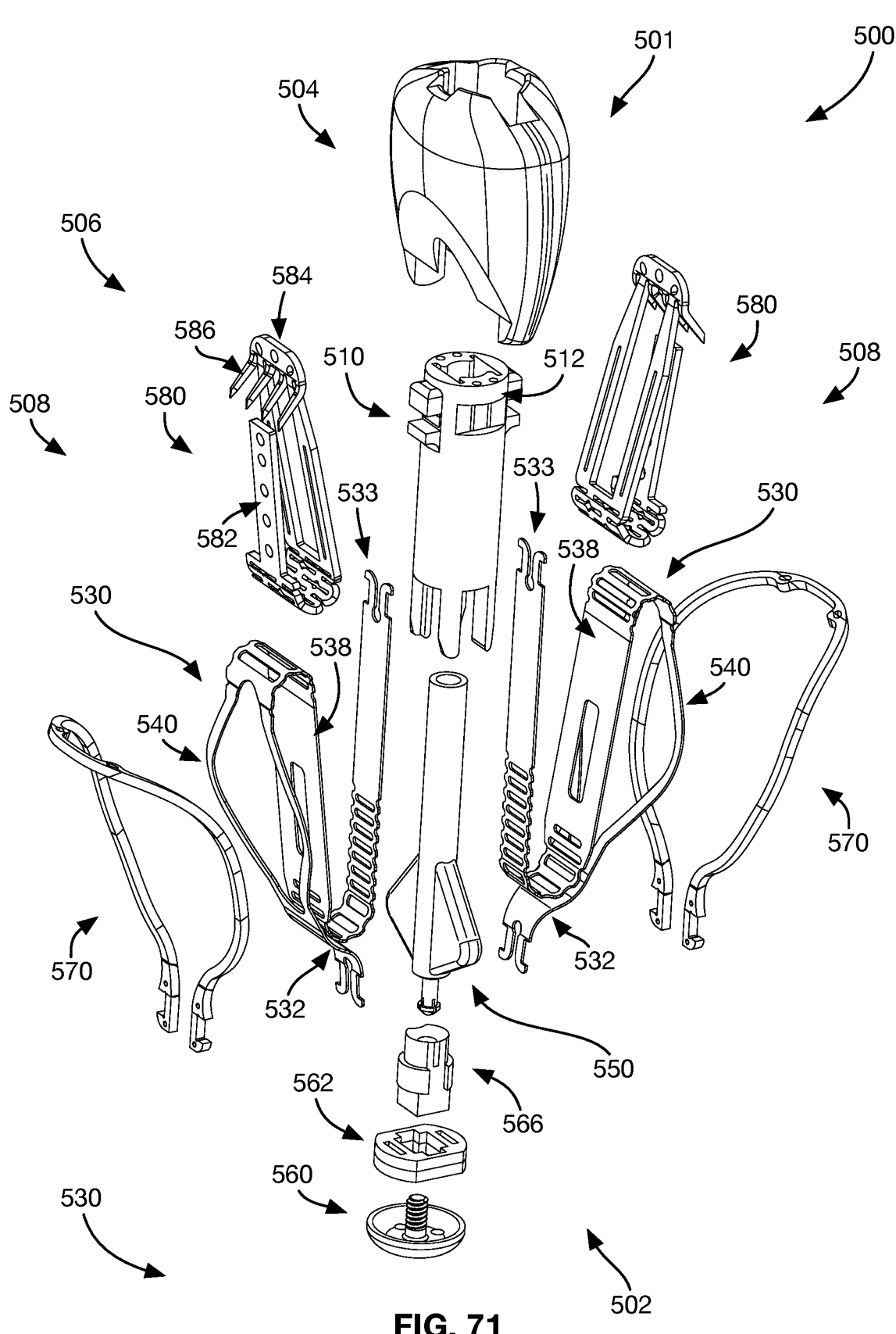
FIG. 71 shows a perspective exploded view of the components of the implantable prosthetic device of FIG. 65.
Figure 71A:
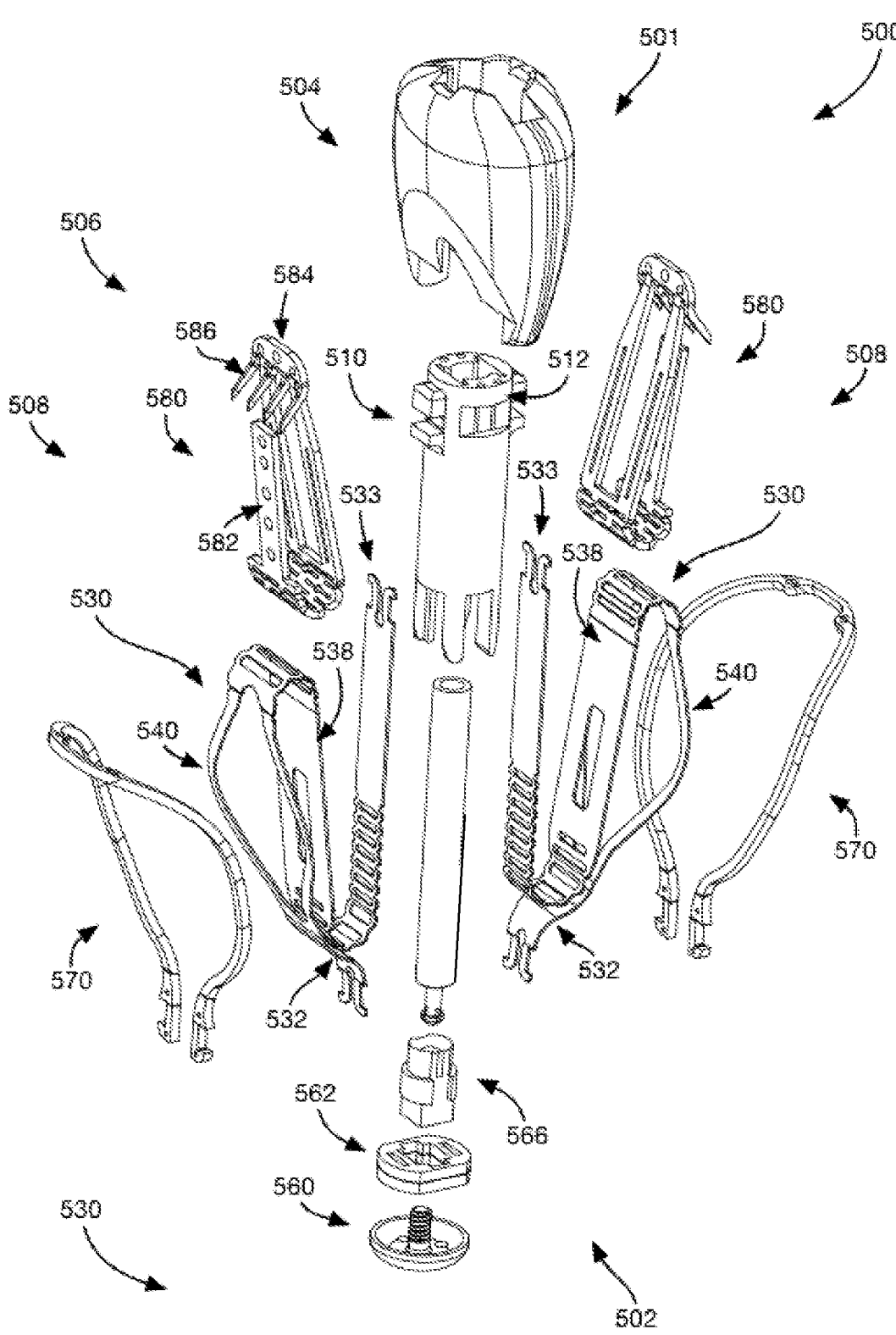
FIG. 71A shows a perspective view of the components of an example implantable prosthetic device.

In the illustrated embodiment of FIG. 71, the implantable prosthetic device 500 includes the optional spreading member 550, as described above. However, the implantable prosthetic device 500 may have other configurations. For example, as shown in FIG. 71A, the implantable prosthetic device does not include the optional spreading member 500.

Figure 78:
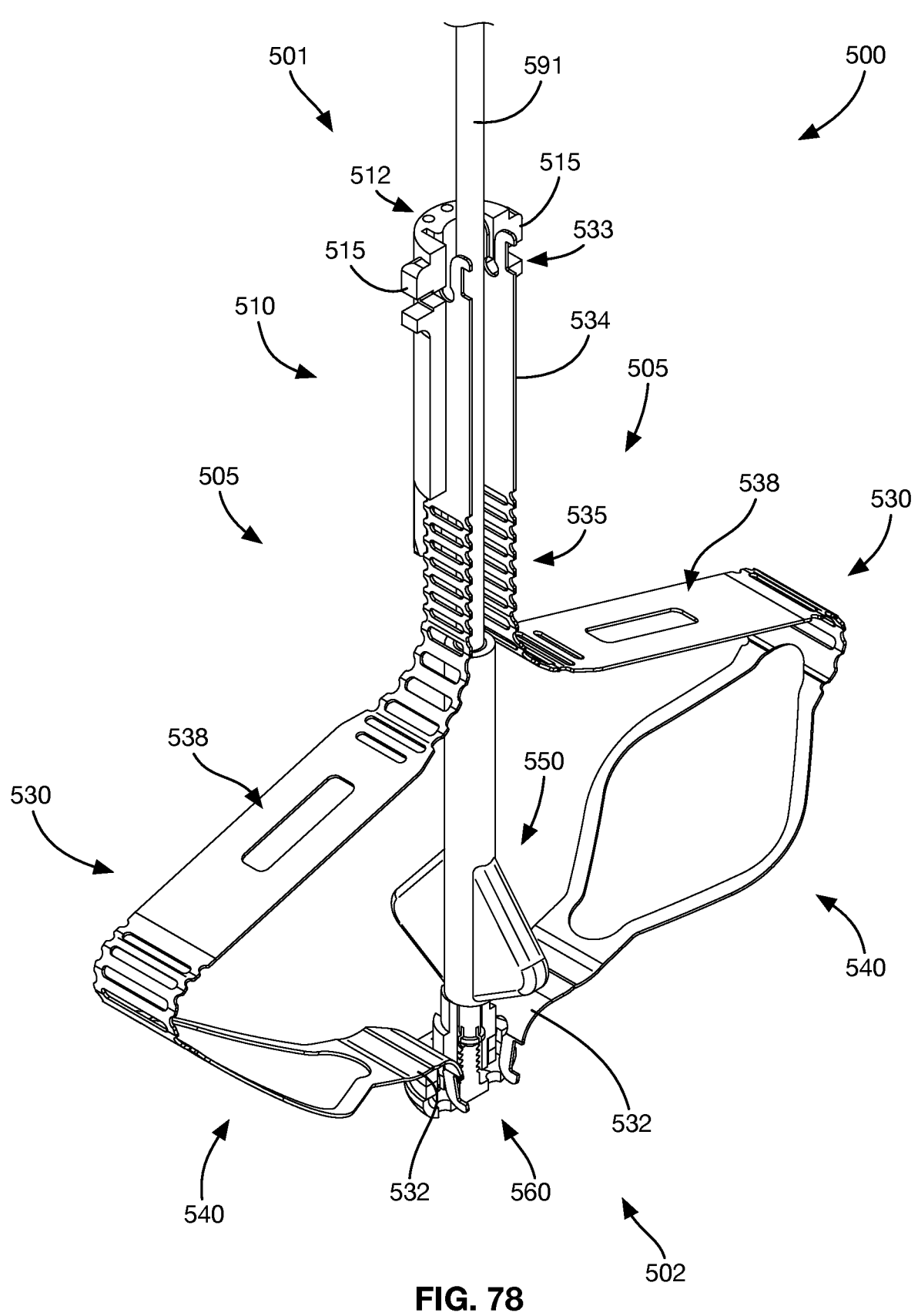
FIG. 78 shows a top perspective view of the paddles and actuating components of the implantable prosthetic device of FIG. 72.
Figure 79:
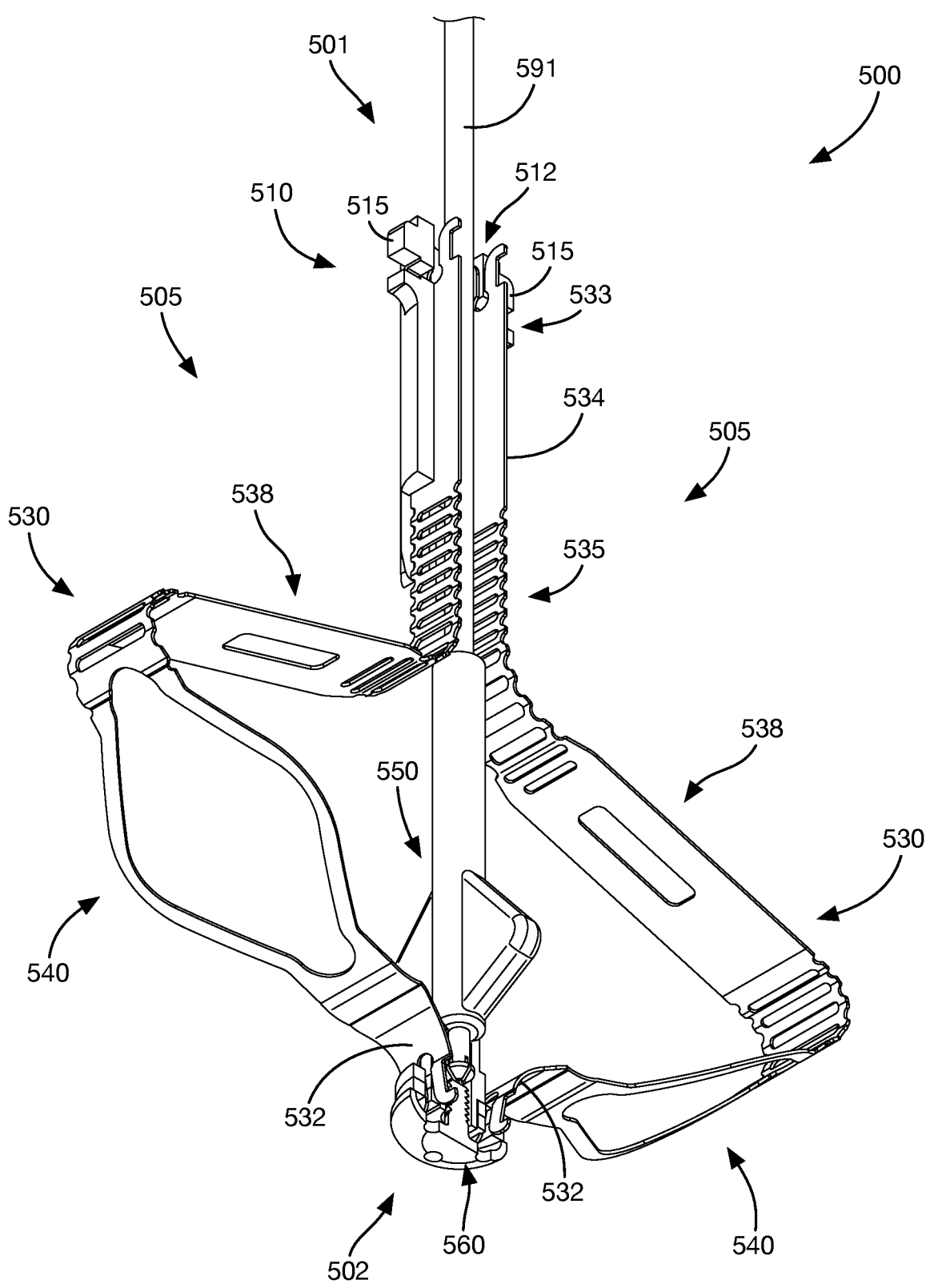
FIG. 79 shows a bottom perspective view of the implantable prosthetic device of FIG. 78.
Figure 80:
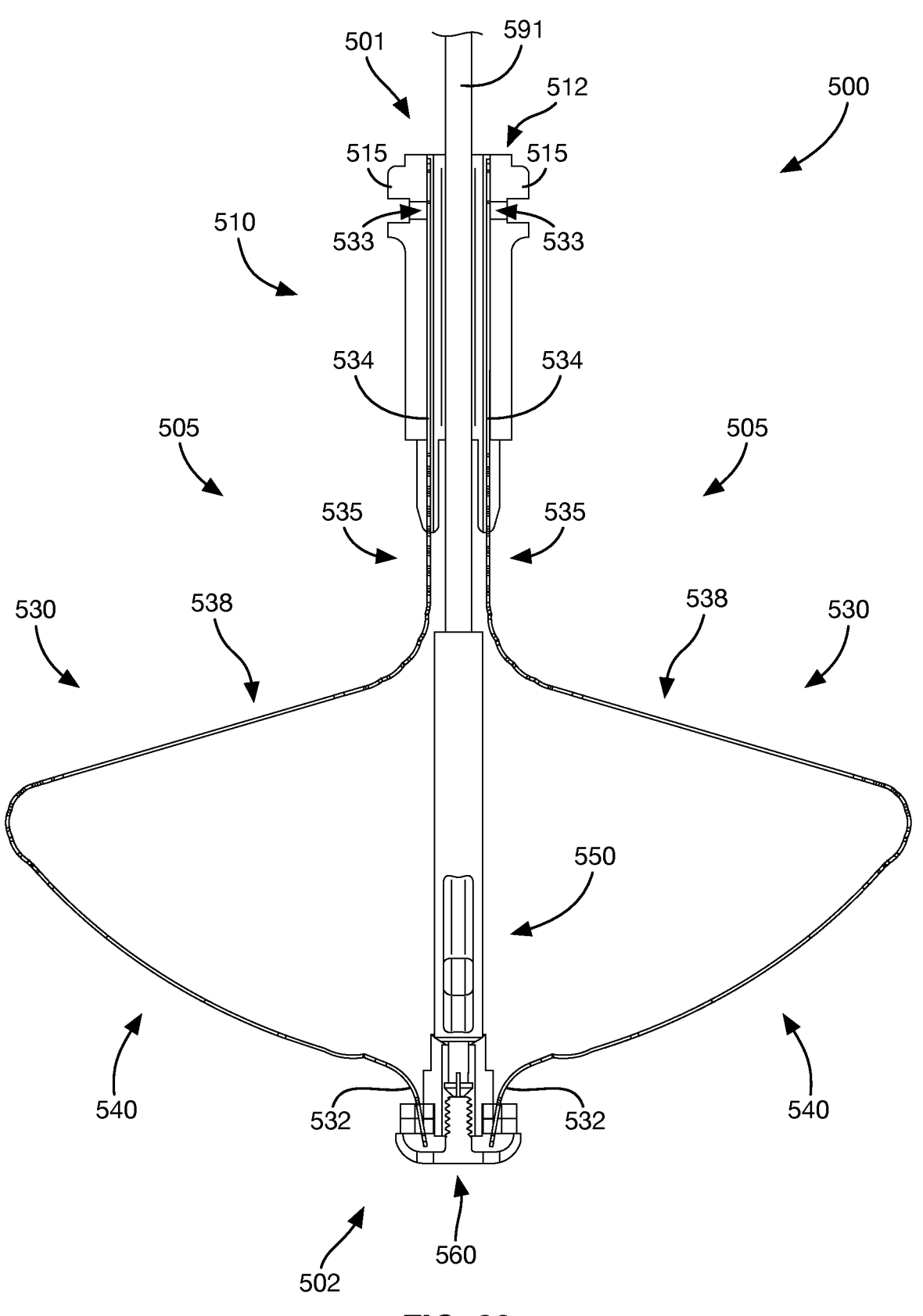
FIG. 80 shows a front view of the implantable prosthetic device of FIG. 78.
Figure 81:
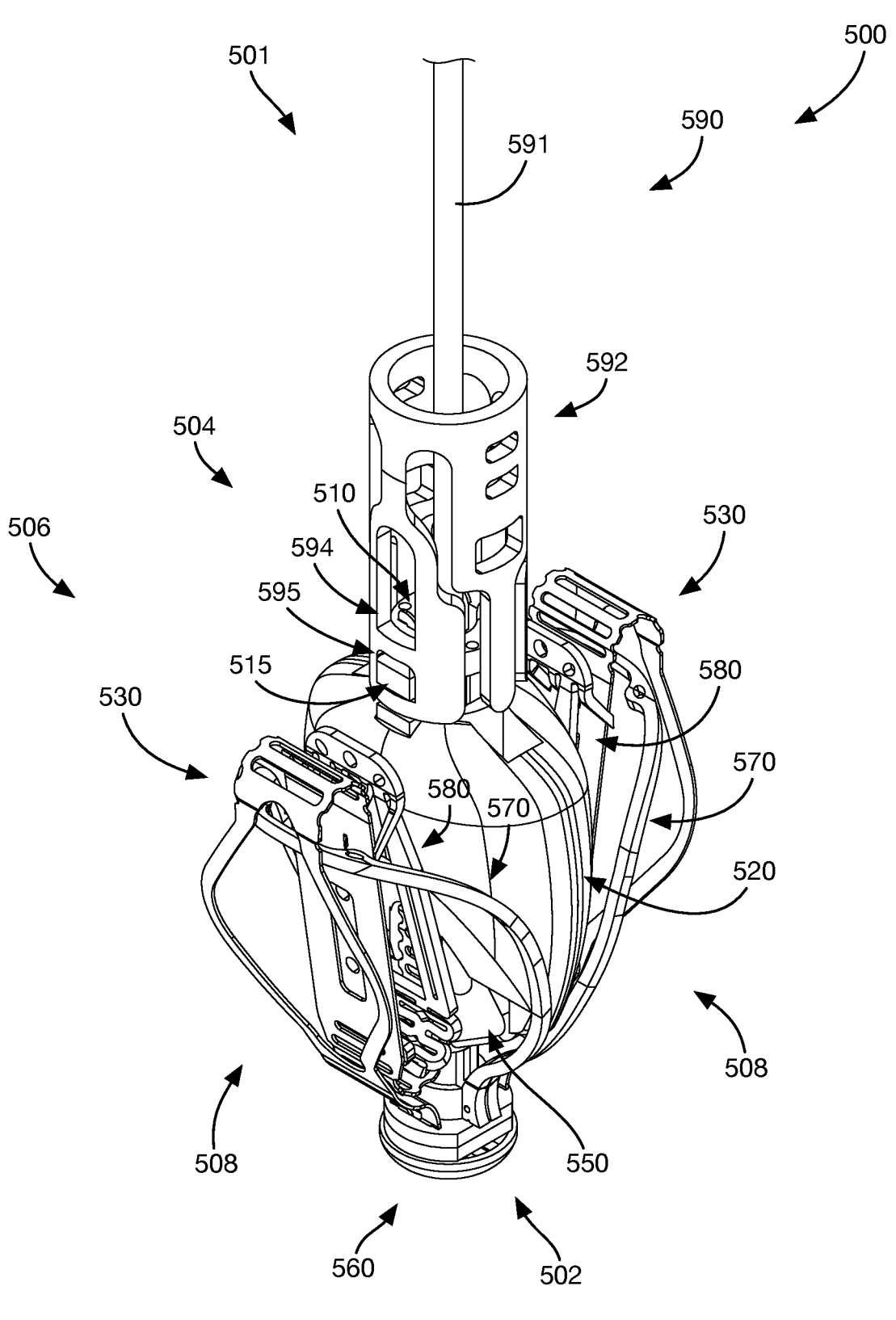
FIG. 81 shows a top perspective view of an example implantable prosthetic device attached to a delivery system.
Figure 82:
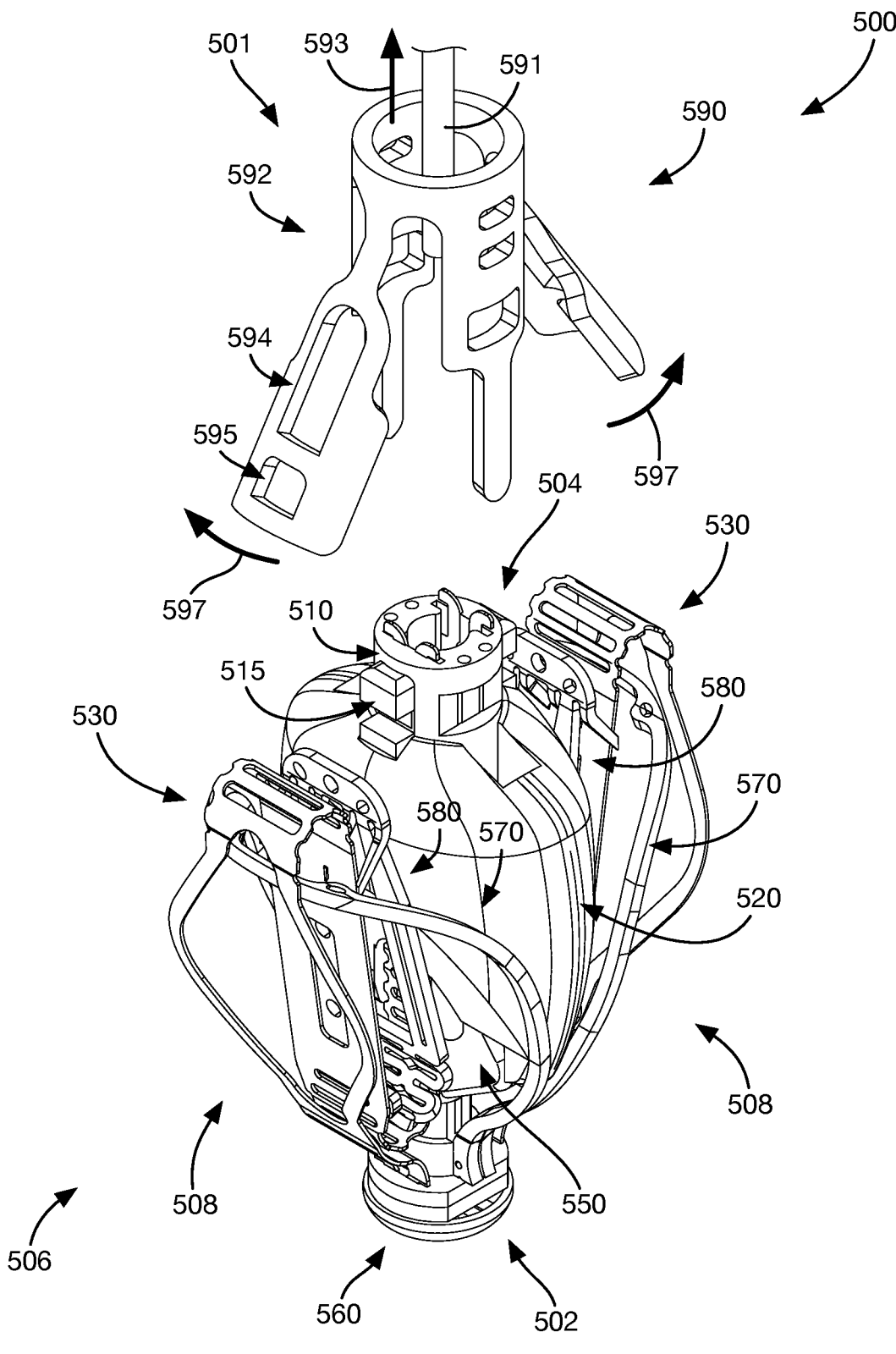
FIG. 82 shows a top perspective view of the implantable prosthetic device of FIG. 81 with the delivery system in an open and retracted position.
Figure 83:
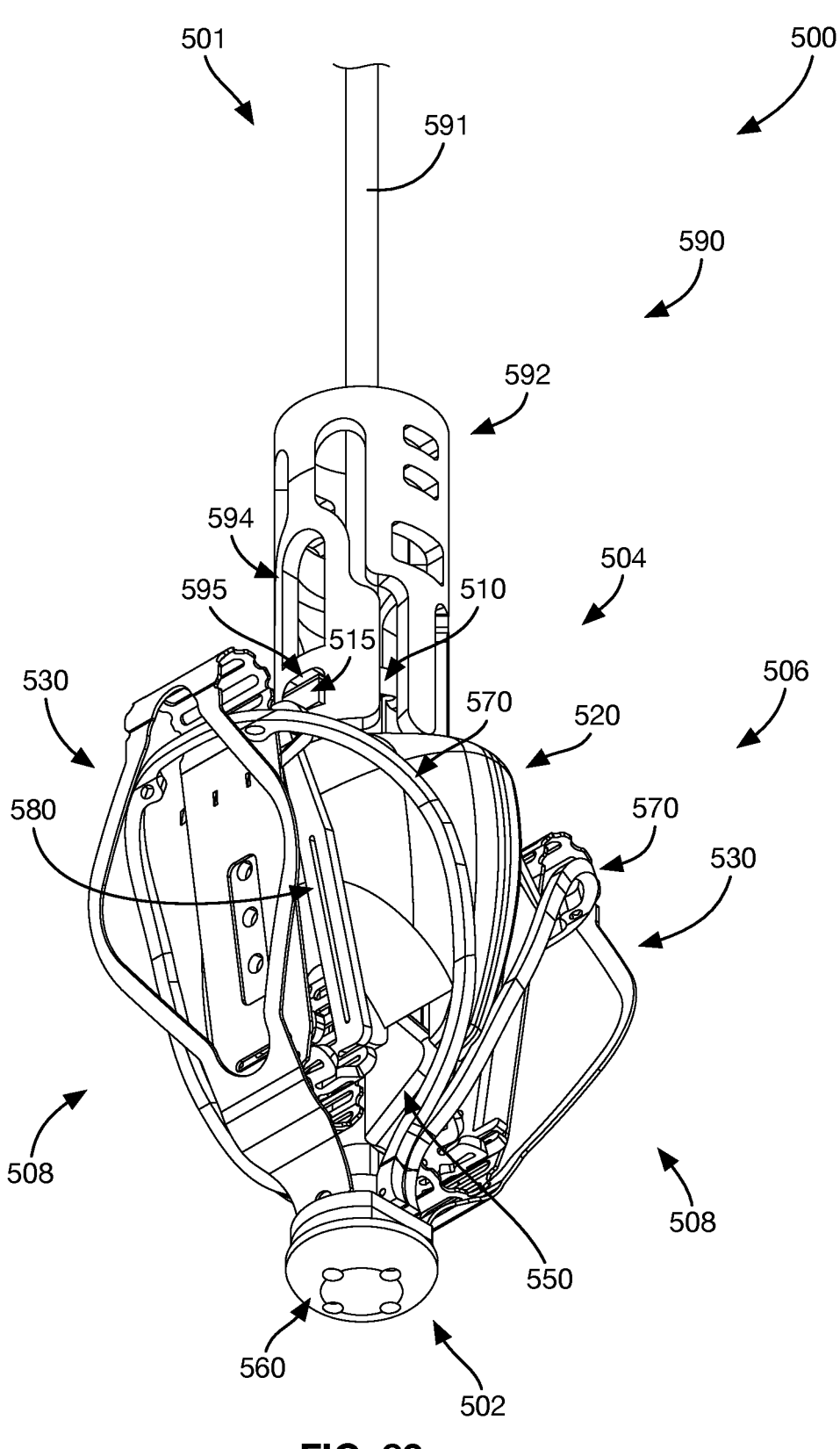
FIG. 83 shows a bottom perspective view of the example implantable prosthetic device of FIG. 81.
Figure 84:
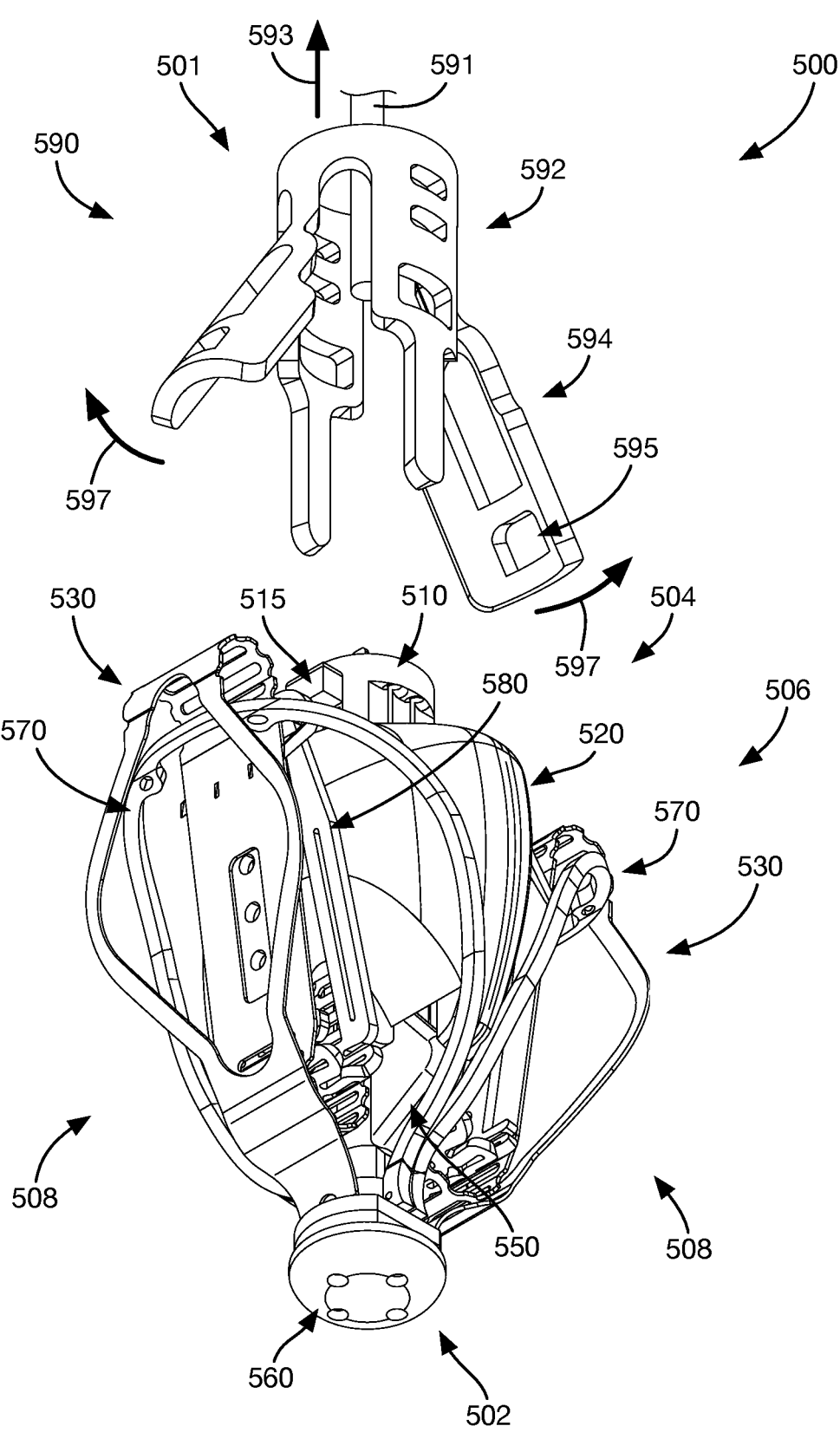
FIG. 84 shows a bottom perspective view of the implantable prosthetic device of FIG. 82.
Figure 85:
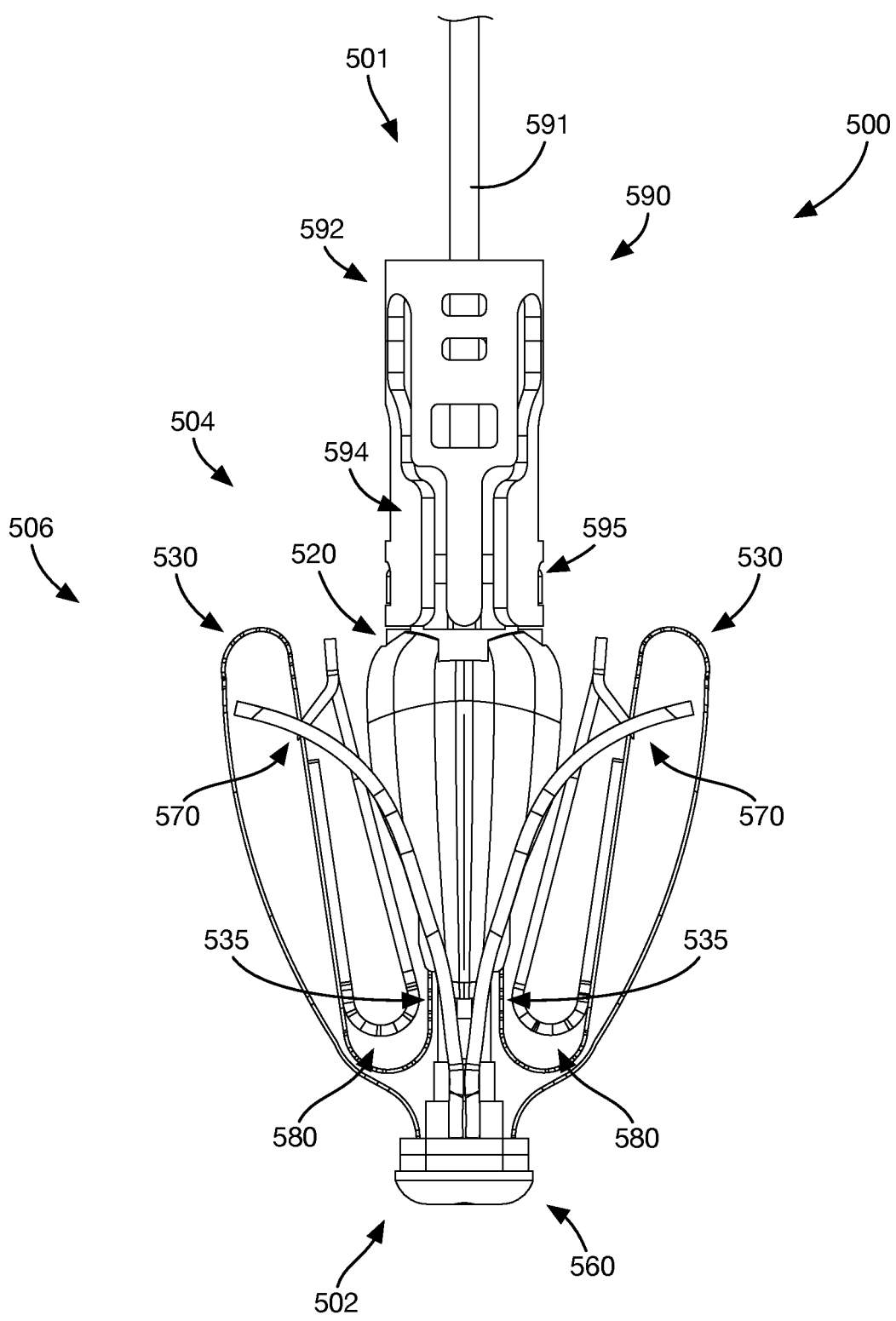
FIG. 85 shows a front view of the example implantable prosthetic device of FIG. 81.
Figure 86:
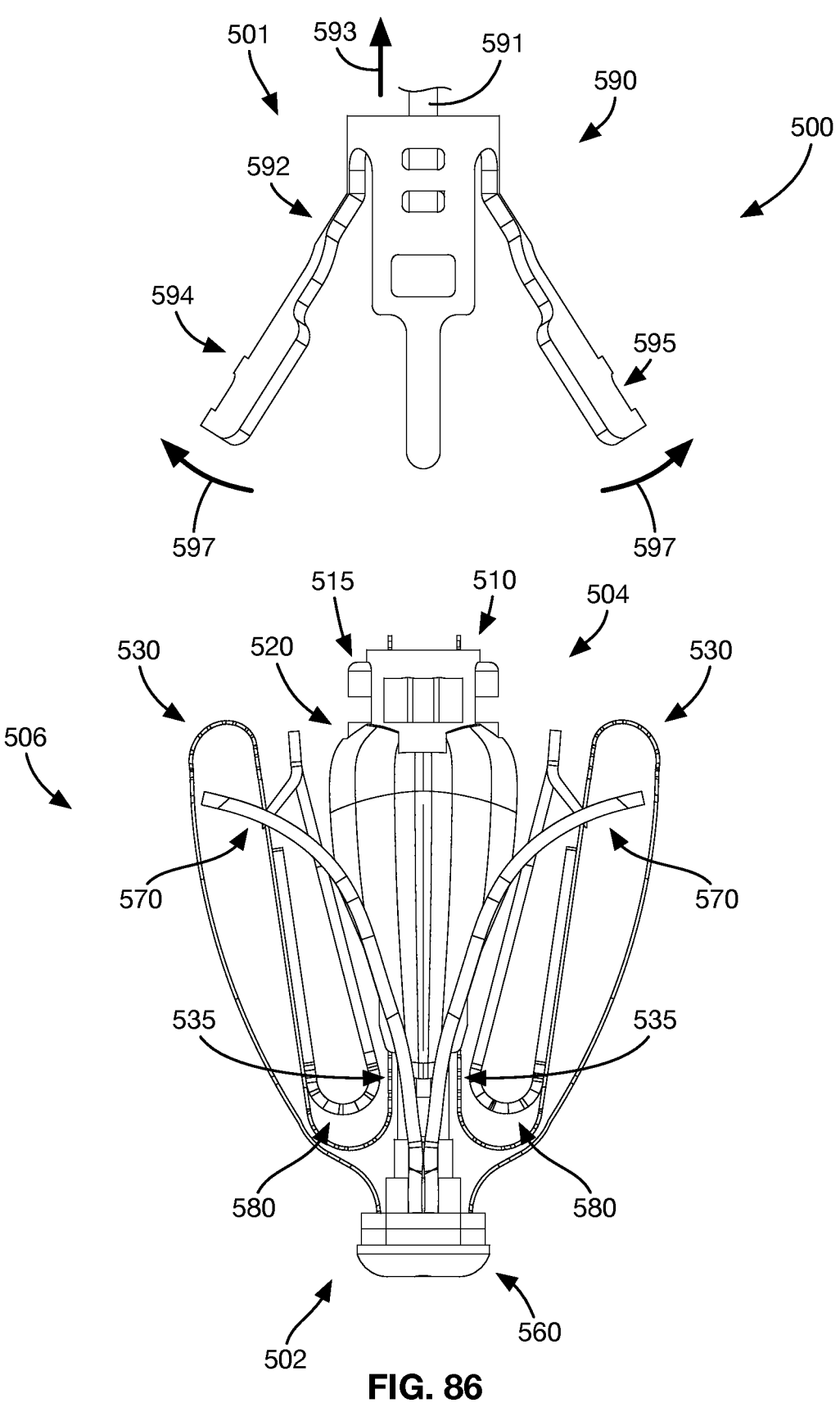
FIG. 86 shows a front view of the implantable prosthetic device of FIG. 82.
Figure 87:
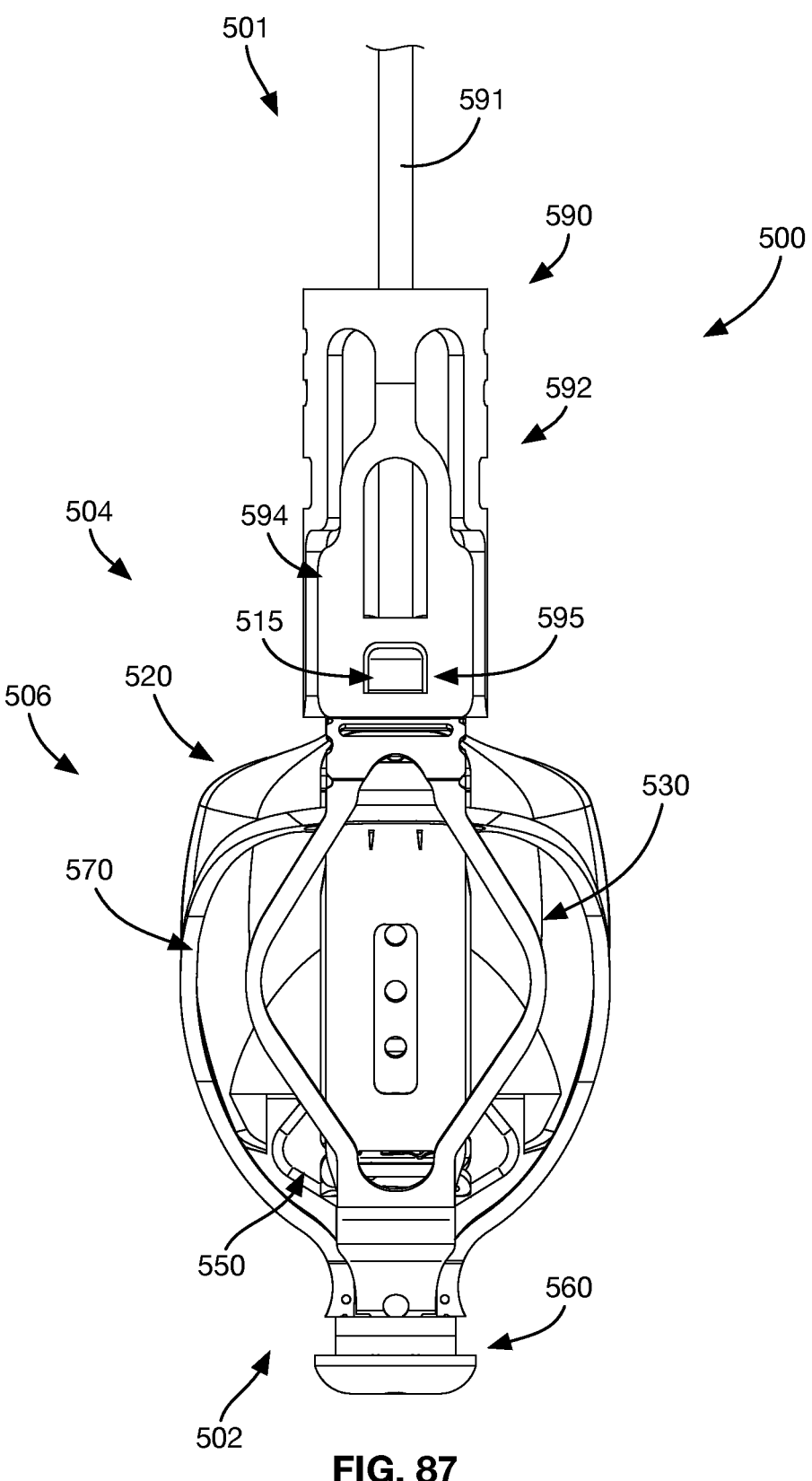
FIG. 87 shows a front view of the example implantable prosthetic device of FIG. 81.
Figure 89:
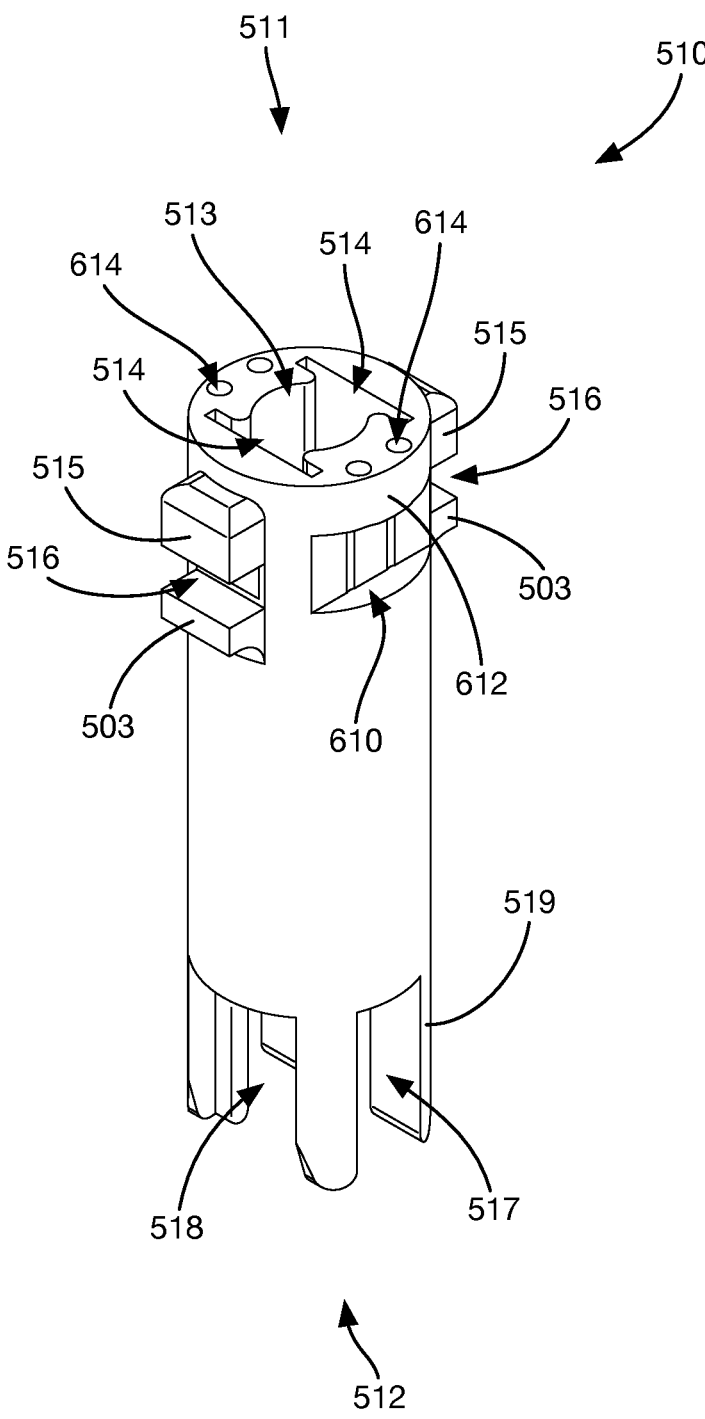
FIG. 89 shows a top perspective view of a main shaft of an example implantable device.
Figure 90:
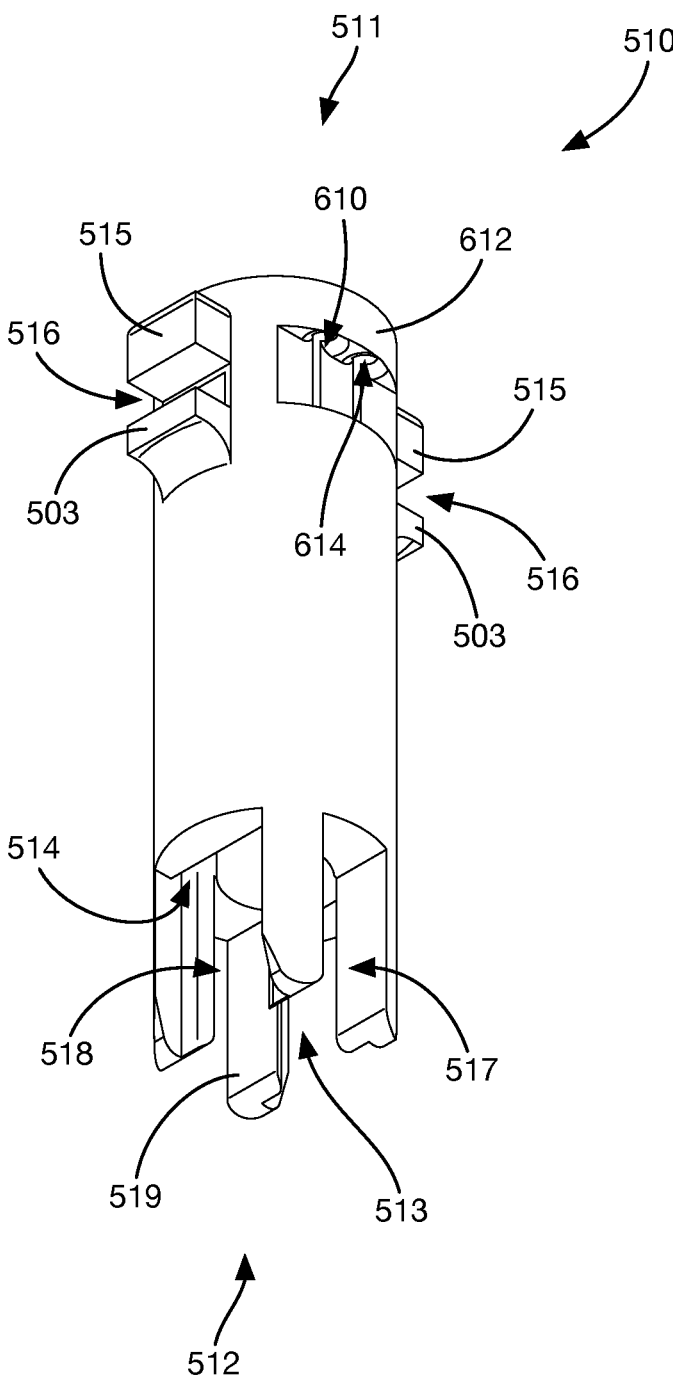
FIG. 90 shows a bottom perspective view of the main shaft of FIG. 89.
Figure 91:
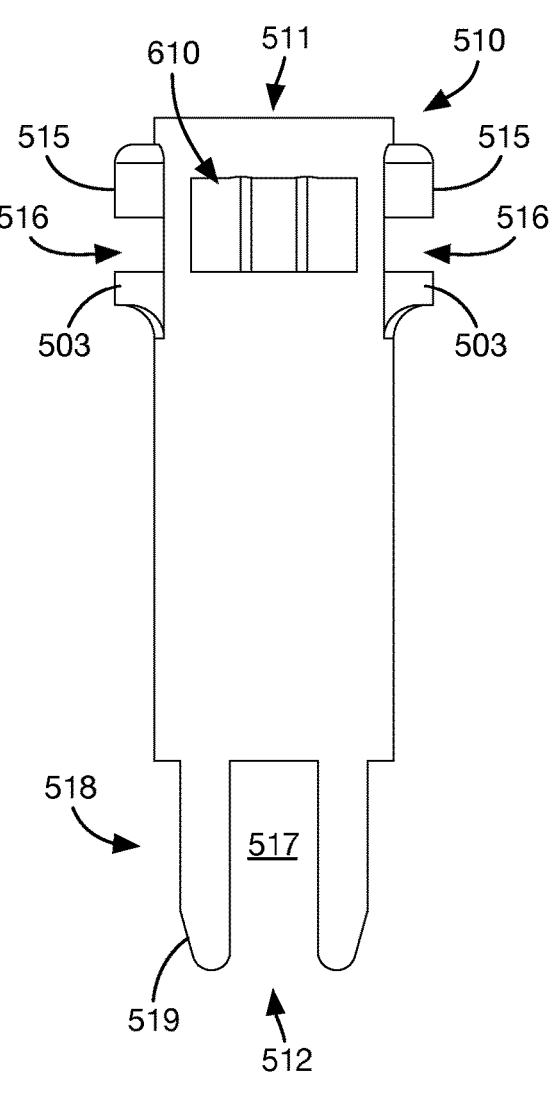
FIG. 91 shows a front view of the main shaft of FIG. 89.
Figure 92:
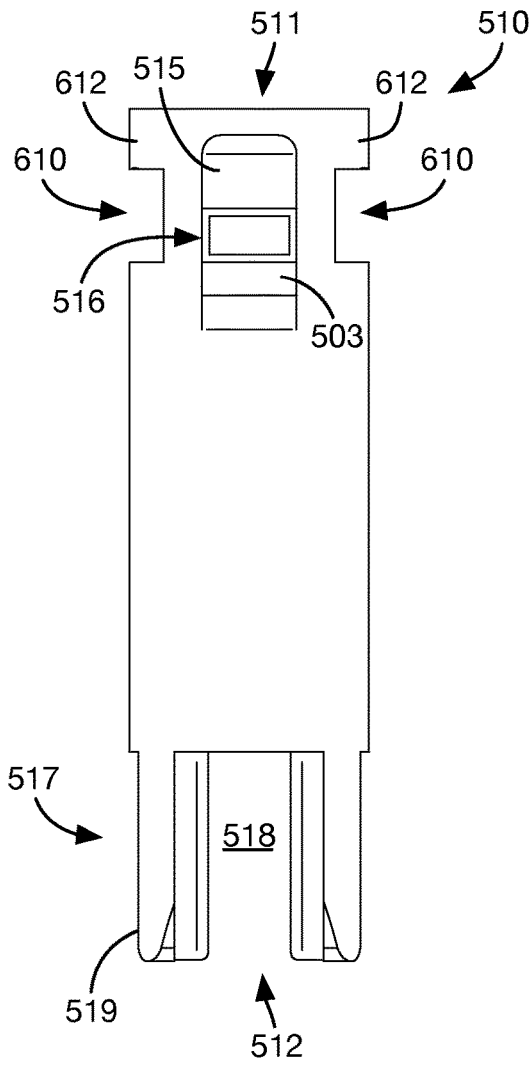
FIG. 92 shows a side view of the main shaft of FIG. 89.
Figure 93:
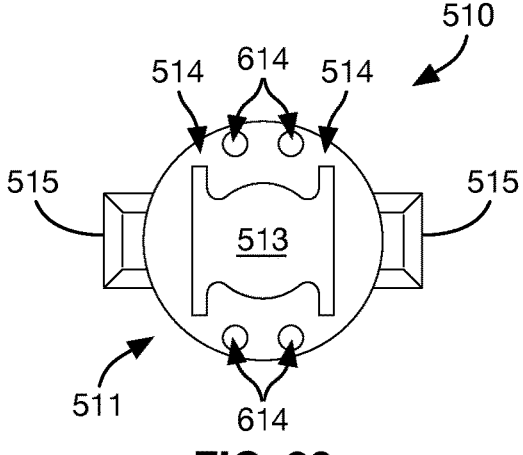
FIG. 93 shows a top view of the main shaft of FIG. 89.
Figure 94:
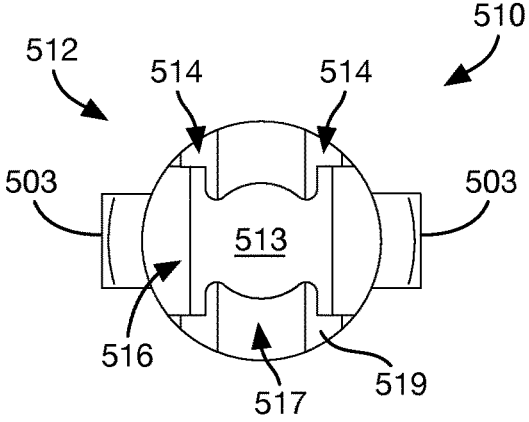
FIG. 94 shows a bottom view of the main shaft of FIG. 89.
Figure 95:
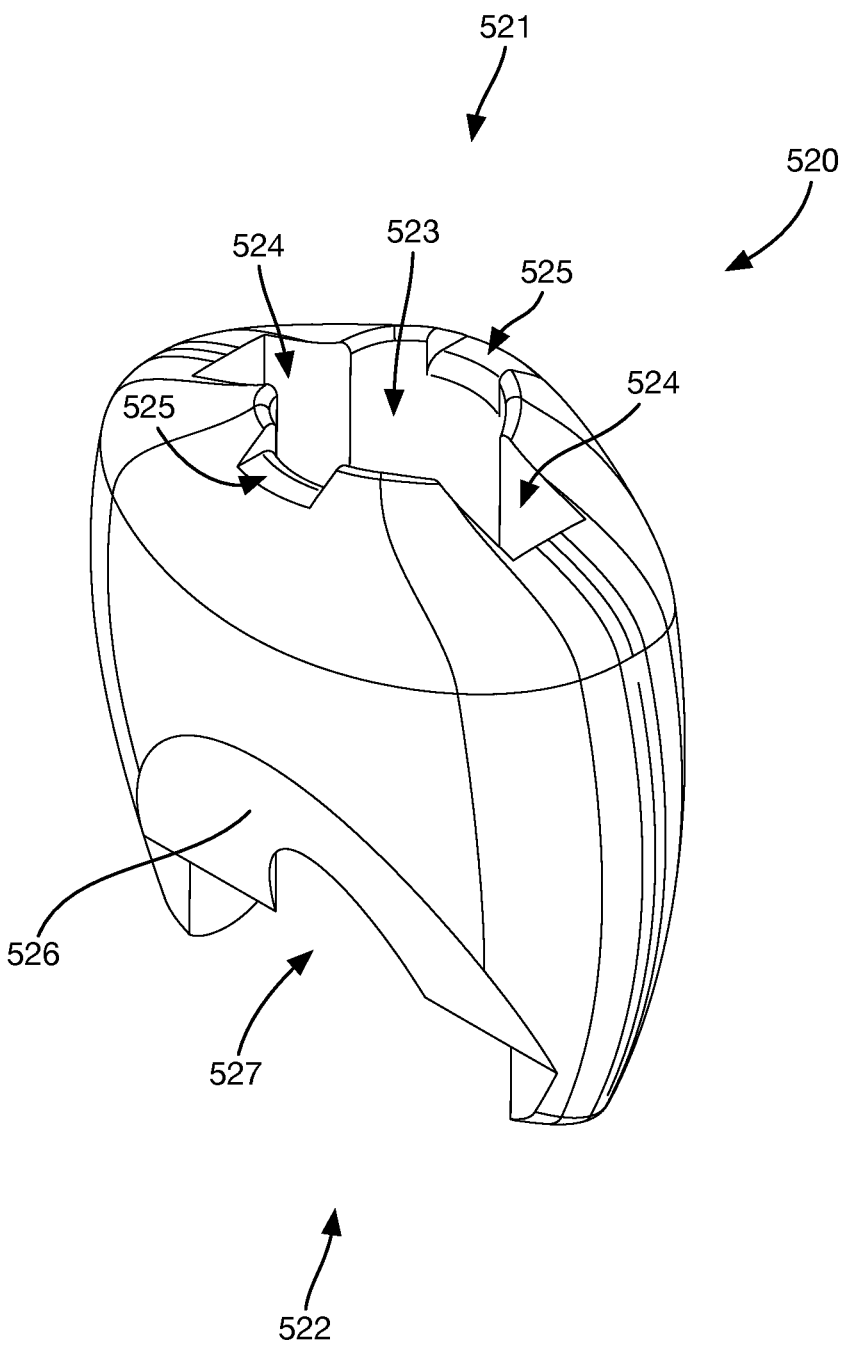
FIG. 95 shows a top perspective view of a coaption element of an example implantable device.
Figure 96:
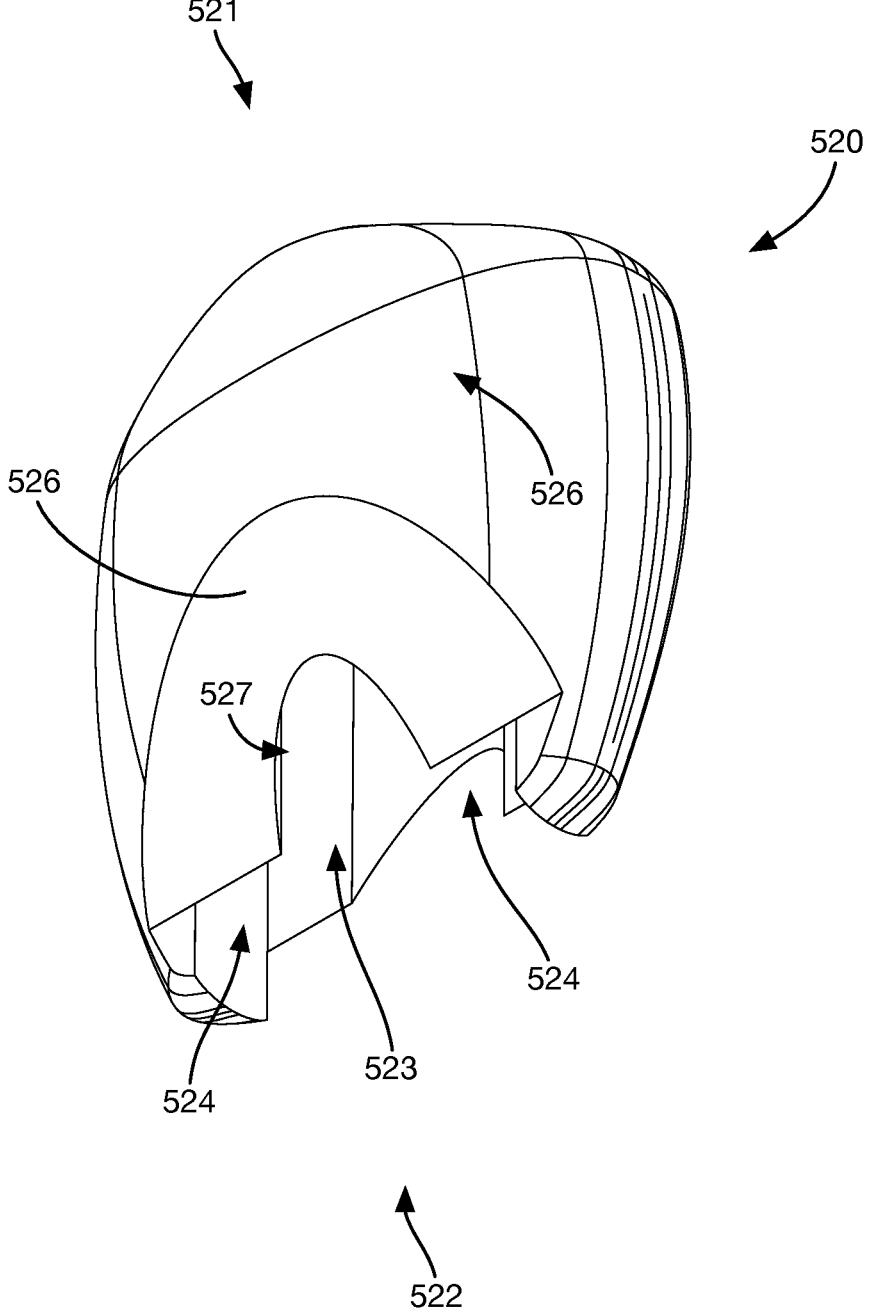
FIG. 96 shows a bottom perspective view of the coaption element of FIG. 95.
Figure 97:
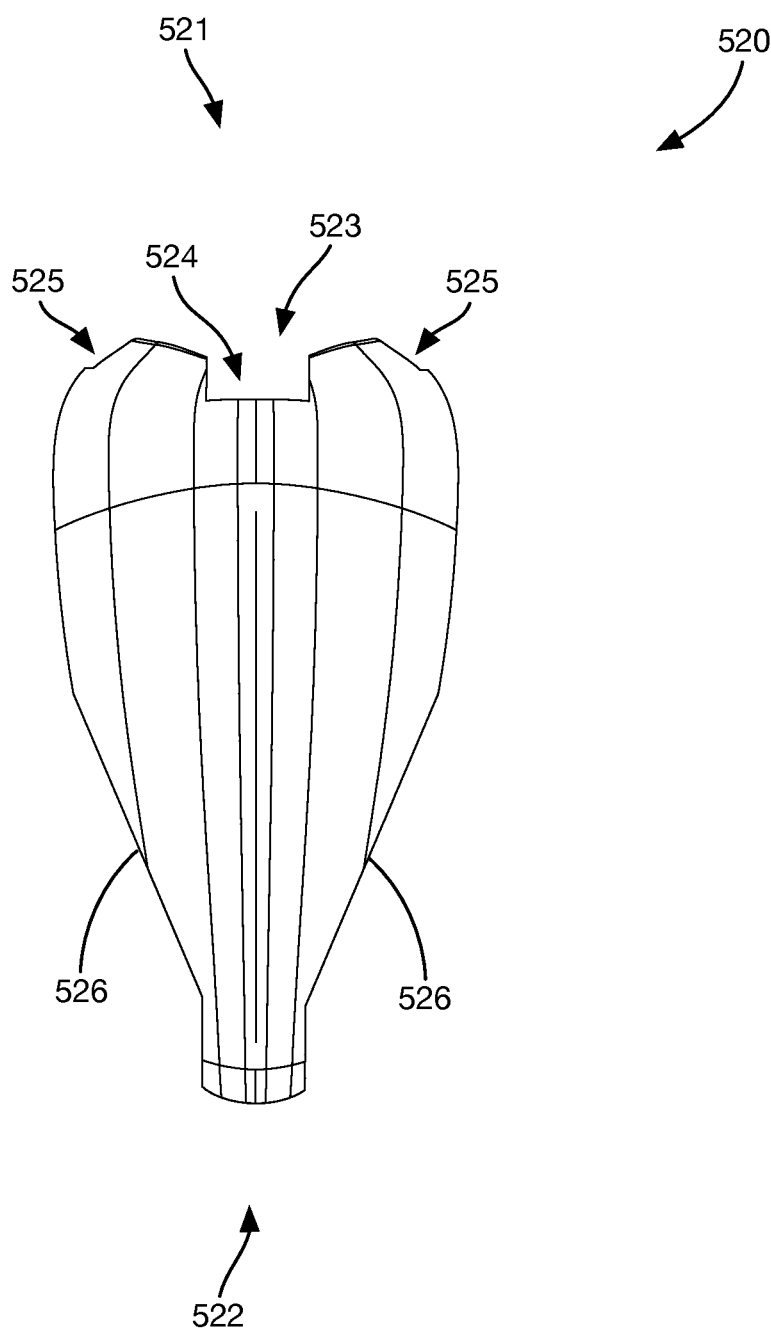
FIG. 97 shows a front view of the coaption element of FIG. 95.
Figure 98:
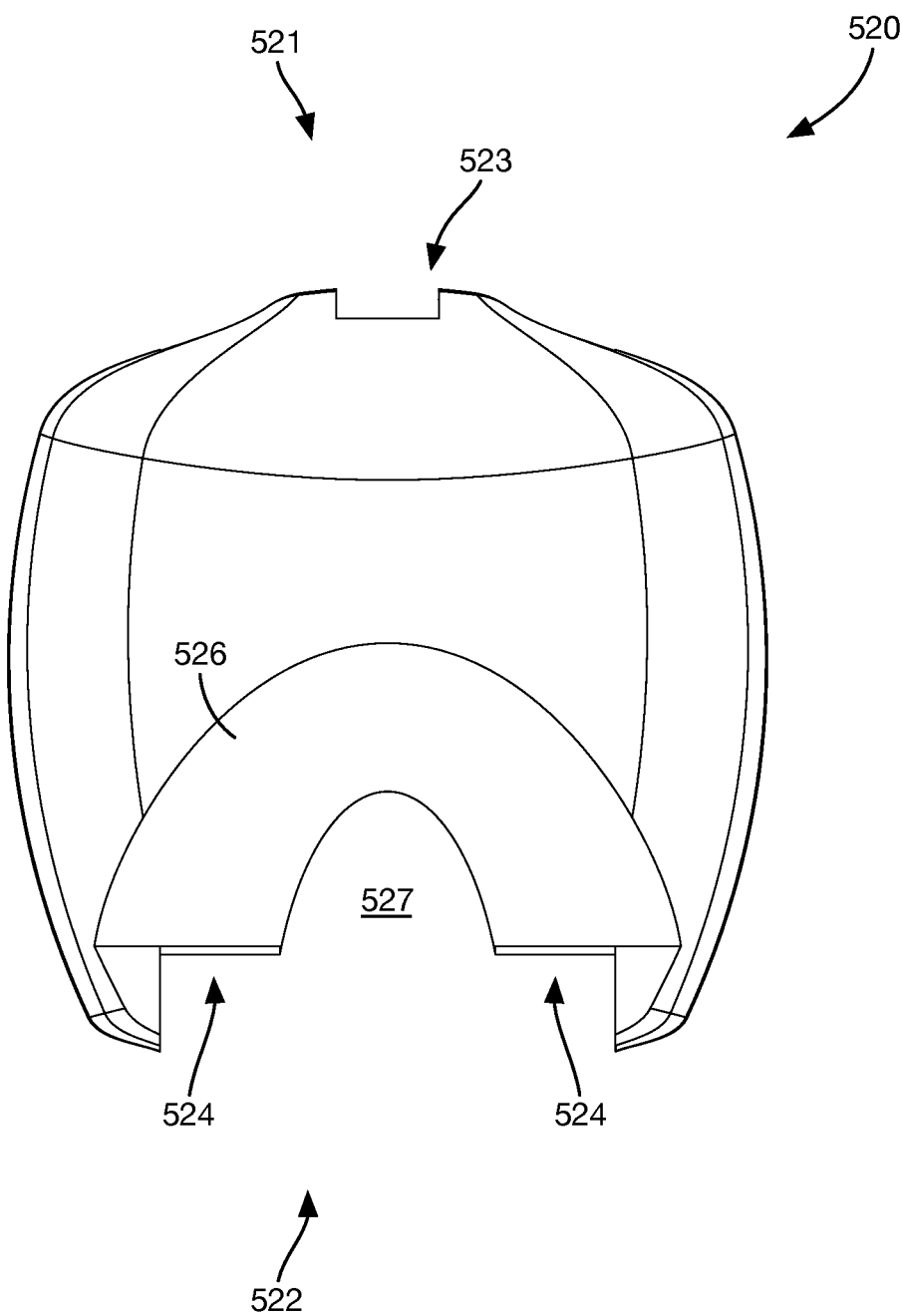
FIG. 98 shows a side view of the coaption element of FIG. 95.
Figure 99:
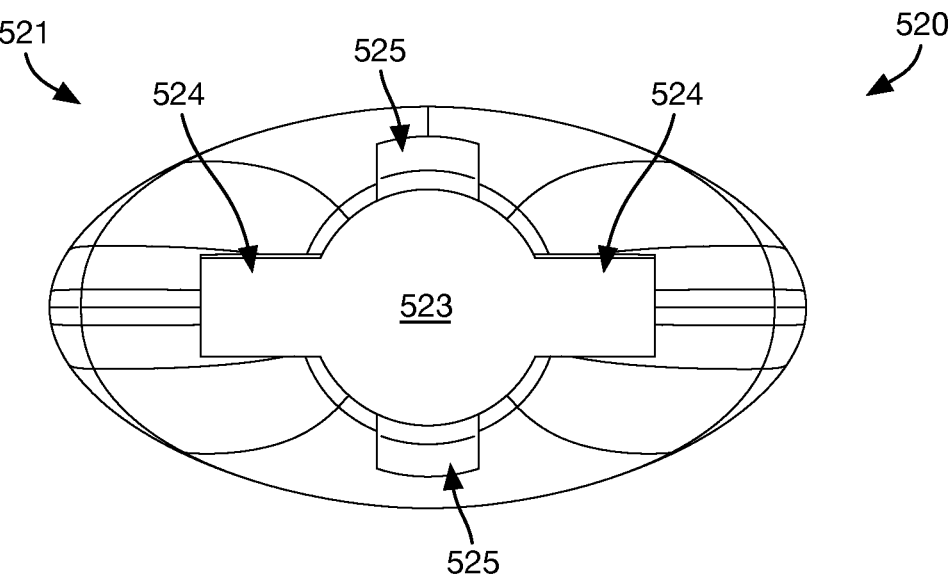
FIG. 99 shows a top view of the coaption element of FIG. 95.
Figure 100:
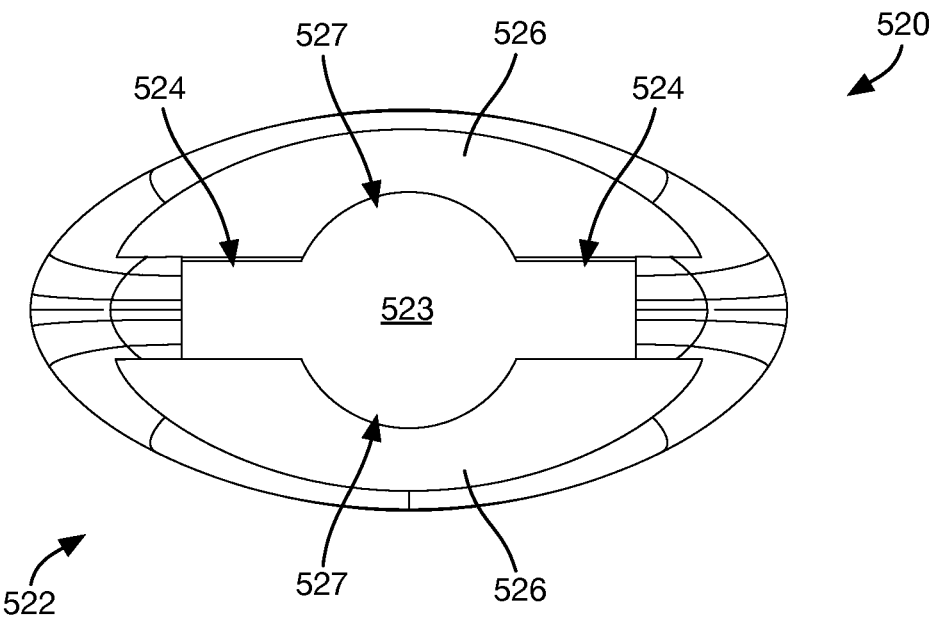
FIG. 100 shows a bottom view of the coaption element of FIG. 95.

Referring now to FIGS. 72-77, the implantable prosthetic device 500 is shown in a partially or approximately three-quarters extended position. Like the device 200 described above, the device 500 is capable of being actuated from closed, to partially open, to fully open, and any position in between, as the circumstance requires. The paddles 530 of the device 500 transition between the closed position shown in FIGS. 65-70 to the open position shown in FIGS. 72-80 upon extension of the actuation element 591 from a fully retracted or closed position to the three-quarter extended position. The implantable prosthetic device 500 is shown in FIGS. 78-80 with various components removed and the main shaft 510 and distal cap assembly 560 cutaway to better show how the paddles 530 connect to the other components to facilitate opening and closing the device 500.

Extending the actuation element 591 pulls down on distal ends 532 of the paddles 530 that are attached to the distal cap assembly 560. The paddles 530 include inner and outer paddle portions 538, 540. The paddle frames 570 are connected by a connector 579 (as shown schematically in the FIGS. 72-74) to the paddles 530 between the inner and outer paddle portions 538, 540 and also to the distal cap assembly 560. The connection 579 can take a wide variety of different forms. For example, the connection 579 can be to the inner paddle portion 538, to the outer paddle portion 540, or on a transition between the inner paddle portion and the outer paddle portion. Pulling down on the distal ends 532 pulls down on the outer paddle portions 540 and paddle frames 570. In turn, the outer paddle portions 540 and paddle frames 570 pull down on the inner paddle portions 538 that are connected to proximal attachment interfaces 533 that are fixedly attached to the main shaft 510. Because the main shaft 510 is held in place by the capture mechanism 592, the inner paddle portions 538 are caused to move, pivot, flex, etc. in an opening direction. When the actuation element 591 is extended sufficiently, the inner paddle portions 538, outer paddle portions 540, and paddle frames 570 all flex to the position shown in FIGS. 72-77. That is, opening the paddles 530 and frames 570 forms a gap 505 between the coaption element 520 and the inner paddle portions 538 that can receive the native leaflets 20, 22. This movement also exposes the barbed clasps 580 that can be moved between closed (FIG. 65) and open (FIG. 72) positions to form another gap 507 for grasping the native leaflets 20, 22. The extent of the gap 507 of the clasp 580 is limited to the extent that the inner paddle portion 538 has spread away from the coaption element 520.

Continuing to extend the actuation element 591 pulls down on the paddles 530 and paddle frames 570, thereby causing the inner paddle portions 538 to spread apart further from the coaption element 520. When fully extended, the outer paddle portions 540 and paddle frames 570 move to a position where they are close to the actuation element 591. In the fully extended position, the inner paddle portions 538 are open to an approximately 180-degree angle with the coaption element 520 (See FIGS. 36 and 37). The inner and outer paddle portions 538, 540 are stretched straight in the fully extended position to form an approximately 180-degree angle between the paddle portions 538, 540 (See FIGS. 36 and 37). The fully extended position of the device 500 provides the maximum size of the gap between the coaption element 520 and inner paddle portions 530, and, in some embodiments, allows clasps 580 to also open fully to approximately 180 degrees (e.g., FIG. 37) between the fixed and moveable arms 582, 584 of the clasp 580. The position of the device 500 is the longest and the narrowest configuration. Thus, the fully extended position of the implantable prosthetic device 500 can be the position for placement of the device in a delivery catheter, or the like, can be the position for initial deployment of the device in the atrium (See FIG. 38), and/or can be the position for bailout of the device 500 from an attempted implantation.

Configuring the implantable prosthetic spacer device 500 such that the anchors 508 can extend to a straight or approximately straight configuration (e.g. approximately 120-180 degrees relative to the coaption element 520) can provide several advantages. For example, this configuration can reduce the radial crimp profile of the prosthetic spacer device 500. It can also make it easier to grasp the native leaflets 20, 22 by providing a larger opening between the coaption element 520 and the inner paddle portions 538 in which to grasp the native leaflets 20, 22. Additionally, the relatively narrow, straight configuration can prevent or reduce the likelihood that the prosthetic spacer device 500 will become entangled in native anatomy (e.g., chordae tendineae CT shown in FIGS. 3 and 4) when positioning and/or retrieving the prosthetic spacer device 500 into the delivery system 590. The clasps can be fully open while the prosthetic spacer device is in the fully elongated position the facilitate disentanglement from the native anatomy.

The implantable prosthetic spacer device 500 is similar in many ways to the devices 200, 300 described above. Like the implantable prosthetic spacer device 200, the implantable prosthetic spacer device 500 can include a cover (not shown). In some embodiments, the cover can be disposed on the coaption member 520, the paddles 530, and/or the paddle frames 570. The cover can be configured to prevent or reduce blood-flow through the prosthetic spacer device 500 and/or to promote native tissue ingrowth. In some embodiments, the cover can be a cloth or fabric such as PET, velour, or other suitable fabric. In some embodiments, in lieu of or in addition to a fabric, the cover can include a coating (e.g., polymeric) that is applied to the implantable prosthetic spacer device 500. In some embodiments, in lieu of or in addition to a fabric, the coaption member cam be made from any of the cover materials described herein.

Referring to FIGS. 81-88, the implantable prosthetic device 500 is retained by a capture mechanism 592 of a delivery system 590. The capture mechanism 592 can be opened and/or closed in a variety of different ways. In one example embodiment, the capture mechanism is opened by retracting the actuation element, wire, or shaft 591. Moveable portions 594 of the capture mechanism 592 removably attach the main shaft 510 to the delivery system 590. Referring to FIGS. 81, 83, 85, and 87, in the illustrated embodiment, the capture mechanism 592 is held closed around the main shaft 510 by the actuation element 591. For example, the actuation element can engage eyelets or other structures that are attached to the insides of the moveable portions 594 to hold the moveable portions closed. Referring to FIGS. 82, 84, 86, and 88, removal of the actuation element 591 in a removal direction 593 allows the moveable portions 594 of the capture mechanism 592 to spring open in an opening direction 597 and release the main shaft 510 to decouple the capture mechanism 592 from the implantable prosthetic device 500 after the device 500 has been successfully implanted. The movable portions 594 include openings 595 that receive portions of attachment projections 515 near the proximal end 512 of the main shaft 510.

Referring now to FIGS. 89-94, various views of the central or main shaft 510 are shown with the main shaft 510 separate from other components of the implantable prosthetic device 500. The main shaft 510 extends from a first or proximal end 511 to a second or distal end 512. A central opening 513 extends through the main shaft 510 from the proximal end 511 to the distal end 512. The central opening 513 has a round shape for receiving and sliding along the optional spreading member 550 and the actuation element 591. Parallel paddle slots 514 extend opposite each other from the proximal end 511 to the distal end 512 for receiving the ribbon paddles 530. The paddle slots 514 can be open to the central opening 513 to form a larger and irregularly shaped central opening 513 that can be formed in a single manufacturing operation. Pairs of spacer connection projections 503 and delivery attachment projections 515 extend outward from opposite sides of the main shaft 510 near the proximal end 511. A gap 516 between each pair of spacer connection projections 503 and attachment projections 515 can be shaped to receive at least part of the moveable portion 594 of the attachment mechanism 592. The gap is sized so that at least a portion of the attachment projections 515 protrude into openings 595 of the moveable portion 594.

A first cam slot 517 extends from the front to back of the main shaft 510 between the paddle slots 514 and has a width that is about the same or slightly larger than a width of cam portions 556 of the spreading member 550. The first slot 517 receives cam portions 556 of the spreading member 550 when the spreading member 550 is in a stowed position and orientation. A second cam slot 518 extends from the distal end 512 on each side of the main shaft 510 to intersect with the paddle slots 514. The second cam slot 518 is orthogonal to the first cam slot 517 and is narrower in near the middle of the main shaft 510—having a width approximately the same as the first cam slot 517—and spreads out to the width of the paddle slots 514 to provide room for the paddles 530 to open and spread apart. The second cam slot 518 receives the cam portions 556 of the spreading member 550 when the spreading member 550 is in a deployed position and orientation. The first and second cam slots 517, 518 receive cam portions 556 of the spreading member 550 when the spreading member 550 is retracted into the main shaft 510 to fully close the implantable prosthetic device 500. Distal projections 519 extend between the first and second cam slots 517, 518 to engage the cam portions 556 and to restrict the rotation of the spreading member 550 between the active and inactive rotational positions.

Still referring to FIGS. 89-94, the optional cutouts 610 form optional flanges 612 at the proximal end 511 of the central shaft. Optional recapture tether passages 614 extend through the flanges 612. Optional recapture tethers can be routed through the passages 614 to allow the device to be recaptured after an initially unsuccessful deployment.

Still referring to FIGS. 89-94, the main shaft 510 can be made from a wide variety of different materials. For example, the main shaft can be made of plastic, such as PET, PTFE, ePTFE, metal, foam, fabric, braided material, etc.

Referring now to FIGS. 95-100, various views of the coaption member or element 520 are shown with the coaption element 520 separate from other components of the implantable prosthetic device 500. The coaption element 520 extends from a proximal end 521 to a distal end 522 and has a generally elongated and round shape. In particular, the coaption element 520 has an elliptical shape or cross-section when viewed from above (FIG. 99) and has a tapered shape or cross-section when seen from a front view (e.g., FIG. 97) and a round shape or cross-section when seen from a side view (e.g., FIG. 98). A blend of these three geometries can result in the three-dimensional shape of the illustrated coaption element 520 that achieves the benefits described herein. To adequately fill the gap 26 between the leaflets 20, 22, the device 500 and the components thereof can have a wide variety of different shapes and sizes. For example, the paddles 530 and paddle frames 570 can be configured to conform to the shape or geometry of the coaption element 520 as is shown in FIGS. 50-54. With regards to the device 500, the round shape of the coaption element 520 can be seen, when viewed from above, to substantially follow or be close to the shape of the paddle frames 570.

The size of the coaption element 520 can be selected to minimize the number of implants that a single patient will require (preferably one), while at the same time maintaining low transvalvular gradients. In one example embodiment, the anterior-posterior distance at the top of the spacer is about 5 mm, and the medial-lateral distance of the spacer at its widest is about 10 mm. In one example embodiment, the overall geometry of the separate coaption element 520 can be based on these two dimensions and the overall shape strategy described above. It should be readily apparent that the use of other anterior-posterior distance anterior-posterior distance and medial-lateral distance as starting points for the device will result in a coaption element 520 having different dimensions. Further, using other dimensions and the shape strategy described above will also result in a coaption element 520 having different dimensions.

A central opening 523 extends through the coaption member 520 from the proximal end 521 to the distal end 522. The central opening 523 has a diameter that is about the same or is slightly larger than a diameter of the main shaft 510 so that the main shaft 510 can be received within the central opening 523 of the coaption element 520. The central opening 523 includes assembly slots or grooves 524 that run along the full length of the central opening 523. The assembly grooves 524 allow the coaption element 520 to slide over the projections 503, 515 during assembly to the main shaft 510 from the proximal end 511, as shown in FIGS. 101-105, which are described below. The assembly grooves 524 are also wide and long enough to receive the cam portions 556 of the spreading member 550 so that the spreading member 550 can be fully retracted in the proximal direction without interfering with the coaption element 520. Engagement or locking recesses 525 are arranged in the proximal end 521 of the coaption element 520 at about a 90-degree offset from the assembly grooves 524. The locking recesses 525 receive the distal end of the projections 503 of the main shaft 510 to complete assembly of the coaption element 520 to the main shaft 510 to "lock" the two components together by prohibiting rotation of the coaption element 520. The distal end 522 of the coaption element 520 includes tapered cuts 526 that intersect the central opening 523 to form a rounded slot or clearance opening 527 that is orthogonal to the assembly grooves 524 and runs through the coaption element from side-to-side. The tapered cuts 526 provide the coaption element 520 with the tapered shape described above, and the clearance opening 527 provides room for the paddles 530 and the spreading member 550, as shown in FIGS. 155-168, which are described below.

In some embodiments, the coaption element 520 is a solid or hollow body instead of being formed from a braided material. Forming the coaption element 520 as a or hollow or solid body also enables the coaption element 520 to be formed by injection molding, casting, machining, additive manufacturing, such as 3D printing, or the like rather than being braided out of strands of material. The coaption element 520 can be formed from any suitable material for use in the human body, such as, for example, various plastics, rubber, foam, and/or metal materials. Forming the coaption element 520 with a molding process also facilitates the creation of custom shaped coaption elements 520 based on the heart anatomy of a particular patient. In some cases, the coaption element 520 can also be removed and replaced with a different coaption element 520 having a different size or shape. In one example embodiment, additive manufacturing techniques are used to form a custom-shaped coaption element that is shaped according to scans of the native anatomy of the patient that will receive the implant. The additive manufacturing techniques, such as 3D printing, allow a custom-shaped coaption element to be produced quickly, even intraoperatively, based on images of the patient. The coaption element 520 can also be made, shaped, or otherwise configured to be compressible. The coaption element 520 can be made to be compressible in a wide variety of ways, such as the ways described below.

Referring now to FIGS. 101-105, the steps to assemble the coaption element 520 to the main shaft 510 of the implantable prosthetic device 500 are shown. When the implantable prosthetic device 500 is fully assembled, the paddles 530 will extend from the distal end 512 of the main shaft 510 thereby preventing the coaption element 520 from being assembled from the distal end 512 of the main shaft. Thus, assembly of the coaption element 520 to the main shaft 510 is accomplished by placing the distal end of the coaption element 520 over the proximal end 511 of the shaft 510.

Figure 102:
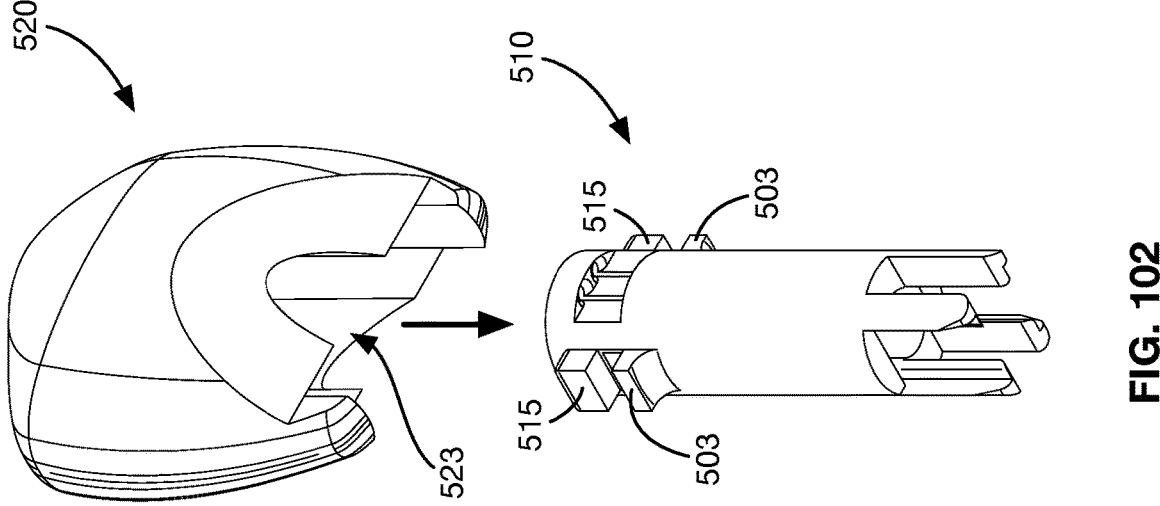
FIGS. 101-105 show the assembly of an example coaption element and main shaft.
Figure 101:
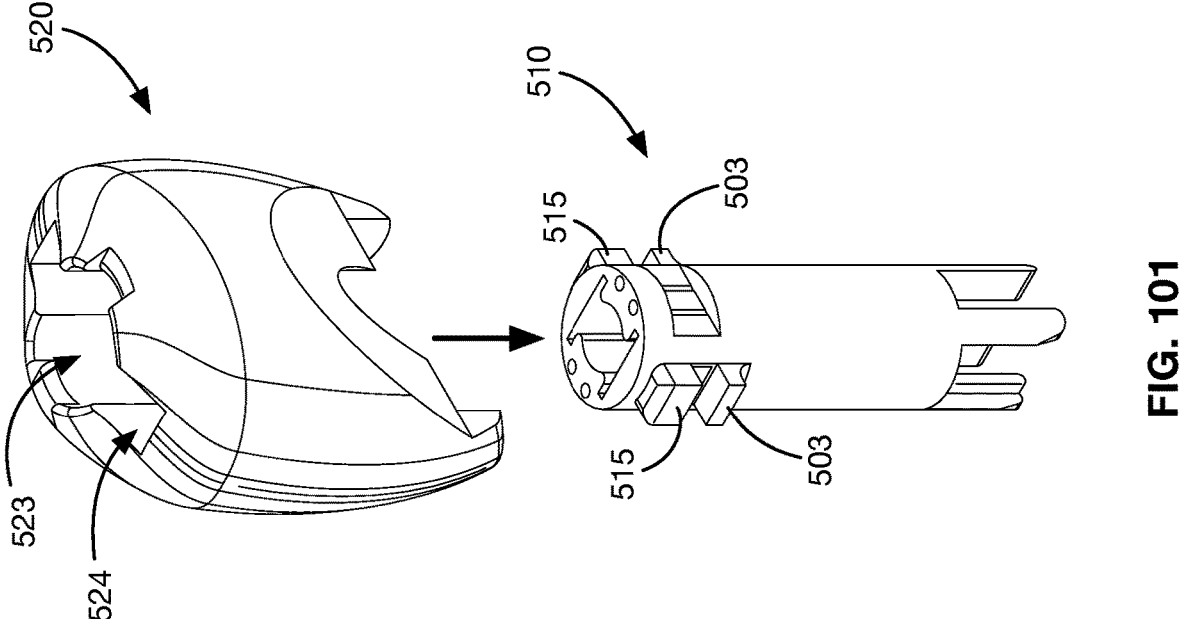
Figures 103, 104, 105:
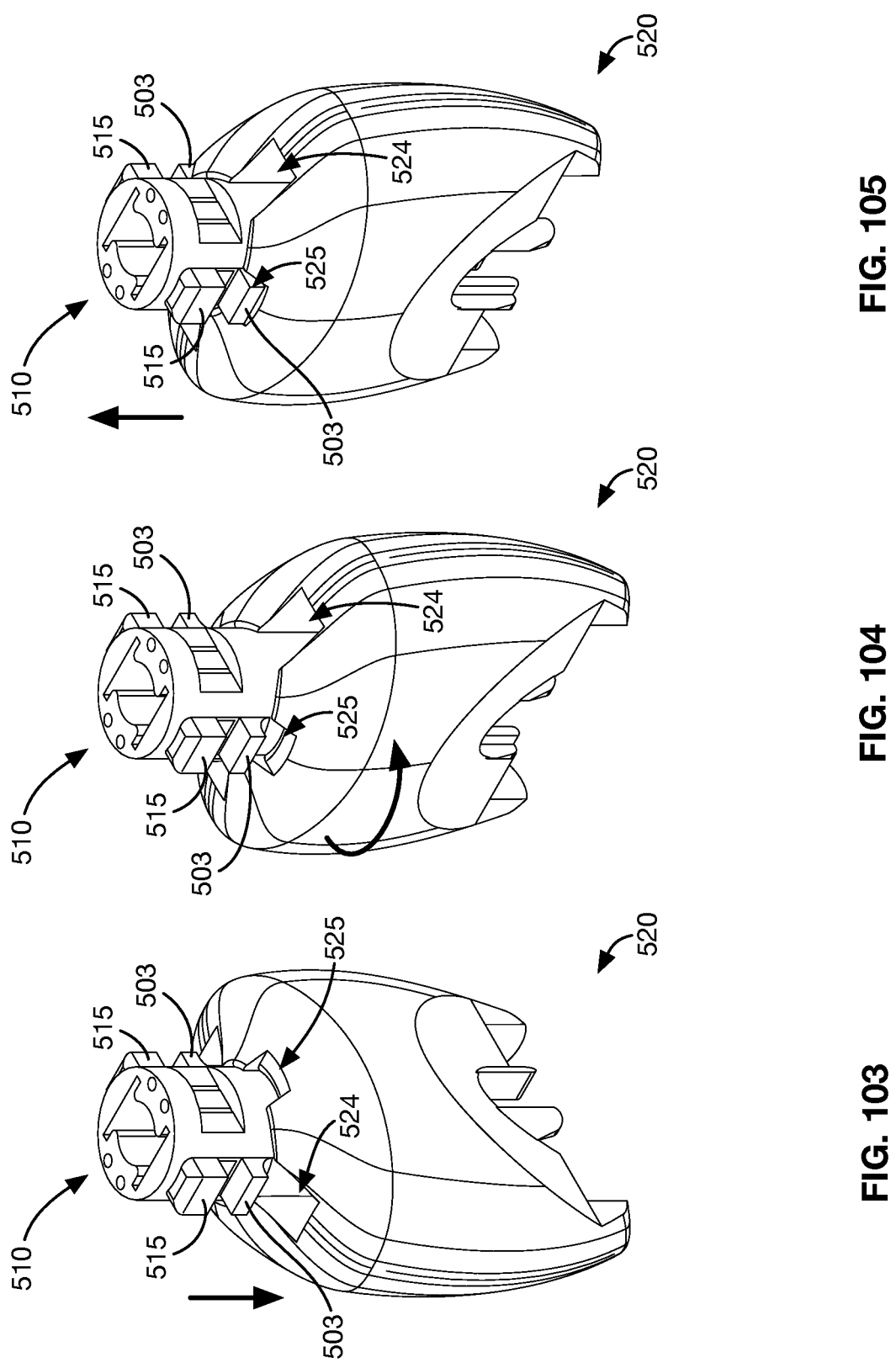
Figure 106:
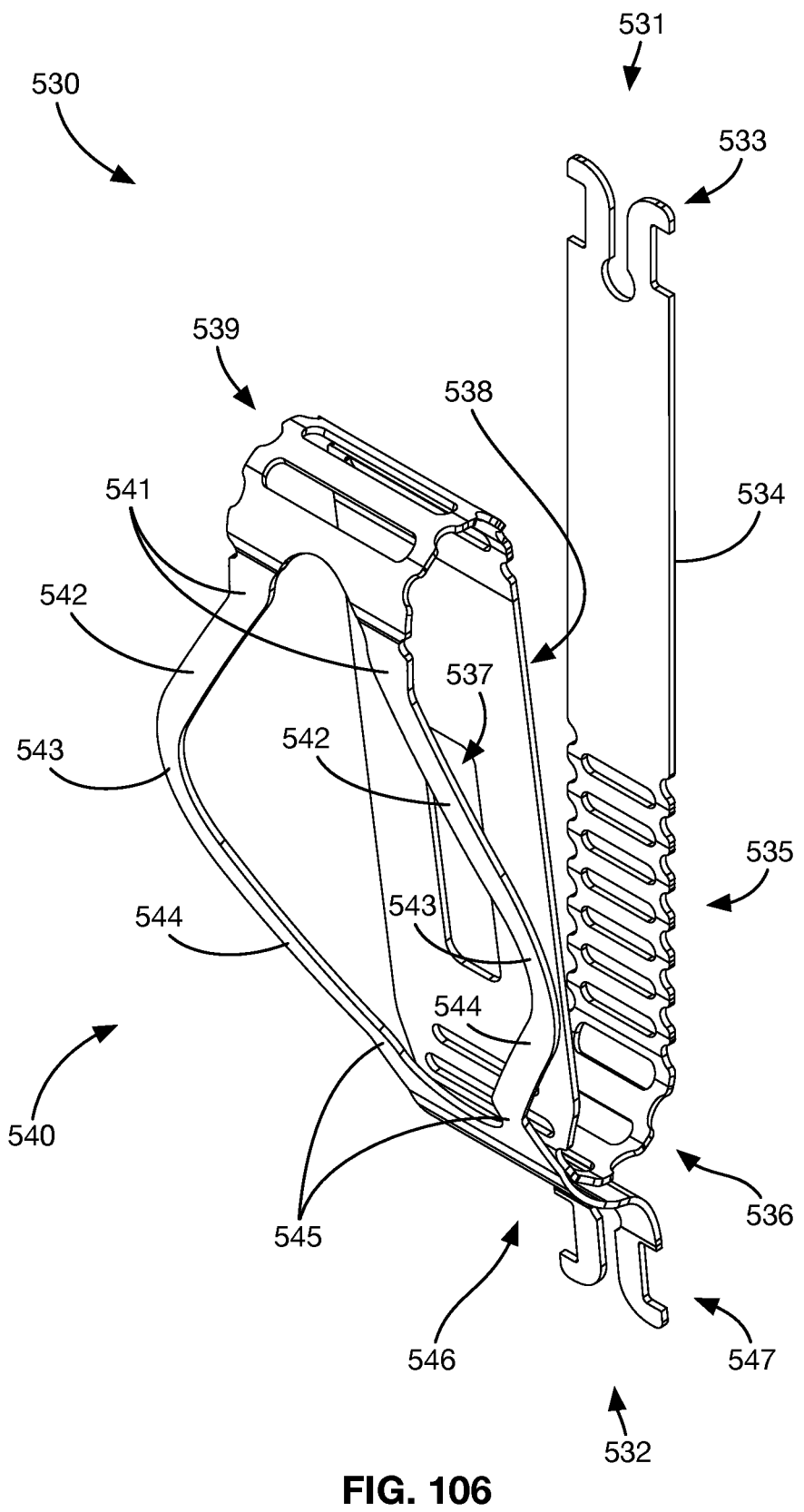
FIG. 106 shows a top perspective view of a paddle of an example implantable prosthetic device.
Figure 107:
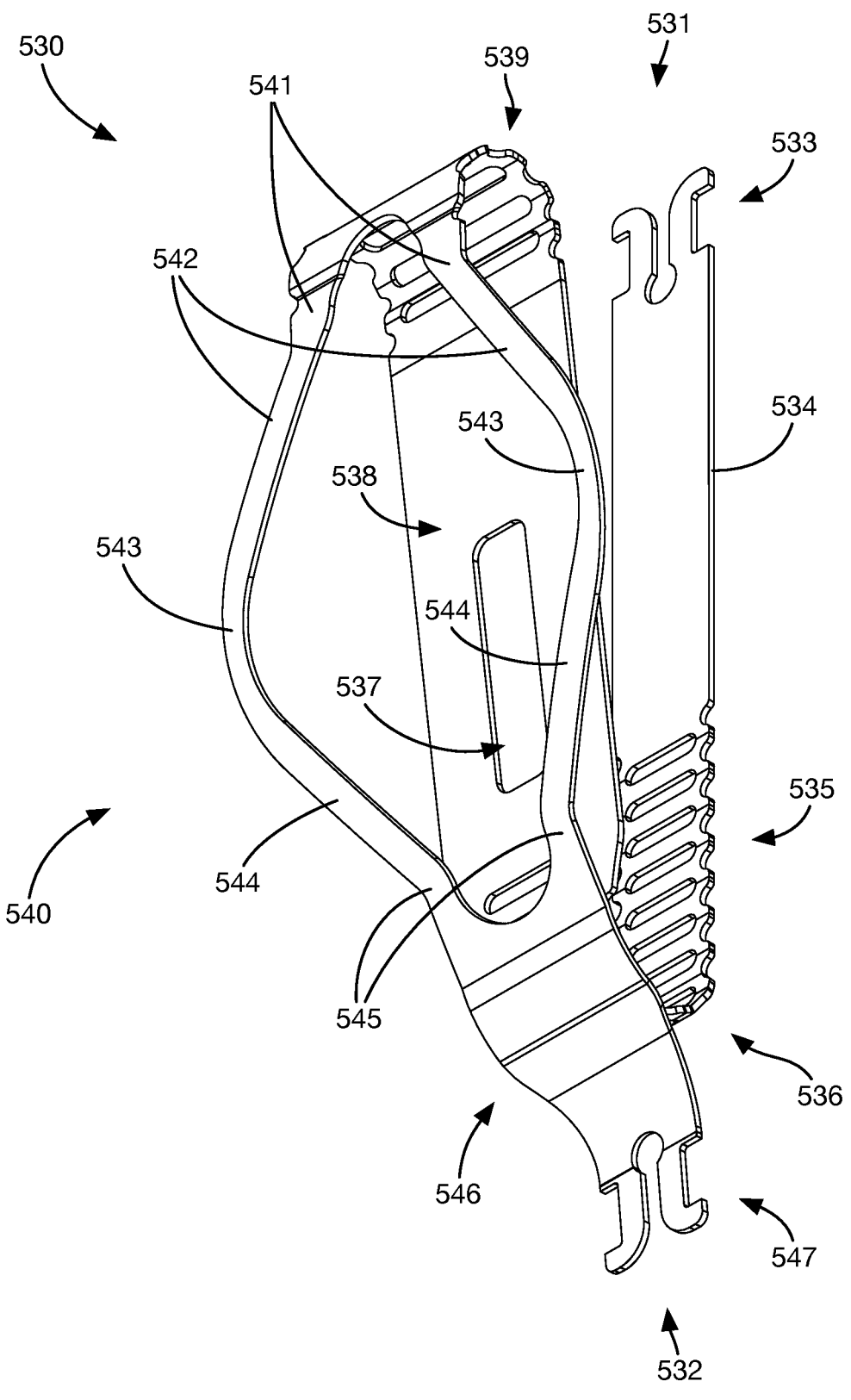
FIG. 107 shows a bottom perspective view of the paddle of FIG. 106.
Figures 108, 109, 110, 111, 112:
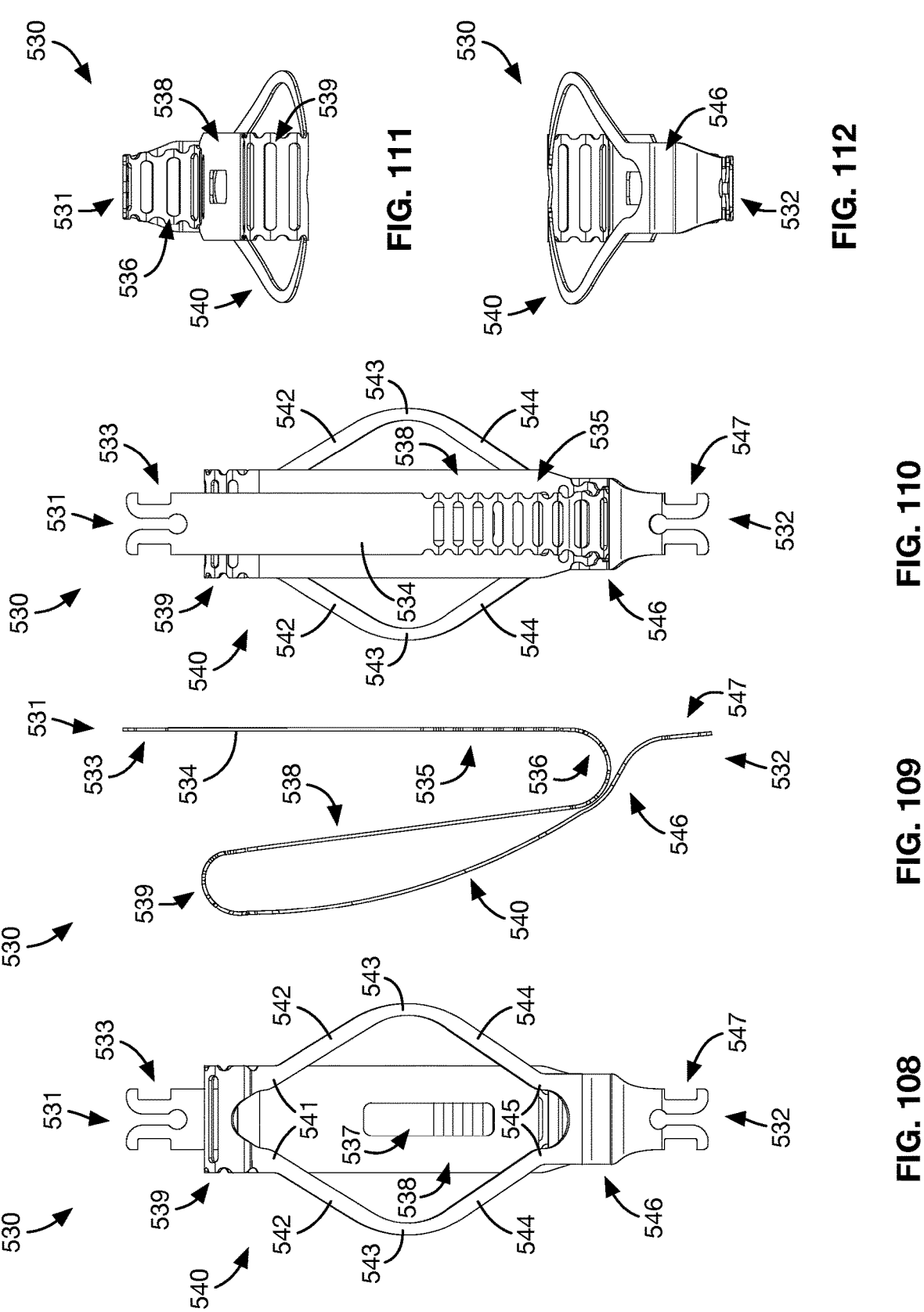
FIG. 108 shows a left side view of the paddle of FIG. 106.
FIG. 109 shows a front view of the paddle of FIG. 106.
FIG. 110 shows a right-side view of the paddle of FIG. 106.
FIG. 111 shows a top view of the paddle of FIG. 106.
FIG. 112 shows a bottom view of the paddle of FIG. 106.
Figures 113, 114:
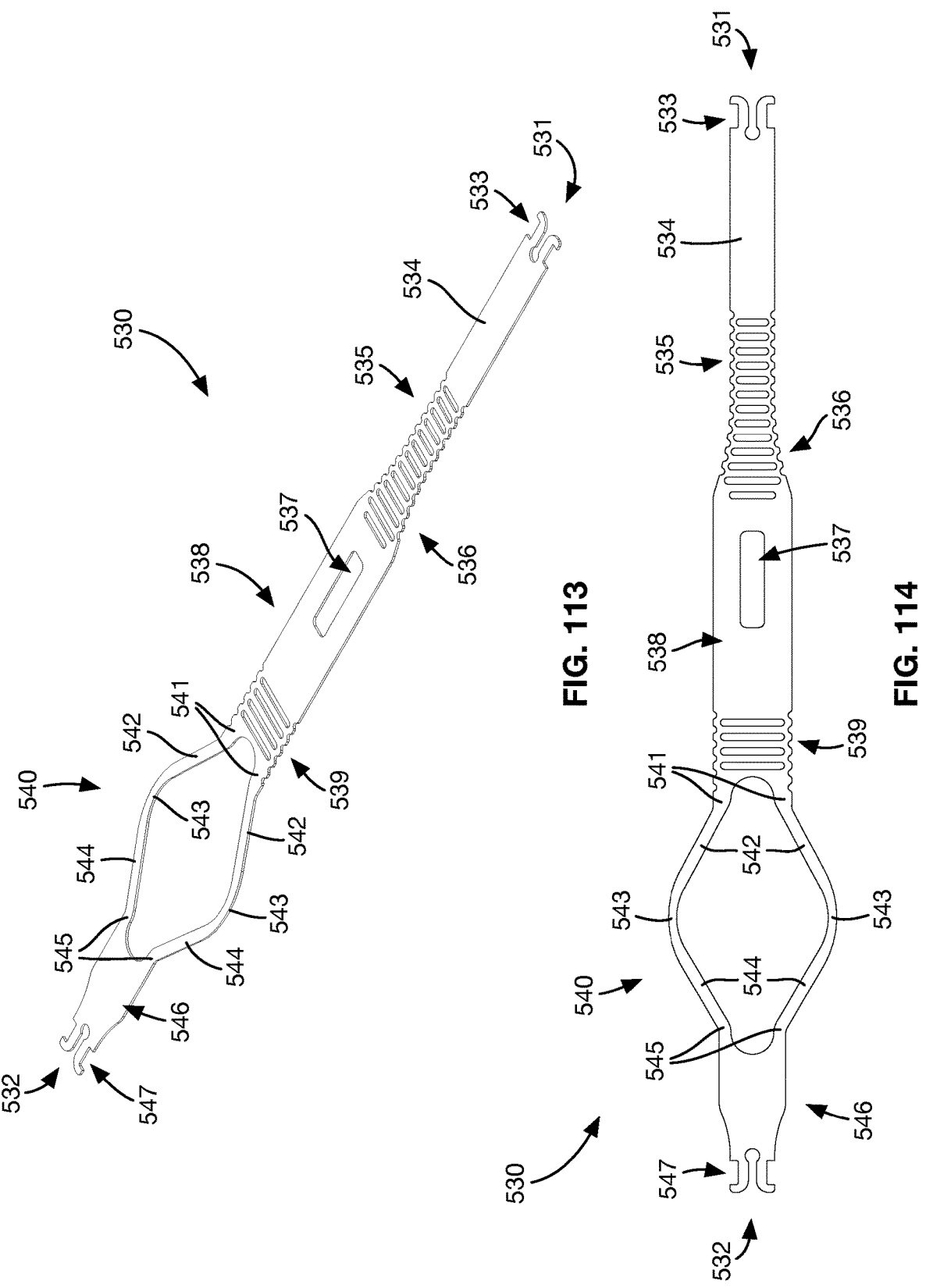
FIGS. 113-114 show the paddle of FIG. 106 laser cut from a flat sheet of material.
Figure 115:
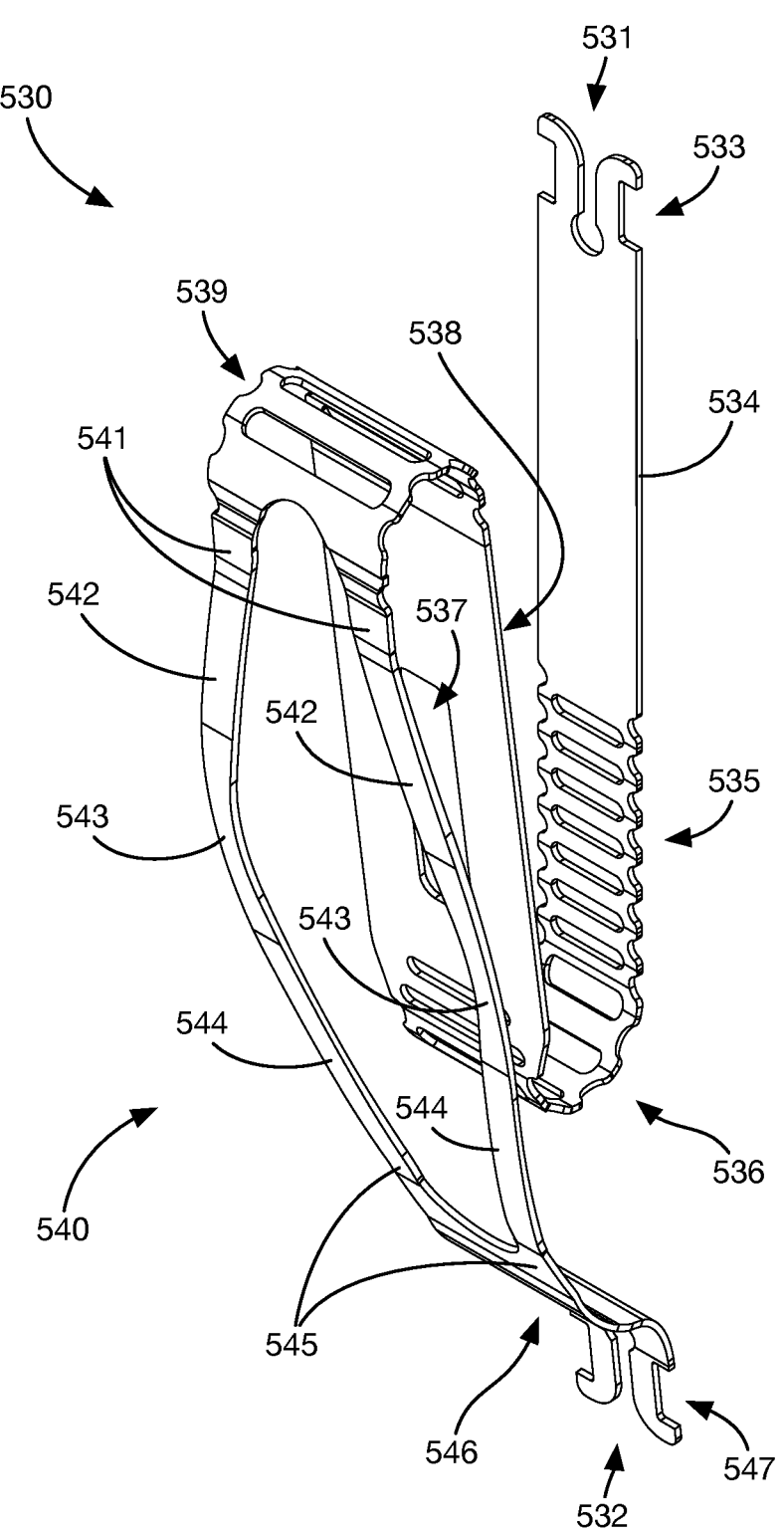
FIG. 115 shows a top perspective view of a paddle of an example implantable prosthetic device.
Figure 116:
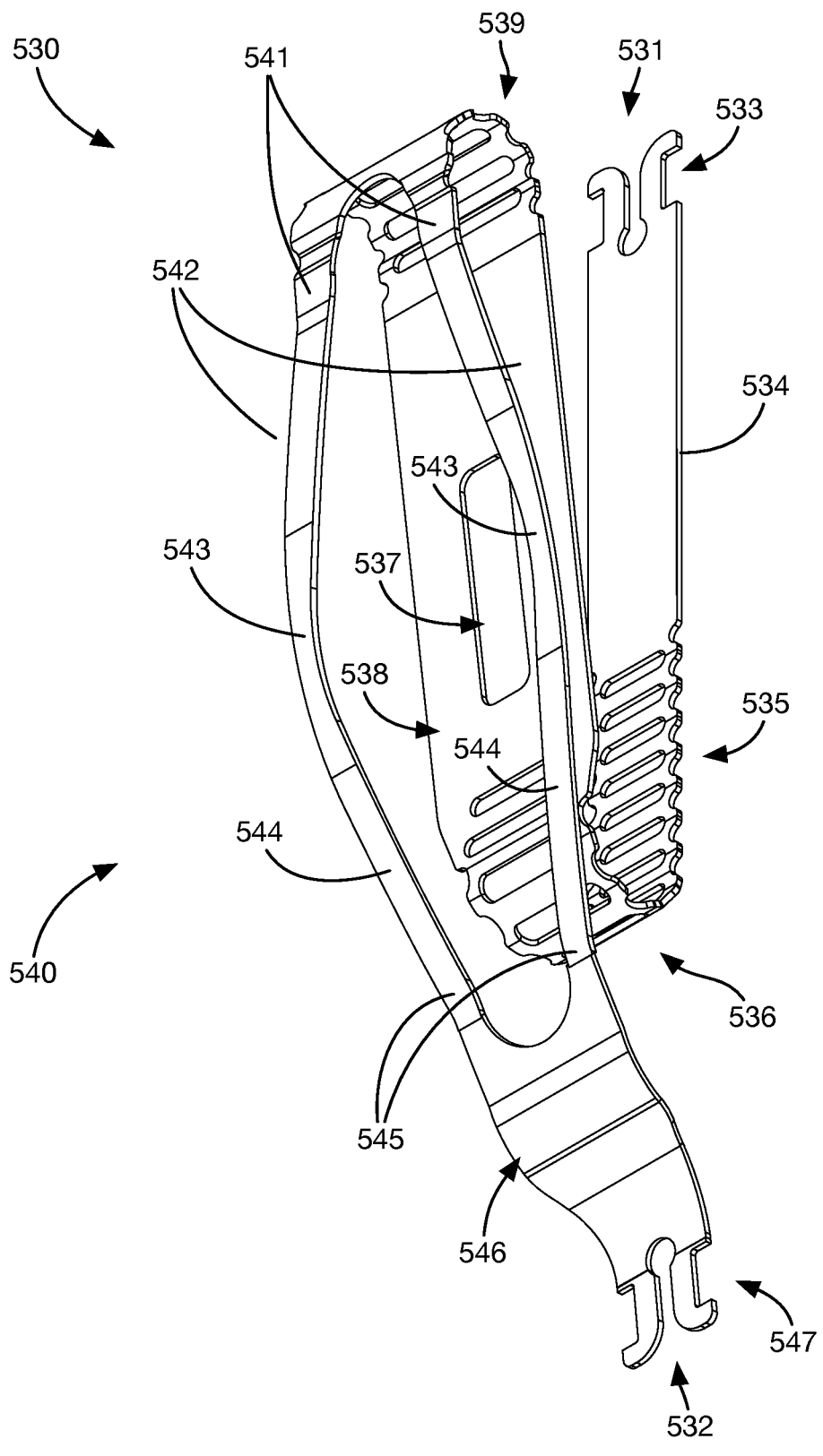
FIG. 116 shows a bottom perspective view of the paddle of FIG. 106.
Figures 117, 118, 119, 120, 121:
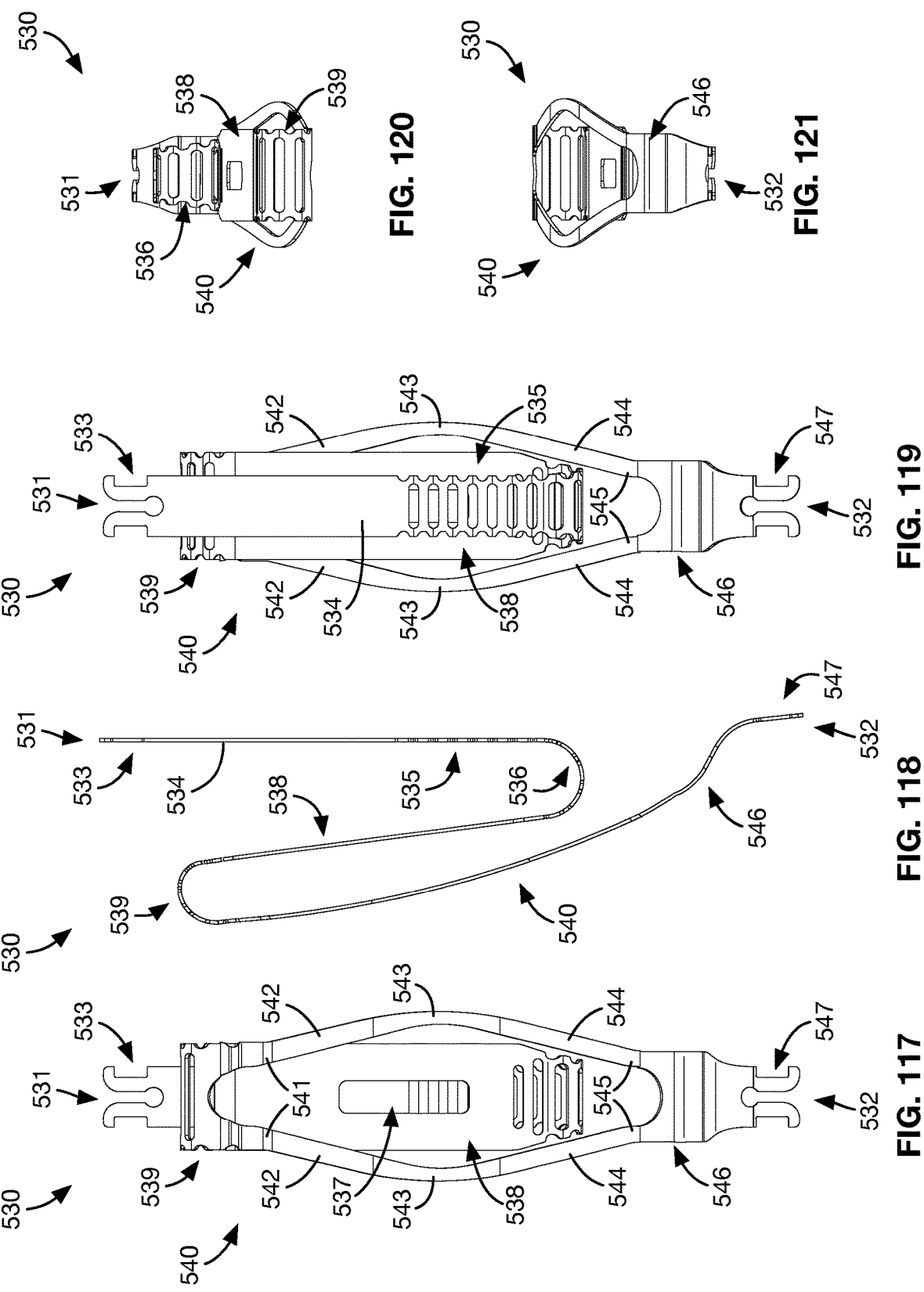
FIG. 117 shows a left side view of the paddle of FIG. 106.
FIG. 118 shows a front view of the paddle of FIG. 106.
FIG. 119 shows a right-side view of the paddle of FIG. 106.
FIG. 120 shows a top view of the paddle of FIG. 106.
FIG. 121 shows a bottom view of the paddle of FIG. 106.
Figures 122, 123, 124, 125, 126, 127:
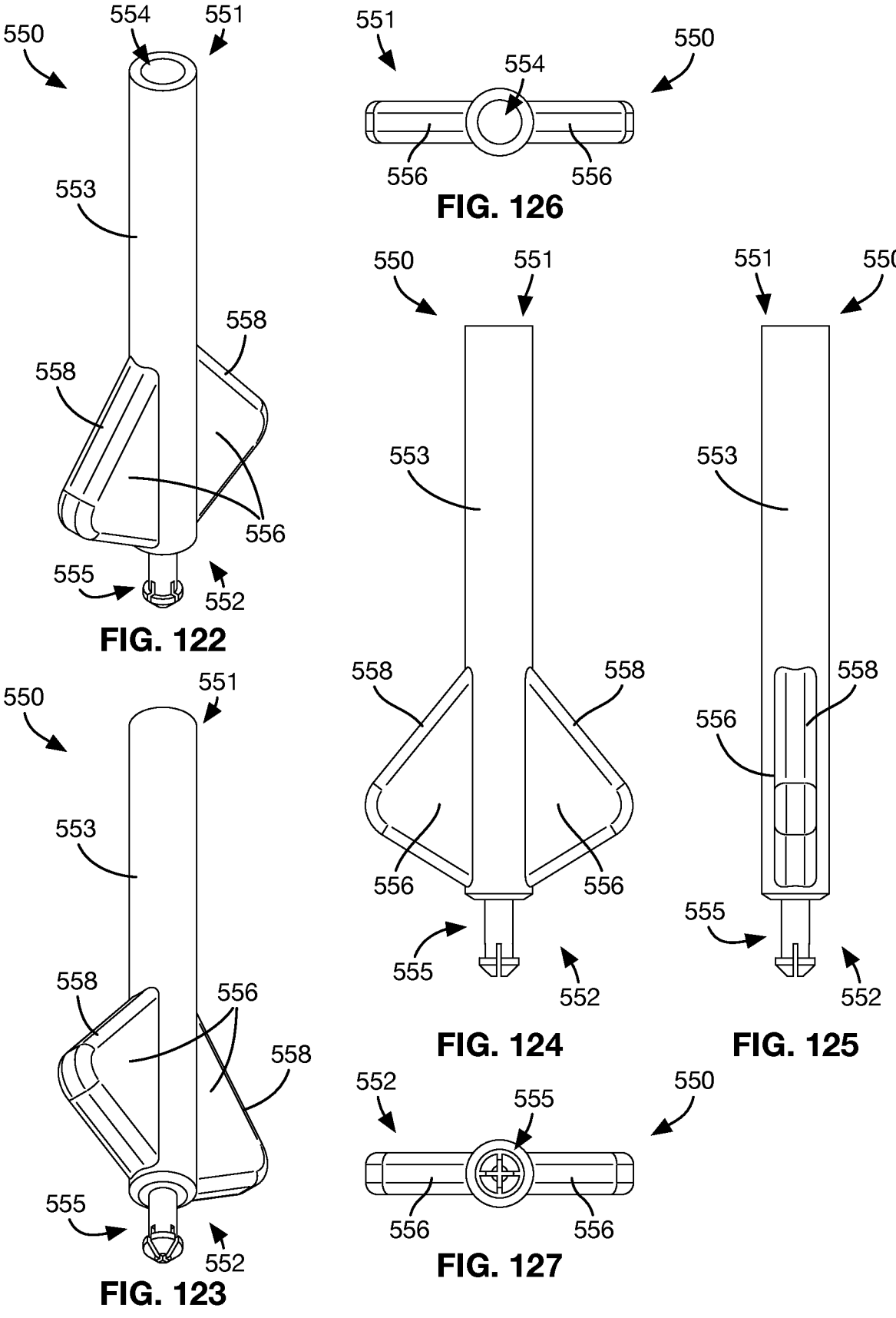
FIG. 122 shows a top perspective view of a spreading member of an example implantable device.
FIG. 123 shows a bottom perspective view of the spreading member of FIG. 122.
FIG. 124 shows a side view of the spreading member of FIG. 122.
FIG. 125 shows a front view of the spreading member of FIG. 122.
FIG. 126 shows a top view of the spreading member of FIG. 122.
FIG. 127 shows a bottom view of the spreading member of FIG. 122.

In some embodiments, as can be seen in FIGS. 101 and 102, prior to assembly the coaption element 520 is arranged at the proximal end 511 of the main shaft 510 and is oriented so that the assembly grooves 524 of the coaption element 520 align with the attachment projections 515 of the main shaft 510. The coaption element 520 is then moved downward onto the main shaft 510 until the proximal end 521 of the coaption element 520 is below the distal end of the attachment projections 515 as can be seen in FIG. 103. Now looking to FIG. 104, the coaption element 520 is then rotated 90 degrees until the engagement recesses 525 are aligned with the attachment projections 503. Finally, the coaption element 520 is moved in a proximal direction so that the distal ends of the attachment projections 503 are inserted into the engagement recesses 525 of the coaption element 520. Optionally, the attachment projections 503 can latch into or otherwise be secured or locked in the engagement recesses to prevent disassembly of the main shaft 510 from the coaption element.

Assembly of the coaption element 520 to the main shaft 510 can be performed prior to implantation or during the implantation process. Such as, for example, once the native leaflets 20, 22 have been captured by the clasps 580 but the paddles 530 are not yet closed. In some embodiments, the coaption element 520 can be removed after implantation and replaced with a new coaption element 520. A re-capture system (not shown) could be used to re-capture an already implanted device 500 which could then be opened, the coaption element removed while the implanted device remains attached to the native valve leaflets, a new coaption element would be installed, and then the device would be closed around the new coaption element.

A wide variety of different connection arrangements can be used to connect the coaption element 520 to the main shaft 510. The illustrated quarter turn connection mechanism is just one of the many connection arrangements that can be used. The illustrated quarter-turn locking mechanism used to join the coaption element 520 to the main shaft 510 allows different coaption elements 520 to be interchanged rapidly. Quick changeover between different coaption elements 520 can enable the physician to adapt to new information learned during the implantation procedure. For example, it may turn out that the size or shape of the gap 26 in the native valve, e.g., native mitral valve, is different than expected or has changed and now requires a different size spacer device than initially planned. Providing the physician with a package or kit containing different size and shape coaption elements 520 along with the implantable prosthetic device 500 allows the physician to choose which size or shape coaption element 520 is needed based on all available information. Or, one or more custom molded coaption elements 520 can also be planned for in advance and provided along with the device 500 so that the fit of each can be tested. Rather than making entire devices having different sized coaption portions, a single implantable prosthetic device 500 can be configured with any number of coaption elements 520 having a wide variety of sizes and shapes thereby improving the fit of the implanted device and reducing manufacturing costs.

Referring now to FIGS. 106-121, various views of one of the pair of paddles 530 are shown with the paddle 530 separate from other components of the implantable prosthetic device 500. The paddles 530 have a ribbon-like form that extends from a proximal end 531 to a distal end 532 and includes three primary segments: a connection portion 534, an inner paddle portion 538, and an outer paddle portion 540. The inner and outer paddle portions 538, 540 of the paddles 530 are configured similar to legs in that the inner paddle portions 538 are like upper portions of the legs, the outer paddle portions 540 are like lower portions of the legs, and a middle connection portion 539 between the inner and outer paddle portions 538, 540 are like knee portions of the legs. The inner paddle portions 538 are stiff, relatively stiff, rigid, have rigid portions and/or are stiffened by a stiffening member or a fixed portion 582 of the clasps 580. As shown, the inner paddle portion 538 can include more material than the other portions of the paddle 530 and can therefore be stiffer. The stiffening of the inner paddle portions 538 allows the device 500 to move to the various different positions shown and described herein.

The proximal end 531 includes the proximal attachment interface 533 that engages with the main shaft 510 to secure the proximal end 531 of the paddle 530 near the proximal end 511 of the main shaft 510. The fixed or connection portion 534 extends from the proximal end 531 to a flexible or spreading portion 535 that is engaged by the cam portions 556 of the spreading member 550. In embodiments where the spreading member 550 is not included, the portion 535 can be rigid or substantially rigid. A hinge or connection portion 536 connects the spreading portion 535 to the inner paddle portion 538. The inner paddle portion 538 can include an optional opening 537 for securing the barbed clasps 580 via sutures or some other attachment means. A hinge or connection portion 539 connects the inner paddle portion 538 to the outer paddle portion 540 that is connected to the distal end 532 via a lower hinge or connection portion 546. Like the proximal end 531, the distal end 532 includes an attachment interface 547 that engages with the distal cap assembly 560.

The paddles 530 can be made from a wide variety of different materials and can be made in a wide variety of different ways. In one example embodiment illustrated by FIGS. 113 and 114, the paddles 530 are laser cut from a flat layer of shape-memory, material such as Nitinol. The various portions of the paddles 530 lay flat in the same plane when cutout of the layer of material. Referring to FIGS. 106-112, the flat paddle 530 is bent into a desired shape in a shape-setting jig and then subjected to a shape-setting process. After shape-setting, deforming the paddle 530 by bending or stretching the various components thereof will generate a spring force that tends to return the components of the paddle 530 to their shape-set position. Because the paddles 530 are shape-set in a roughly closed condition, the various connection portions act as spring-loaded hinges that tend to close the paddles 530.

The outer paddle portion 540 includes upper and lower flexible members 542, 544 that enable the outer paddle portion 540 to stretch to a longer and narrower stretched condition, shown in FIGS. 115-121. The upper and lower flexible members 542, 544 are connected by various hinge or connection portions: first connection portions 541 connect the upper flexible members 542 to the middle connection portion 539; second connection portions 543 connect the upper flexible members 542 to the lower flexible members 544; and third connection portions 545 connect the lower flexible members 544 to the lower connection portion 546. During stretching of the outer paddle portions 540 the upper flexible members 542 move, pivot, or flex toward each other and the lower flexible members 544 also move, pivot, or flex toward each other so that the outer paddle portion 540 lengthens and narrows. This lengthening and narrowing occurs when the device is moved from the closed condition to the open position and/or to the fully elongated position. In particular, pulling down on the attachment interface 547 to open and/or elongate the device 500 applies a tensile force to the outer paddle portions 540 and the illustrated configuration of the outer paddle portions allows the outer paddle portions to elongate and narrow.

When force is applied to the implantable prosthetic device 500 to stretch the outer paddle portion 540, the angles between the various components connected by each of the first, second, and third connection portions 541, 543, 545 increases. This increase in angle is resisted by a restorative spring force caused by the shape-memory nature of the material of the paddles 530 that resists the expanding of the connection portions 541, 543, 545. Thus, when stretching forces are removed, the outer paddle portion 540 contracts to an original length and widens to an original width.

In some embodiments, the connection portions 536, 539, 546 are formed by a plurality of spring or connecting segments arranged in a repeating pattern of cutouts that are formed when the paddle 530 is laser cut from a flat sheet of material. The thinner sections of the segments provide flexibility along a mid-plane of the paddle 530 and the symmetrical shape of each segment resists bending moments that may twist the paddle 530 outside of the mid-plane during bending. These connecting segments allow the connection portions 536, 539, 546 to bend a considerable amount while avoiding plastic deformation of the material as the individual connecting segments are bent.

Referring now to FIGS. 122-127, various views of embodiments of the optional spreading member 550 are shown with the spreading member 550 separate from other components of the implantable prosthetic device 500. The spreading member 550 extends from a proximal end 551 that attaches to the actuation element 591 to a distal end 552 that attaches to the distal cap 560. A central rod 553 of the spreading member 550 includes a threaded opening 554 at the proximal end 551 of the spreading member 550. The central rod 553 extends from the proximal end 551 to the distal end 552 that includes an attachment portion 555. Cam portions 556 extend laterally in the bottom half of the spreading member 550. The cam portions 556 have a rounded triangular shape and include an external rounded cam surface 558 that engages with the paddles 530. Though the spreading member 550 is shown as an elongated body with ramp-like portions extending laterally, the spreading member 550 can be any device or mechanism that spreads the paddles 530 laterally.

The cam portions 556 can take on a wide variety of shapes and sizes. Also, the cam portions 556 can be formed from a solid piece of material or can be expandable by inflation or other suitable means so that the cam portions 556 can change size, shape, and/or position. In certain embodiments, the cam portions 556 are expandable or inflatable such that no rotation of the spreading member 550 is necessary to engage the paddles 530 with the cam surfaces 558. That is, inflating the cam portions 556 engages the paddles 530 and deflating the cam portions 556 disengages the paddles 530.

Figure 129:
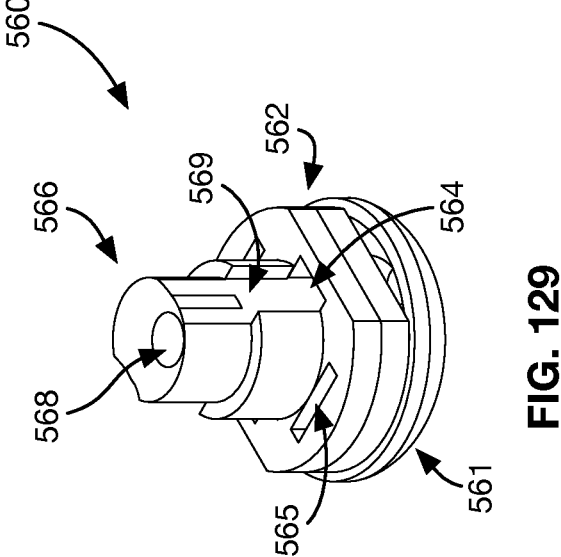
FIG. 129 shows the distal nut assembly of FIG. 128 in an assembled condition.
Figure 128:
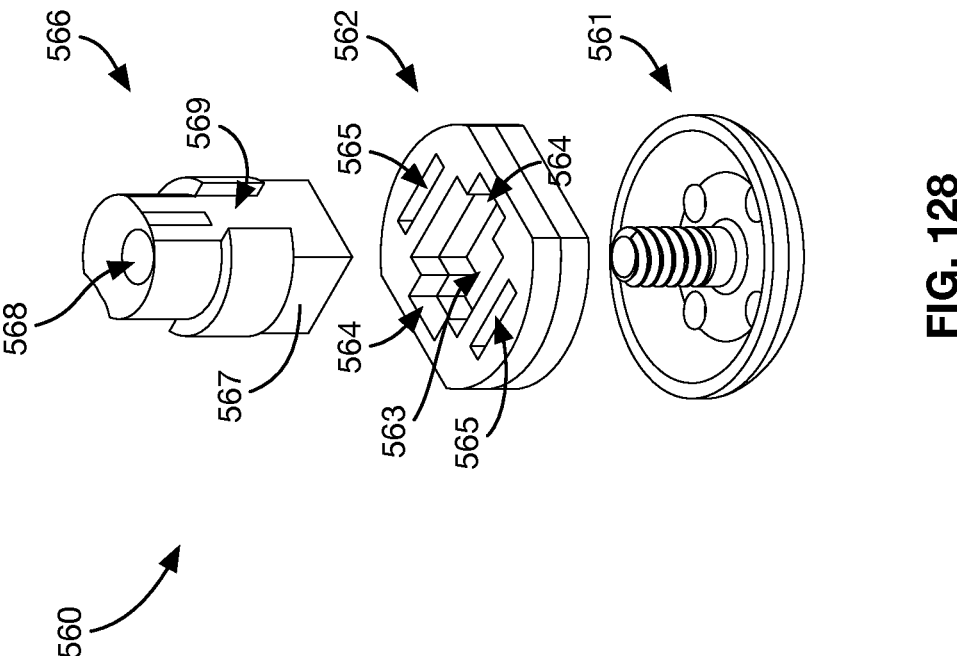
FIG. 128 shows a top perspective view of the components of a distal nut assembly of an example implantable device in a disassembled condition.
Figures 130, 131, 132, 133:
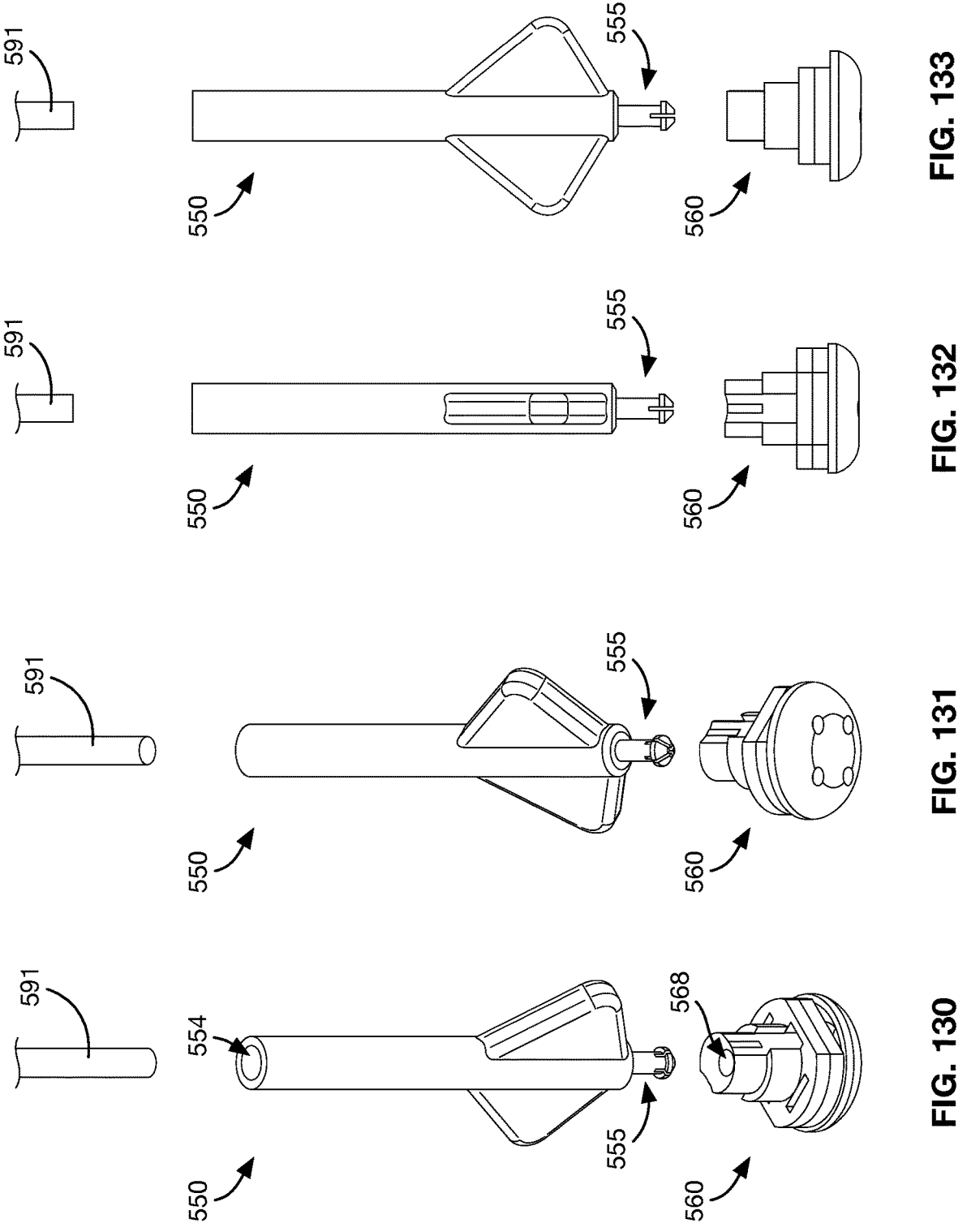
FIG. 130 shows a top perspective view of an actuation element, a spreading member, and a distal nut assembly of an example implantable device in a disassembled condition.
FIG. 131 shows a bottom perspective view of the components of FIG. 130.
FIG. 132 shows a front view of the components of FIG. 130.
FIG. 133 shows a side view of the components of FIG. 130.
Figures 134, 135, 136, 137:
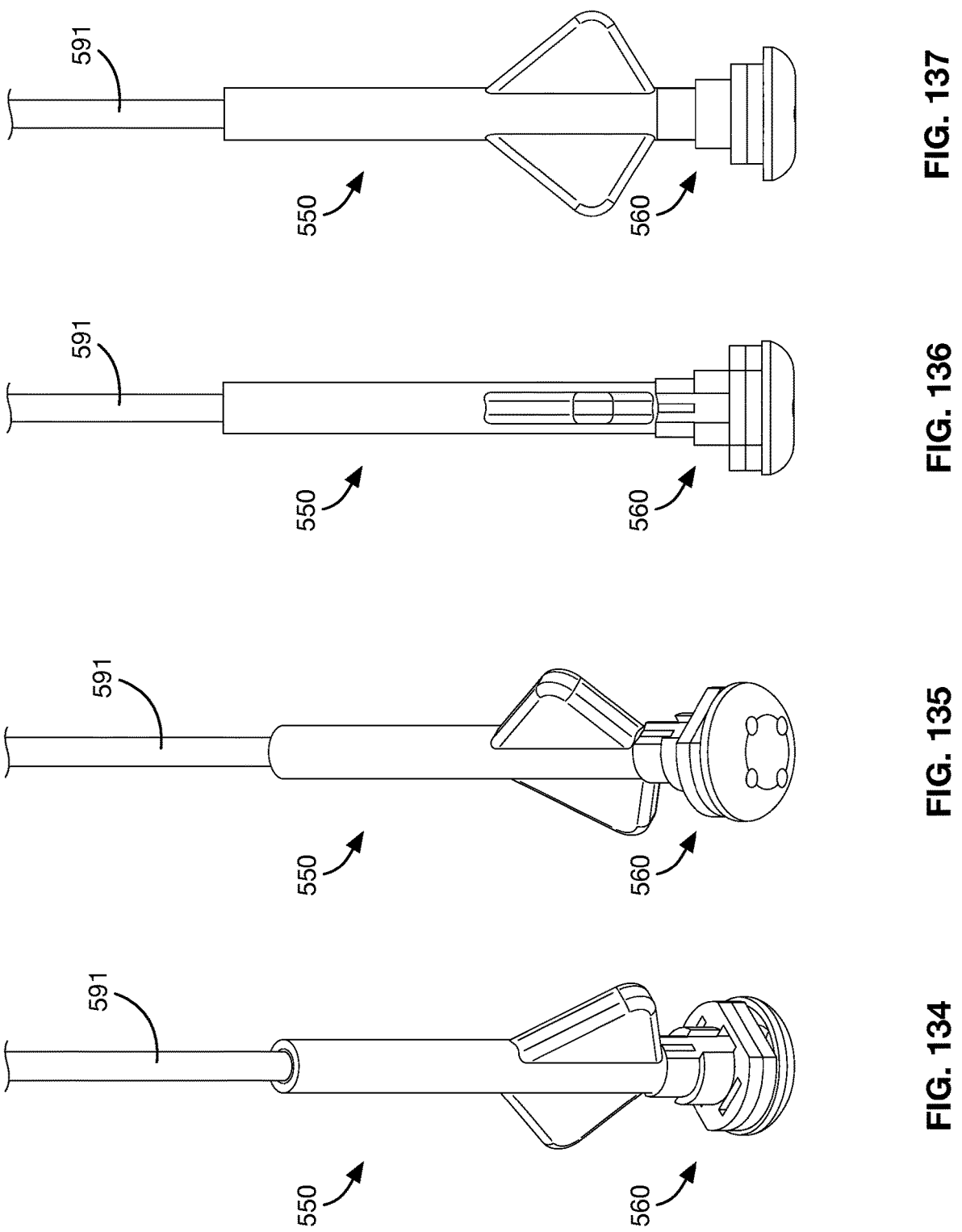
FIG. 134 shows a top perspective view of an actuation element, a spreading member, and a distal nut assembly of an example implantable device in an assembled condition.
FIG. 135 shows a bottom perspective view of the components of FIG. 134.
FIG. 136 shows a front view of the components of FIG. 134.
FIG. 137 shows a side view of the components of FIG. 134.
Figures 138, 139, 140, 141:
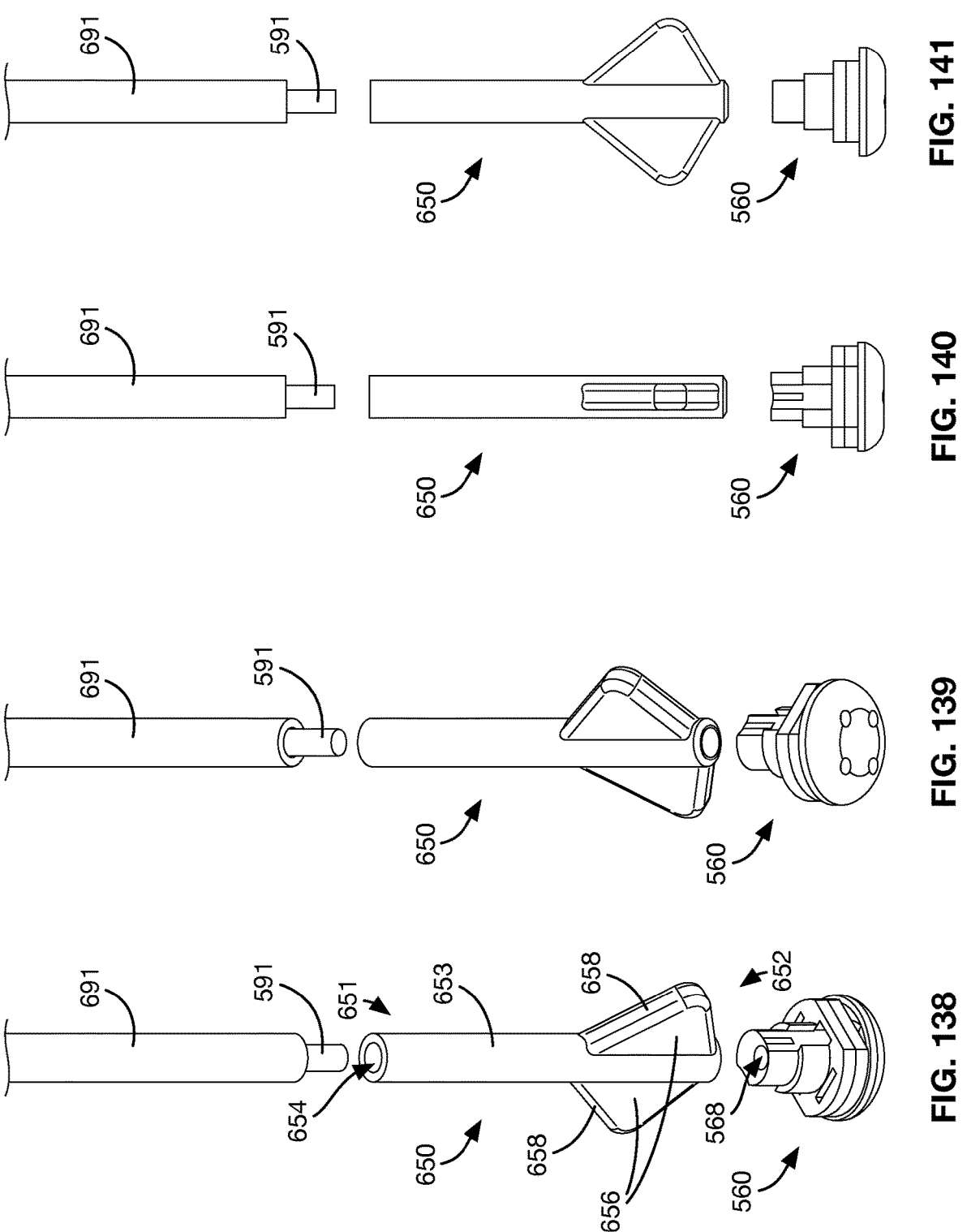
FIG. 138 shows a top perspective view of an actuation element, a spreading member, and a distal nut assembly of an example implantable device in a disassembled condition.
FIG. 139 shows a bottom perspective view of the components of FIG. 138.
FIG. 140 shows a front view of the components of FIG. 138.
FIG. 141 shows a side view of the components of FIG. 138.
Figures 142, 143, 144, 145:
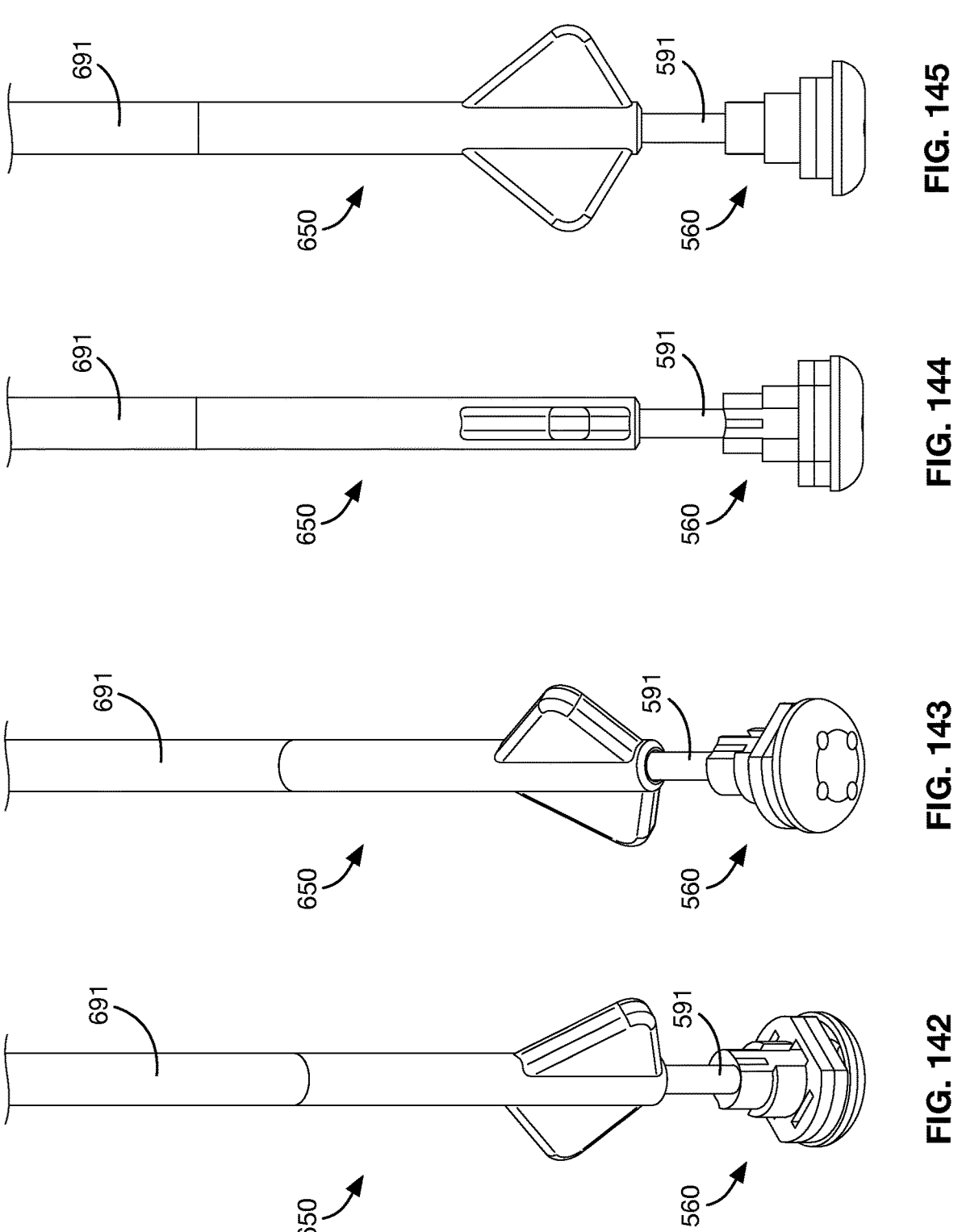
FIG. 142 shows a top perspective view of an actuation element, a spreading member, and a distal nut assembly of an example implantable device in an assembled condition.
FIG. 143 shows a bottom perspective view of the components of FIG. 142.
FIG. 144 shows a front view of the components of FIG. 142.
FIG. 145 shows a side view of the components of FIG. 142.
Figure 146:
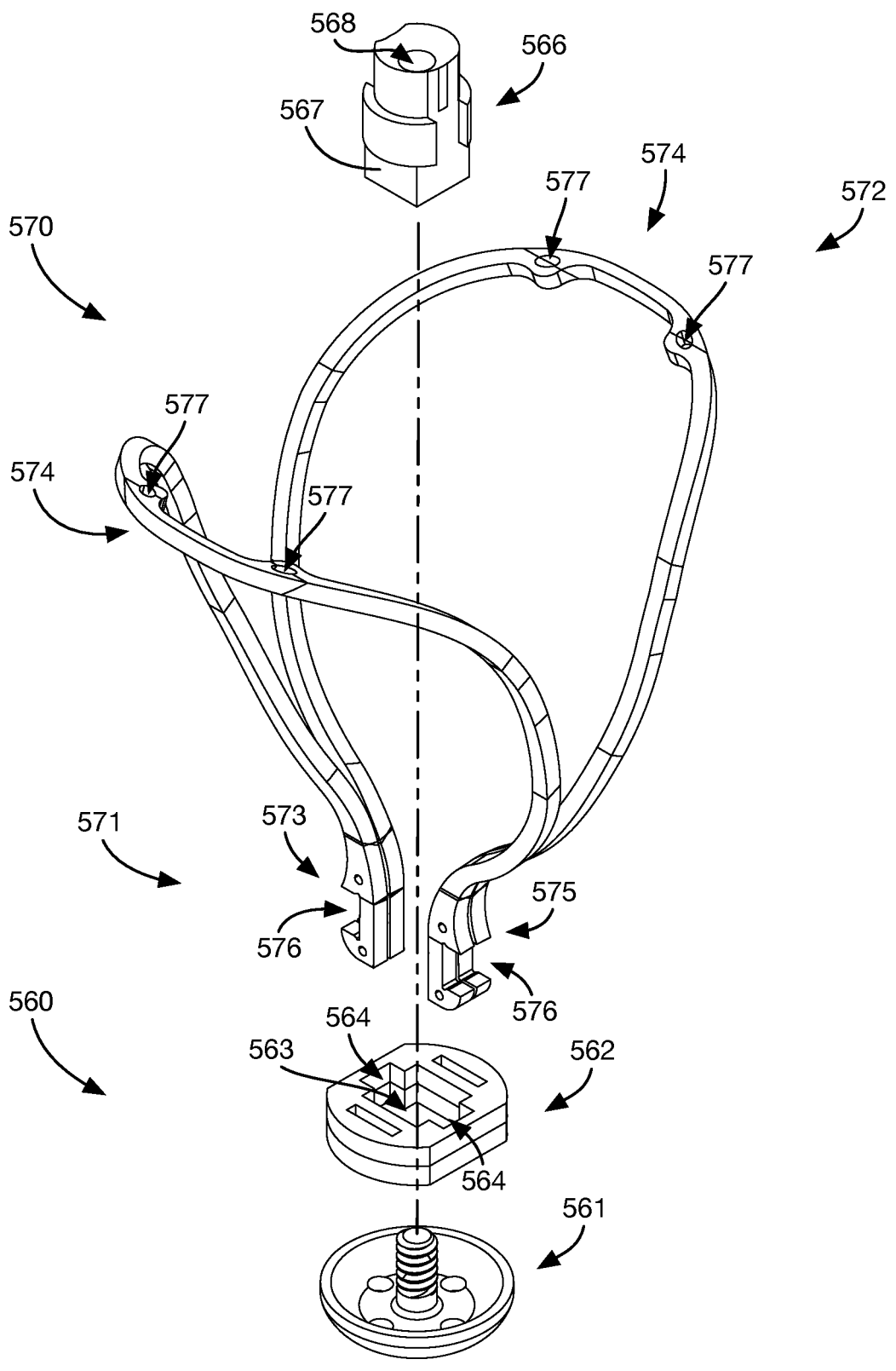
FIG. 146 shows a top perspective view of paddle frames and a distal nut assembly of an example implantable device in a disassembled condition.
Figure 147:
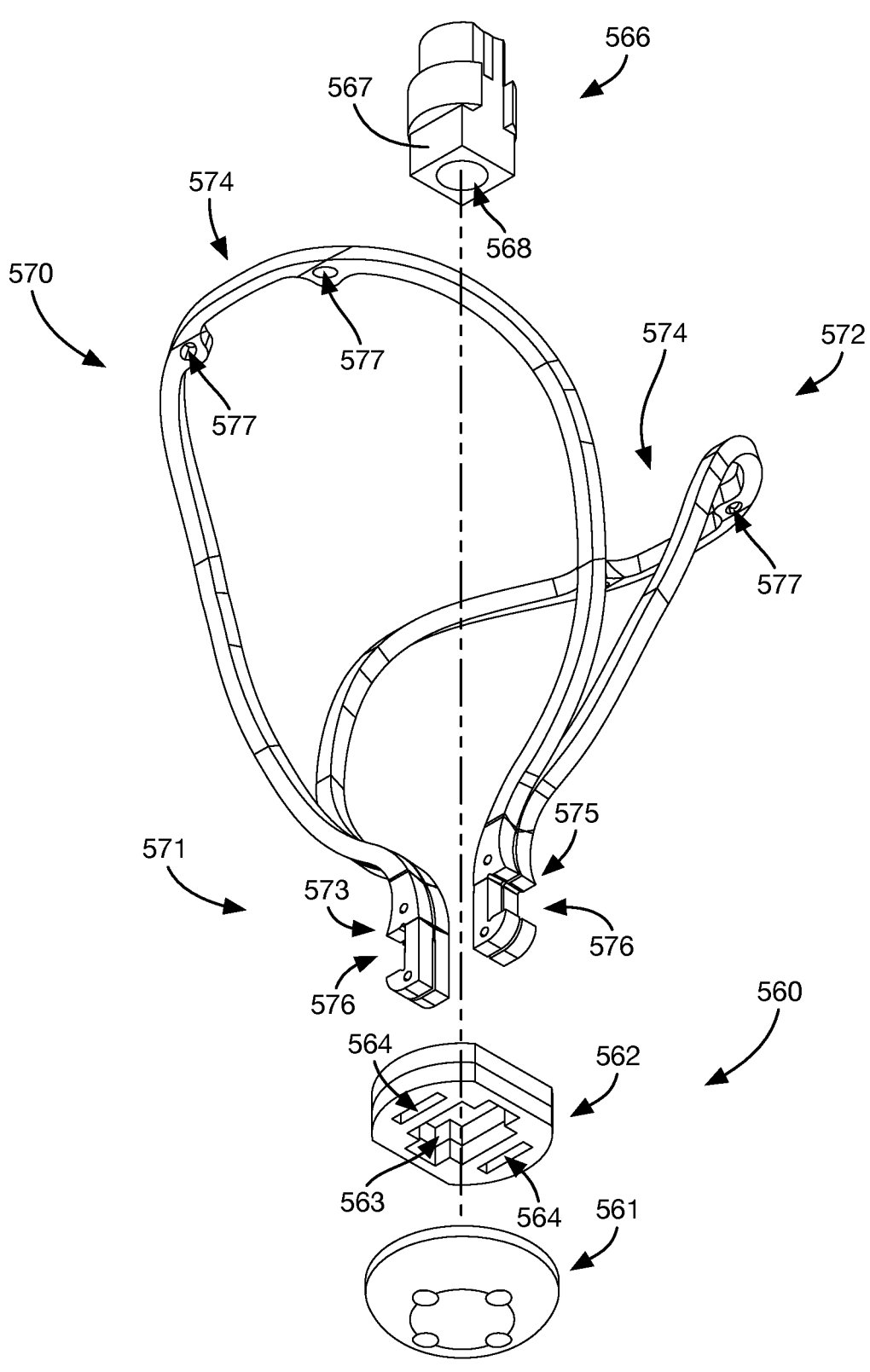
FIG. 147 shows a bottom perspective view of the components of FIG. 146.
Figure 148:
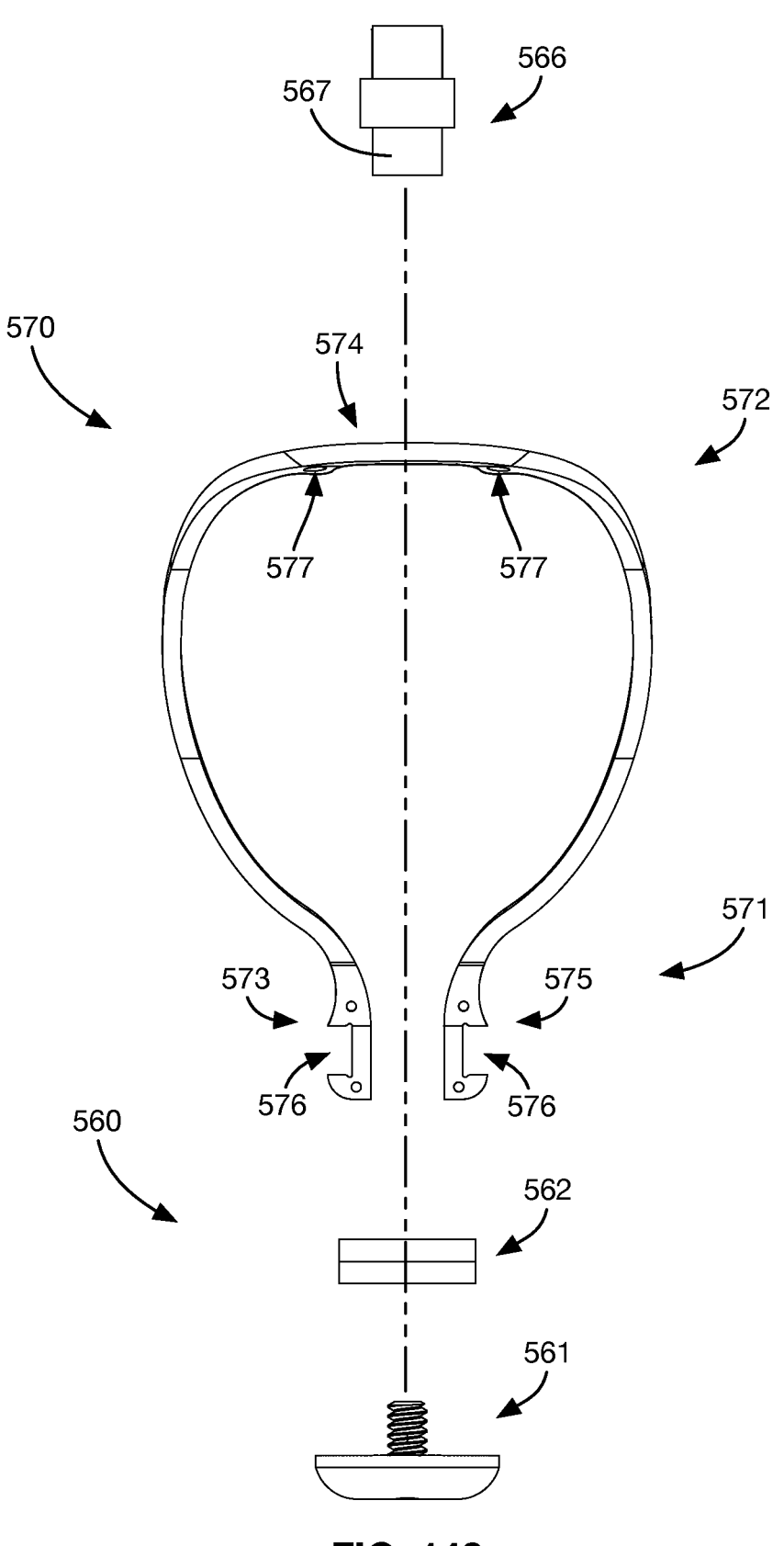
FIG. 148 shows a side view of the components of FIG. 146.

Referring now to FIGS. 128-129, an example distal cap assembly 560 is shown in an exploded view (FIG. 128) and an assembled view (FIG. 129). The distal cap assembly 560 holds the distal end 502 of the device 500 and enables the device 500 to be opened and closed, e.g., by extending and retracting the actuation element 591. The base of the distal cap assembly 560 is a threaded bolt 561 that extends from a rounded head. Washers 562 fit over the bolt 561 and include a square-shaped central opening 563 for receiving a distal retaining nut 566 and rectangular side openings 564 for receiving the paddle frames 570. The washers 562 also include paddle slots 565 for receiving the distal ends 532 of the paddles 530. The retaining nut 566 includes a square or locking end 567 that fits within the central opening 563 and closes off the side openings 564 to retain the paddle frames 570. A threaded opening 568 extends through the length (threads can be included on all or a portion of the length of the opening) of the retaining nut 566 and is engaged by the bolt 561, thereby holding the distal cap assembly 560 together. Side slots 569 align with the side openings 564 of the washers 562 to provide further engagement with the paddle frames 570.

Referring now to FIGS. 130-137, various views of an example assembly of the spreading member 550, distal cap assembly 560, and actuation element 591 in an exploded condition (FIGS. 130-133) and an assembled condition (FIGS. 134-137) are shown. The two connections of the assembly—between the spreading member 550 and the distal cap assembly 560 and between the spreading member 550 and the actuation element 591—are different in their nature and purpose. That is, the connection between the distal cap assembly 560 and the spreading member 550 allows the two components to rotate relative to each other without coming undone, as would be the case with a typical threaded connection. A wide variety of different rotatable couplings between the distal cap assembly 560 and the spreading member 550 can be used. In contrast, the connection between the spreading member 550 and the actuation element 591 is a fixed connection, such as a threaded connection that fixes the spreading member 550 to the actuation element but disassembles when the actuation element 591 is rotated in a counter-tightening direction while the spreading member 550 is retained in a fixed position. However, any fixed, but releasable, connection can be used between the actuation element 591 and the spreading member 550.

In the illustrated example, the rotatable coupling between the spreading member 550 and the distal cap assembly 560 is made by inserting the attachment portion 555 of the spreading member 550 into the opening 568 of the distal nut 566. The opening 568 includes a radially inwardly extending projection that engages the radially outwardly extending end of the attachment portion. The attachment portion 555 engages internal projection in the opening 568 to join the spreading member 550 to the distal nut 566 so that the spreading member 550 is free to rotate relative to the distal nut 566. The attachment portion 555 engages the opening 568 by snapping the two components together with cam surfaces at the end of the attachment portion 555 engaging the protrusion on the interior of the opening 568. The connection between the spreading member 550 and distal nut 566 allows the spreading member 550 to rotate freely relative to the distal nut 566 without coming apart, in contrast to a fixed threaded connection. Thus, the spreading member 550 can be rotated between the resting and engaged positions by the wire 591, as described below.

In one example embodiment, the connection between the spreading member 550 and the actuation element 591 is made by threading the actuation element 591 into the threaded opening 568 of the distal cap assembly 560. When fully attached, the connection between the spreading member 550 and the actuation 591 is rotationally fixed so that rotation of the actuation element 591 also rotates the spreading member 550. The connection between the spreading member 550 and the actuation element 591 can be unscrewed when the spreading member 550 is fully retracted into the main shaft 510 and prevented from rotating by the projections 519. For example, once implantation of the device 500 is completed, the actuation element 591 can be unscrewed from the spreading member 550 and retracted into the delivery system 590.

Referring now to FIGS. 138-145, various views of an example assembly of a spreading member 650, the distal cap assembly 560, the actuation element 591, and an actuation tube 691 in an exploded condition (FIGS. 138-141) and an assembled condition (FIGS. 142-145) are shown. The spreading member 650 is similar in shape and function to the spreading member 550 but can be actuated independently from the distal cap assembly 560 to provide additional control over the lateral position of the paddles 530 that is independent from the open condition of the paddles 530. That is, the spreading member 650 can be actuated when the implantable prosthetic device 500 is partially opened, half opened, three-quarters open, fully open, or opened any other amount.

In some embodiments, the spreading member 650 extends from a proximal end 651 that attaches to the actuation tube 691 to a distal end 652. The actuation element 591 extends through the actuation tube 691 to attach to the opening 568 of the distal cap assembly 560. A central rod 653 of the spreading member 650 includes a central opening 654 that extends through the spreading member 650. The actuation element 591 extends through the central opening 654 so that the spreading member 650 can slide along the actuation element 591. The central rod 653 extends from the proximal end 651 to the distal end 652. Cam portions 656 extend laterally in the bottom half of the spreading member 650. The cam portions 656 have a rounded triangular shape and include an external rounded cam surface 658 that engages with the paddles 530.

The two connections of the assembly—between the actuation element 591 and the distal cap assembly 560 and between the spreading member 650 and the actuation tube 691—are similar in their nature and purpose. That is, both connections are fixed connections that enable the actuation element 591 and tube 691 to extend and retract the connected component—i.e., the distal cap assembly 560 and the spreading member 650, respectively. For example, a threaded connection can be used between the actuation element 591 and distal cap assembly 560 and between the spreading member 650 and the actuation tube 691 so that the connections can be released by rotating the actuation element 591 or tube 691 in a counter-tightening direction while the distal cap assembly 560 or spreading member 650 are retained in a fixed position. However, any fixed, but releasable, connection can be used between the actuation element 591 and the distal cap assembly 560 and between the actuation tube 691 and the spreading member 650.

Referring now to FIGS. 146-152, various views of the example distal cap assembly 560 and paddle frames 570 are shown separate from other components of the implantable prosthetic device 500. The paddle frames 570 extend from a cap attachment portion 571 to a paddle connection portion 572. The paddle frames 570 are formed from a piece of material such as nitinol, or any other suitable material, that extends from a first end 573 at the cap attachment portion 571, through a middle or loop portion 574 at the paddle connection portion 572 and returns to a second end 575 at the cap attachment portion 571. The first and second ends 573, 575 of the paddle frame 570 each include an attachment notch or recess 576 that helps to secure the paddle frames 570 to the distal cap assembly 560. The paddle frames 570 also include attachment holes 577 in the loop portion 574 for securing the paddles 530 to the paddle frame 570. In some embodiments, the paddle frames 224 are formed of a material that is more rigid and stiff than the material forming the paddles 222, 220 so that the paddle frames 224 provide support for the paddles 222, 220. The paddle frames 570 can be formed from a flat blank that is cut from a flat sheet of material, for example, by laser cutting. The cut blank can then be bent to form the three-dimensional shape of the paddle frames 570.

The paddle frames 570 provide additional pinching force between the paddles 530 and the coaption element 520 and assist in wrapping the leaflets 20, 22 around the sides of the coaption element 520 for a better seal between the coaption element 520 and the leaflets 20, 22, as can be seen in FIG. 51. That is, the paddle frames 570 can be configured with a round three-dimensional shape extending from the distal cap assembly 560 to the middle hinge portion 539 between the inner and outer paddle portions 538, 540. The connections between the main shaft 510, paddles 530, the distal cap assembly 560, paddle frames 570 can constrain each of these parts to the movements and positions described herein. In particular the middle hinge portion 539 is constrained by its connection between the inner and outer paddle portions 538, 540 and by its connection to the paddle frame 570. Similarly, the paddle frame 570 is constrained by its attachment to the paddles 530 (by way of the middle hinge portion 539) and to the distal cap assembly 560.

In some embodiments, the loop portions 574 of the paddle frames 570 form a generally rounded, three-dimensional shape that—as discussed above and as can be seen in FIGS. 65 and 69—generally conforms to the shape of the coaption element 520. The sides of the paddle frames 570 between the cap attachment portion 571 and the paddle connection portion 572 have a rounded, wing-like shape that engages the curved surface of the coaption element 520 during grasping of native leaflets 20, 22 between the paddle 530 and coaption element 520 of an implantable device of the present invention, as can be seen in FIGS. 50 and 51. Configuring the paddle frames 570 in this manner provides increased surface area compared to the paddles 530 alone. This can, for example, make it easier to grasp and secure the native leaflets 20, 22. The increased surface area can also distribute the clamping force of the paddles 530 and paddle frames 570 against the native leaflets 20, 22 over a relatively larger surface of the native leaflets 20, 22 in order to further protect the native leaflet tissue. Similar to the frames 224 shown in FIG. 51, the increased surface area of the paddle frames 570 can also allow the native leaflets 20, 22 to be clamped to the implantable prosthetic spacer device 500, such that the native leaflets 20, 22 coapt entirely around the coaption member 520. This can, for example, improve sealing of the native leaflets 20, 22 and thus prevent or further reduce valvular regurgitation.

Figure 149:
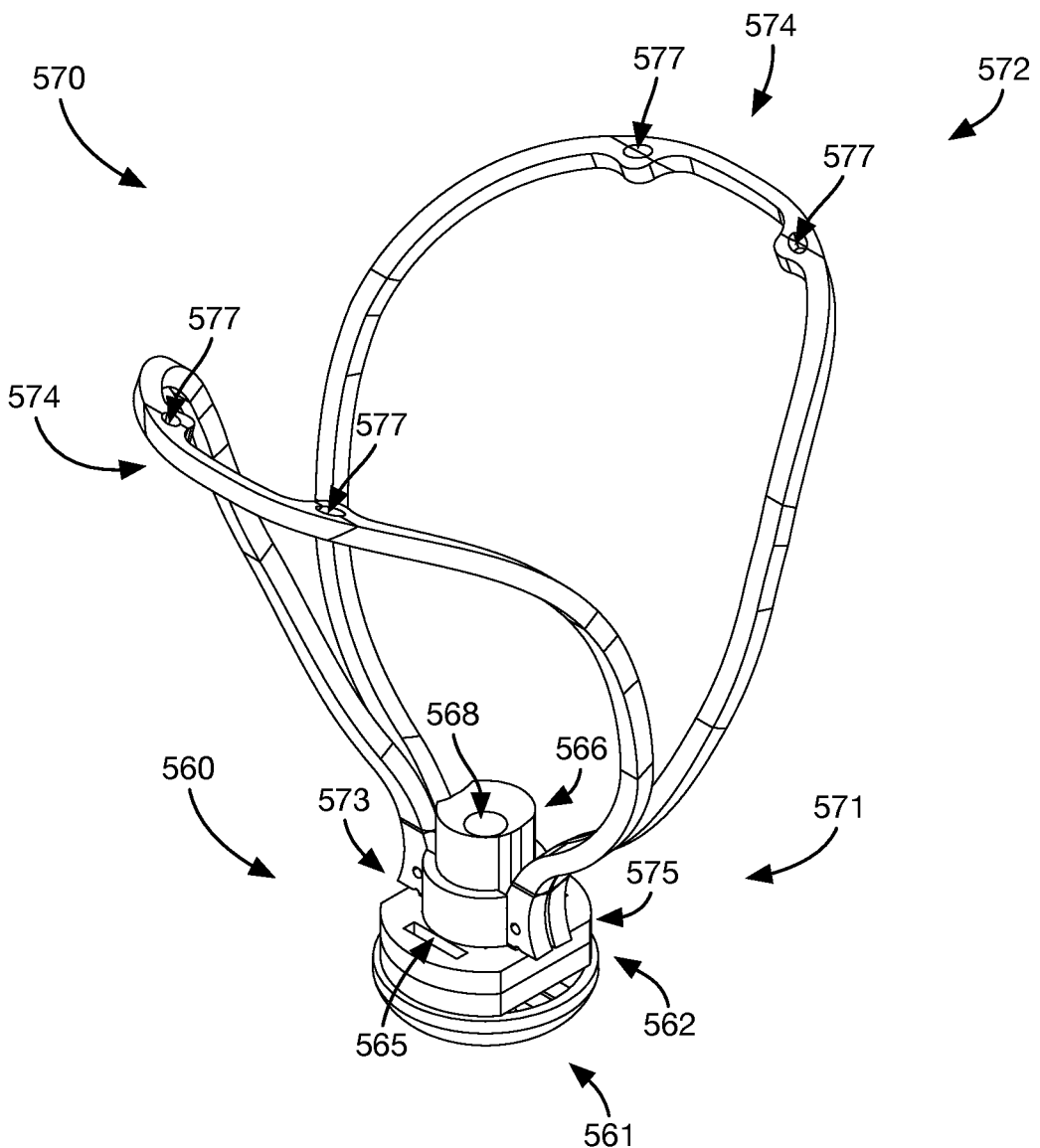
FIG. 149 shows a top perspective view of paddle frames and a distal nut assembly of an example implantable device in an assembled condition.
Figure 150:
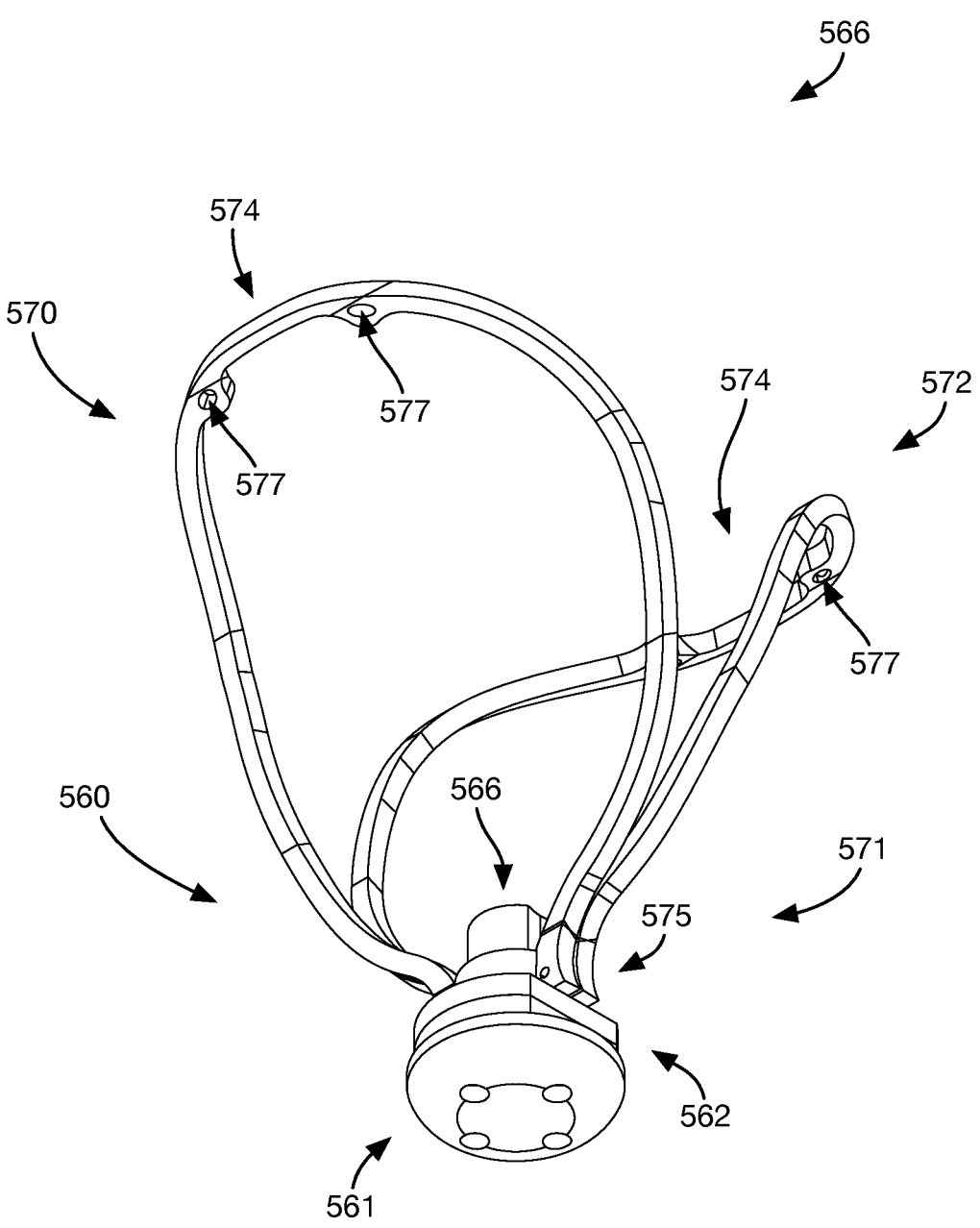
FIG. 150 shows a bottom perspective view of the components of FIG. 149.
Figure 151:
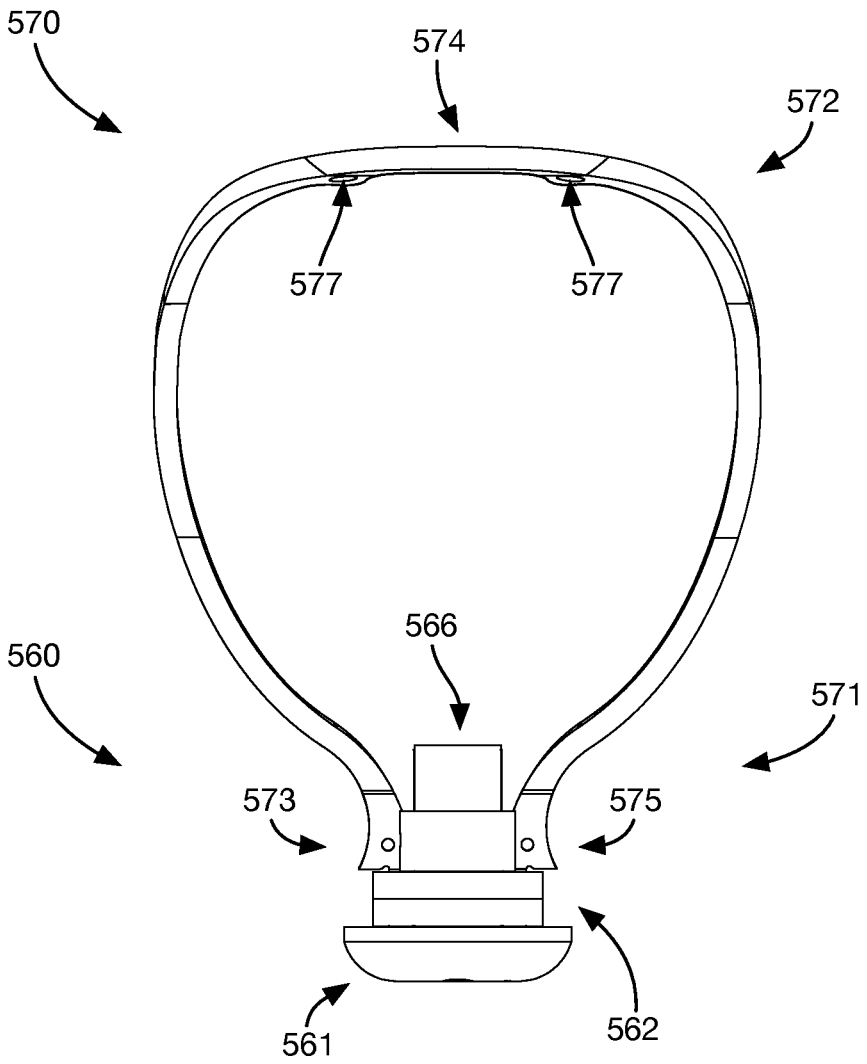
FIG. 151 shows a side view of the components of FIG. 149.

Referring again to FIGS. 146-148, the example distal cap assembly 560 and paddle frames 570 are shown in an exploded condition prior to being joined together. To assemble the paddle frames 570 to the distal cap assembly 560 the first and second ends 573, 575 are squeezed together to narrow the width of the cap attachment portion 571 so that the first and second ends 573, 575 can be inserted into the side openings 564 of the washers 562. When the paddle frames 570 are allowed to expand, the first and second ends 573, 575 expand outwards so that the attachment recesses 576 receive and hook around a portion of the washers 562. The retaining nut 566 is then inserted into the opening 563 so that the locking end 567 fits between the ends 573, 575 of the paddle frames 570, thereby locking the paddle frames 570 in engagement with the washers 562. The bolt 561 is then threaded into the retaining nut 566 and tightened until the flange or cap of the bolt 561 engages the washers 562, as is shown in FIGS. 149-151.

Figure 152:
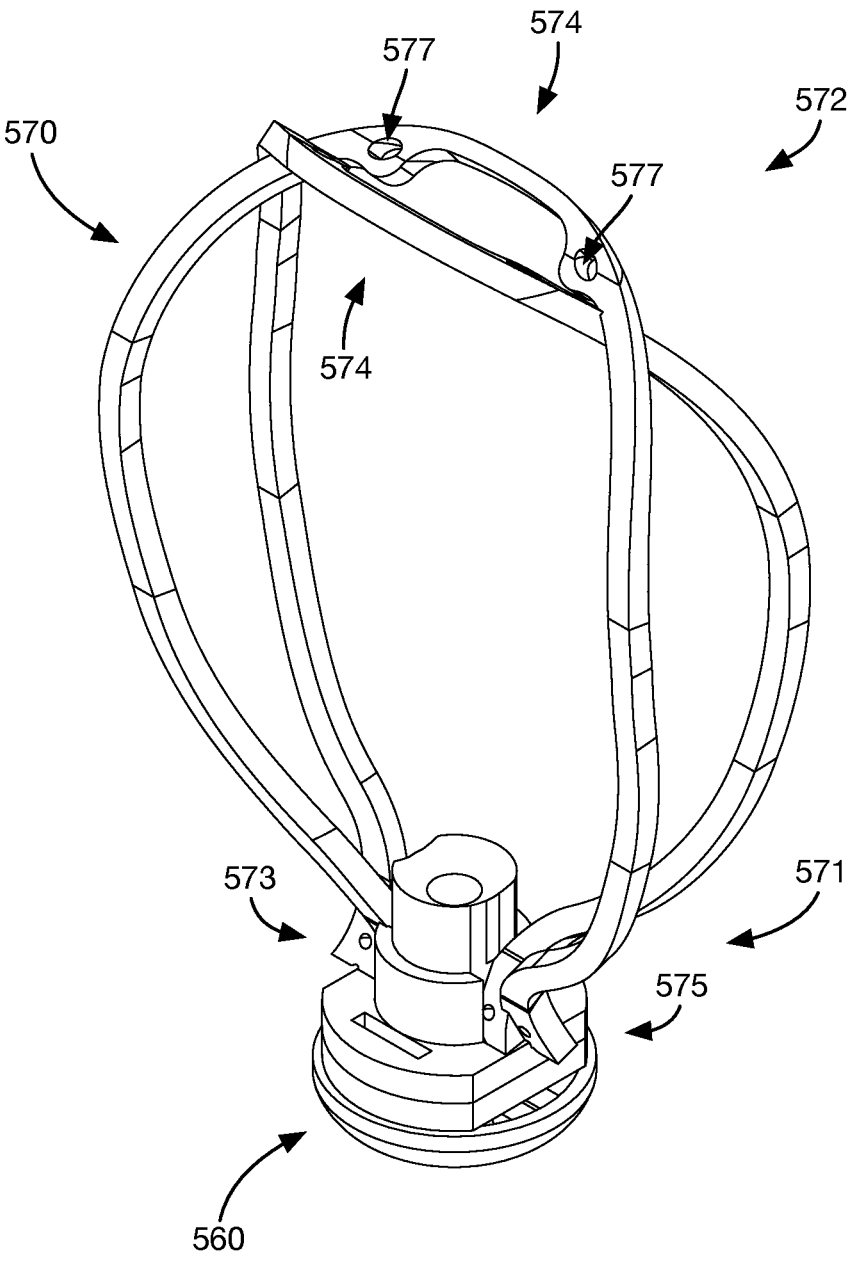

Referring to FIG. 152, the paddle frames 570 are shown assembled to the distal cap assembly 560. The paddle frames 570 can be shape set to provide increased clamping force against or toward the coaption element 520 when the paddles 530 are in the closed configuration. This is because the paddle frames 570 are shape-set relative to the closed position (e.g., FIG. 149) to a first position (e.g., FIG. 152) which is beyond the position where the paddle 530 would engage the coaption element 520, such as beyond a central plane of the device 500, such as beyond the opposite side of the coaption element 520, such as beyond the outer paddle 570 on the opposite side of the coaption element 520. In the first position the loop portions 574 of the paddle frames 570 are intertwined in that the sides of one paddle frame 570 are moved slightly laterally to allow movement past the sides of the other paddle frame 570 until the paddle connection portions 572 of each frame 570 contact each other and the sides and prevent further movement.

Figure 153:
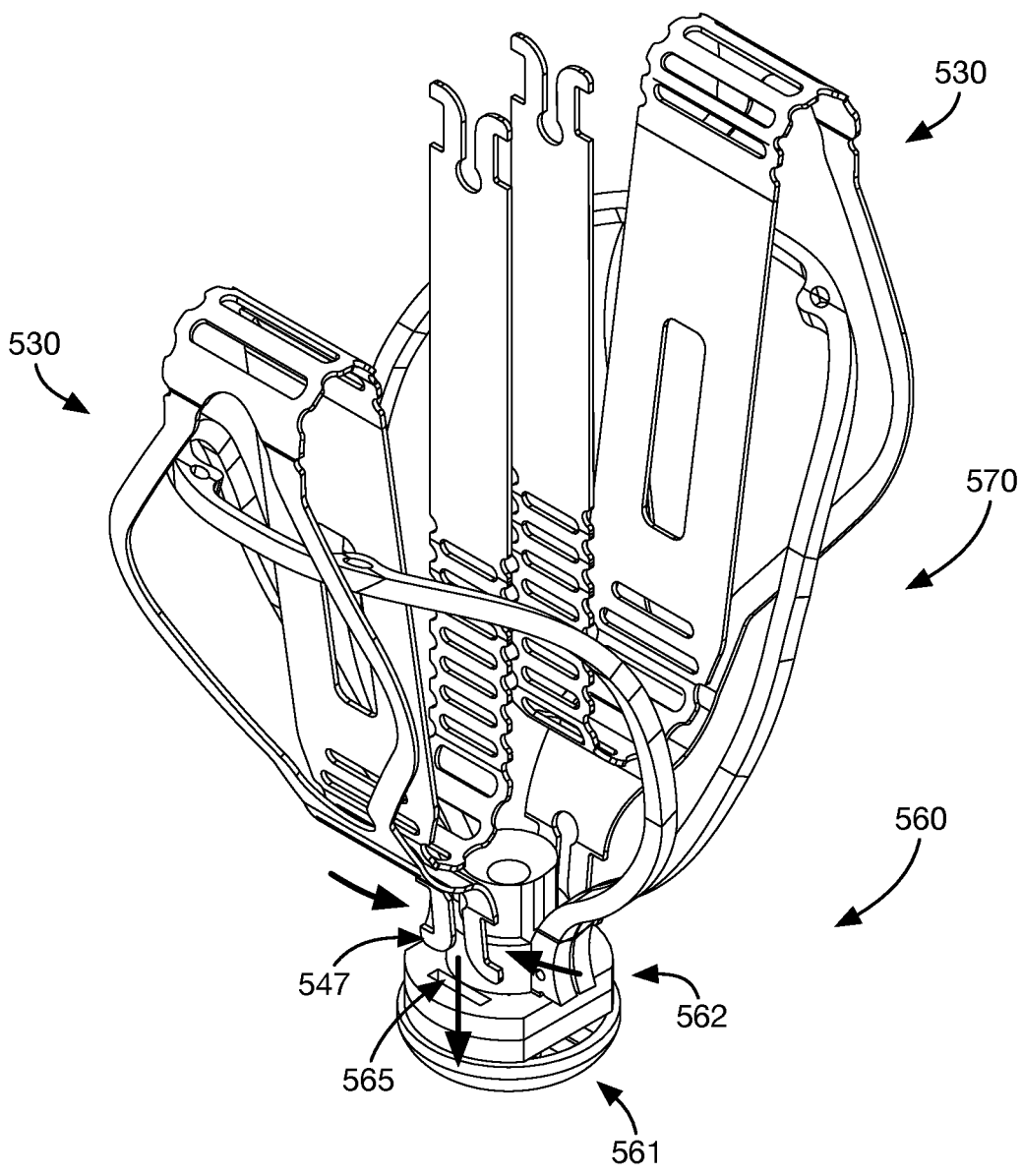
Figure 154:
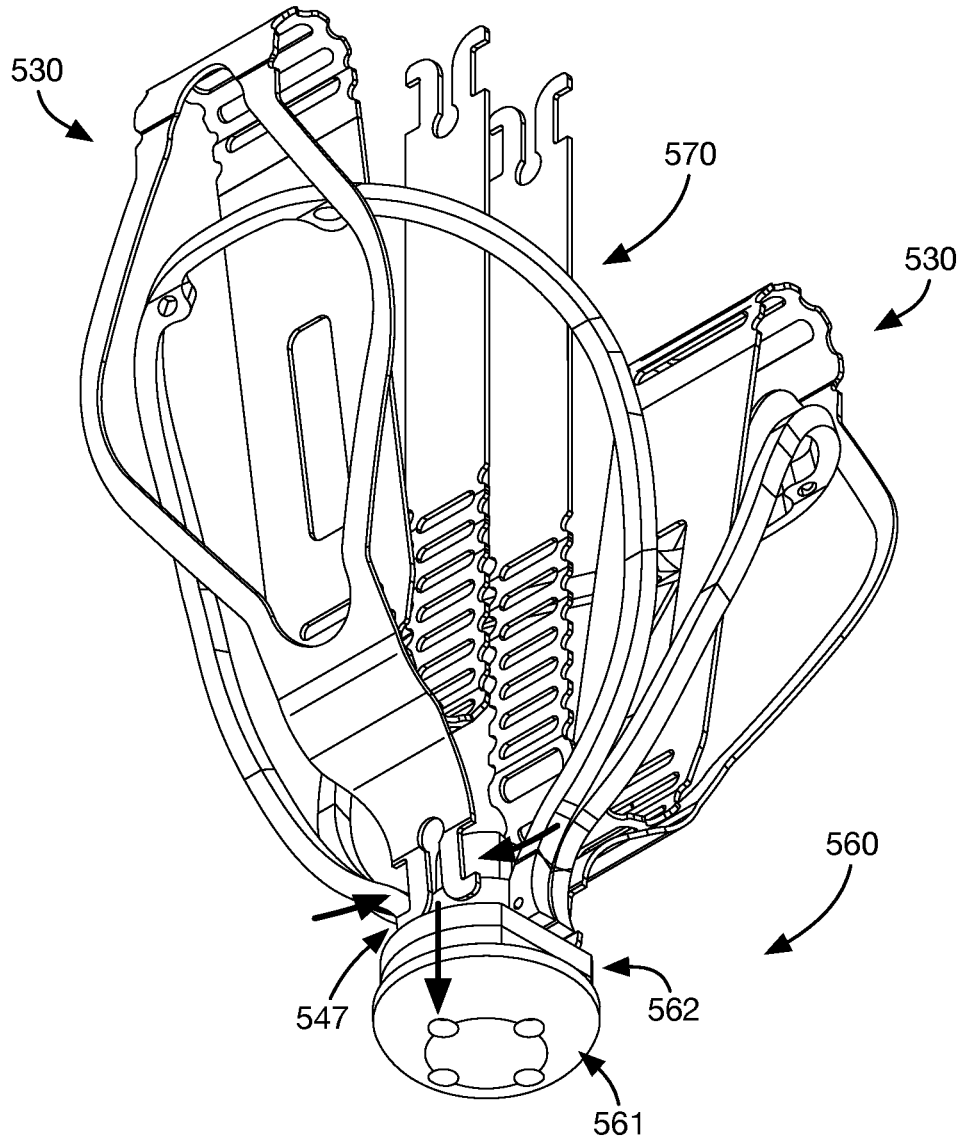
Figure 155:
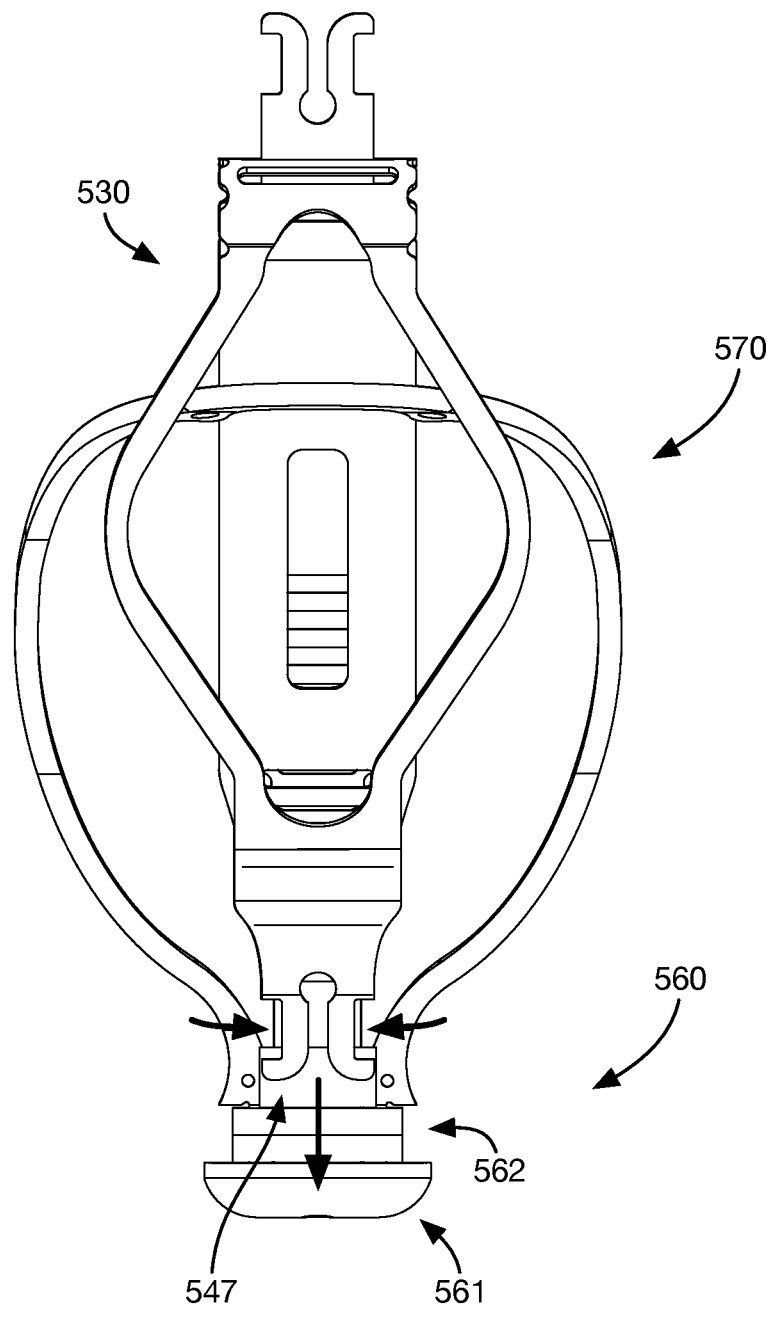
Figure 156:
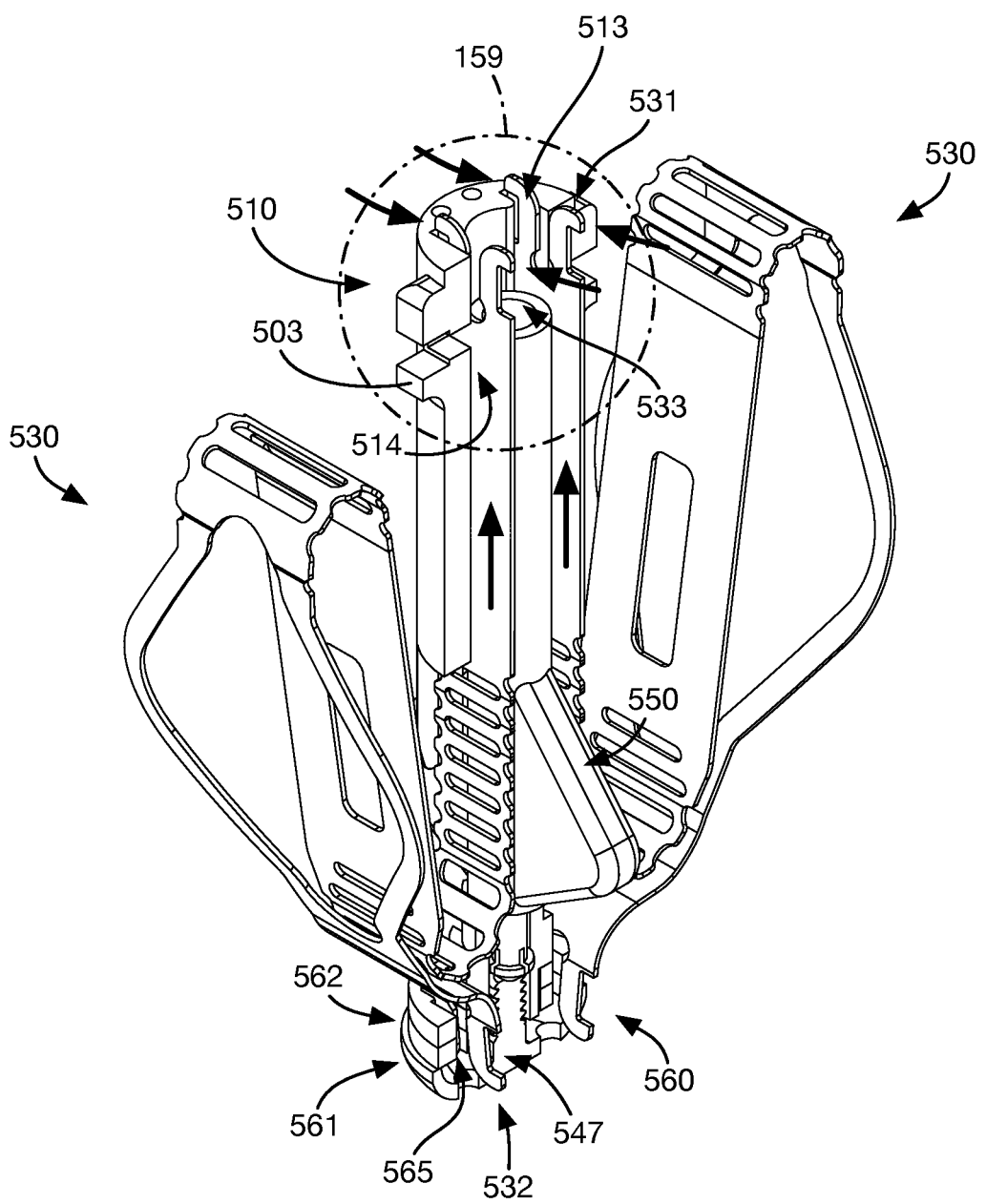
Figure 157:
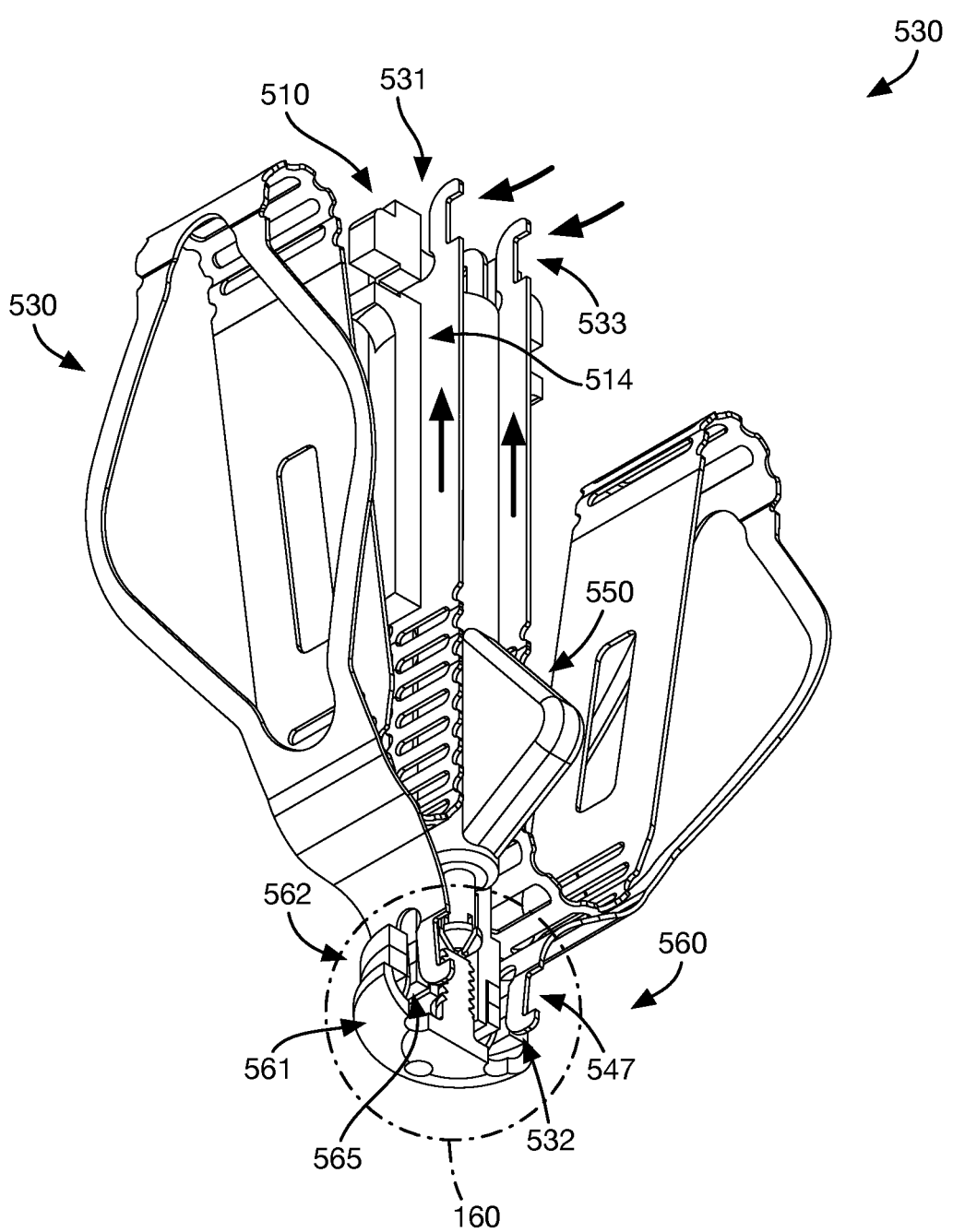
Figure 158:
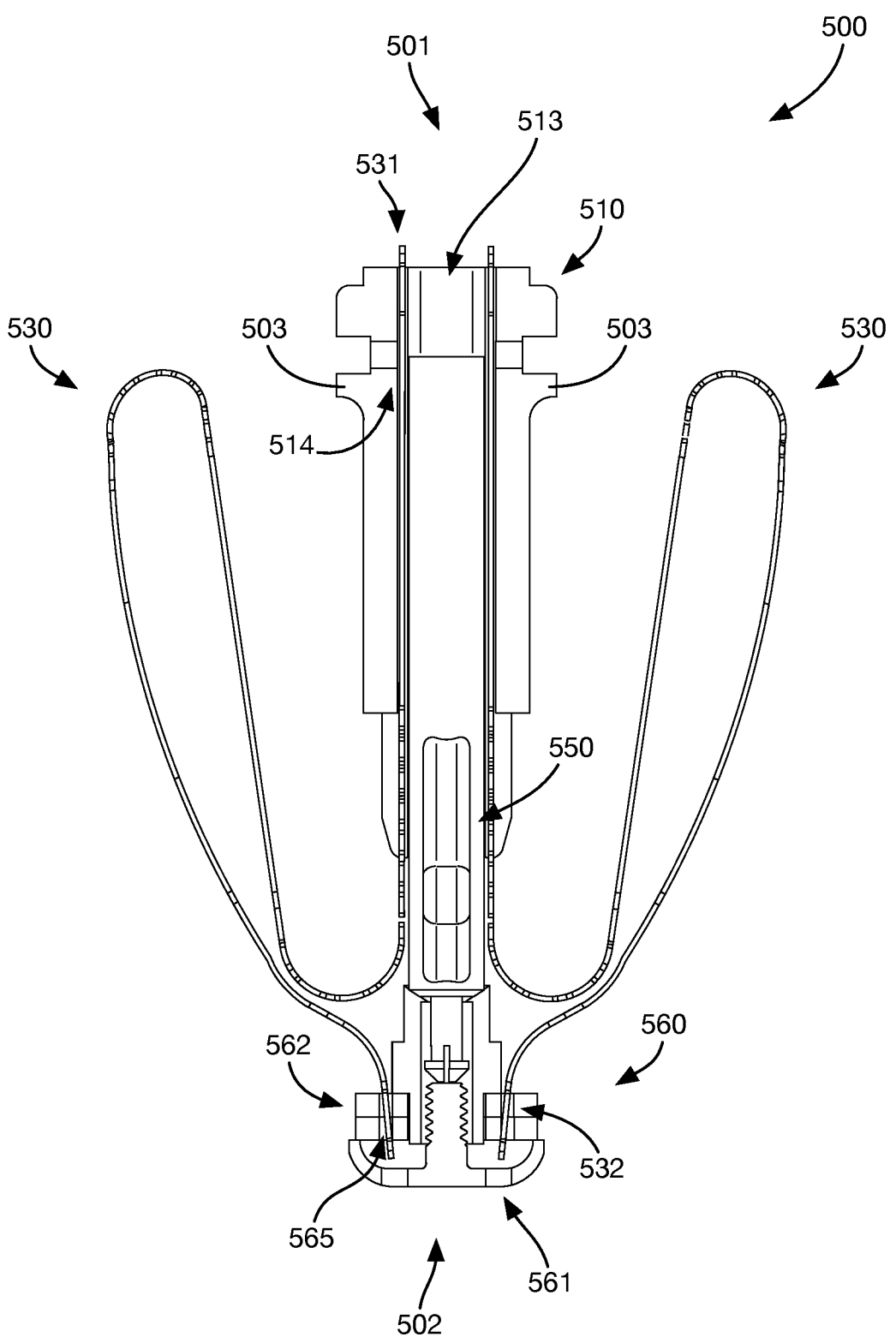
Figure 159:
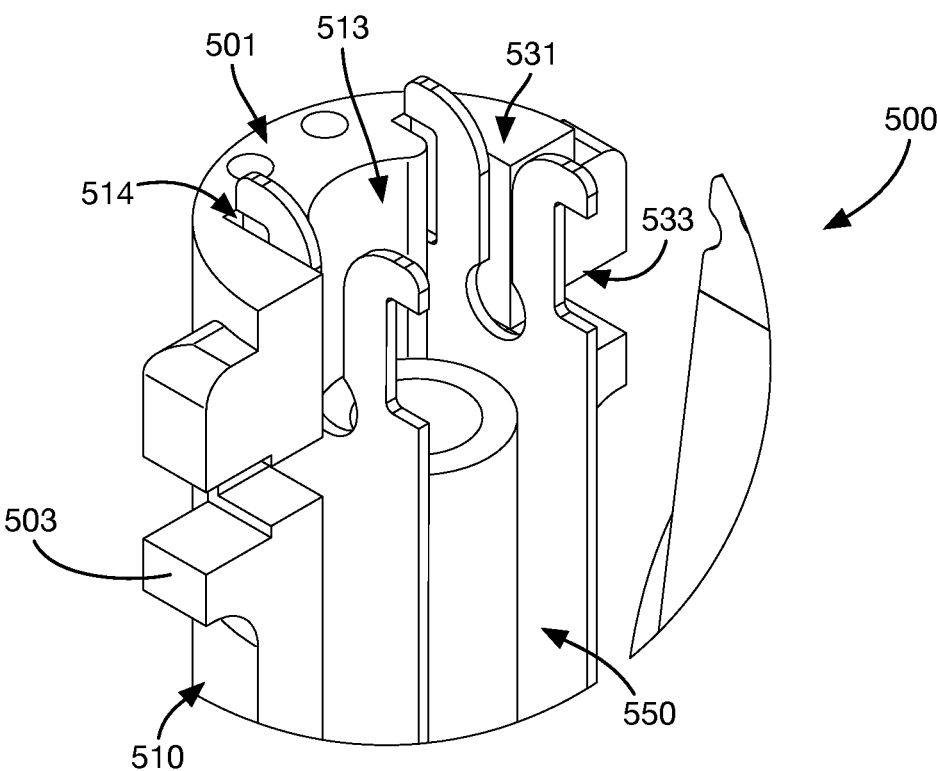
Figure 160:
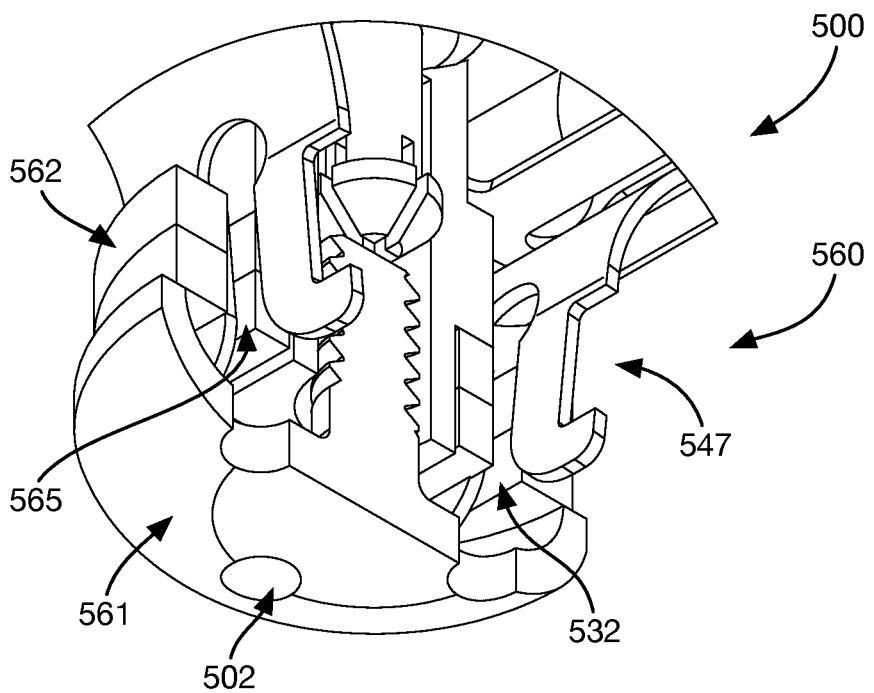
Figure 161:
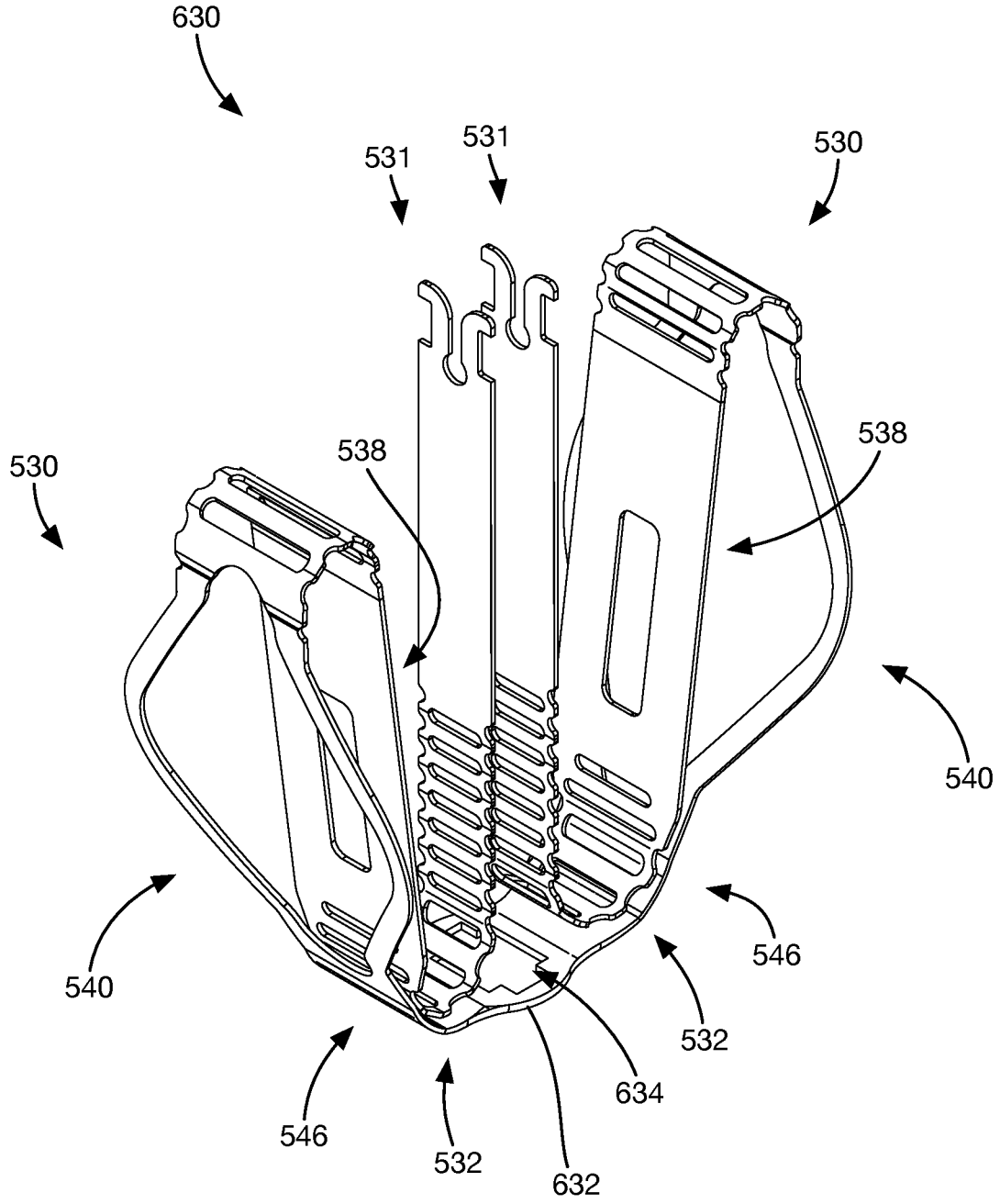
Figure 162:
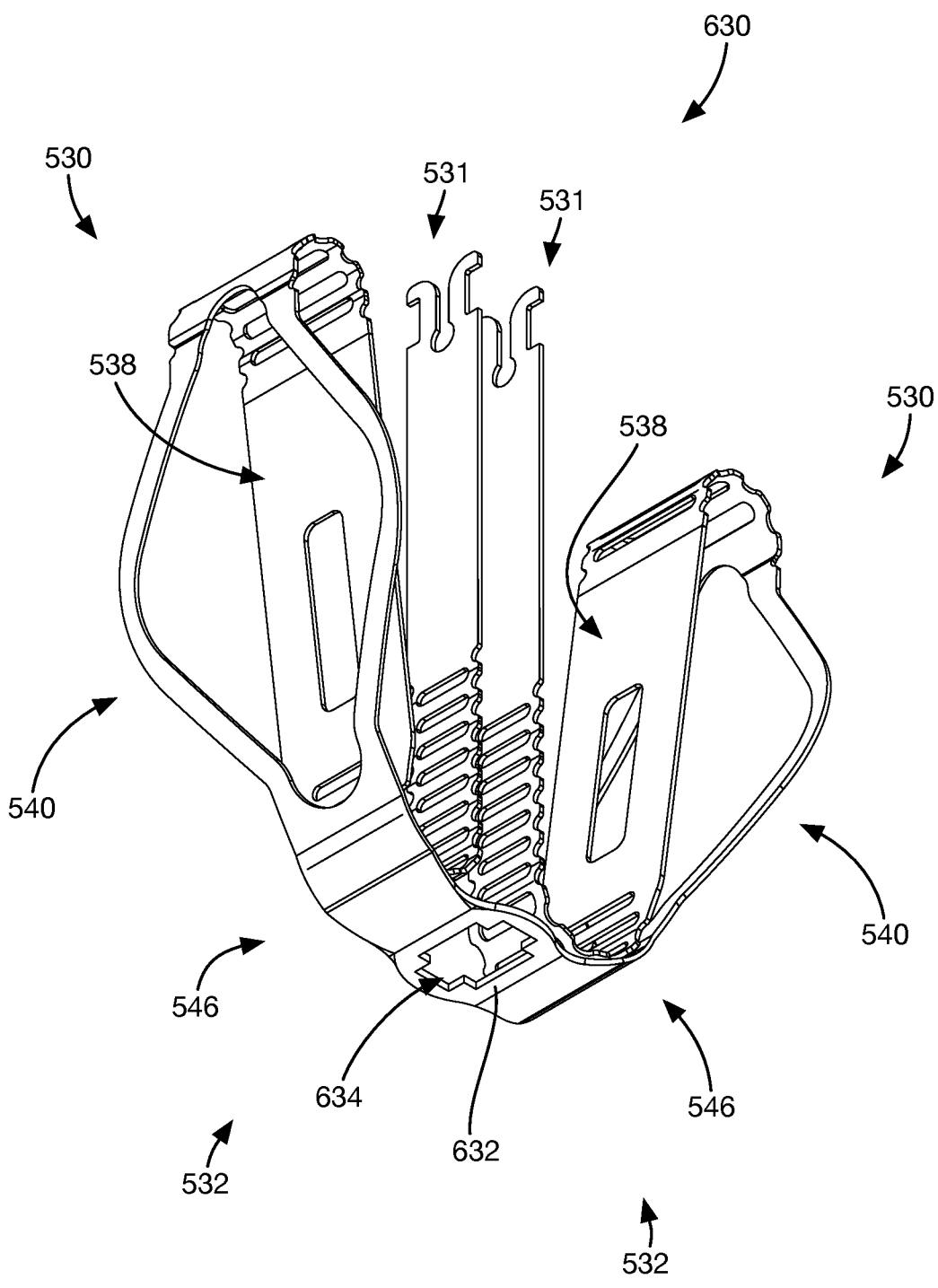

Referring now to FIGS. 153-155, the paddles 530 are shown spaced apart from the connected distal nut assembly that forms the distal cap 560 and paddle frames 570. To attach the paddles 530 to the distal cap assembly 560, the distal ends 532 of the paddles 530 are aligned with the paddle slots 565 in the washers 562. The distal attachment interface 547 of the paddles 530 is squeezed laterally to fit within the paddle slot 565 and is then inserted into the paddle slot 565 until the attachment interface 547 bottoms out on the washer 562. Then the attachment interface 547 is allowed to expand to secure the distal end 532 of the paddle 530 within the paddle slot 565, as is shown in FIGS. 156-158 and 160.

Referring to FIGS. 156-159, the paddles 530 and the main shaft 510 are assembled by inserting the proximal attachment interfaces 533 through the slots 514 at the distal end 512 of the main shaft. The attachment interfaces 533 are advanced through the slots 514, until the attachment interfaces reach the proximal end 511 of the main shaft 510. The proximal attachment interfaces 533 expand laterally to secure the proximal ends 531 of the paddles 530 to the proximal end 511 of the main shaft 510. Though the proximal attachment interfaces 533 are shown slightly protruding from the proximal end 511 of the main shaft 510, the proximal attachment interfaces 533 can be flush with the proximal end of the main shaft 510 or recessed within the proximal end of the main shaft 510.

Referring to FIGS. 156-159, the proximal end 551 of the shaft 553 of the spreading member 550 is inserted through the passage 513 at the distal end 512 of the main shaft 510. The shaft 553 of the spreading member 550 is advanced through the passage 513 toward the proximal end 511 of the main shaft 510.

Figure 163:
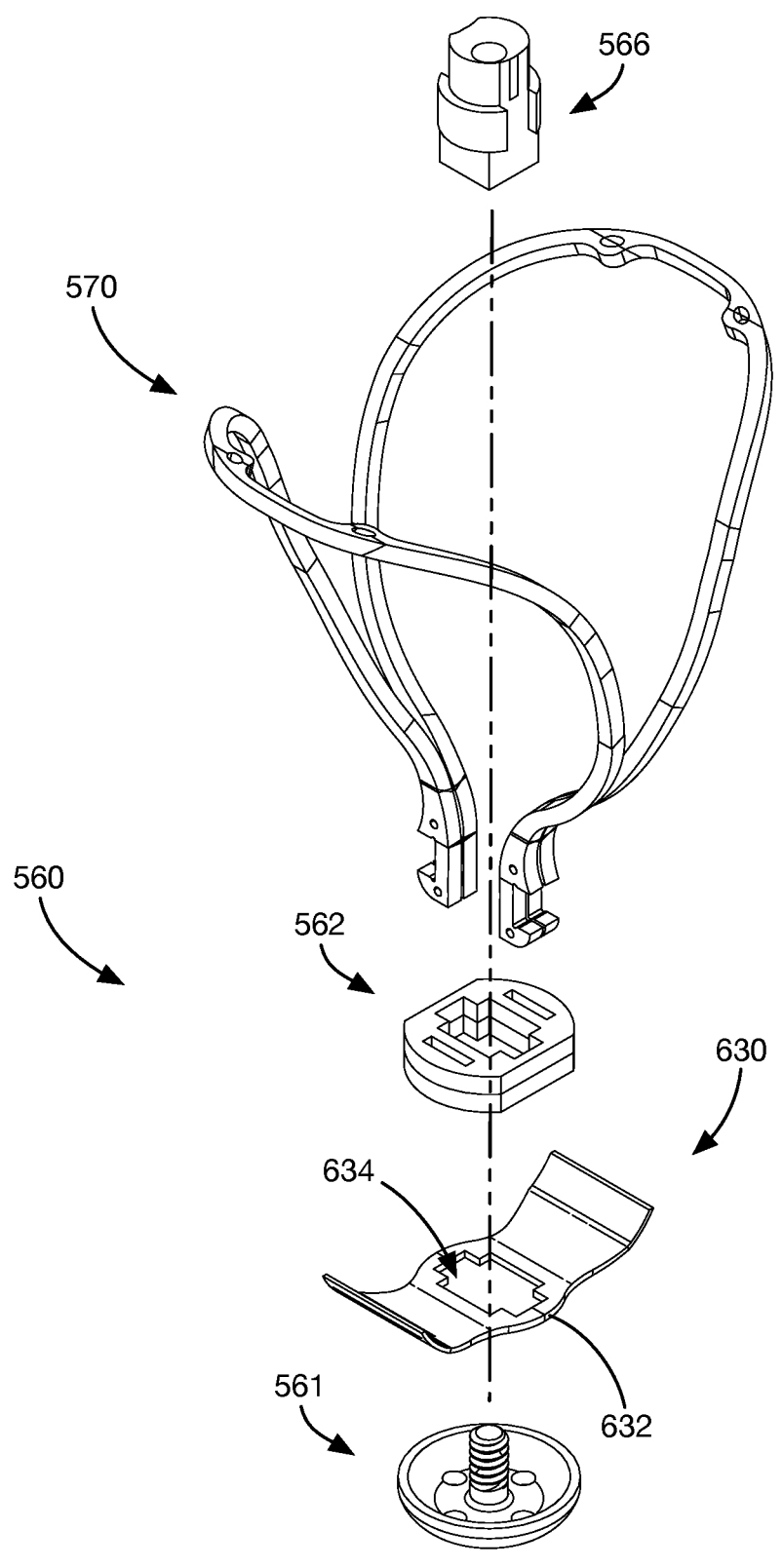

Referring now to FIGS. 161-164, another example embodiment of paddles 630 for an example implantable are shown. The paddles 630 are formed by joining distal ends 532 of the two of the paddles 530 (described above) together with a connecting portion 632. The connecting portion 632 includes an opening 634 for receiving the distal retaining nut 566 (FIG. 163) so that the paddles 630 are sandwiched between the bolt 561 and the washers 562 (FIG. 163). Optionally, the paddles 530 can be joined by a connecting portion (not shown) at their proximal ends 532. Attaching the paddles 630 in this way enables both paddles 530 to be formed in a single operation.

Referring now to FIGS. 165-167, various views of one of the barbed clasps 580 are shown with the barbed clasp 580 separate from other components of the implantable prosthetic device 500. The barbed clasp 580 can be substantially the same as the barbed clasp 330 shown in FIG. 56, but the size of the clasp 580 can be different than the size of the clasp 330, since the device 300 shown in FIG. 55 can be a different size than the device 500. However, a wide variety of different barbed clasps can be used in the devices disclosed herein. Examples of barbed clasps that can be used include but are not limited the barbed clasp illustrated by FIG. 29 and/or any of the barbed clasps disclosed in the present application and any of the applications that are incorporated herein by reference and/or that the present application claims priority to. The barbed clasps 580 grasp the native leaflets 20, 22 in a similar manner to that shown in FIG. 29 and described above.

The barbed clasps 580 include a base or fixed arm 582, a moveable arm 584, barbs 586, and a joint or hinge portion 588. The fixed arms 582 are attached to the paddles 530, with the joint portion 588 disposed proximate the coaption element 520. The joint portion 588 is spring-loaded so that the fixed and moveable arms 582, 584 are biased toward each other when the barbed clasp 580 is in a closed condition, as well as the open portion. The hinge portion 588 is formed from a plurality of spring segments arranged in a repeating pattern extending between the fixed arm 582 and the movable arm 584. Joining multiple segments together allows the hinge portion 588 to bend a considerable amount while avoiding plastic deformation of the material as the individual spring segments are twisted. For example, in certain embodiments, the fixed arm 582 can be moved, flexed, rotated, or pivoted from a neutral position that is approximately 125 degrees beyond the moveable arm 584 to a fully open position that is approximately 180 degrees from the moveable arm 584 without plastically deforming the clasp material. In certain embodiments, the clasp material plastically deforms during opening without reducing or without substantially reducing the pinch force exerted between the fixed and moveable arms in the closed position.

The fixed arms 582 are attached to the openings 537 of the paddles 530 through holes or slots 581 with sutures (not shown). The fixed arms 582 can be attached to the paddles 530 with any suitable means, such as screws or other fasteners, crimped sleeves, mechanical latches or snaps, welding, adhesive, or the like. The fixed arms 582 remain substantially stationary relative to the paddles 530 when the moveable arms 584 are opened to open the barbed clasps 580 and expose the barbs 586. The barbed clasps 580 are opened by applying tension to actuation lines 596 (FIGS. 72-75) attached to holes 585 in the moveable arms 584, thereby causing the moveable arms 584 to move, pivot, flex, etc. on the joint portions 588.

In some embodiments, the barbed clasps 580 are laser cut from a layer of shape-memory alloy, such as Nitinol. As is shown in FIGS. 166-167, the barbs 586 lay flat in the same plane as the rest of the clasp 580 when cut out of the layer of material. The moveable arms 584 and barbs 586 are then bent and/or twisted and are then subjected to a shape setting process. These can be formed in other ways as well.

Referring again to FIGS. 115-121, the outer paddle portion 540 of the paddles 530 can be stretched to extend the length and decrease the width of the implantable prosthetic device 500. The paddle frames 570 can also be lengthened and narrowed by stretching. In some embodiments, the width of the paddle frames 570 can decrease from about 10 millimeters to about 8 millimeters during stretching. Stretching of the paddles 530 and paddle frames 570 can be achieved by applying force to the actuation element 591 to push the distal cap assembly 560 away from the main shaft 510 while simultaneously maintaining tension on the actuation lines 596. Movement of the distal cap assembly 560 away from the main shaft 510 pulls down on the distal ends 532 of the paddles 530 which in turn apply a tensile force to the outer paddle portions 540. The force applied to the actuation lines can be less than the force required to open the clasps 580 while still being sufficient to maintain the position of the clasps 580 as the actuation element 591 is extended. Consequently, the inner paddle portion 538 attached to the clasp 580 and the paddle connection portions

572 of the paddle frames 570 are also restrained from moving. Thus, the outer paddle portions 540 and the paddle frames 570 are stretched between the distal cap assembly 560 and the paddle connection portions 572 so that the outer paddle portions 540 are extended from the resting position shown in FIGS. 106-112 to the extended position shown in FIGS. 115-121 and the paddle frames 570 are similarly extended (not shown). In embodiments of the implantable prosthetic device 500 that include a spreading member 650 (FIGS. 138-145) that can be actuated independently from the movement of the distal cap assembly 560, the paddles 530 and paddle frames 570 can be spread apart while they are maintained in an open position. That is, the position of the distal cap assembly 560 (which controls the opening and closing of the paddles) can be maintained by the control wire, while the spreading member 650 is moved to engage the paddles 530. The engagement of the paddles 530 with the spreading member 650, while the position of the cap 560 is maintained, can also increase tension along the outer paddle portions 540 and paddle frames 570. This tension can stretch the outer paddle portions 540 and paddle frames 570 to allow the outer paddle portions and paddle frames to fit between small gaps in the patient's anatomy, such as between chordae tendinea.

As described above, the upper and lower flexible members 542, 544 move together to reduce the overall width of the outer paddle portions 540 as the length of the outer paddle portions 540 is increased. The paddle frames 570 similarly narrow as they are stretched. Accordingly, the width of the outer paddle portions 540 and the paddle frames 570 can be adjusted by stretching the outer paddle portions 540 and the paddle frames 570. In some embodiments, the outer paddle portions 540 are more flexible than the paddle frames 570 such that the outer paddle portions 540 narrow before the paddle frames 570 and, consequently, the paddle frames 570 carry more of the load exerted on the device 500 from stretching. Conversely, in some embodiments, the paddle frames 570 are more flexible than the outer paddle portions 540 so that the paddle frames 570 narrow before the outer paddle portions 540 and, consequently, the outer paddle portions 540 carry more of the load exerted on the device 500 from stretching.

During the implantation procedure, native heart structures (e.g., numerous and/or densely packed chordae) can interfere with capture of the leaflets. That is, portions of the implantable prosthetic device 500 may contact the chordae such that the connected leaflet is pushed away as the surgeon attempts to move the implantable prosthetic device 500 toward the leaflet for capture. Enabling the adjustment of the width of the implantable prosthetic device 500 improves maneuverability of the implantable prosthetic device 500 when configured in a "capture ready" configuration during the implantation procedure. When such native structures are encountered, the implantable prosthetic device 500 can be partially extended to stretch the outer paddle portions 540 and paddle frames 570 to reduce the width of the paddles 530 and the paddle frames 570, thereby avoiding the native heart structures and enabling capture of the leaflet. The paddles 530 widen when the implantable prosthetic device 500 is closed to capture the leaflet which provides an increased pinching surface to better secure the leaflet within the implantable prosthetic device 500.

Referring now to FIGS. 168-183, various views of the deployment of the optional spreading member 550 are shown. The spreading member 550 can be selectively deployed to engage and spread apart the paddles 530 to enable the translational movement of the paddles 530 shown in FIGS. 57-64 and described above. That is, deployment and actuation of the spreading member 550 causes the paddles 530 to translate outward to better position the clasps 580 to grasp leaflets 20, 22 of a native valve with a larger gap 26. As is discussed above, the translation of the paddles 530 can occur prior to, during, or after the paddles are rotated or pivoted in an opening direction to prepare to capture the leaflets 20, 22. When the gap 26 is not large enough to require spreading, the device can be used as described above, without using the paddle spreading feature. That is, the paddles 530 are simply opened and closed, by translating the spreading member 550, without rotating the spreading member 550 to enable the paddle spreading feature.

Referring now to FIGS. 168, 172, 176, and 178, when not needed to spread apart the paddles 530, the spreading member 550 is stowed at the distal end 512 of the main shaft 510 such that the cam portions 556 are arranged between and rotationally restricted by the distal projections 519 of the main shaft 510. In the stowed position, the spreading member 550 is also partially located within the central opening 523 and assembly grooves 524 at the distal end 522 of the coaption element 520. The actuation element 591 is extended to deploy the spreading member 550 by first moving the spreading member 550 distally such that the cam portions 556 are free from the distal projections 519 of the main shaft, as shown in FIGS. 169 and 173. This extension of the actuation element 591 can partially open the paddles 530. Optionally, this partial opening can be limited or prevented altogether by applying tension to the actuation lines 596 during extension of the actuation element 591 as described above. That is, the force exerted by extension of the actuation element 591 can be directed to stretching the outer paddle portions 540 and paddle frames 570 rather than opening the paddles 530. In some embodiments, the outer paddle portions 540 and paddle frames 570 are stretched and the paddles 530 are partially opened by extension of the actuation element 591 to deploy the spreading member 550.

Figures 168, 169, 170, 171:
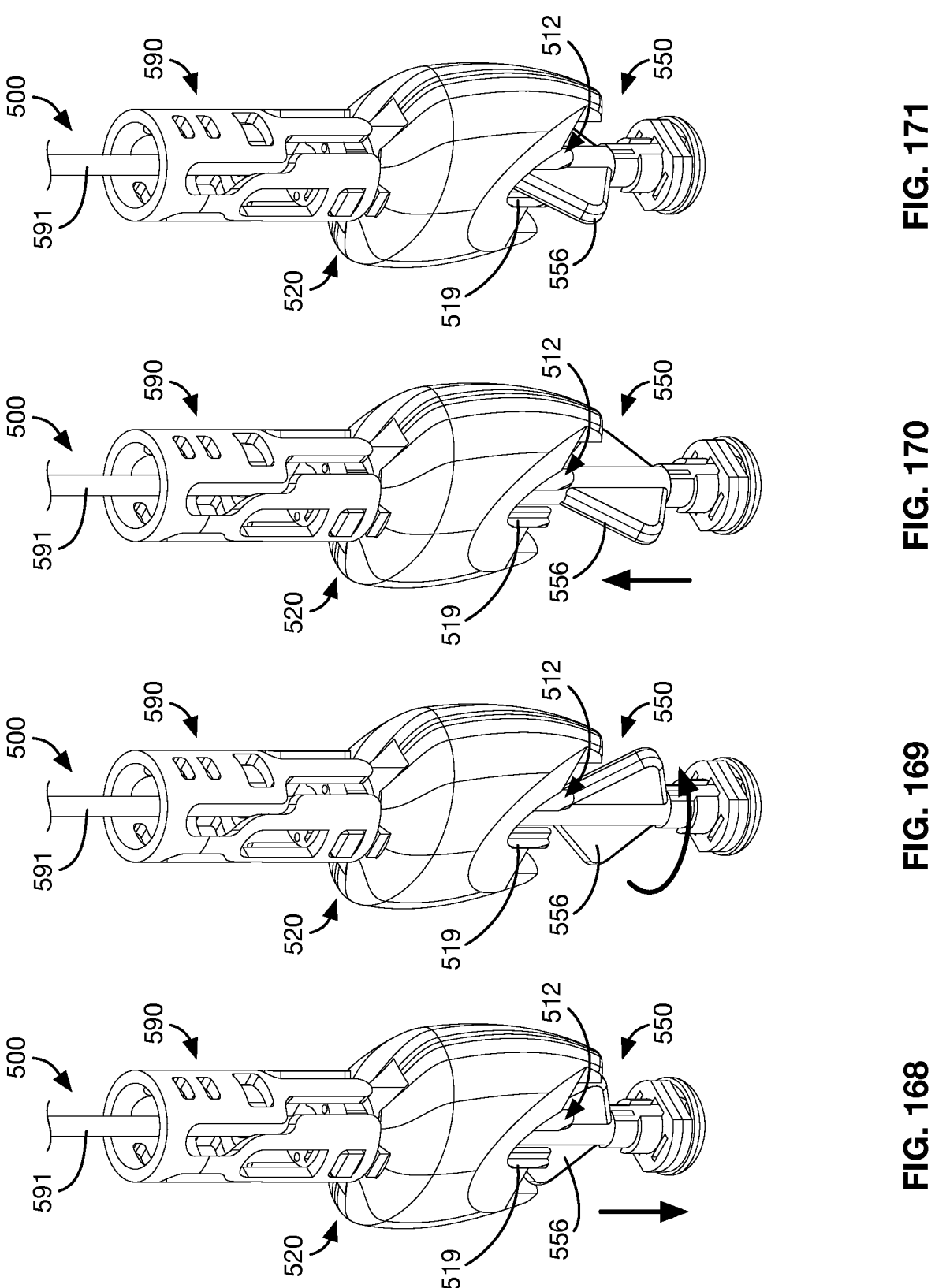
Figures 172, 173, 174, 175:
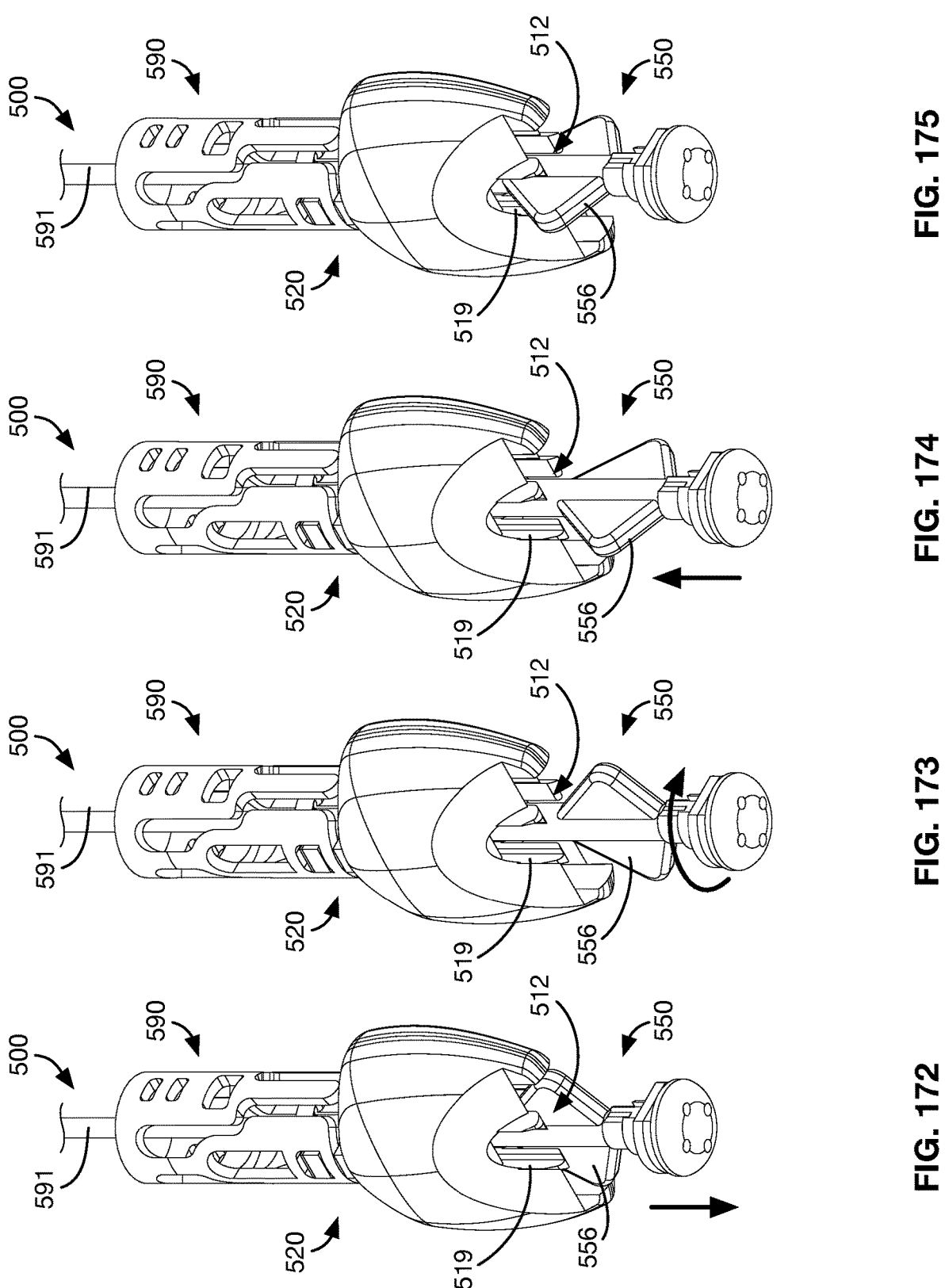

Referring now to FIGS. 170 and 174, the extended actuation element 591 is rotated to rotate the spreading member 550 to a deployed orientation that is 90 degrees from the stowed orientation. This rotation aligns the cam portions 556 of the spreading member 550 with the second cam slot 518 of the main shaft 510 so that the spreading member 550 can be retracted to engage and spread apart the paddles 530 (see FIG. 181). The actuation element 591 and spreading member 550 can be retracted into the second cam slot 518 between the distal projections 519 to engage the paddles 530. The spreading member 550 can be actuated to any position between the extended position shown in FIGS. 170 and 174 and the retracted position shown in FIGS. 171, 175, 177, and 179 to achieve translation of the paddles 530.

In one use, the cam spreader 550 can be configured to remain in the cam spreading position after the leaflets are captured, the clasps 580 are closed, and the paddles 530 are closed around the coaption member 520 by retraction of the cam spreader. In another example embodiment, the cam spreader 550 can be used to widen the spacing between the clasps 580 by rotating the cam spreader 550 to capture the spaced apart leaflets. Once the spaced apart leaflets are grasped by the clasps 580, the cam spreader 550 can be used to return the spacing between the clasps 580 (and the captured leaflets) to the original, narrower spacing by rotating the cam spreader 550 back to the illustrated position. The paddles 530 can then be closed around the captured leaflets by retracting the cam spreader.

Referring now to FIGS. 180-183, portions of the paddles 530 and clasps 580 are shown in addition to the components of the device 500 shown in FIGS. 168-179 to illustrate how the spreading member 550 engages the paddles 530 to facilitate the above described translation movement that spreads apart the paddles 530 to capture leaflets 20, 22. To begin leaflet capture, the device 500 is opened to a capture-ready condition, shown in FIG. 180, with the paddles 530 and clasps 580 opened about half-way (though any amount of opening can be used). The spreading member 550 is in a stowed or disengaged position so that the spreading member 550 fits between and does not engage the paddles 530. In this position, the leaflets 20, 22 are spread apart and would likely not be captured by closing the clasps 580.

To move the clasps 580 into a more desirable capture position, the spreading member 550 can be used to widen the spacing between the clasps 580 by rotating the spreading member 550 to the position illustrated by FIG. 181 to capture the spaced apart leaflets 20, 22. The spreading member 550 is extended (See FIG. 180), rotated, and retracted to move from the stowed position shown in FIG. 179 to the deployed position shown in FIG. 181. During retraction, the optional distal projections 519 of the main shaft 510 can prohibit the rotation of the spreading member 550 out of either the disengaged position or the engaged position during retraction of the spreading member 550 into the main shaft 510 and coaption element 520. This retracting movement causes the cam surfaces 558 of the cam portions 556 engage the spreading portions 535 of the paddles 530 to spread the spreading portions 535 apart. Outward movement of the spreading portions 535 also moves the connection portions 536 and inner paddle portions 538 outward so that the clasps 580 attached to the inner paddle portions 538 also translate in an outward direction. The illustrated ramp-like shape of the cam portions 556 enables the magnitude of the lateral translation of the paddles 530 and clasps 580 to be controlled by controlling the magnitude of the extension and retraction of the actuation element 591 and/or spreading portions. That is, the maximum outward movement of the paddles 530 is reached when the spreading member 550 is retracted to the fullest extent possible. The cam portions 556 are shown with a triangular shape, but and can have a wide variety of shapes to increase or decrease the magnitude and rate at which the paddles 530 are spread during retraction of the spreading member 550 to aid in the capture of the native leaflets 20, 22.

Once the paddles 530 and clasps 580 have been spread apart, the leaflets 20, 22 are captured by closing the clasps 580 and paddles 530. Closing the clasps 580 pinches the leaflets 20, 22 between the fixed and moveable arms 582, 584, as can be seen in FIG. 182. The paddles 530 can also be closed partially to move the leaflets 20, 22 toward the coaption element 520. Once the leaflets 20, 22 are captured, the spreading member 550 can be used to return the spacing between the clasps 580 (and the captured leaflets 20, 22) to the original, narrower spacing by rotating the spreading member 550 back to the stowed or disengaged position illustrated by FIG. 183. The paddles 530 are then closed fully to secure the leaflets 20, 22 against the coaption element 520, as illustrated in FIG. 183. In another use, the spreading member 550 can remain in the spread-out position shown in FIGS. 181 and 182 after the leaflets 20, 22 are captured, the clasps 580 are closed, and the paddles 530 are closed around the coaption member 520 by retraction of the spreading member 550.

Referring now to FIGS. 184-213, a coaption element can be configured in a variety of ways to be compressible. For example, the coaption element 520 described above can be compressible such that it fits within, can be moved through, and/or can be deployed from a delivery catheter or the like. Each of the coaption elements can incorporate any of the features previously described herein, such as the coaption element 520 described in FIGS. 95-100. Additionally, each of the coaption elements can be used with any of the implantable prosthetic spacer devices 100, 200, 300, 400, 500 previously described herein. Each of the coaption elements can be made of a flexible and/or compressible material such as, for example, rubber, foam, plastic, or other suitable material.

Referring to FIGS. 184-188, a coaption element 1520 is depicted according to one embodiment. The coaption element 1520 extends from a proximal end 1521 to a distal end 1522 and has a generally elongated and rounded shape. In particular, the coaption element 1520 has an elliptical shape or cross-section when viewed from above (FIG. 187) and has a tapered shape or cross-section when seen from a front view (FIG. 186) and a rounded shape or cross-section when seen from a side view (FIG. 185). A central opening 1523 extends through a body portion 1528 of the coaption member 1520 from the proximal end 1521 to the distal end 1522. The central opening 1523 has a diameter that is about the same or is slightly larger than a diameter of the main shaft 510 so that the main shaft 510 can be received within the central opening 1523 of the coaption element 1520.

The coaption element 1520 has one or more arm portions 1530 extending outwardly (to the front and rear) from the body portion 1528. The one or more arm portions 1530 connect to the body portion 1528 near the proximal end 1521 and the distal end 1522 of the body portion 1528, thereby defining one or more openings 1531 between the arm portion 1530 and the body portion 1528. The one or more arm portions 1530 can be made from a flexible and/or compressible material such as, for example, foam, rubber, plastic, or other suitable material.

Optionally, the coaption element 1520 can also include a distal arm 1532 defining a distal opening 1533 between the body portion 1528 and the distal arm 1532. The distal arm 1532 can be made from a flexible and/or compressible material such as, for example, foam, rubber, plastic, or other suitable material. In one example embodiment, the entire coaption element 1520 is a single molded component.

As shown in FIG. 188, a force can be applied to the one or more arm portions 1530 such that the arm portions 1530 bend, move, or are otherwise flexed medially or inwardly toward the body portion 1528, thereby decreasing the size of the one or more openings 1531 or eliminating the one or more openings. As such, the arm portions 1530 are compressed toward the body portion 1528 and the overall size of the coaption element 1520 is decreased. In the illustrated embodiment, a force is applied downwardly (distally) such that the arm portions 1530 are compressed toward the body portion 1528. However, it will be appreciated that the arm portions 1530 can be compressed toward the body portion 1528 in a variety of ways. For example, a medial inward force can be applied to the arm portions 1530 such that the arm portions 1530 are compressed toward the body portion 1528.

Referring to FIGS. 189-193, a coaption element 2520 is depicted according to one embodiment. The coaption element 2520 extends from a proximal end 2521 to a distal end 2522 and has a generally elongated and rounded shape. In particular, the coaption element 2520 has an elliptical shape or cross-section when viewed from above (FIG. 192) and has a tapered shape or cross-section when seen from a front view (FIG. 191) and a rounded shape or cross-section when seen from a side view (FIG. 190). A central opening 2523 extends through a body portion 2528 of the coaption member 2520 from the proximal end 2521 to the distal end 2522. The central opening 2523 has a diameter or size that is about the same or is slightly larger than a diameter of the main shaft 510 so that the main shaft 510 can be received within the central opening 2523 of the coaption element 2520.

The coaption element 2520 has a plurality of protrusions or wing portions 2530 extending outwardly (to the front and rear) from the body portion 2528. The protrusions or wing portions 2530 are generally oriented perpendicularly to the central opening 2523. The one or more protrusions or wing portions 2530 connect to the body portion 2528 at two points thereby defining longitudinal openings 2531 between the body portion 2528 and each of the wing portions 2530. The longitudinal openings 2531 on each side of the body portion 2528 can be at least partially aligned. In some embodiments, there are 2-20 protrusions/wing portions, and the protrusions/wing portions are spaced apart anywhere from 0.1 mm to 3 mm. The one or more protrusions/wing portions 2530 can be made from a flexible and/or compressible material such as, for example, foam, rubber, plastic, silicone, or other suitable material.

As shown in FIG. 193, the coaption element 2520 can be compressed. A force can be applied to the protrusions/wing portions 2530 such that the protrusions/wing portions 2530 angle downwardly or distally in the direction of the distal portion 2522. The outer portion of each protrusion/wing portion 2530 can be moved downwardly or distally such that the outer portion of each protrusion/wing portion 2530 nests or fits within the longitudinal opening 2531 defined by the protrusion/wing portion 2530 distally below. As such, the overall size of the coaption element 2520 is decreased. In the illustrated embodiment, a force is applied downwardly (distally) and inwardly (medially) to each wing portion 2530 such that the protrusions/wing portions 2530 are compressed toward the body portion 2528. However, it will be appreciated that the protrusions/wing portions 2530 can be compressed toward the body portion 2528 in a variety of ways. For example, a downward or an inward force can be applied to the protrusions/wing portions 2530 such that the protrusions/wing portions 2530 are compressed toward the body portion 2528.

Referring to FIGS. 194-198, a coaption element 3520 is depicted according to one embodiment. The coaption element 3520 extends from a proximal end 3521 to a distal end 3522 and has a generally elongated and rounded shape. In particular, the coaption element 3520 has an elliptical shape or cross-section when viewed from above (FIG. 197) and has a tapered shape or cross-section when seen from a front view (FIG. 196) and a rounded shape or cross-section when seen from a side view (FIG. 195). A central opening 3523 extends through a body portion 3528 of the coaption member 3520 from the proximal end 3521 to the distal end 3522. The central opening 3523 has a diameter or shape that is about the same or is slightly larger than a diameter of the main shaft 510 so that the main shaft 510 can be received within the central opening 3523 of the coaption element 3520.

The coaption element 3520 has a plurality of protrusions or wing portions 3530 extending outwardly (to the front and rear) from the body portion 3528. Similarly to the coaption element 2520 of FIGS. 189-193, the protrusions or wing portions 3530 are generally oriented perpendicularly to the central opening 3523 and the one or more wing portions 3530 connect to the body portion 3528 at two points thereby defining longitudinal openings 3531 between the body portion 3528 and each of the protrusions/wing portions 3530.

However, the protrusions/wing portions 3530 are thinner and spaced farther apart (e.g., 1-3 times farther apart) than the protrusions/wing portions 2530 of the coaption element 2520 shown in FIGS. 189-193. The one or more wing portions 3530 can be made from a flexible and/or compressible material such as, for example, foam, rubber, plastic, or other suitable material. In some embodiments, there are 2-20 protrusions/wing portions, and the protrusions/wing portions are spaced apart anywhere from 0.1 mm to 5 mm.

As shown in FIG. 198, the coaption element 3520 can be compressed. A force can be applied to the protrusions/wing portions 3530 such that the protrusions/wing portions 3530 angle downwardly or distally. The outer portion of each protrusion/wing portion 3530 can be moved downwardly or distally such that the outer portion of each protrusion/wing portion 3530 nests or fits within the opening 3531 defined by the protrusion/wing portion 3530 below. Due to the configuration and spacing of the protrusions/wing portions 3530, each protrusion/wing portion 3530 can extend farther outwardly (toward the front and rear) than the protrusion/wing portion 3530 proximally above. As such, the protrusions/wing portions 3530 can nest more easily which can facilitate the overall compression of the coaption element 3520. In the illustrated embodiment, a force is applied downwardly (distally) and inwardly (medially) to each protrusion/wing portion 3530 such that the protrusions/wing portions 2530 are compressed toward the body portion 3528. However, it will be appreciated that the protrusions/wing portions 3530 can be compressed toward the body portion 3528 in a variety of ways. For example, a downward or an inward force can be applied to the protrusions/wing portions 3530 such that the protrusions/wing portions 3530 are compressed toward the body portion 3528.

Referring to FIGS. 199-203, a coaption element 4520 is depicted according to one embodiment. The coaption element 4520 extends from a proximal end 4521 to a distal end 4522 and is depicted with a generally elongated and rounded shape. In particular, the coaption element 4520 is depicted with an elliptical shape or cross-section when viewed from above (FIG. 202) and has a tapered shape or cross-section when seen from a front view (FIG. 201) and a rounded shape or cross-section when seen from a side view (FIG. 200), though variations and other shapes are possible. A central opening 4523 extends through a body portion 4528 of the coaption member 4520 from the proximal end 4521 to the distal end 4522. The central opening 4523 has a diameter or shape that is about the same or is slightly larger than a diameter of the main shaft 510 so that the main shaft 510 can be received within the central opening 4523 of the coaption element 4520.

The coaption element 4520 has a plurality of protrusions or wing portions 4530 extending outwardly (to the front and rear) from the body portion 4528. The protrusions/wing portions 4530 are angled distally and outwardly from the body portion 4528, with the distal protrusions/wing portions 4530 being oriented more downwardly (i.e., toward the distal end 4522 of the coaption element 4520). Optionally, the one or more protrusions/wing portions 4530 connect to the body portion 4528 at two points thereby defining openings 4531 between the body portion 4528 and each of the protrusions/wing portions 4530. The coaption element 4520 also includes grooves 4533 between that the protrusions/wing portions 4530 that are narrowly tapered toward the body portion 4528. The distal grooves 4533 can be wider than the proximal grooves 4533. The one or more protrusions/wing portions 4530 can be made from a flexible and/or compressible material such as, for example, foam, rubber, plastic, or other suitable material.

As shown in FIG. 203, a force can be applied to the protrusions/wing portions 4530 such that the outer portion of the wing protrusions/portions 4530 are moved downwardly (distally) and inwardly (toward the body portion 4528). The grooves 4533 can be configured such that the longer protrusions/wing portions 4530 move farther downward than the other protrusions/wing portions 4530. Optionally, portions of the protrusions/wing portions 4530 can fit or nest in the longitudinal opening 4531 defined by the protrusion/wing portion 4530 distally below. As such, the overall size of the coaption element 4520 can be compressed or otherwise decreased. In the illustrated embodiment, a force is applied downwardly (distally) and inwardly (medially) to each protrusion/wing portion 4530 such that the protrusions/wing portions 4530 are compressed toward the body portion 4528. However, it will be appreciated that the protrusions/wing portions 4530 can be compressed toward the body portion 4528 in a variety of ways. For example, a downward or an inward force can be applied to the protrusions/wing portions 4530 such that the protrusions/wing portions 4530 are compressed toward the body portion 4528.

Referring to FIGS. 204-208, a coaption element 5520 is depicted according to one embodiment. The coaption element 5520 extends from a proximal end 5521 to a distal end 5522 and has a generally elongated and rounded shape. In particular, the coaption element 5520 has an elliptical shape or cross-section when viewed from above (FIG. 207) and has a tapered shape or cross-section when seen from a front view (FIG. 206) and a rounded shape or cross-section when seen from a side view (FIG. 205). A central opening 5523 extends through a body portion 5528 of the coaption member 5520 from the proximal end 5521 to the distal end 5522. The central opening 5523 has a diameter or size that is about the same or is slightly larger than a diameter of the main shaft 510 so that the main shaft 510 can be received within the central opening 5523 of the coaption element 5520.

The coaption element 5520 has a plurality of protrusions or wing portions 5530 extending outwardly (to the front and rear) from the body portion 5528. The protrusions/wing portions 5530 are angled or generally angled distally and outwardly from a point substantially in the middle of the body portion 5528. The protrusions/wing portions 5530 closer to the proximal end 5521 can be angled upwardly away from the body portion 5528 and the protrusions/wing portions 5530 closer to the distal end 5522 can be angled downwardly away from the body portion 5528. Optionally, the one or more protrusions/wing portions 5530 connect to the body portion 5528 at two points thereby defining openings 5531 between the body portion 5528 and each of the protrusions/wing portions 5530. The coaption element 4520 also includes grooves 5533 between that the protrusions/wing portions 5530 that are narrowly tapered toward the body portion 5528. The grooves 5533 extend medially toward a center of the body portion 5528. The one or more protrusions/wing portions 5530 can be made from a flexible and/or compressible material such as, for example, foam, rubber, plastic, or other suitable material.

As shown in FIG. 208, forces can be applied to the protrusions/wing portions 5530 to compress the coaption element 5520. An upward (proximal) and inward (toward the body portion 5528) force can be applied to the protrusions/wing portions 5530 that are closer to the proximal end 5521 and a downward (distal) and inward (toward the body portion 5528) force can be applied to the protrusions/wing portions 5530 that are closer to the distal end 5522. The grooves 5533 can be configured such that the protrusions/wing portions 5530 can move toward the body portion 5528 as much as possible. Optionally, portions of the protrusions/wing portions 5530 can fit or nest in the longitudinal opening 5531 defined by the protrusion/wing portion 5530 toward which the protrusion/wing portion 5530 is moved. As such, the overall size of the coaption element 5520 can be compressed. In the illustrated embodiment, a force is applied upwardly (proximally) and inwardly to the protrusions/wing portions 5530 that are closer to the proximal end 5521 and a force is applied downwardly (distally) and inwardly to the protrusions/wing portions 5530 closer to the distal end 5522 such that the protrusions/wing portions 5530 are compressed toward the body portion 5528. However, the protrusions/wing portions 5530 can be compressed toward the body portion 5528 in a variety of ways. For example, the protrusions/wing portions 5530 can be oriented, shaped, and/or configured such that a medially inward force can be applied to all the protrusions/wing portions 5530 to compress the protrusions/wing portions 5530 toward the body portion 5528.

Referring to FIGS. 209-213, a coaption element 6520 is depicted according to one embodiment. The coaption element 6520 extends from a proximal end 6521 to a distal end 6522 and has a generally elongated and rounded shape. In particular, the coaption element 6520 has an elliptical shape or cross-section when viewed from above (FIG. 212) and has a tapered shape or cross-section when seen from a front view (FIG. 211) and a rounded shape or cross-section when seen from a side view (FIG. 210). A central opening 6523 extends through a body portion 6528 of the coaption member 5520 from the proximal end 6521 to the distal end 6522. The central opening 6523 has a diameter or size that is about the same or is slightly larger than a diameter of the main shaft 510 so that the main shaft 510 can be received within the central opening 6523 of the coaption element 6520.

The coaption element 6520 has a plurality of protrusions or wing portions 6530 extending radially outwardly (to the front and rear) from the body portion 6528. The protrusions or wing portions 6530 are separated by one or more longitudinal grooves 6531 which extends radially inwardly toward the body portion 6528. The longitudinal grooves 6531 can be tapered inwardly toward the body portion 6528. The protrusions/wing portions 6530 and the longitudinal grooves 6531 can be configured such that the protrusions/wing portions 6530 are thicker at the radial outer portions. The one or more protrusions/wing portions 6530 can be made from a flexible and/or compressible material such as, for example, foam, rubber, plastic, or other suitable material.

As shown in FIG. 213, forces can be applied to the protrusions/wing portions 6530 to compress the coaption element 6520. Radially inward forces can be applied to the protrusions/wing portions 6530 to radially compress the protrusions/wing portions 6530 and thereby decrease the overall size of the coaption element 6520. The longitudinal grooves 6531 can be configured such that the protrusions/wing portions 6530 can move toward the body portion 6528 as much as possible. As such, the overall size of the coaption element 6520 can be compressed.

In the illustrated embodiment, inward radial forces are applied to the protrusions/wing portions 6530 such that the protrusions/wing portions 6530 are compressed toward the body portion 6528. However, it will be appreciated that the protrusions/wing portions 6530 can be compressed toward the body portion 6528 in a variety of ways. For example, a lateral force, either forward or backward, can be applied to the protrusions/wing portions 6530 such that the protrusions/wing portions are compressed toward the body portion 6528.

While the coaption elements have been described according to specific embodiments, the various features of any of the coaption elements 520, 1520, 2520, 3520, 4520, 5520, 6620 can be used in many alternative embodiments, either individually or in various combinations and sub-combinations thereof.

The coaption element 7020 can be sized, shaped, and configured to fit in the native anatomy of the patient that will receive the implant. For example, any of the coaption elements 520, 1520, 2520, 3520, 4520, 5520, 6620, or a coaption element incorporating any of the various features of any of the coaption elements 520, 1520, 2520, 3520, 4520, 5520, 6620 can be employed. The coaption element 520 can be sized, shaped, and configured specifically for the native anatomy of the patient that will receive the implant. Optionally, the person performing the procedure can have a variety of coaption elements available to him or her during the procedure, e.g., in a kit, which can include any of the associated tools and other elements. The person performing the procedure can select the coaption element with the desired size, shape, and configuration corresponding to the native anatomy of the patient that will receive the implant.

While various inventive aspects, concepts and features of the disclosures may be described and illustrated herein as embodied in combination in the example embodiments, these various aspects, concepts, and features can be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. Further, the treatment techniques, methods, operations, steps, etc. described or suggested herein can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

We claim:

1. A valve repair system for repairing a native valve of a patient, the valve repair system comprising:
    a valve repair device comprising:
        a main shaft;
        a plastic hollow coaptation element mounted over the main shaft;
        a pair of paddles, each paddle comprising a connection portion, an inner paddle portion, and an outer paddle portion;
        wherein each connection portion of the pair of paddles is connected to the main shaft;
        at least one clasp attached to each paddle of the pair of paddles;
        an actuation shaft extending through the main shaft;
        a cap attached to the actuation shaft such that the cap can be moved by the actuation shaft away from the main shaft; and
        wherein movement of the cap toward the main shaft causes the pair of paddles to move to a closed position, and movement of the cap away from the main shaft causes the pair of paddles to move to an open position.

2. The valve repair system of claim 1, wherein the connection portion, the inner paddle portion, and the outer paddle portion are formed from a single strip of metal.

3. The valve repair system of claim 1, wherein the connection portion, the inner paddle portion, and the outer paddle portion have a ribbon-like form.

4. The valve repair system of claim 1 wherein the pair of paddles are configured to narrow and widen.

5. The valve repair system of claim 4 wherein the pair of paddles are configured to narrow and widen during opening and closing of the pair of paddles.

6. The valve repair system of claim 1 wherein each inner paddle portion of the pair of paddles is configured to narrow and widen.

7. The valve repair system of claim 1 wherein the pair of paddles are formed from a single ribbon of material.

8. The valve repair system of claim 7 wherein the single ribbon of material is attached to a distal cap and wherein movement of the distal cap moves the pair of paddles between the open position and the closed position.

9. The valve repair system of claim 1, further comprising a cover disposed over the plastic hollow coaptation element.

\* \* \* \* \*